United States Patent
Zhou et al.

(10) Patent No.: US 9,670,203 B2
(45) Date of Patent: Jun. 6, 2017

(54) FUSED TRICYCLIC UREA COMPOUNDS AS RAF KINASE AND/OR RAF KINASE DIMER INHIBITORS

(71) Applicant: BeiGene, LTD., Camana Bay (KY)

(72) Inventors: Changyou Zhou, Princeton, NJ (US); Guoliang Zhang, Beijing (CN)

(73) Assignee: BeiGene, Ltd., Grand Cayman (KY)

( * ) Notice: Subject to any disclaimer, the term of this patent is extended or adjusted under 35 U.S.C. 154(b) by 0 days.

(21) Appl. No.: 14/901,634

(22) PCT Filed: Jun. 27, 2014

(86) PCT No.: PCT/CN2014/080983
§ 371 (c)(1),
(2) Date: Dec. 28, 2015

(87) PCT Pub. No.: WO2014/206343
PCT Pub. Date: Dec. 31, 2014

(65) Prior Publication Data
US 2016/0368914 A1 Dec. 22, 2016

(30) Foreign Application Priority Data

Jun. 28, 2013 (WO) ................ PCT/CN2013/078338

(51) Int. Cl.
| | | |
|---|---|---|
| C07D 519/00 | (2006.01) | |
| C07D 405/12 | (2006.01) | |
| C07D 471/04 | (2006.01) | |
| C07D 498/04 | (2006.01) | |
| C07D 473/30 | (2006.01) | |

(52) U.S. Cl.
CPC ......... *C07D 471/04* (2013.01); *C07D 405/12* (2013.01); *C07D 473/30* (2013.01); *C07D 498/04* (2013.01)

(58) Field of Classification Search
CPC .. C07D 519/00; C07D 405/12; C07D 471/04; C07D 498/04
See application file for complete search history.

(56) References Cited

U.S. PATENT DOCUMENTS

| | | |
|---|---|---|
| 2010/0197924 A1 | 8/2010 | Gould et al. |
| 2016/0159820 A1 | 6/2016 | Zhou et al. |

FOREIGN PATENT DOCUMENTS

| | | |
|---|---|---|
| WO | WO 02/070516 A2 | 9/2002 |
| WO | WO 2004/021969 | 3/2004 |
| WO | WO 2005/062795 A2 | 7/2005 |
| WO | WO 2006/066913 A2 | 6/2006 |
| WO | WO 2007/067444 A1 | 6/2007 |
| WO | WO 2007/136572 A2 | 11/2007 |
| WO | WO 2008/028617 A1 | 3/2008 |
| WO | WO 2008/079906 A1 | 7/2008 |
| WO | WO 2008/079909 A1 | 7/2008 |
| WO | WO 2009/012283 A1 | 1/2009 |
| WO | WO 2010/064722 A1 | 6/2010 |
| WO | WO 2011/092088 A1 | 8/2011 |
| WO | WO 2013/097224 | 7/2013 |
| WO | WO 2014/206343 | 12/2014 |
| WO | WO 2014/206344 A1 | 12/2014 |

OTHER PUBLICATIONS

Supplementary European Search Report for European Application No. 14818636.4, mailed Jan. 10, 2017, 4 pages.
International Search Report and Written Opinion for International Application No. PCT/CN2014/080986, mailed Sep. 30, 2014, 11 pages.
International Preliminary Report on Patentability for International Application No. PCT/CN2014/080986, mailed Dec. 29, 2015, 8 pages.
Supplementary European Search Report for European Application No. 14816633.3, mailed Nov. 7, 2016, 4 pages.
International Search Report and Written Opinion for International Application No. PCT/CN2014/080983, mailed Oct. 9, 2014, 12 pages.
International Preliminary Report on Patentability for International Application No. PCT/CN2014/080983, mailed Dec. 29, 2015, 8 pages.

*Primary Examiner* — Rebecca Anderson
(74) *Attorney, Agent, or Firm* — Cooley LLP

(57) ABSTRACT

Provided are certain fused tricyclic urea compounds and salts thereof, compositions thereof, and methods of use therefor.

24 Claims, No Drawings

FUSED TRICYCLIC UREA COMPOUNDS AS RAF KINASE AND/OR RAF KINASE DIMER INHIBITORS

CROSS-REFERENCE TO RELATED APPLICATION

This application is a U.S. National Stage Application under 35 U.S.C.§371 of International Application No. PCT/CN2014/080983, filed on Jun. 27, 2014 and entitled "FUSED TRICYCLIC UREA COMPOUNDS AS RAF KINASE AND/OR RAF KINASE DIMER INHIBITORS", which claims the benefit of priority to International Application No. PCT/CN2013/078338, filed Jun. 28, 2013.

Disclosed herein are fused tricyclic urea compounds, pharmaceutical compositions comprising at least one such fused tricyclic urea compound, processes for the preparation thereof, and the use thereof in therapy. Disclosed herein are certain tricyclic urea compounds that can be useful for inhibiting Raf kinase and/or Raf kinase dimer and for treating disorders mediated thereby.

The Raf/MEK/ERK pathway is of interest for cell survival, growth, proliferation and tumorigenesis (Zebisch et al., Curr Med Chem. 14(5): 601-623, 2007; Roberts and Der, Oncogene 26 (22): 3291-3310, 2007; Montagut and Settleman, Cancer Lett. 283(2): 125-134, 2009). Stimulation of the Raf/MEK/ERK signal transduction pathway may occur after binding of a ligand to the membrane-bound receptor tyrosine kinase. GTP-bound RAS can be activated, which can subsequently promote the activation of the Raf family proteins (A-Raf, B-Raf and Raf1, formerly known as C-Raf) (Wellbrock et al., Nat. Rev. Mol. Cell Biol. 5: 875-885, 2004). Mutations in various RAS GTPases and B-Raf kinase in the Raf/MEK/ERK signal pathway have been reported to constitutively activate the MAPK pathway, resulting in increased cell division and survival (Bos, Cancer Res. 49: 4682-4689, 1989; Hoshino et al., Oncogene. 18(3): 813-822, 1999). For example, B-Raf mutations are reportedly found in a large percentage of human melanomas and thyroid cancers (Davies et al., Nature 417: 949-954, 2002) (Cohen et al., J. Nat. Cancer Inst. 95(8): 625-627, 2003; Kimura et al., Cancer Res. 63(7): 1454-1457, 2003; Pollock and Meltzer, Cancer Cell 2: 5-7, 2002). In addition, lower, but still significant frequency of B-Raf mutations have been reported in Barret's adenocarcinoma (Garnett et al., Cancer Cell 6:313-319, 2004; Sommerer et al., Oncogene 23(2): 554-558, 2004), breast cancer (Davies et al., Nature 417: 949-954, 2002), cervical cancer (Moreno-Bueno et al., Clin. Cancer Res. 12(12): 365-3866, 2006), cholangiocarcinoma (Tannapfel et al., Gut. 52(5): 706-712, 2003), glioblastoma (Knobbe et al., Acta Neuropathol. (Berl.). 108(6): 467-470, 2004), colorectal cancer (Yuen et al., Cancer Res. 62(22): 6451-6455, 2002; Davies et al., Nature 417: 949-954, 2002), gastric cancer (Lee et al., Oncogene 22(44): 6942-6945), lung cancer (Brose et al., Cancer Res. 62(23): 6997-7000, 2002), ovarian cancer (Russell and McCluggage, J. Pathol. 203(2): 617-619, 2004; Davies et al., Nature 417: 949-954, 2002), pancreatic cancer (Ishimura et al., Cancer Lett. 199(2): 169-173, 2003), prostate cancer (Cho et al., Int. J. Cancer. 119(8): 1858-1862, 2006), and hematologic cancers (Garnett and Marais, Cancer Cell 6: 313-319, 2004). These reports suggest that B-Raf is one of the most frequently mutated genes in human cancers. B-Raf kinase can represent an excellent target for anticancer therapy based on preclinical target validation, epidemiology and drugability. Recent approval of B-raf inhibitors, vemurafenib and dabrafenib, validated the utility of B-raf inhibitors in treatment of B-raf mutant melanoma.

In addition to B-raf mutation that activate the Raf/MEK/ERK pathway, mutations in RAS GTPase or aberrations of growth factor receptors that are upstream of Raf/MEK/ERK signaling also lead to constant activation of the pathway that gives rise to cancer. Approximately 30% of human tumors contain mutations in one of the three Ras genes (Downward, Nat Rev Cancer. 2003 January; 3(1):11-22); K-Ras, N-Ras and H-Ras that are associated with increased level of Ras-GRP and thus constitutive activation of downstream signaling pathways. K-ras or N-ras mutations account for 59% of pancreatic cancer, 39% of colorectal cancer, 30% of cancer of Billary Tract, 17% of Non-small-cell-lung cancer, 15% of ovarian cancer, 15% of endometrium cancer, and 23% of blood cancer (Sanger Institut, Cosmic Database Janurary 2013, cancer.sanger.ac.uk). Despite the spectacular success of first generation B-RAF inhibitor, such as vemurafenib and dabrafenib, in treatment of B-RAF V600E melanoma, it is ineffective against tumors with activating RAS mutations and in some cases it can even promote tumor growth (Niault et al., J Cell Biol. 2009 Nov. 2; 187(3):335-42). Preclinical data demonstrated that this could be caused by paradoxical increase in MAPK signalling by RAF inhibitors through induction of B-RAF/C-RAF heterodimer in the context of mutated of activated RAS that RAF inhibitors bind to one RAF protomer in the dimer transactivates the other protomer (Hatzivassiliou et al., Nature. 2010 Mar. 18; 464(7287):431-5; Poulikakos et al., Nature. 2010 Mar. 18; 464(7287):427-30; Heidorn et al., Cell. 2010 Jan. 22; 140(2):209-21). The expression of B-RAF V600E splice variant (p61) with enhanced dimerization potential has also be shown to contribute to resistant to RAF inhibitors (Poulikakos et al., Nature. 2011 Nov. 23; 480(7377):387-90). It is also reported that C-RAF/B-RAF dimers are much better MEK kinases than the respective monomers or homodimers (Rushworth et al., Mol Cell Biol. 2006 March; 26(6):2262-72). These findings suggest that RAF dimer play an important role in disease association. Therefore, inhibiting the activity of RAF dimer represents a novel stand-alone approach to block aberrant RAF signalling triggered not only by V600E mutation, but also by oncogenic RAS mutations and aberrations of growth factor receptors.

As mentioned earlier, the presence of constitutively dimerized p61 contribute to resistant to vemurafenib and this splice variant were identified in 6 of 9 melanoma patients with acquired vemurafenib resistance (Poulikakos et al., Nature. 2011 Nov. 23; 480(7377):387-90). The ineffectiveness of vemurafenib in p61 expressing cells and the paradoxical activation of MAPK pathway by vemurafenib in wild-type B-RAF cells predict that any cell that can induce dimeric RAF will be able to induce resistant to the first generation B-RAF inhibitors. In fact, this has been reported through a number of different mechanisms including upregulation of receptor tyrosine kinases and the acquisition of additional genetic mutations such as concomitant B-RAF and N-RAS mutations (Nazarian et al., Nature. 2010 Dec. 16; 468(7326):973-7; Tap et al., Neoplasia 2010 August; 12(8):637-49). Therefore, inhibitors of RAF dimers could also potentially be effective in treating tumors that are resistant to the first generation B-RAF inhibitors, such as vemurafenib and dabrafenib.

To evaluate the inhibitory effect of compounds on RAF dimers, it is important to first induce the dimer formation of RAF proteins. The expression of p61 B-RAF splice variant drives activation of MAPK pathway through its ability to form constitutive p61 homodimer (Poulikakos et al., Nature. 2011 Nov. 23; 480(7377):387-90), therefore A375 stably expressing p61 (A375-p61) was also utilized to evaluate compounds' effect on RAF dimer through measuring $IC_{50}$ of ERK phosphorylation. Since A375-p61 cells are addicted to p61, the measurement of half-maximal effect concentration ($EC_{50}$) on cell proliferation was also utilized for this purpose. Finally, it is also reported that mutant Ras induce RAF dimers (Luo et al., Nature. 1996 Sep. 12; 383(6596):181-5; Weber et al., Cancer Res. 2001 May 1; 61(9):3595-8; Garnett et al., Mol Cell. 2005 Dec. 22; 20(6):963-9) The ability of compounds to inhibit ERK phosphorylation in RAS mutant cell such as Calu-6 serves as another way to evaluate compounds' ability to inhibit the RAF dimer activities.

Inhibitors of Raf kinases have been discussed for use in disruption of tumor cell growth and hence in the treatment of cancers, e.g. melanoma, colorectal cancer including large intestinal colon carcinoma, histiocytic lymphoma, lung adenocarcinoma, small cell lung cancer, and pancreatic and breast carcinoma (Crump, Current Pharmaceutical Design 8: 2243-2248, 2002; Sebastien et al., Current Pharmaceutical Design 8: 2249-2253, 2002), and/or in the treatment or prophylaxis of disorders associated with neuronal degeneration resulting from ischemic events, including cerebral ischemia after cardiac arrest, stroke and multi-infarct dementia. Inhibitors of Raf kinases have also been discussed for use after cerebral ischemic events such as those resulting from head injury, surgery and/or during childbirth (York et al., Mol. and Cell. Biol. 20(21): 8069-8083, 2000; Chin et al., Neurochem. 90: 595-608, 2004), as well as in polycystic kidney disease (Nagao et al., Kidney Int. 63(2): 427-437, 2003).

In addition, certain hyperproliferative disorders may be characterized by the over activation of Raf kinase functions, for example, by mutations or over expression of the protein. Accordingly, inhibitors of Raf kinases can be useful in the treatment of hyperproliferative disorders, such as cancer.

Small molecule inhibitors of B-Raf kinases are being developed for anticancer therapy. Nexavar® (sorafenib tosylate) is a multikinase inhibitor, which includes inhibition of B-Raf kinases, and is approved for the treatment of patients with advanced renal cell carcinoma and unresectable hepatocellular carcinoma. Vemurafenib and dabrafenib have recently approved for the treatment of metastatic melanoma with Braf-V600E mutation. Other Raf inhibitors have also been disclosed or have entered clinical trials, for example, SB-590885, RAF-265, and XL-281. Other B-Raf inhibitors are also known. See, for example, U.S. Patent Application Publication 2006/0189627, U.S. Patent Application Publication 2006/0281751, U.S. Patent Application Publication 2007/0049603, International Patent Application Publication WO 2007/002325, International Patent Application Publication WO 2007/002433, International Patent Application Publication WO 03/068773, International Patent Application Publication WO 2007/013896, International Patent Application Publication WO 2011/097526, International Patent Application Publication WO 2011/117382 and International Patent Application Publication WO2012/118492

Certain nitrogen-containing heteroaryl-substituted aryl bicyclic compounds have been identified as Raf inhibitors. See, for example, International Patent Application Publication WO 2007/067444 and U.S. Patent Application Publication 2010/0197924.

Certain Raf kinase inhibitors have also been identified. See, for example, International Patent Application Publication WO 2005/062795, International Patent Application Publication WO 2008/079906, International Patent Application Publication WO 2008/079909, International Patent Application Publication WO 2006/066913, International Patent Application WO 2008/028617, International Patent Application Publication WO 2009/012283, International Patent Application Publication WO 2010/064722 and International Patent Application Publication WO 2011/092088.

Disclosed herein are methods to evaluate inhibition of RAF dimer activity in cells and compounds that can inhibit Raf kinases, including wild-type B-RAF and V600E B-RAF mutant and the Raf dimer activity in cells.

Provided is at least one compound selected from compounds of Formula I:

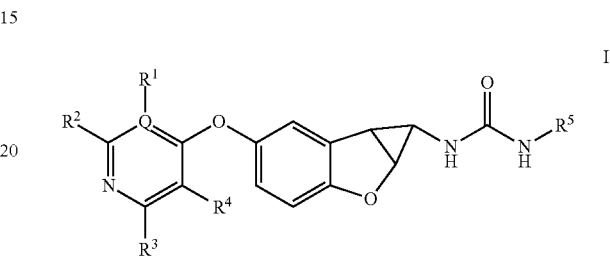

stereoisomers thereof, and pharmaceutically acceptable salts thereof,
wherein:

Q is selected from C and N;

$R^1$, $R^2$, $R^3$, and $R^4$, which may be the same or different, are each selected from hydrogen, halogen, alkyl, alkenyl, cycloalkyl, aryl, heterocyclyl, heteroaryl, alkynyl, —CN, —$NR^6R^7$, —$OR^6$, —$COR^6$, —$CO_2R^6$, —$CONR^6R^7$, —C(=$NR^6$)$NR^7R^8$, —$NR^6COR^7$, —$NR^6CONR^7R^8$, —$NR^6CO_2R^7$, —$SO_2R^6$, —$NR^6SO_2NR^7R^8$, —$NR^6SO_2R^7$, and —$NR^6SO_2$aryl, wherein the alkyl, alkenyl, alkynyl, cycloalkyl, heteroaryl, aryl, and heterocyclyl are independently optionally substituted with at least one substituent $R^9$, or ($R^1$ and $R^2$), and/or ($R^3$ and $R^4$), together with the ring to which they are attached, form a fused ring selected from heterocyclyl and heteroaryl rings optionally substituted with at least one substituent $R^9$; provided that $R^1$ is absent when Q is N;

$R^5$ is each selected from alkyl, cycloalkyl, heterocyclyl, aryl, heteroaryl rings, each of which is optionally substituted with at least one substituent $R^9$;

$R^6$, $R^7$ and $R^8$, which may be the same or different, are each selected from H, alkyl, alkenyl, alkynyl, cycloalkyl, heterocyclyl, aryl, and heteroaryl; or ($R^6$ and $R^7$), and/or ($R^7$ and $R^8$) together with the atom(s) to which they are attached, each form a ring selected from heterocyclyl and heteroaryl rings optionally substituted with at least one substituent $R^9$;

$R^9$ is selected from halogen, haloalkyl, alkyl, alkenyl, cycloalkyl, aryl, heteroaryl, heterocyclyl, alkynyl, oxo, -alkyl-NR'R", —CN, —OR', —NR'R", —COR', —$CO_2R'$, —CONR'R", —C(=NR')NR"R'", nitro, —NR'COR", —NR'CONR'R", —NR'$CO_2R$", —$SO_2R'$, —$SO_2$aryl, —NR'$SO_2$NR"R'", NR'$SO_2R$", and —NR'$SO_2$aryl, wherein the cycloalkyl, aryl, heteroaryl, or heterocyclyl group are each independently optionally substituted by one, two or three substituents selected from halo, alkyl and haloalkyl, wherein R', R", and R'" are independently selected from H, haloalkyl, alkyl, alkenyl, alkynyl, cycloalkyl, heterocyclyl, aryl, and heteroaryl, or (R' and R"), and/or (R" and R'") together with the atoms to which they are attached, form a ring selected from heterocyclyl optionally substituted by halogen and alkyl, and heteroaryl rings optionally substituted by halogen and alkyl.

Also provided is a pharmaceutical composition comprising at least one pharmaceutically acceptable carrier and at least one compound selected from compounds of Formula (I), stereoisomers thereof, and pharmaceutically accept salts thereof described herein.

Also provided is a method of treating cancer responsive to inhibition of Raf kinase comprising administering to a subject in need of treating for such cancer an amount of at least one compound selected from compounds of Formula (I), stereoisomers thereof, and pharmaceutically accept salts thereof described herein effective to treat the cancer.

Also provided is a use of at least one compound selected from compounds of Formula (I), stereoisomers thereof, and pharmaceutically acceptable salts thereof described herein in manufacture of a medicament for inhibiting Raf kinases.

Also provided is a use of at least one compound selected from compounds of Formula (I), stereoisomers thereof, and pharmaceutically acceptable salts thereof described herein in manufacture of a medicament for inhibiting Raf kinase dimers.

Also provided is a use of at least one compound selected from compounds of Formula (I), stereoisomers thereof, and pharmaceutically acceptable salts thereof described herein in manufacture of a medicament for inhibiting Raf kinases and/or Raf kinase dimers.

Also provided is a use of at least one compound selected from compounds of Formula (I), stereoisomers thereof, and pharmaceutically acceptable salts thereof described herein in manufacture of a medicament for treating tumors that are resistant to the first generation B-RAF inhibitors.

Also provided is a use of at least one compound selected from compounds of Formula (I), stereoisomers thereof, and pharmaceutically acceptable salts thereof described herein in the manufacture of a medicament for treating cancer.

As used herein, the following words, phrases and symbols are generally intended to have the meanings as set forth below, except to the extent that the context in which they are used indicates otherwise. The following abbreviations and terms have the indicated meanings throughout:

The term "alkyl" herein refers to a hydrocarbon group selected from linear and branched saturated hydrocarbon groups comprising from 1 to 18, such as from 1 to 12, further such as from 1 to 10, more further such as from 1 to 6, carbon atoms. Examples of the alkyl group can be selected from methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group can be selected from 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ $CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$) and 3,3-dimethyl-2-butyl (—$CH(CH_3)C$ $(CH_3)_3$) groups.

The term "alkenyl" herein refers to a hydrocarbon group selected from linear and branched hydrocarbon groups comprising at least one C=C double bond and from 2 to 18, such as from 2 to 6, carbon atoms. Examples of the alkenyl group may be selected from ethenyl or vinyl (—$CH=CH_2$), prop-1-enyl (—$CH=CHCH_3$), prop-2-enyl (—$CH_2CH=CH_2$), 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as from 2 to 6, carbon atoms. Examples of the alkynyl group include ethynyl (—C≡CH), 1-propynyl (—C≡$CCH_3$), 2-propynyl (propargyl, —$CH_2$C≡CH), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as 3 to 8, further such as 3 to 6, 3 to 5, or 3 to 4 carbon atoms. Even further for example, the cycloalkyl group may be selected from monocyclic group comprising from 3 to 12, such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further examples of the bicyclic cycloalkyl groups include those arranged as a bicyclic ring selected from [5,6] and [6,6] ring systems, such as

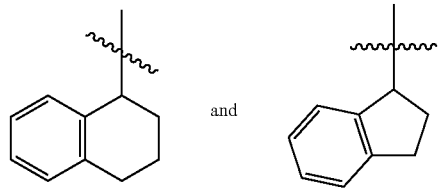 [SMILES: *C1CCCc2ccccc21 ; *C1CCc2ccccc21]

wherein the wavy lines indicate the points of attachment. The ring may be saturated or have at least one double bond (i.e. partially unsaturated), but is not fully conjugated, and is not aromatic, as aromatic is defined herein.

The term "Aryl" herein refers to a group selected from:
  5- and 6-membered carbocyclic aromatic rings, for example, phenyl;
  bicyclic ring systems such as 7 to 12 membered bicyclic ring systems wherein at least one ring is carbocyclic and aromatic, selected, for example, from naphthalene, indane, and 1,2,3,4-tetrahydroquinoline; and
  tricyclic ring systems such as 10 to 15 membered tricyclic ring systems wherein at least one ring is carbocyclic and aromatic, for example, fluorene.

For example, the aryl group is selected from 5 and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" herein refers to F, Cl, Br or I.

The term "heteroaryl" herein refers to a group selected from:
  5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;
  8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and
  11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

Compounds described herein may contain an asymmetric center and may thus exist as enantiomers. Where the compounds described herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoiosomer(s).

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH$_2$)$_n$—COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "pharmaceutically acceptable salts thereof" include salts of at least one compound of Formulae I, II, and/or III, and salts of the stereoisomers of at least one compound of Formulae I, II, and/or III, such as salts of enantiomers, and/or salts of diastereomers.

"Treating," "treat," or "treatment" or "alleviation" refers to administering at least one compound and/or at least one stereoisomer thereof, and/or at least one pharmaceutically acceptable salt thereof disclosed herein to a subject in recognized need thereof that has, for example, cancer.

The term "effective amount" refers to an amount of at least one compound and/or at least one stereoisomer thereof, and/or at least one pharmaceutically acceptable salt thereof disclosed herein effective to "treat," as defined above, a disease or disorder in a subject.

The term "at least one substituent" disclosed herein includes, for example, from 1 to 4, such as from 1 to 3, further as 1 or 2, substituents, provided that the valency allows. For example, "at least one substituent R$^9$" disclosed herein includes from 1 to 4, such as from 1 to 3, further as 1 or 2, substituents selected from the list of R$^9$ as described herein.

Provided is at least one compound selected from compounds of Formula I:

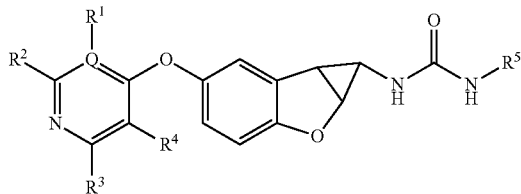

stereoisomers thereof, and pharmaceutically acceptable salts thereof,
wherein:

Q is selected from C and N;

$R^1$, $R^2$, $R^3$, and $R^4$, which may be the same or different, are each selected from hydrogen, halogen, alkyl, alkenyl, cycloalkyl, aryl, heterocyclyl, heteroaryl, alkynyl, —CN, —$NR^6R^7$, —$OR^6$, —$COR^6$, —$CO_2R^6$, —$CONR^6R^7$, —C(=$NR^6$)$NR^7R^8$, —$NR^6COR^7$, —$NR^6CONR^7R^8$, —$NR^6CO_2R^7$, —$SO_2R^6$, —$NR^6SO_2NR^7R^8$, —$NR^6SO_2R^7$, and —$NR^6SO_2aryl$, wherein the alkyl, alkenyl, alkynyl, cycloalkyl, heteroaryl, aryl, and heterocyclyl are independently optionally substituted with at least one substituent $R^9$, or ($R^1$ and $R^2$), and/or ($R^3$ and $R^4$), together with the ring to which they are attached, form a fused ring selected from heterocyclyl and heteroaryl rings optionally substituted with at least one substituent $R^9$; provided that $R^1$ is absent when Q is N;

$R^5$ is each selected from alkyl, cycloalkyl, heterocyclyl, aryl, heteroaryl rings, each of which is optionally substituted with at least one substituent $R^9$;

$R^6$, $R^7$ and $R^8$, which may be the same or different, are each selected from H, alkyl, alkenyl, alkynyl, cycloalkyl, heterocyclyl, aryl, and heteroaryl; or ($R^6$ and $R^7$), and/or ($R^7$ and $R^8$) together with the atom(s) to which they are attached, each form a ring selected from heterocyclyl and heteroaryl rings optionally substituted with at least one substituent $R^9$;

$R^9$ is selected from halogen, haloalkyl, alkyl, alkenyl, cycloalkyl, aryl, heteroaryl, heterocyclyl, alkynyl, oxo, -alkyl-NR'R", —CN, —OR', —NR'R", —COR', —$CO_2R'$, —CONR'R", —C(=NR')NR"R'", nitro, —NR-'COR", —NR'CONR'R", —$NR'CO_2R"$, —$SO_2R'$, —$SO_2aryl$, —$NR'SO_2NR"R'''$, $NR'SO_2R"$, and —$NR'SO_2aryl$, wherein the cycloalkyl, aryl, heteroaryl, or heterocyclyl group are each independently optionally substituted by one, two or three substituents selected from halo, alkyl and haloalkyl, wherein R', R", and R'" are independently selected from H, haloalkyl, alkyl, alkenyl, alkynyl, cycloalkyl, heterocyclyl, aryl, and heteroaryl, or (R' and R"), and/or (R" and R'") together with the atoms to which they are attached, form a ring selected from heterocyclyl optionally substituted by halogen and alkyl, and heteroaryl rings optionally substituted by halogen and alkyl.

In some embodiments of Formula (I), Q is C.

In some embodiments of Formula (I), Q is N and $R^1$ is absent.

In some embodiments of Formula (I), $R^1$ and $R^2$, which may be the same or different, are each selected from hydrogen, halogen, and alkyl optionally substituted with at least one substituent $R^9$ (such as unsubstituted alkyl or haloalkyl).

In some embodiments of Formula (I), each of $R^1$ and $R^2$ is hydrogen.

In some embodiments of Formula (I), $R^3$ and $R^4$, which may be the same or different, are each selected from hydrogen, halogen, and alkyl optionally substituted with at least one substituent $R^9$ (such as unsubstituted alkyl or haloalkyl), —$NR^6R^7$, and —$CONR^6R^7$, wherein $R^6$ and $R^7$ are each selected from hydrogen or alkyl.

In some embodiments of Formula (I), $R^3$ is halogen, and alkyl optionally substituted with at least one substituent $R^9$ (such as unsubstituted alkyl or haloalkyl), —$NR^6R^7$, and —$CONR^6R^7$ and $R^4$ is hydrogen, wherein $R^6$ and $R^7$ are each selected from hydrogen or alkyl.

In some embodiments of Formula (I), $R^3$ is —$NR^6R^7$, and —$CONR^6R^7$ and $R^4$ is hydrogen, wherein $R^6$ and $R^7$ are each selected from hydrogen or alkyl.

In some embodiments of Formula (I), $R^3$ and $R^4$ together with the ring to which they are attached, form a fused ring selected from a heterocycle or heteroaryl ring, such as naphthyridinyl (such as dihydronaphthyridinyl, further such as dihydronaphthyridin-4-yl), pyridooxazinyl (such as pyridooxazinyl, further such as dihydro-1H-pyrido[2,3-d][1,3]oxazin-5-yl), pyridopyrimidinyl (such as pyrido[2,3-d]pyrimidinyl, further such as 1,2,3,4-tetrahydropyrido[2,3-d]pyrimidin-5-yl), and purinyl (such as 9H-purin-6-yl), said ring being optionally substituted with at least one substituent $R^9$, such as oxo.

In some embodiments of Formula (I), $R^3$ and $R^4$ together with the ring to which they are attached, form a fused ring selected from heterocyclyl and heteroaryl rings optionally substituted with at least one substituent $R^9$, which is represented by

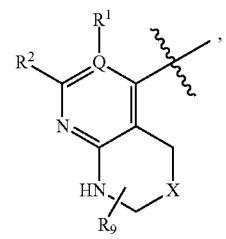

wherein $R^1$, $R^2$ and $R^9$ are defined as in Formula (I), and X is selected from —O—, —NR'— and —CR'R", wherein R' and R" are independently selected from H, haloalkyl, or alkyl.

In some embodiments of Formula (I), $R^3$ and $R^4$ together with the ring to which they are attached, form a fused ring selected from heterocyclyl and heteroaryl rings optionally substituted with at least one substituent $R^9$, which is represented by

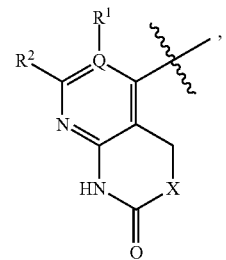

wherein $R^1$ and $R^2$ are defined as in Formula (I), and X is selected from —O—, —NR'— and —CR'R", wherein R' and R" are independently selected from H, haloalkyl, or alkyl.

In some embodiments of Formula (I), $R^3$ and $R^4$ together with the ring to which they are attached, form a fused ring selected from heterocyclyl and heteroaryl rings, which is represented by

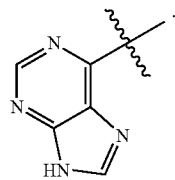 [SMILES: *c1ncnc2[nH]cnc12]

In some embodiments of Formula (I), $R^5$ is alkyl optionally substituted with at least one substituent $R^9$ as defined in Formula (I), for example, optionally substituted with one or two or three halogen.

In some embodiments of Formula (I), $R^5$ is methyl, ethyl, propyl, isopropyl, butyl, tert-butyl, pentyl, neopentyl, hexyl, octyl, nonyl or decyl, each of which is optionally substituted with one or two or three halogen.

In some embodiments of Formula (I), $R^5$ is aryl optionally substituted with at least one substituent $R^9$ as defined in Formula (I), for example optionally substituted with one or two or three substituent $R^9$ as defined in Formula (I).

In some embodiments of Formula (I), $R^5$ is phenyl or naphthyl or indanyl, each of which is optionally substituted with one or two or three substituent $R^9$ as defined in Formula (I).

In some embodiments of Formula (I), $R^5$ is phenyl or naphthyl or indanyl, each of which is optionally substituted with one or two or three substituent $R^9$ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.

In some embodiments of Formula (I), $R^5$ is heteroaryl optionally substituted with at least one substituent $R^9$ as defined in Formula (I), for example optionally substituted with one or two or three substituent $R^9$ as defined in Formula (I).

In some embodiments of Formula (I), $R^5$ is pyridinyl or pyrimidinyl, each of which is optionally substituted with one or two or three substituent $R^9$ as defined in Formula (I).

In some embodiments of Formula (I), $R^5$ is pyridinyl or pyrimidinyl, each of which is optionally substituted with one or two or three substituent $R^9$ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.

In some embodiments of Formula (I), $R^5$ is heterocyclyl optionally substituted with at least one substituent $R^9$ as defined in Formula (I), for example optionally substituted with one or two or three substituent $R^9$ as defined in Formula (I).

In some embodiments of Formula (I), $R^5$ is tetrapyranyl or piperidinyl, each of which is optionally substituted with one or two or three substituent $R^9$ as defined in Formula (I).

In some embodiments of Formula (I), $R^5$ is tetrapyranyl or piperidinyl, each of which is optionally substituted with one or two or three substituent $R^9$ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.

In some embodiments of Formula (I), $R^5$ is cycloalkyl optionally substituted with at least one substituent $R^9$ as defined in Formula (I), for example optionally substituted with one or two or three substituent $R^9$ as defined in Formula (I).

In some embodiments of Formula (I), $R^5$ is monocyclic or bicyclic cycloalkyl group each of which is optionally substituted with one or two or three substituent $R^9$ as defined in Formula (I).

In some embodiments of Formula (I), $R^5$ is monocyclic cycloalkyl group selected from cyclopropyl, cyclobutyl, cyclopentyl, cyclohexyl, cycloheptyl and cyclooctyl; or bicyclic cycloalkyl group selected from those arranged as a bicyclic ring selected from [4,4], [4,5], [5,5], [5,6] and [6,6] ring systems (such as

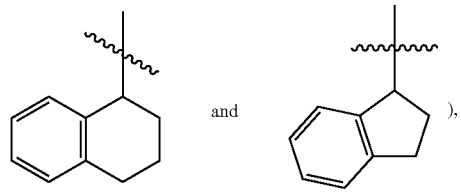 [SMILES: *C1CCCc2ccccc21 ; *C1CCc2ccccc21]

each of which is optionally substituted with one or two or three substituent $R^9$ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.

In some embodiments of Formula (I), the compound is in either of the following configurations:

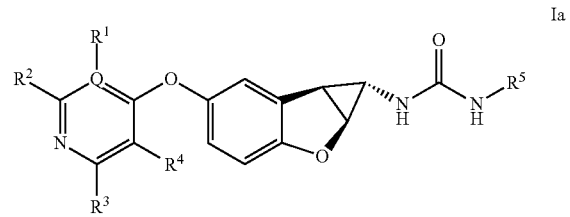

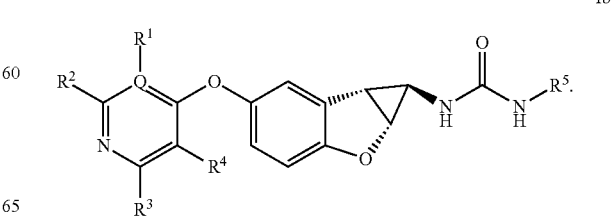

In some embodiments of Formula (I), the compounds of Formula (I) are represented by Formula (II)

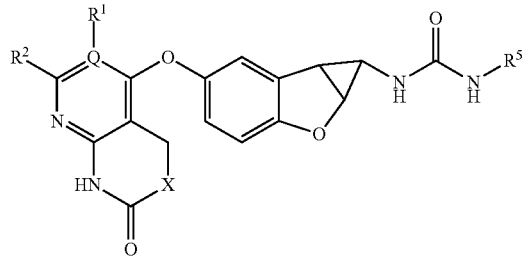

stereoisomers thereof, and pharmaceutically acceptable salts thereof,
wherein:
Q is selected from C and N;
$R^1$, and $R^2$, which may be the same or different, are each selected from hydrogen, halogen, alkyl, alkenyl, cycloalkyl, aryl, heterocyclyl, heteroaryl, alkynyl, —CN, —NR$^6$R$^7$, —OR$^6$, —COR$^6$, —CO$_2$R$^6$, —CONR$^6$R$^7$, —C(=NR$^6$)NR$^7$R$^8$, —NR$^6$COR$^7$, —NR$^6$CONR$^7$R$^8$, —NR$^6$CO$_2$R$^7$, —SO$_2$R$^6$, —NR$^6$SO$_2$NR$^7$R$^8$, —NR$^6$SO$_2$R$^7$, and —NR$^6$SO$_2$aryl, wherein the alkyl, alkenyl, alkynyl, cycloalkyl, heteroaryl, aryl, and heterocyclyl are independently optionally substituted with at least one substituent $R^9$, or ($R^1$ and $R^2$) together with the ring to which they are attached, form a fused ring selected from heterocyclyl and heteroaryl rings optionally substituted with at least one substituent $R^9$; provided that $R^1$ is absent when Q is N;
X is selected from —O—, —NR'— and —CR'R", wherein R' and R" are independently selected from H, haloalkyl, or alkyl;
$R^5$ is each selected from alkyl, cycloalkyl, heterocyclyl, aryl, heteroaryl rings, each of which is optionally substituted with at least one substituent $R^9$;
$R^6$, $R^7$ and $R^8$, which may be the same or different, are each selected from H, alkyl, alkenyl, alkynyl, cycloalkyl, heterocyclyl, aryl, and heteroaryl; or ($R^6$ and $R^7$), and/or ($R^7$ and $R^8$) together with the atom(s) to which they are attached, each form a ring selected from heterocyclyl and heteroaryl rings optionally substituted with at least one substituent $R^9$;
$R^9$ is selected from halogen, haloalkyl, alkyl, alkenyl, cycloalkyl, aryl, heteroaryl, heterocyclyl, alkynyl, oxo, -alkyl-NR'R", —CN, —OR', —NR'R", —COR', —CO$_2$R', —CONR'R", —C(=NR')NR"R"', nitro, —NR'COR", —NR'CONR'R", —NR'CO$_2$R", —SO$_2$R', —SO$_2$aryl, —NR'SO$_2$NR"R"', NR'SO$_2$R", and —NR'SO$_2$aryl, wherein the cycloalkyl, aryl, heteroaryl, or heterocyclyl group are each independently optionally substituted by one, two or three substituents selected from halo, alkyl and haloalkyl, wherein R', R", and R"' are independently selected from H, haloalkyl, alkyl, alkenyl, alkynyl, cycloalkyl, heterocyclyl, aryl, and heteroaryl, or (R' and R"), and/or (R" and R"') together with the atoms to which they are attached, form a ring selected from heterocyclyl optionally substituted by halogen and alkyl, and heteroaryl rings optionally substituted by halogen and alkyl.

In some embodiments of Formula (II), Q is C.
In some embodiments of Formula (II), Q is N and $R^1$ is absent.
In some embodiments of Formula (II), $R^1$ and $R^2$, which may be the same or different, are each selected from hydrogen, halogen, and alkyl optionally substituted with at least one substituent $R^9$ (such as unsubstituted alkyl or haloalkyl).

In some embodiments of Formula (II), each of $R^1$ and $R^2$ is hydrogen.
In some embodiments of Formula (II), X is —O—.
In some embodiments of Formula (II), X is —CR'R", wherein R' and R" are independently selected from H, haloalkyl, or alkyl.
In some embodiments of Formula (II), X is —NR'—, wherein R' is selected from H, haloalkyl, or alkyl.
In some embodiments of Formula (II), $R^5$ is alkyl optionally substituted with at least one substituent $R^9$ as defined in Formula (II), for example, optionally substituted with one or two or three halogen.
In some embodiments of Formula (II), $R^5$ is methyl, ethyl, propyl, isopropyl, butyl, tert-butyl, pentyl, neopentyl, hexyl, octyl, nonyl or decyl, each of which is optionally substituted with one or two or three halogen.
In some embodiments of Formula (II), $R^5$ is aryl optionally substituted with at least one substituent $R^9$ as defined in Formula (II), for example optionally substituted with one or two or three substituent $R^9$ as defined in Formula (II).
In some embodiments of Formula (II), $R^5$ is phenyl or naphthyl or indanyl, each of which is optionally substituted with one or two or three substituent $R^9$ as defined in Formula (II).
In some embodiments of Formula (II), $R^5$ is phenyl or naphthyl or indanyl, each of which is optionally substituted with one or two or three substituent $R^9$ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.
In some embodiments of Formula (II), $R^5$ is heteroaryl optionally substituted with at least one substituent $R^9$ as defined in Formula (II), for example optionally substituted with one or two or three substituent $R^9$ as defined in Formula (II).
In some embodiments of Formula (II), $R^5$ is pyridinyl or pyrimidinyl, each of which is optionally substituted with one or two or three substituent $R^9$ as defined in Formula (II).
In some embodiments of Formula (II), $R^5$ is pyridinyl or pyrimidinyl, each of which is optionally substituted with one or two or three substituent $R^9$ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.
In some embodiments of Formula (II), $R^5$ is heterocyclyl optionally substituted with at least one substituent $R^9$ as defined in Formula (II), for example optionally substituted with one or two or three substituent $R^9$ as defined in Formula (II).
In some embodiments of Formula (II), $R^5$ is tetrapyranyl or piperidinyl, each of which is optionally substituted with one or two or three substituent $R^9$ as defined in Formula (II).
In some embodiments of Formula (II), $R^5$ is tetrapyranyl or piperidinyl, each of which is optionally substituted with one or two or three substituent $R^9$ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R")

together with the nitrogen atom to which they are attached, form a ring selected from heterocyclyl optionally substituted by halogen and alkyl.

In some embodiments of Formula (II), $R^5$ is cycloalkyl optionally substituted with at least one substituent $R^9$ as defined in Formula (II), for example optionally substituted with one or two or three substituent $R^9$ as defined in Formula (II).

In some embodiments of Formula (II), $R^5$ is monocyclic or bicyclic cycloalkyl group each of which is optionally substituted with one or two or three substituent $R^9$ as defined in Formula (II).

In some embodiments of Formula (II), $R^5$ is monocyclic cycloalkyl group selected from cyclopropyl, cyclobutyl, cyclopentyl, cyclohexyl, cycloheptyl and cyclooctyl; or bicyclic cycloalkyl group selected from those arranged as a bicyclic ring selected from [4,4], [4,5], [5,5], [5,6] and [6,6] ring systems (such as

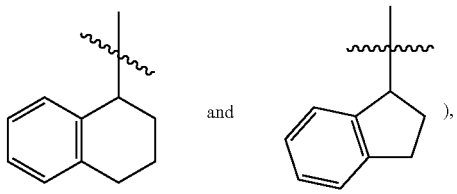 [SMILES: *C1CCCc2ccccc21 ; *C1CCc2ccccc21]

), each of which is optionally substituted with one or two or three substituent $R^9$ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.

In some embodiments of Formula (II), the compound is in either of the following configurations:

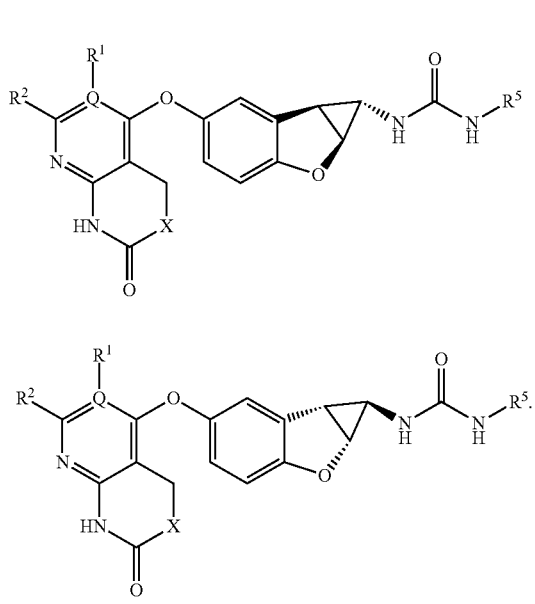

In some embodiments of Formula (II), the compounds of Formula (I) are represented by Formula (III)

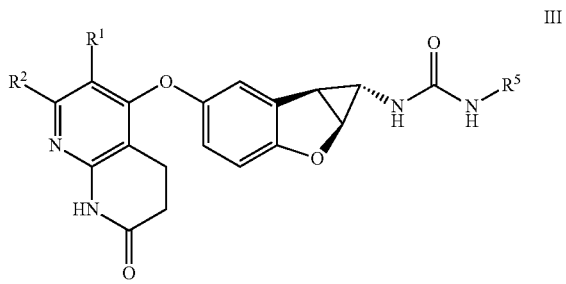

stereoisomers thereof, and pharmaceutically acceptable salts thereof,
wherein:
$R^1$, and $R^2$, which may be the same or different, are each selected from hydrogen, halogen, alkyl, alkenyl, cycloalkyl, aryl, heterocyclyl, heteroaryl, alkynyl, —CN, —NR$^6$R$^7$, —OR$^6$, —COR$^6$, —CO$_2$R$^6$, —CONR$^6$R$^7$, —C(=NR$^6$)NR$^7$R$^8$, —NR$^6$COR$^7$, —NR$^6$CONR$^7$R$^8$, —NR$^6$CO$_2$R$^7$, —SO$_2$R$^6$, —NR$^6$SO$_2$NR$^7$R$^8$, —NR$^6$SO$_2$R$^7$, and —NR$^6$SO$_2$aryl, wherein the alkyl, alkenyl, alkynyl, cycloalkyl, heteroaryl, aryl, and heterocyclyl are independently optionally substituted with at least one substituent $R^9$, or ($R^1$ and $R^2$) together with the ring to which they are attached, form a fused ring selected from heterocyclyl and heteroaryl rings optionally substituted with at least one substituent $R^9$; provided that $R^1$ is absent when Q is N;

$R^5$ is each selected from alkyl, cycloalkyl, heterocyclyl, aryl, heteroaryl rings, each of which is optionally substituted with at least one substituent $R^9$;

$R^6$, $R^7$ and $R^8$, which may be the same or different, are each selected from H, alkyl, alkenyl, alkynyl, cycloalkyl, heterocyclyl, aryl, and heteroaryl; or ($R^6$ and $R^7$), and/or ($R^7$ and $R^8$) together with the atom(s) to which they are attached, each form a ring selected from heterocyclyl and heteroaryl rings optionally substituted with at least one substituent $R^9$;

$R^9$ is selected from halogen, haloalkyl, alkyl, alkenyl, cycloalkyl, aryl, heteroaryl, heterocyclyl, alkynyl, oxo, -alkyl-NR'R", —CN, —OR', —NR'R", —COR', —CO$_2$R', —CONR'R", —C(=NR')NR"R'", nitro, —NR'COR", —NR'CONR'R", —NR'CO$_2$R", —SO$_2$R', —SO$_2$aryl, —NR'SO$_2$NR"R'", NR'SO$_2$R", and —NR'SO$_2$aryl, wherein the cycloalkyl, aryl, heteroaryl, or heterocyclyl group are each independently optionally substituted by one, two or three substituents selected from halo, alkyl and haloalkyl, wherein R', R", and R'" are independently selected from H, haloalkyl, alkyl, alkenyl, alkynyl, cycloalkyl, heterocyclyl, aryl, and heteroaryl, or (R' and R"), and/or (R" and R'") together with the atoms to which they are attached, form a ring selected from heterocyclyl optionally substituted by halogen and alkyl, and heteroaryl rings optionally substituted by halogen and alkyl.

In some embodiments of Formula (III), $R^1$ and $R^2$, which may be the same or different, are each selected from hydrogen, halogen, and alkyl optionally substituted with at least one substituent $R^9$ (such as unsubstituted alkyl or haloalkyl).

In some embodiments of Formula (III), each of $R^1$ and $R^2$ is hydrogen.

In some embodiments of Formula (III), $R^5$ is alkyl optionally substituted with at least one substituent $R^9$ as defined in Formula (III), for example, optionally substituted with one or two or three halogen.

In some embodiments of Formula (III), R⁵ is methyl, ethyl, propyl, isopropyl, butyl, tert-butyl, pentyl, neopentyl, hexyl, octyl, nonyl or decyl, each of which is optionally substituted with one or two or three halogen.

In some embodiments of Formula (III), R⁵ is aryl optionally substituted with at least one substituent R⁹ as defined in Formula (III), for example optionally substituted with one or two or three substituent R⁹ as defined in Formula (III).

In some embodiments of Formula (III), R⁵ is phenyl or naphthyl or indanyl, each of which is optionally substituted with one or two or three substituent R⁹ as defined in Formula (III).

In some embodiments of Formula (III), R⁵ is phenyl or naphthyl or indanyl, each of which is optionally substituted with one or two or three substituent R⁹ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.

In some embodiments of Formula (III), R⁵ is phenyl optionally substituted with one or two or three substituent R⁹ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.

In some embodiments of Formula (III), R⁵ is heteroaryl optionally substituted with at least one substituent R⁹ as defined in Formula (III), for example optionally substituted with one or two or three substituent R⁹ as defined in Formula (III).

In some embodiments of Formula (III), R⁵ is pyridinyl or pyrimidinyl, each of which is optionally substituted with one or two or three substituent R⁹ as defined in Formula (III).

In some embodiments of Formula (III), R⁵ is pyridinyl or pyrimidinyl, each of which is optionally substituted with one or two or three substituent R⁹ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.

In some embodiments of Formula (III), R⁵ is heterocyclyl optionally substituted with at least one substituent R⁹ as defined in Formula (III), for example optionally substituted with one or two or three substituent R⁹ as defined in Formula (III).

In some embodiments of Formula (III), R⁵ is tetrapyranyl or piperidinyl, each of which is optionally substituted with one or two or three substituent R⁹ as defined in Formula (III).

In some embodiments of Formula (III), R⁵ is tetrapyranyl or piperidinyl, each of which is optionally substituted with one or two or three substituent R⁹ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.

In some embodiments of Formula (III), R⁵ is cycloalkyl optionally substituted with at least one substituent R⁹ as defined in Formula (III), for example optionally substituted with one or two or three substituent R⁹ as defined in Formula (III).

In some embodiments of Formula (III), R⁵ is monocyclic or bicyclic cycloalkyl group each of which is optionally substituted with one or two or three substituent R⁹ as defined in Formula (III).

In some embodiments of Formula (III), R⁵ is monocyclic cycloalkyl group selected from cyclopropyl, cyclobutyl, cyclopentyl, cyclohexyl, cycloheptyl and cyclooctyl; or bicyclic cycloalkyl group selected from those arranged as a bicyclic ring selected from [4,4], [4,5], [5,5], [5,6] and [6,6] ring systems (such as

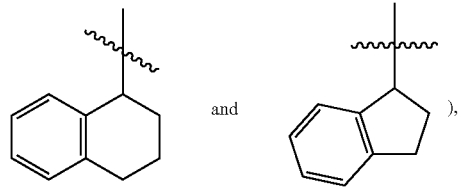 [SMILES: *C1CCCc2ccccc21 ; *C1CCc2ccccc21]

and ), each of which is optionally substituted with one or two or three substituent R⁹ selected from halogen, haloalkyl, alkyl, alkenyl, alkynyl, -alkyl-NR'R", —CN, —OR', —NR'R", and nitro, wherein R' and R" are independently selected from H, haloalkyl, and alkyl, or (R' and R") together with the nitrogen atom to which they are attached, form a ring selected from heterocyclyl optionally substituted by halogen and alkyl.

In some embodiments of Formula (III), R⁵ is monocyclic cycloalkyl group selected from cyclopropyl, cyclobutyl, cyclopentyl, cyclohexyl, cycloheptyl and cyclooctyl.

Also provided herein is at least one compound selected from the following compounds, stereoisomers thereof, and pharmaceutically acceptable salts thereof:

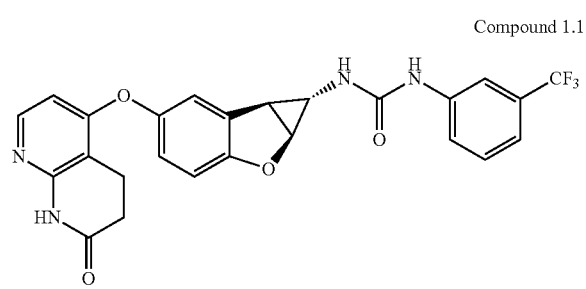

Compound 1.1

Compound 1.2

-continued
Compound 1.3
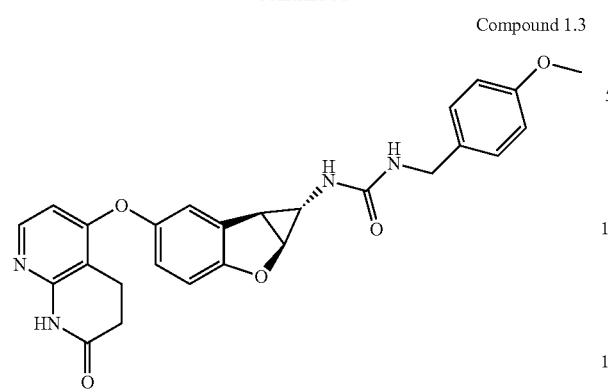
Compound 1.4
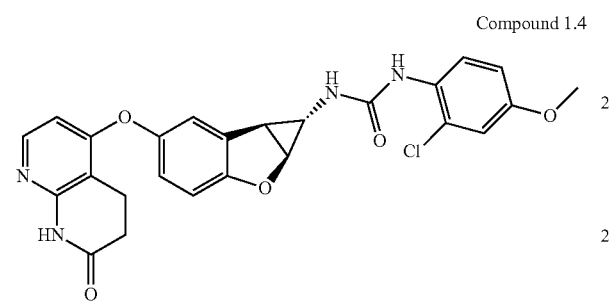
Compound 1.5
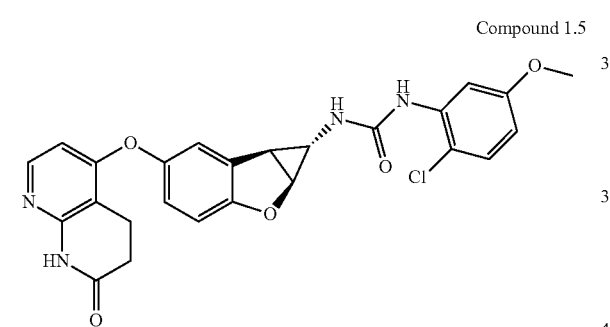
Compound 1.6
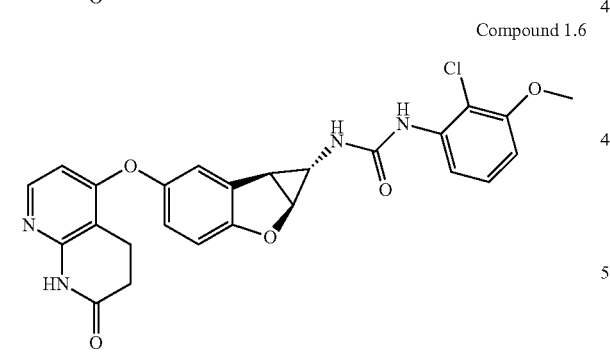
Compound 1.7
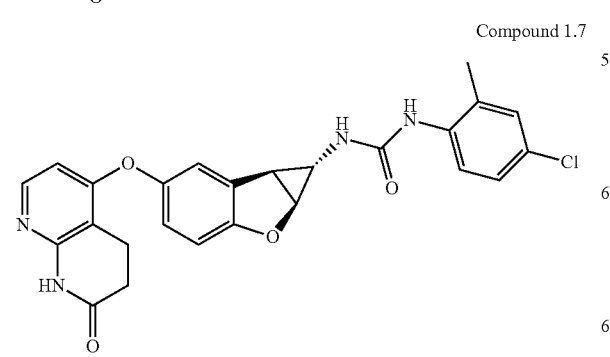
-continued
Compound 1.8
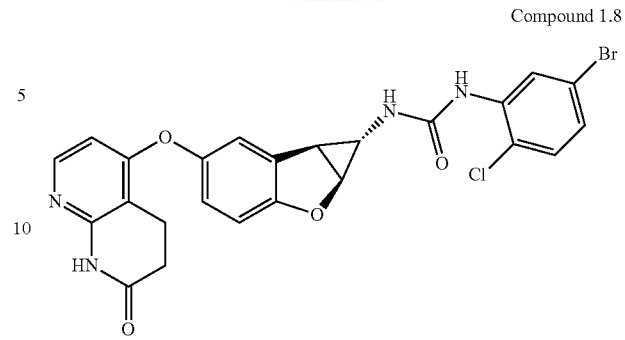
Compound 1.9
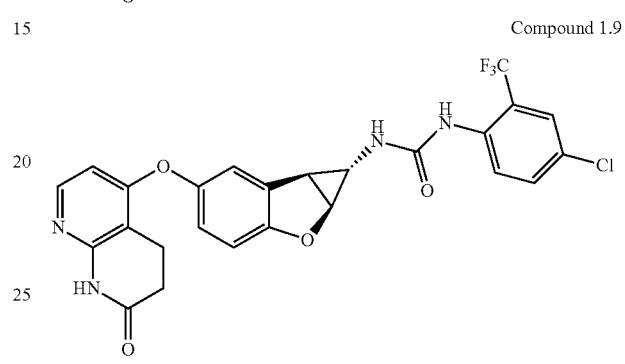
Compound 1.10
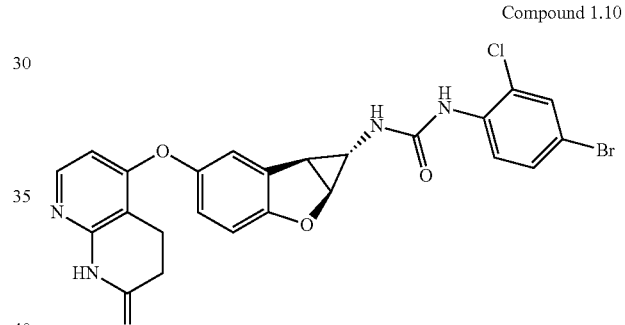
Compound 1.11
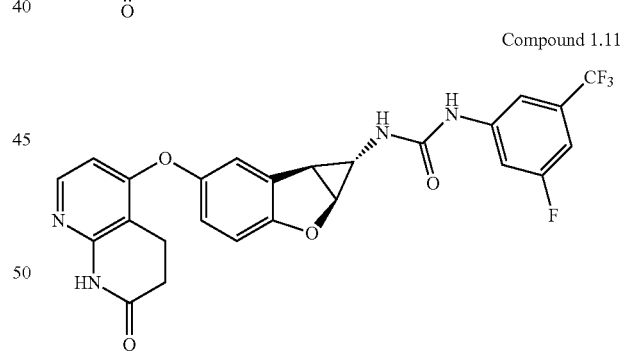
Compound 1.12
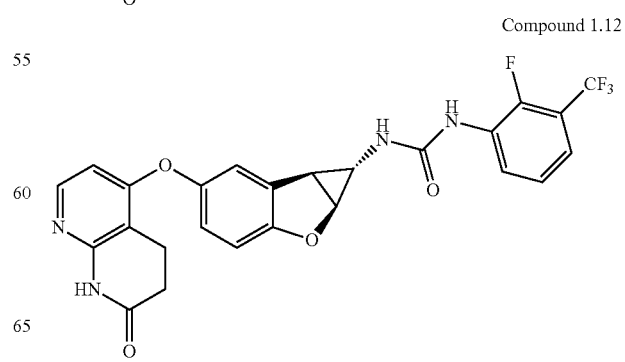

Compound 1.13
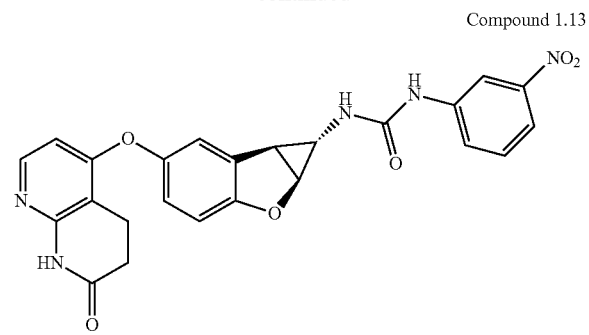
Compound 1.14
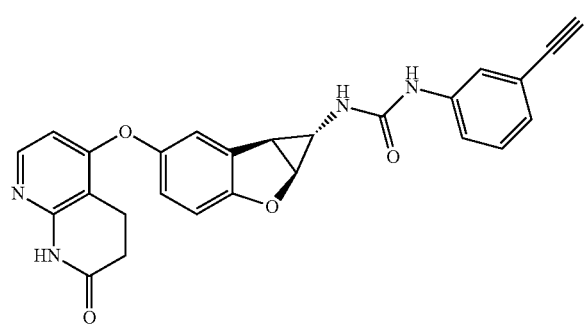
Compound 1.15
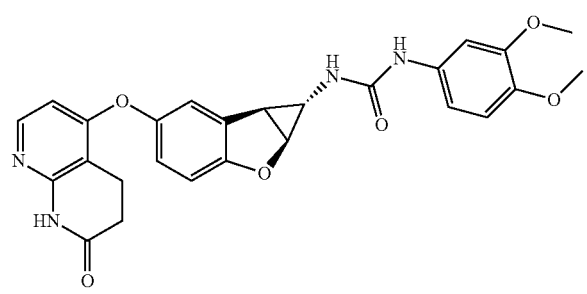
Compound 1.16
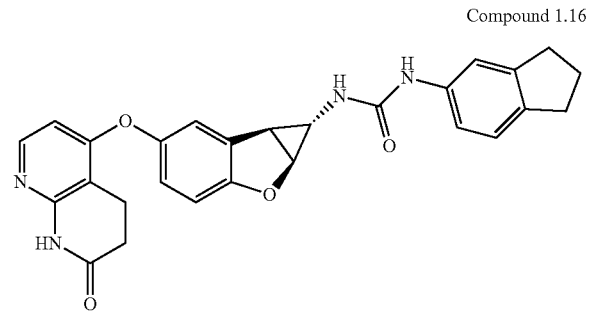
Compound 1.17
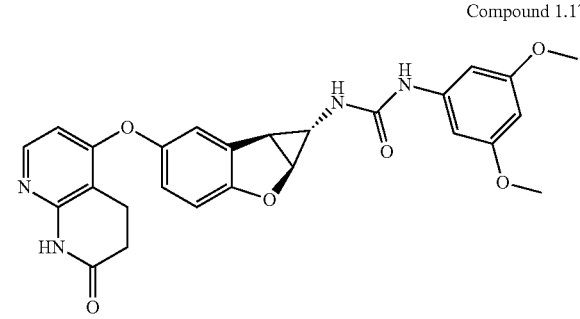
Compound 1.18
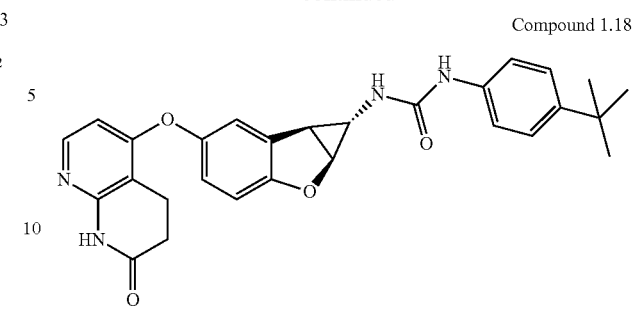
Compound 1.19
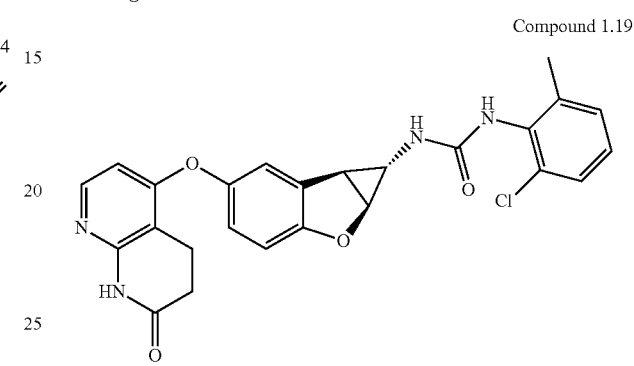
Compound 1.20
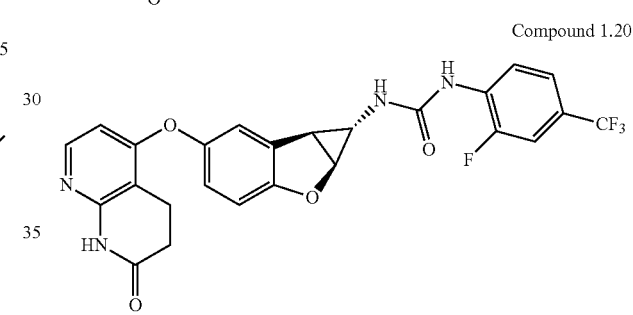
Compound 1.21
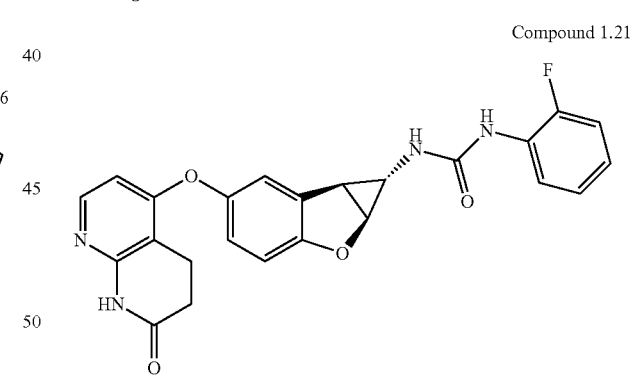
Compound 1.22
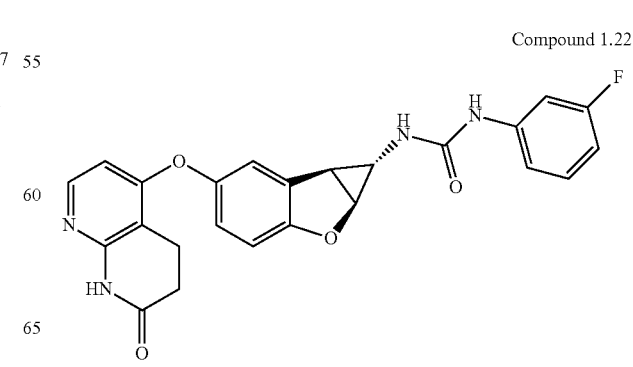

Compound 1.23
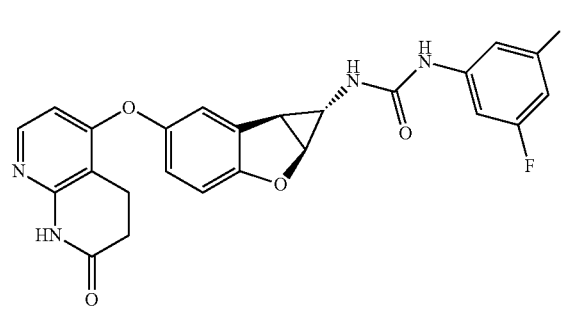
Compound 1.28
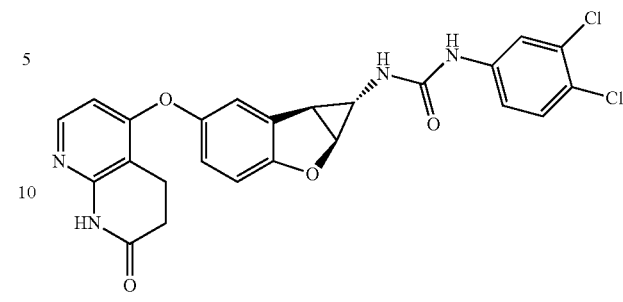
Compound 1.24
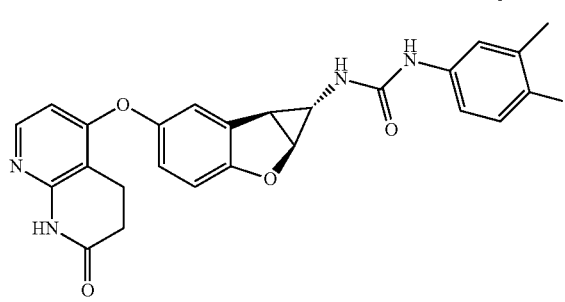
Compound 1.29
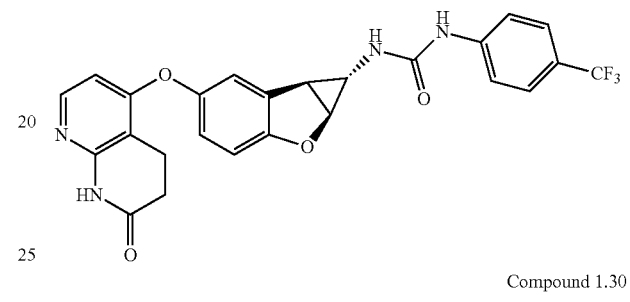
Compound 1.25
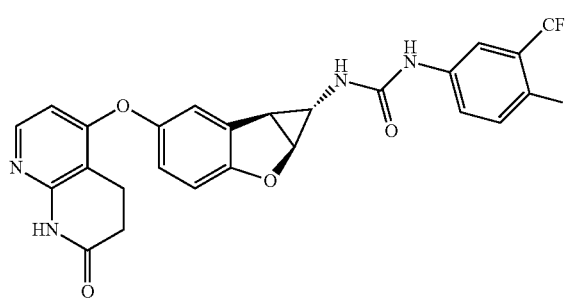
Compound 1.30
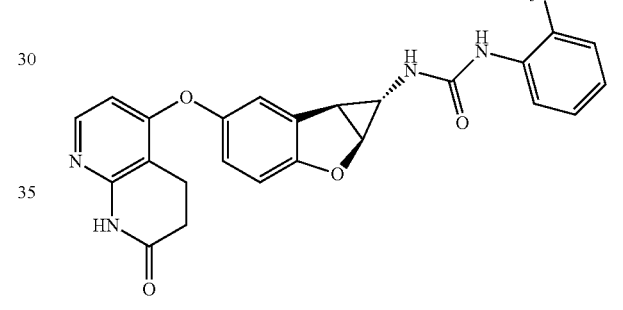
Compound 1.26
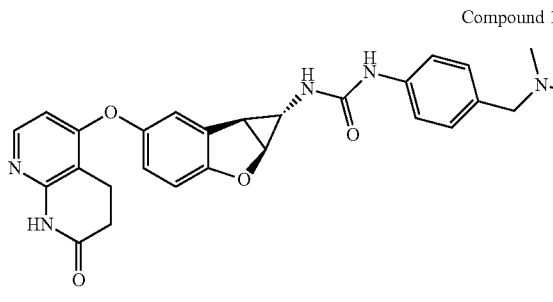
Compound 1.31
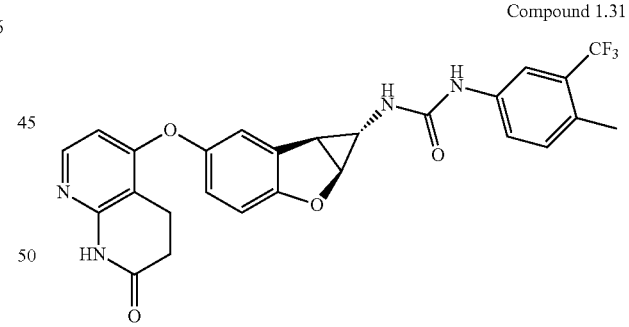
Compound 1.27
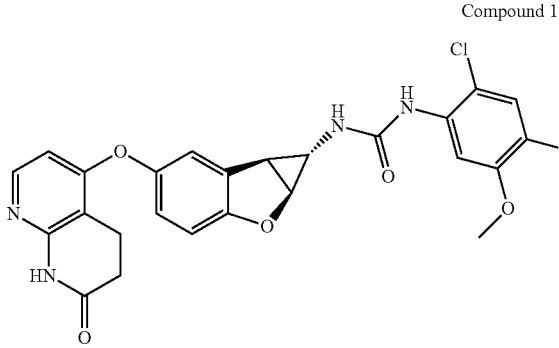
Compound 1.32
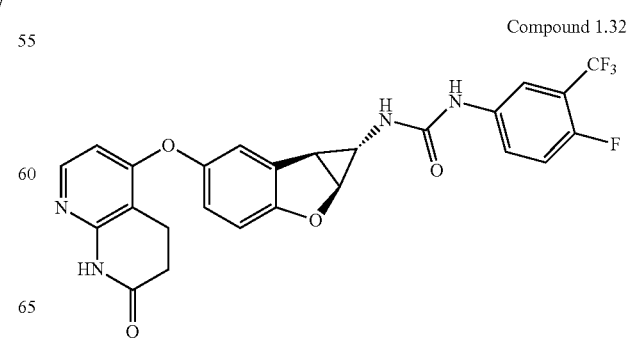

Compound 1.33
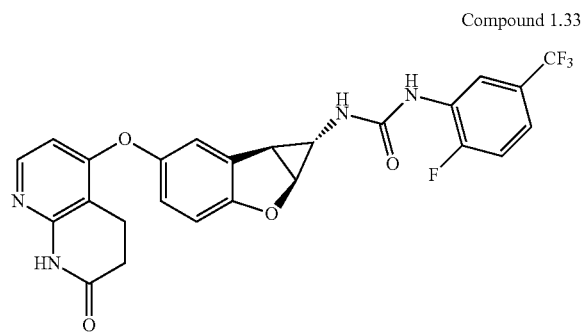
Compound 1.34
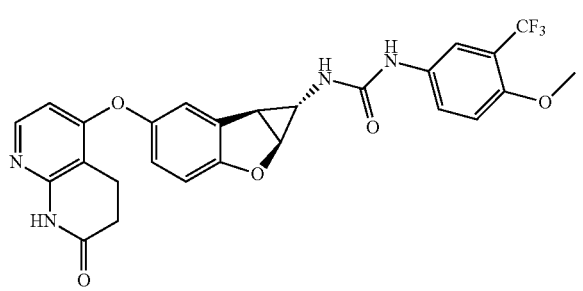
Compound 1.35
Compound 1.36
Compound 1.37
Compound 1.38
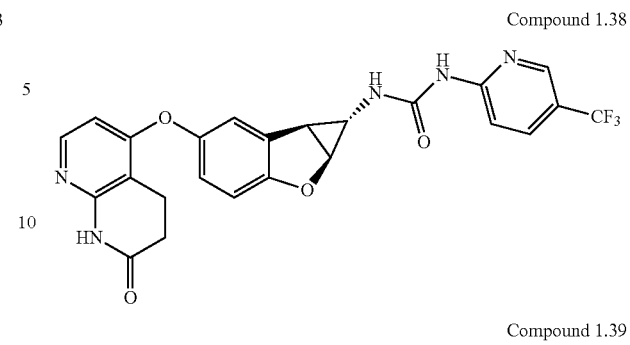
Compound 1.39
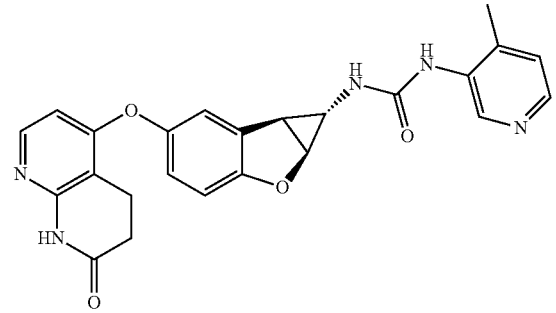
Compound 1.40
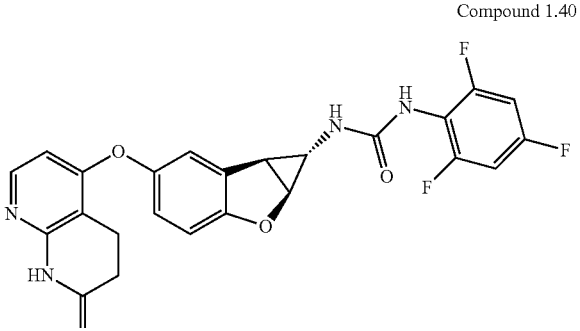
Compound 1.41
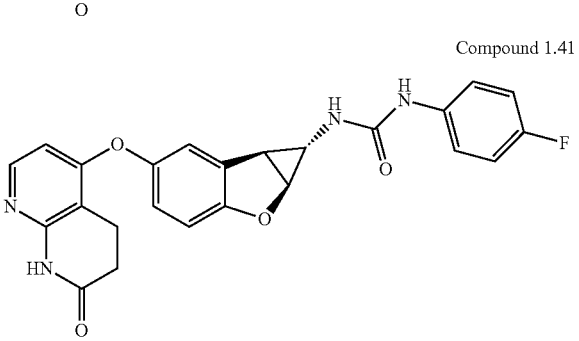
Compound 1.42
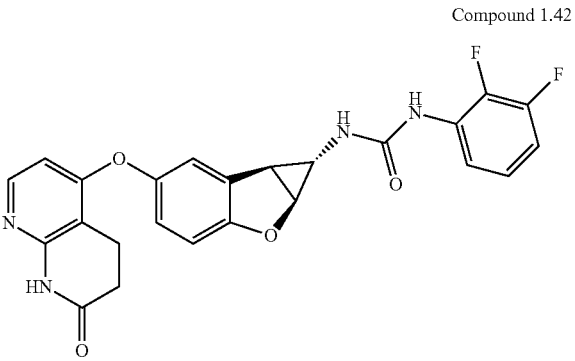

Compound 1.43
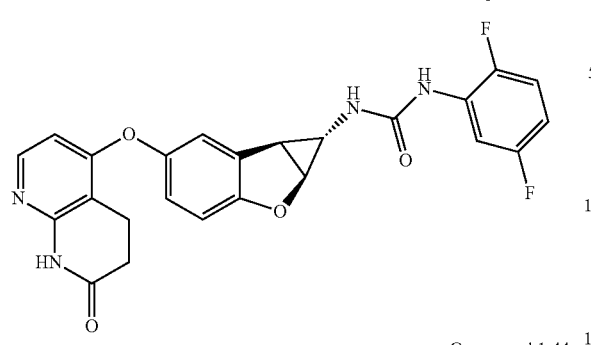
Compound 1.44
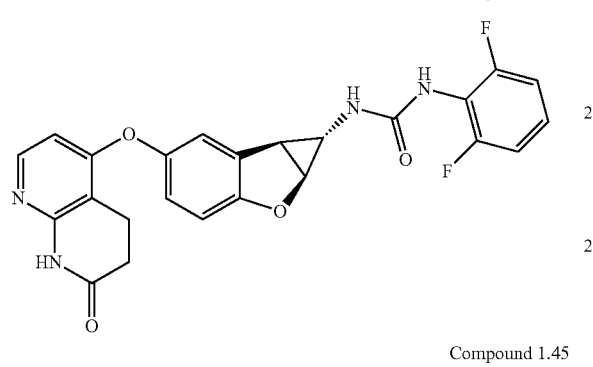
Compound 1.45
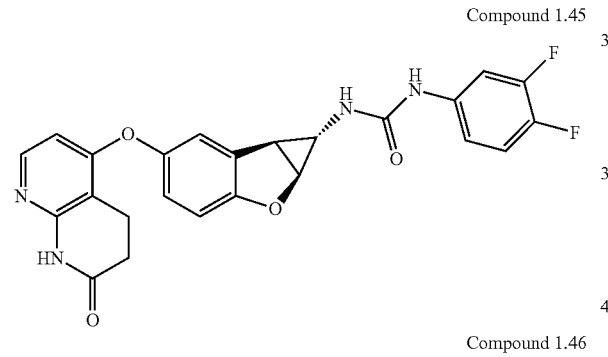
Compound 1.46
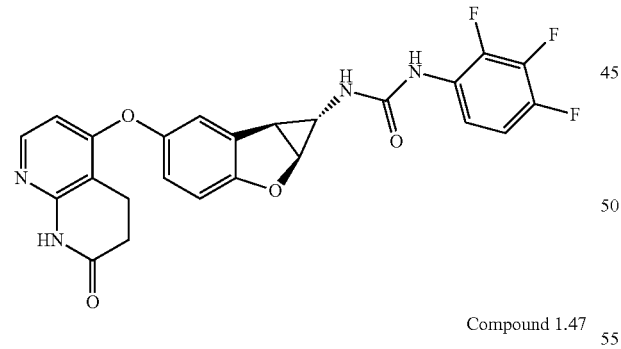
Compound 1.47
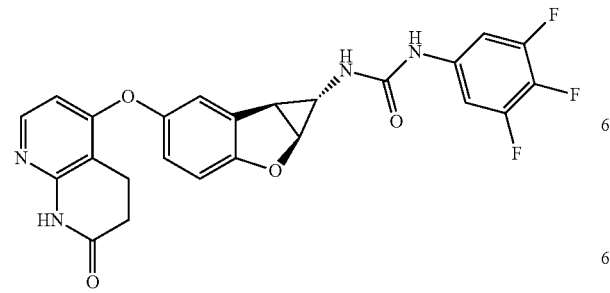
Compound 1.48
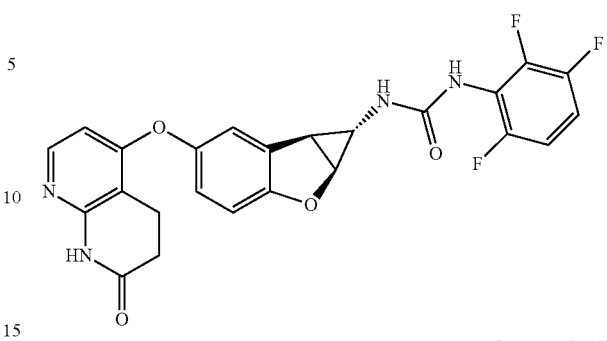
Compound 1.49
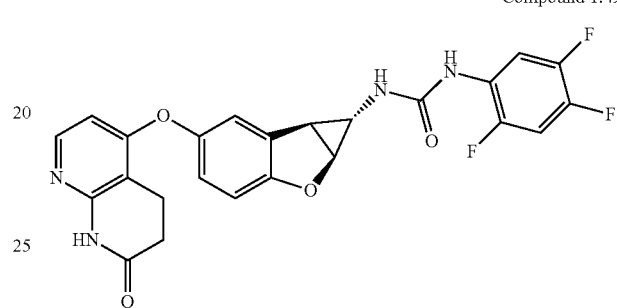
Compound 1.50
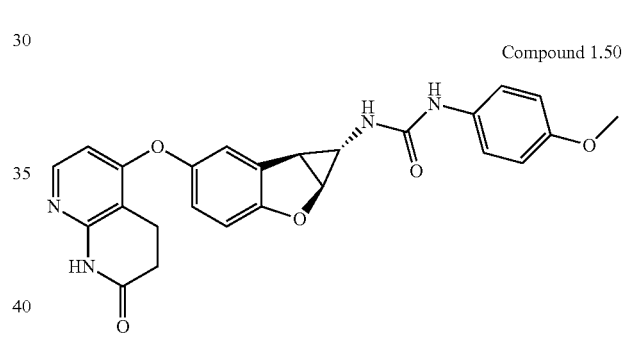
Compound 1.51
Compound 1.52
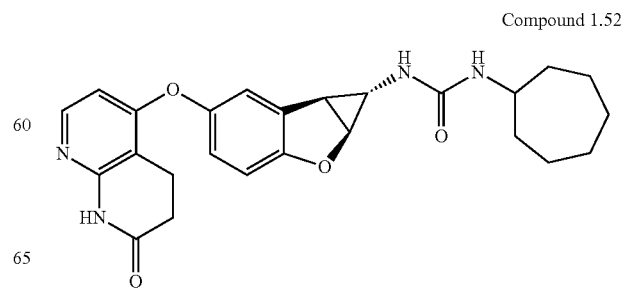

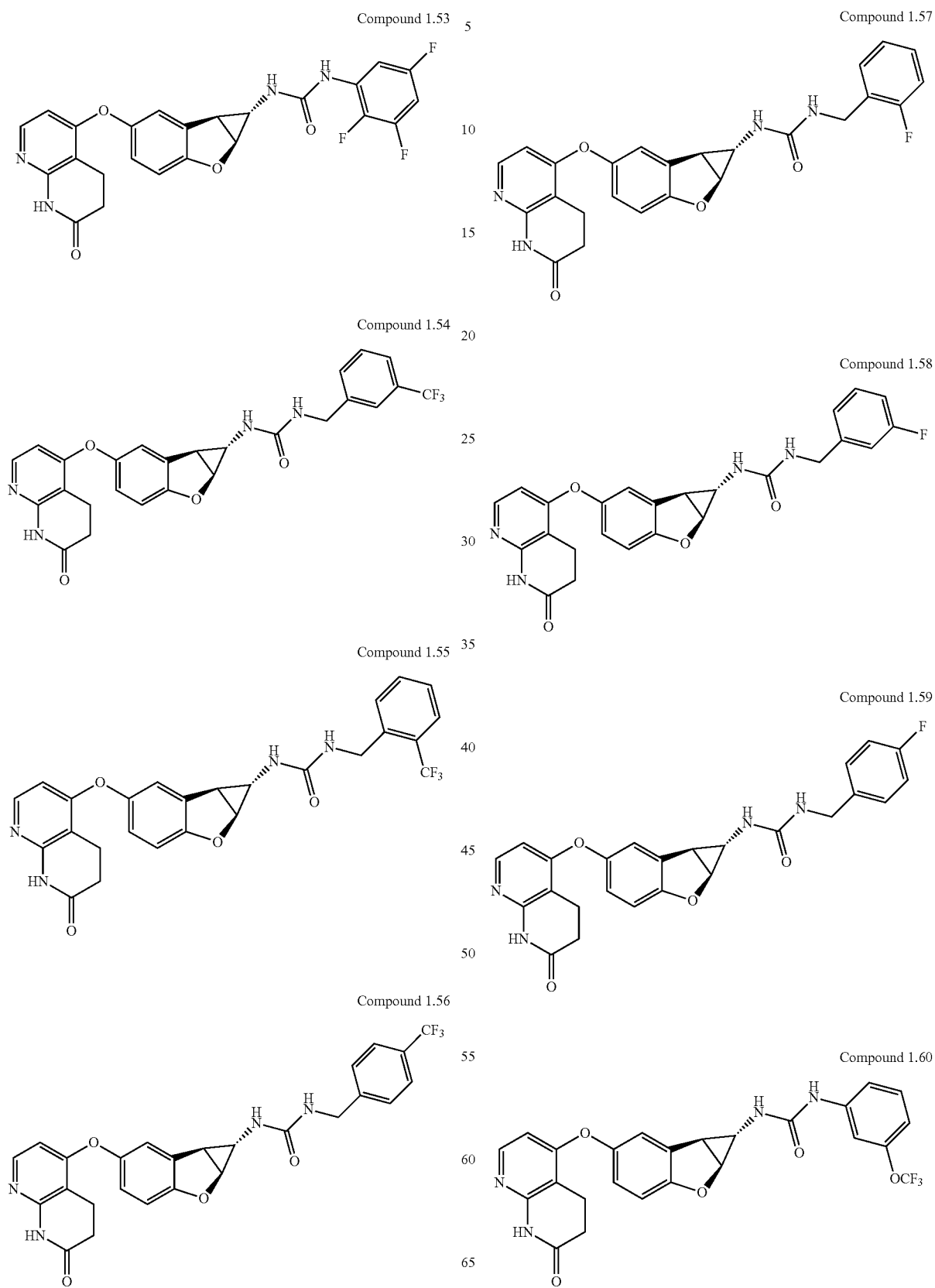

Compound 1.61
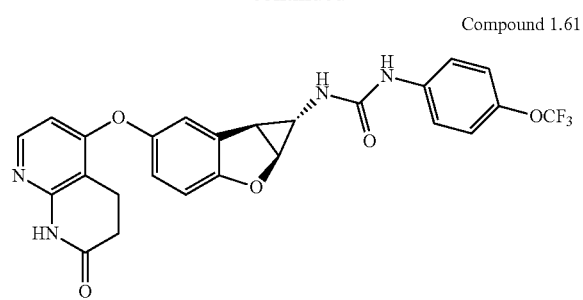
Compound 1.62
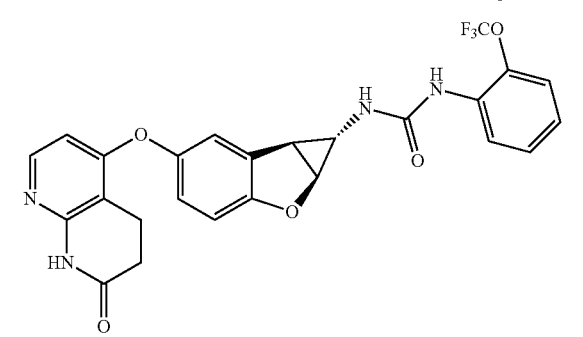
Compound 1.63
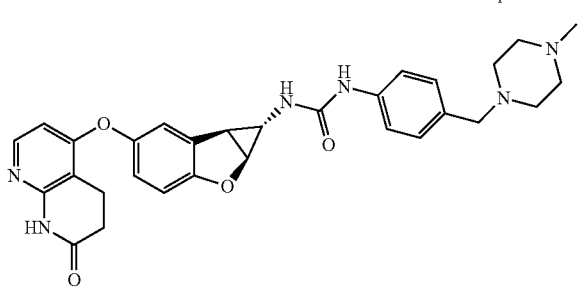
Compound 1.64
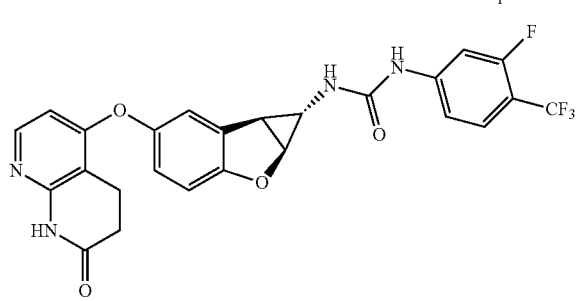
Compound 1.65
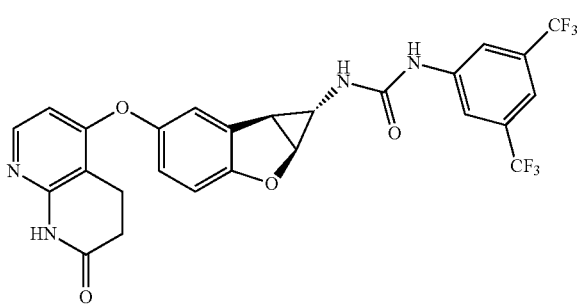
Compound 1.66
Compound 1.67
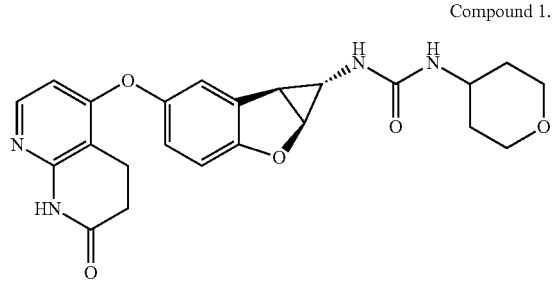
Compound 1.68
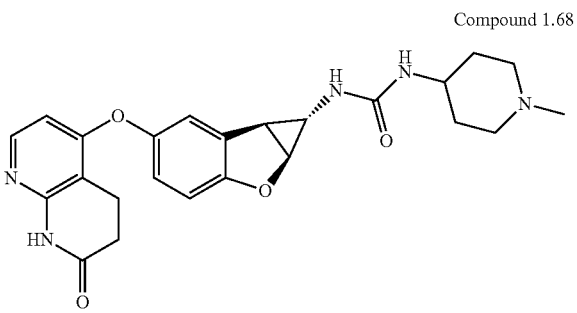
Compound 1.69
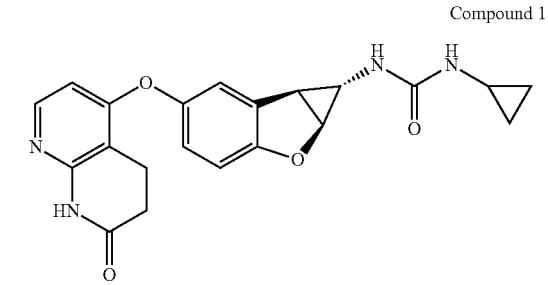
Compound 1.70
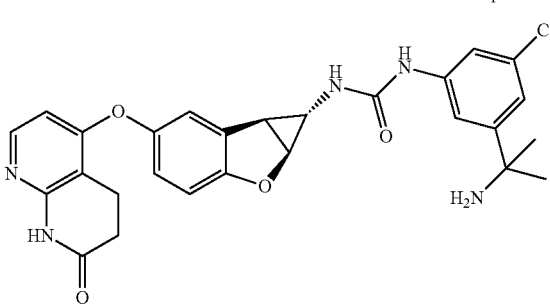

-continued
Compound 1.71
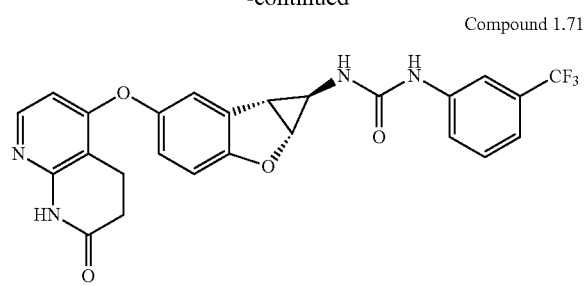
Compound 1.72
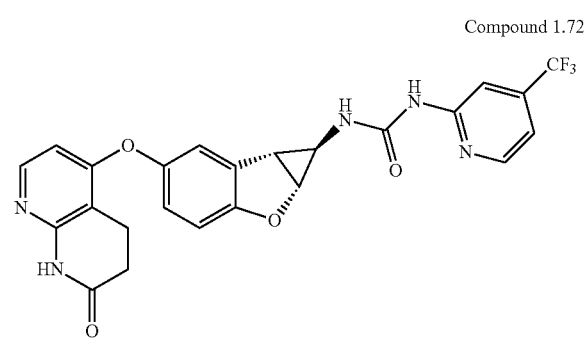
Compound 1.73
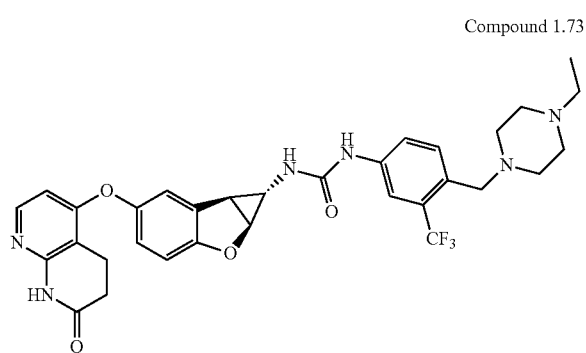
Compound 1.74
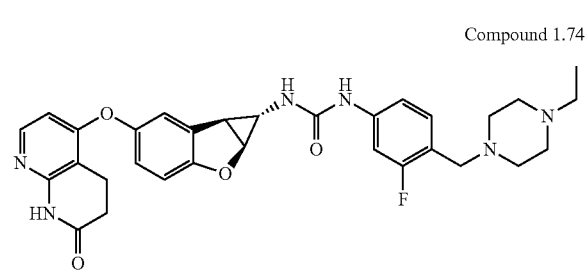
Compound 1.75
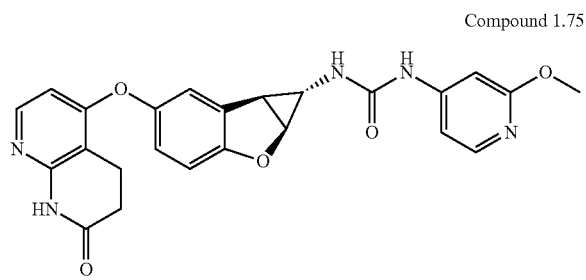
-continued
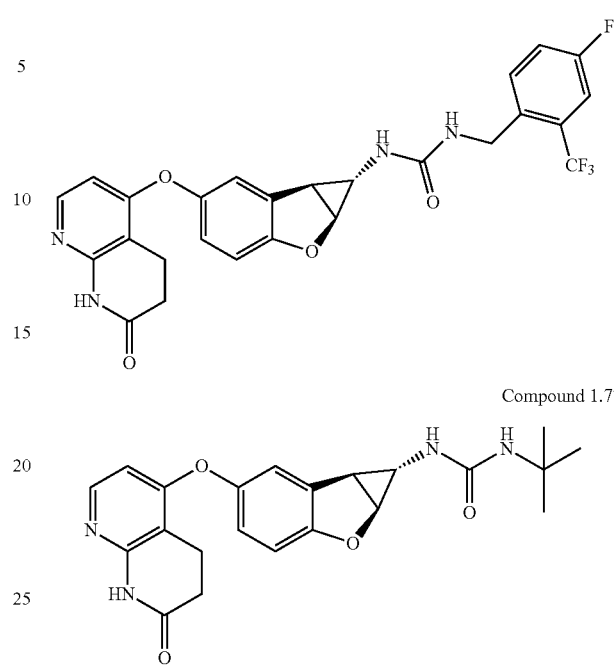

Compound 1.81
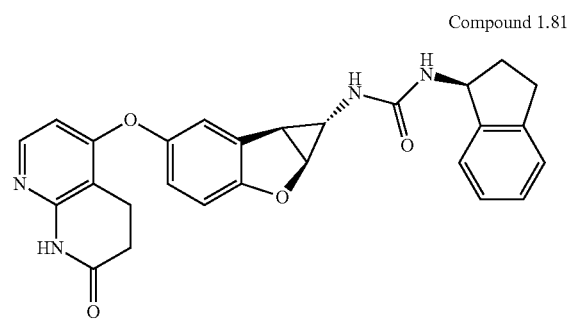
Compound 1.82
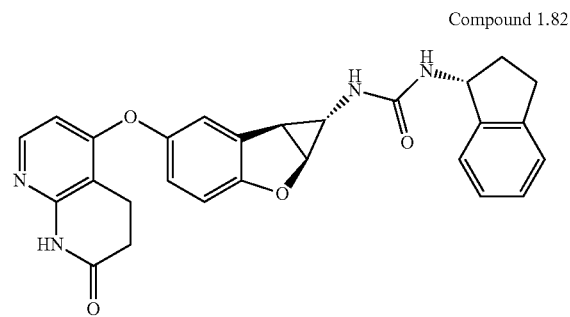
Compound 1.83
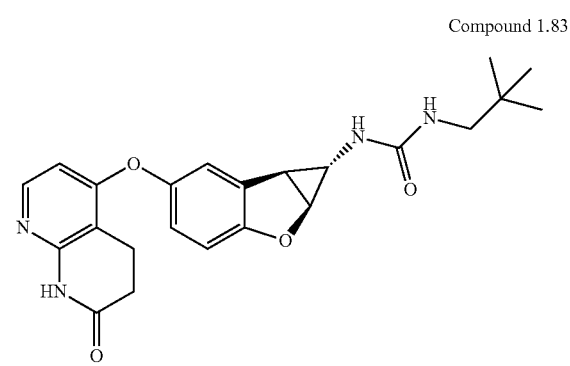
Compound 1.84
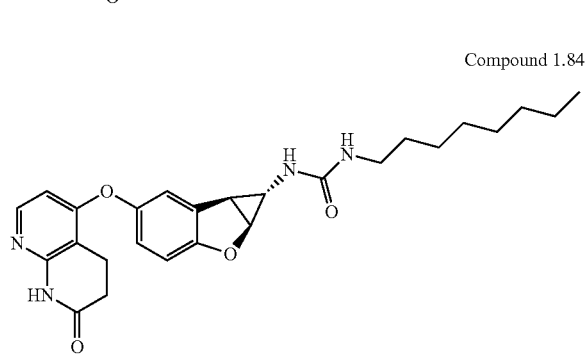
Compound 1.85
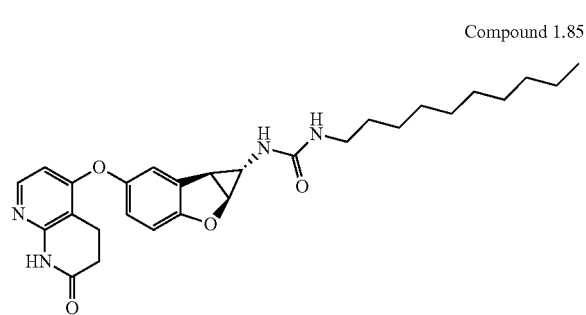
Compound 1.86
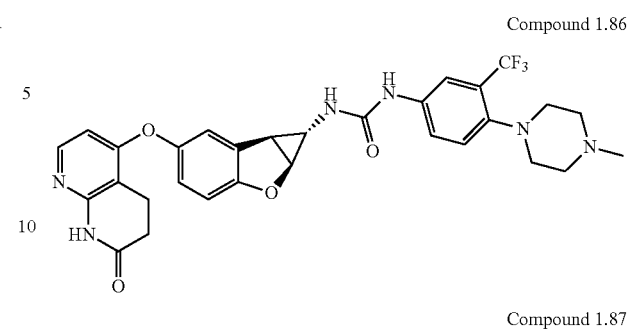
Compound 1.87
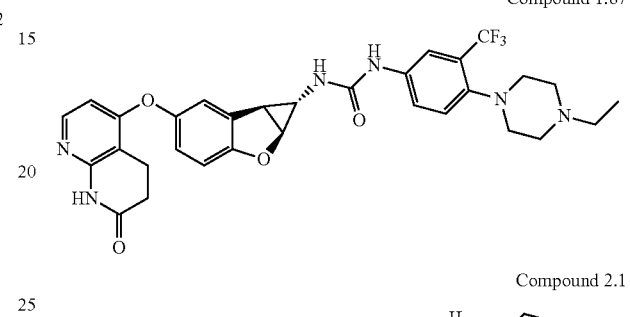
Compound 2.1
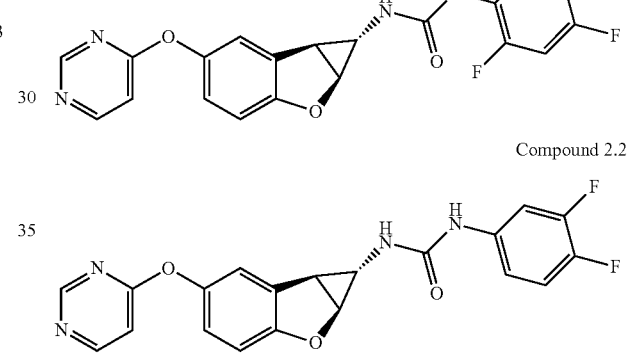
Compound 2.2
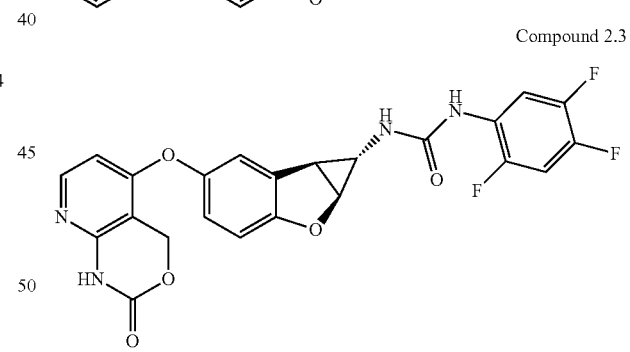
Compound 2.3
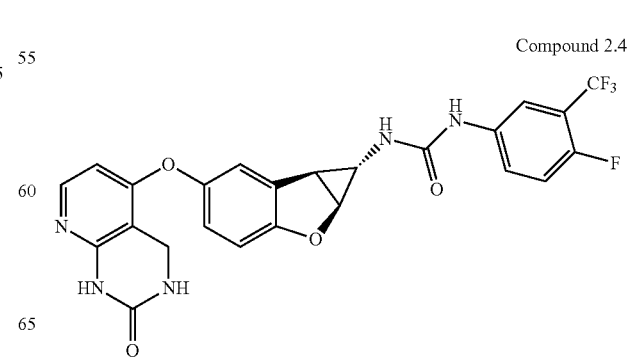
Compound 2.4

Compound 2.5
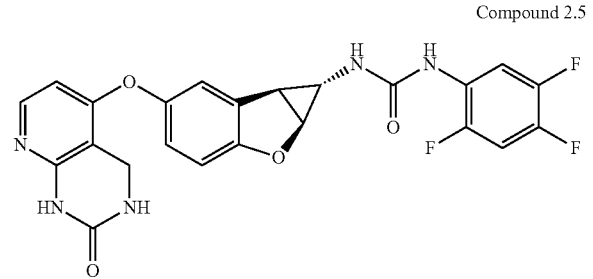
Compound 2.6
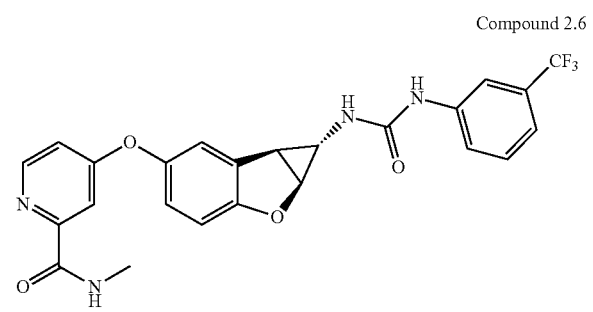
Compound 2.7
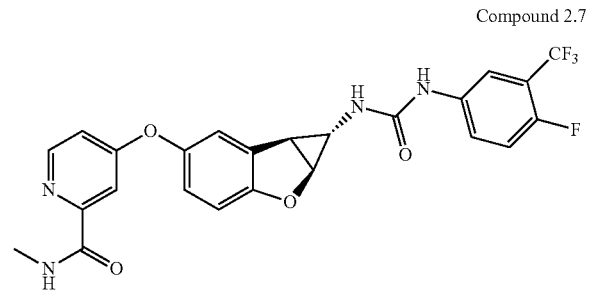
Compound 2.8
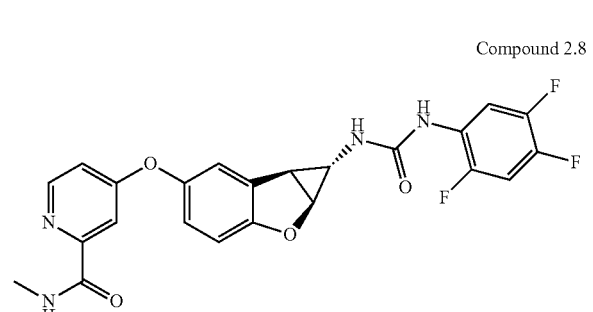
Compound 2.9
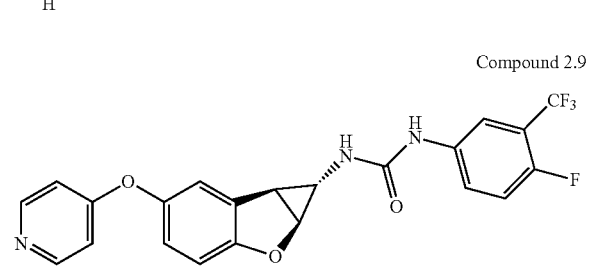
Compound 2.10
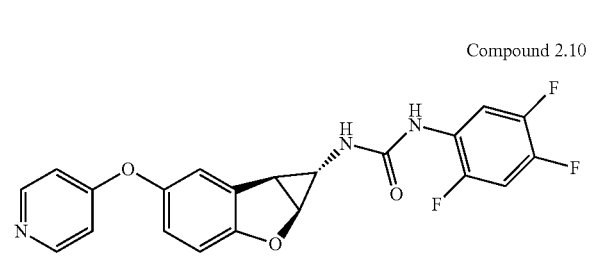
Compound 2.11
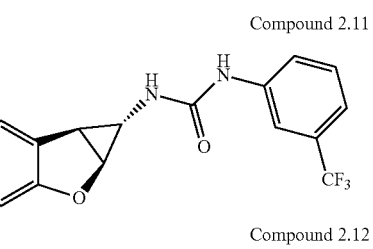
Compound 2.12
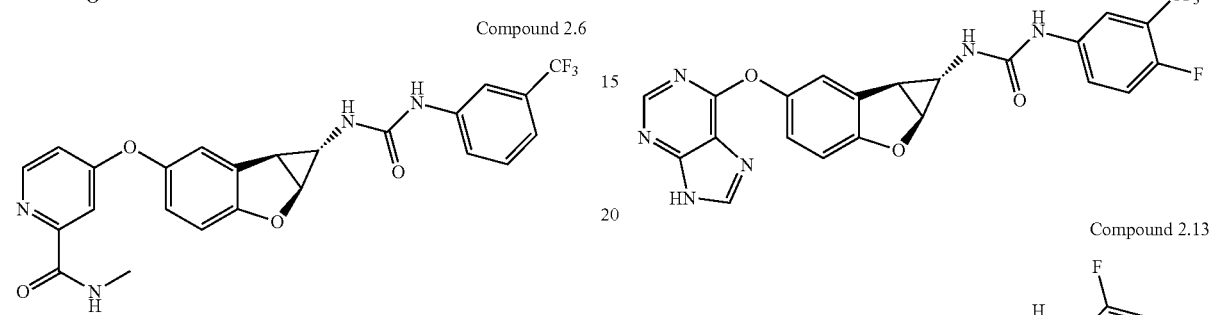
Compound 2.13
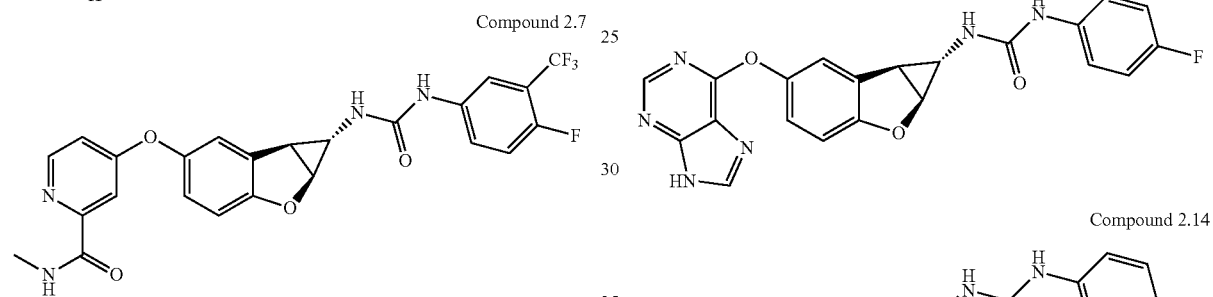
Compound 2.14
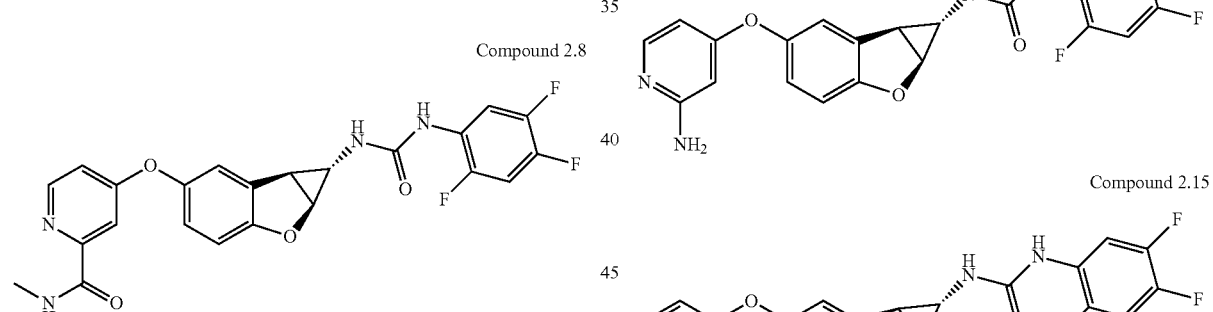
Compound 2.15
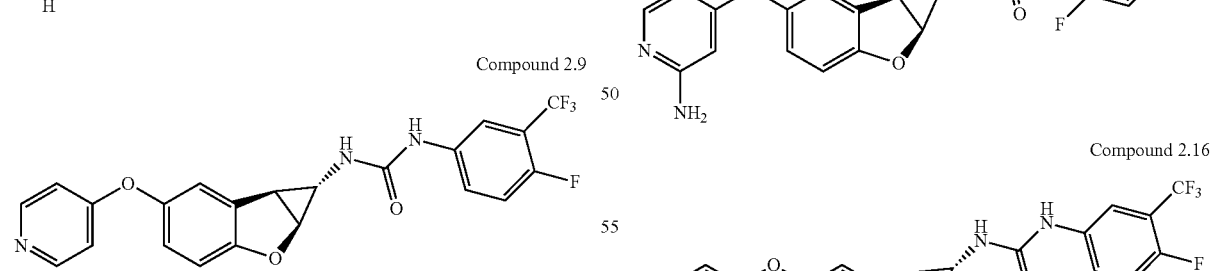
Compound 2.16
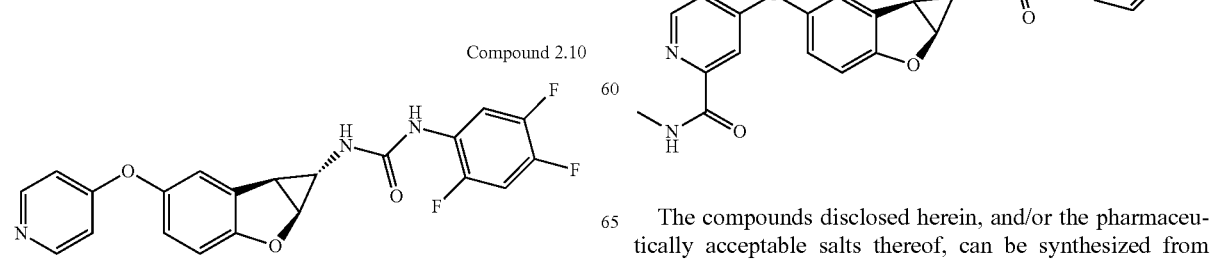
The compounds disclosed herein, and/or the pharmaceutically acceptable salts thereof, can be synthesized from commercially available starting materials taken together with the disclosure herein. The following scheme illustrates methods for preparation of some of the compounds disclosed herein.

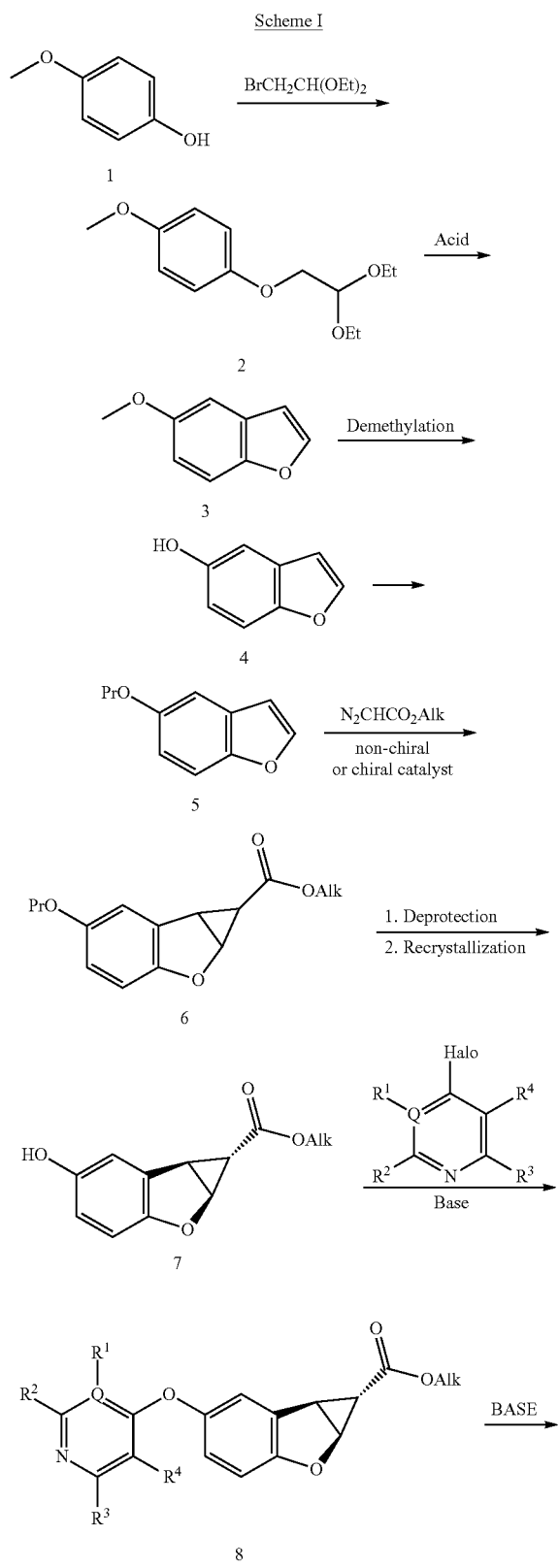

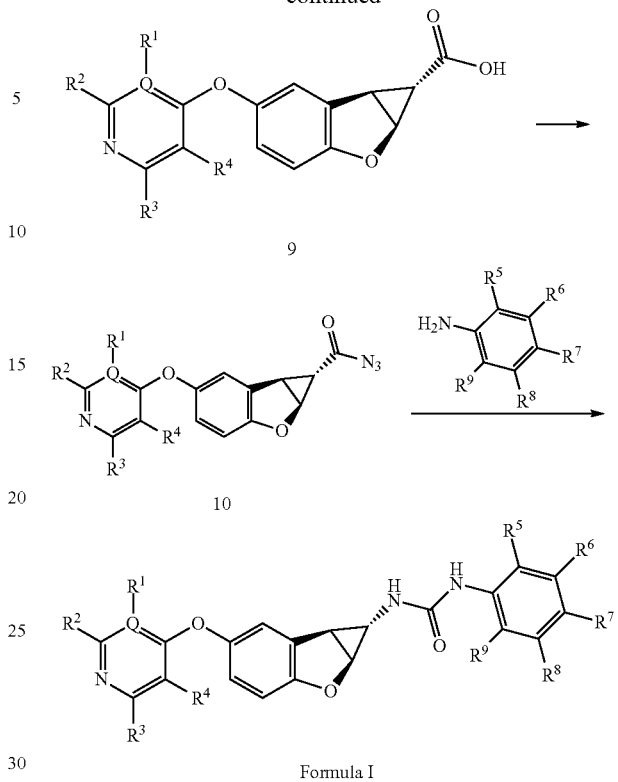

Formula I

Pr = protecting group;
PrO = protected hydroxy group;
Alk = alkyl group;
Halo = halogen;

In this scheme, a commercially available 4-methoxyphenol 1 is reacted with 2-bromo-1,1-diethoxyethane to form formula 2, then the ring is closed in the presence of acidic condition to give 5-methoxybenzofuran 3. Then the methyl group is removed and the hydroxy group of formula 4 is protected with a hydroxy protecting group (such as methyl, ethyl, isopropyl, benzyl, p-methoxybenzyl, trityl, methoxymethyl, tetrahydropyranyl acetyl, benzoate, trimethylsilyl, triethylsilyl, tri-isopropylsilyl, tert-butyldimethylsilyl or tert-butyldiphenylsilyl, further such as benzyl from benzyl bromide, and tert-butyldiphenylsilyl from TBSCl) to provide a protected hydroxybenzofuran of formula 5. The compound of formula 5 is reacted with alkyl diazo-acetate (such as ethyl diazo-acetate) in the presence of a Rh or Cu catalyst to provide a cyclopropane derivative of formula 6. The chiral derivative of formula 6 may be obtained by using a chiral catalyst formed in situ from $Cu(OOCCF_3)_2$ and a chiral amino alcohol or by using a commercially available chiral Rh catalyst. The compound of formula 6 is deprotected as described above to provide a phenol derivative (for example, the TMS protecting group may be removed by treating with HCl/EtOH). Formula 7 can be obtained using simple recrystallization. The resulting phenol derivative of formula 7 is reacted with haloheteroaryl derivative (such as fluoro-substituted heteroaryl derivative) to provide a compound of formula 8, which subsequently is hydrolyzed into the free acid of formula 9 by using a base such as sodium hydroxide. A compound of formula 9 is reacted with DPPA (diphenylphosphoryl azide) to form formula 10, which is rearranged to afford a compound of Formula I in the presence of the aniline.

Also provided is a method for treating or preventing hyperproliferative disorders, such as cancer, comprising administrating to a subject, such as a mammal or human in need thereof pharmaceutically-effective amount of at least one compound selected from compounds of Formula (I), (II) or (III), stereoisomers thereof, and pharmaceutically accept salts thereof described herein.

Also provided is a method for treating or preventing hyperproliferative disorders, such as cancer by inhibiting Raf kinases and/or Raf kinase dimmers, comprising administrating to a subject, such as a mammal or human in need thereof pharmaceutically-effective amount of at least one compound selected from compounds of Formula (I), (II) or (III), stereoisomers thereof, and pharmaceutically accept salts thereof described herein.

Also provided is a method for treating or preventing cancer including but not limiting to, for example, melanomas and thyroid cancer, Barret's adenocarcinoma, breast cancer, cervical cancer, colorectal cancer, gastric cancer, lung cancer, ovarian cancer, pancreatic cancer, prostate cancer, hematologic cancers, cancer of Binary Tract, Non-small-cell-lung cancer, endometrium cancer, blood cancer, large intestinal colon carcinoma, histiocytic lymphoma, lung adenocarcinoma, comprising administrating to a subject, such as a mammal or human in need thereof pharmaceutically-effective amount of at least one compound selected from compounds of Formula (I), (II) or (III), stereoisomers thereof, and pharmaceutically accept salts thereof described herein.

Also provided is a method for treating or preventing disorders associated with neuronal degeneration resulting from ischemic events, including cerebral ischemia after cardiac arrest, stroke and multi-infarct dementia, comprising administrating to a subject, such as a mammal or human in need thereof pharmaceutically-effective amount of at least one compound selected from compounds of Formula (I), (II) or (III), stereoisomers thereof, and pharmaceutically accept salts thereof described herein.

Also provided is a method for treating or preventing disorders associated with those after cerebral ischemic events such as those resulting from head injury, surgery and/or during childbirth, as well as in polycystic kidney disease, comprising administrating to a subject, such as a mammal or human in need thereof pharmaceutically-effective amount of at least one compound selected from compounds of Formula (I), (II) or (III), stereoisomers thereof, and pharmaceutically accept salts thereof described herein.

Also provided is a pharmaceutical composition comprising at least one compound selected from compounds of Formula (I), (II) or (III), stereoisomers thereof, and pharmaceutically accept salts thereof described herein and pharmaceutically-acceptable carriers, diluents, or adjuvants.

Also provided herein is a method of treating cancer responsive to inhibition of Raf kinase comprising administering to a subject, such as a mammal or human, in need of treating for the cancer an effective amount of at least one compound selected from compounds of Formula (I), (II), or (III), stereoisomers thereof, and pharmaceutically acceptable salts thereof described herein.

The at least one compound selected from compounds of Formula (I), (II), or (III), stereoisomers thereof, and pharmaceutically acceptable salts thereof may be employed alone or in combination with at least one other therapeutic agent for treatment. In some embodiments, the at least one compound selected from compounds of Formula (I), (II), or (III), stereoisomers thereof, and pharmaceutically acceptable salts thereof can be used in combination with at least one additional therapeutic agent. The at least one additional therapeutics agent can be, for example, selected from anti-hyperproliferative, anti-cancer, and chemotherapeutic agents. The at least one compound and/or at least one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the at least one compound and/or at least one pharmaceutically acceptable salt disclosed herein A "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anti-cancer drugs, toxins, and/or radionuclides; biological response modifiers (e.g., interferons, such as IFN-a and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer); Letrozole (FEMARA®, Novartis); Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG1478, AG1571 (SU 5271, Sugen); Trametinib (GSK1120212); Selumetinib (AZD6244); Binimetinib (MEK162); Pimasertib; alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines such as altretamine, triethylenemelamine, triethylenephosphoramide, triethylenethiophosphoramide and trimethylomelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CB1-TM1; eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, such as calicheamicin gamma1I and calicheamicin omega1I (Angew Chem. Intl. Ed. Engl. (1994) 33:183-186); dynemicin, such as dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; and rogens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ib and ronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (I), (II), or (III) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal gl and s, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti- and rogens such as flutamide, nilutamide, bicalutamide, leuprolide, and goserelin; as well as troxacitabine (a 1,3-dioxolane nucleoside cytosine analog); (iv) protein kinase inhibitors such as MEK1/2 inhibitors, for example, trametinib, selumetinib, pimasertib and GDC-0973; (v) lipid kinase inhibitors; (vi) antisense oligonucleotides, such asthose which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and $HER^2$ expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibodydrug conjugate, gemtuzumab ozogamicin (MYLOTARG®, Wyeth).

Humanized monoclonal antibodies with therapeutic potential as chemotherapeutic agents in combination with the at least one compound selected from compounds of Formula (I), (II), or (III), stereoisomers thereof, and pharmaceutically acceptable salt thereofmay, for example, be selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, visilizumab, nivolumab and Pembroluzimab.

Also provided herein is a composition comprising at least one compound selected from compounds of Formula (I), (II), or (III), stereoisomers thereof, and pharmaceutically acceptable salts thereof, and at least one pharmaceutically acceptable carrier.

The composition comprising at least one compound selected from compounds of Formula (I), (II), or (III), stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The at least one compound selected from Formula (I), (II), or (III), stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The at least one compound selected from compounds of Formula (I), (II), or (III), stereoisomers thereof, and pharmaceutically acceptable salts thereof disclosed herein can also be administered parenterally, in sterile liquid dosage forms, such as dispersions, suspensions or solutions. Other dosages forms that can also be used to administer the at least one compound selected from Formula (I), (II), or (III), stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the at least one compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene glycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in Remington's Pharmaceutical Sciences, A. Osol, a standard reference text in the art.

The at least one compound selected from compounds of Formula (I), (II), or (III), stereoisomers thereof, and pharmaceutically acceptable salts thereof disclosed herein can further be examined for efficacy in treating cancer by in vivo assays. For example, the at least one compound and/or the at least one pharmaceutically acceptable salts thereof disclosed herein can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the at least one compound selected from compounds of Formula (I), (II), or (III), stereoisomers thereof, and pharmaceutically acceptable salts thereof disclosed herein may be conveniently delivered in the form of an aerosol spray presentation from pressurized packs or nebulisers. The at least one compound selected from compounds of Formula (I), (II), or (III), stereoisomers thereof, and pharmaceutically acceptable salts thereof disclosed herein may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of at least one compound selected from compounds of Formula (I), (II), or (III), stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the at least one compound selected from compounds of Formula (I), (II), or (III), stereoisomers thereof, and pharmaceutically acceptable salts thereof disclosed herein in an appropriate ophthalmic vehicle, such that the at least one compound selected from compounds of Formula (I), (II), or (III), stereoisomers thereof, and at least one pharmaceutically acceptable salts thereof disclosed herein is maintained in contact with the ocular surface for a sufficient time period to allow the compound to penetrate the corneal and internal regions of the eye.

Useful pharmaceutical dosage-forms for administration of the at least one compound selected from compounds of Formula (I), (II), or (III), stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the at least one compound selected from compounds of Formula (I), (II), or (III), stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the at least one compound selected from compounds of Formula (I), (II), or (III), stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the at least one compound selected from compounds of Formula (I), (II), or (III), stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the at least one compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided at least one compound selected from compounds of Formula (I), (II), or (III), stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the at least one compound selected from compounds of Formula (I), (II), or (III), stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term "coadministration" is understood to include the administration of at least two agents concomitantly or sequentially, or alternatively as a fixed dose combination of the at least two active components.

The at least one compound selected from compounds of Formula (I), (II), or (III), stereoisomers thereof, and pharmaceutically acceptable salt thereof disclosed herein can be administered as the sole active ingredient or in combination with at least one second active ingredient, selected, for example, from other active ingredients known to be useful for treating cancers in a patient.

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using prepacked silica gel cartridges.

$^1$H NMR spectra were recorded on a Varian instrument operating at 400 MHz. $^1$H-NMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). All compound names except the reagents were generated by ChemDraw version 12.0.

In the following examples, the abbreviations below are used:
AcOH Acetic acid
Aq Aqueous
Brine Saturated aqueous sodium chloride solution
Bn Benzyl
BnBr Benzyl Bromide
$CH_2Cl_2$ Dichloromethane
DMF N,N-Dimethylformamide
Dppf 1,1"-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol
$Et_2O$ or ether Diethyl ether
G grams
h or hr hour
HATU O-(7-Azabenzotriazol-1-yl)-N,N,N',N'-tetramethyluronium hexafluorophosphate
HCl Hydrochloric acid
HPLC High-performance liquid chromatography
IPA 2-propanol
i-PrOH Isopropyl alcohol
Mg milligrams
mL milliliters
Mmol millimole
MeCN Acetonitrile
MeOH Methanol
Min minutes
ms or MS Mass spectrum
$Na_2SO_4$ Sodium sulfate
PE petroleum ether
PPA Polyphosphoric acid
Rt Retention time
Rt or rt Room temperature
TBAF Tetra-butyl ammonium fluoride
TBSCl tert-Butyldimethylsilyl chloride
TFA Trifluoroacetic acid
THF tetrahydrofuran
TLC thin layer chromatography
μL microliters

EXAMPLE 1

Synthesis of Compounds 1.1-1.87

Compound 1.1: 1-((1S,1aS,6bS)-5-((7-oxo-5,6,7,8-tetrahydro-1,8-naphthyridin-4-yl) oxy)-1a,6b-dihydro-1H-cyclopropa[b]benzofuran-1-yl)-3-(3-(trifluoromethyl) phenyl)urea

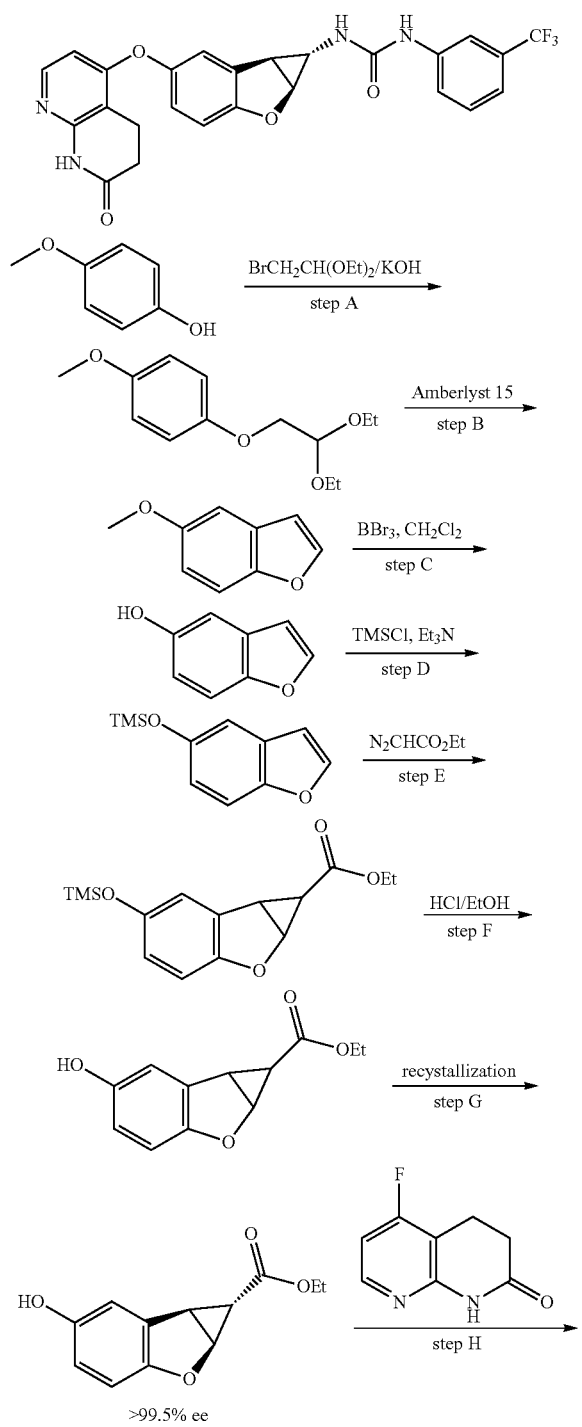

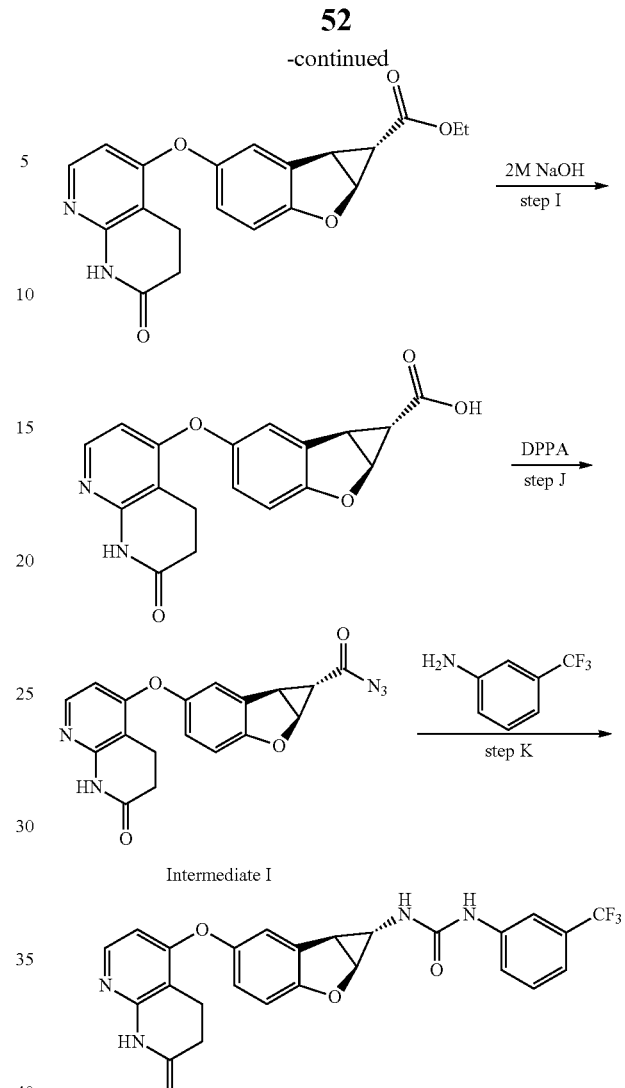

Step A: 1-(2,2-diethoxyethoxy)-4-methoxybenzene

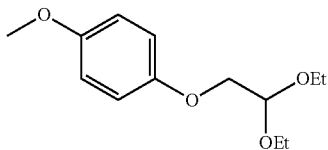 [SMILES: CCOC(COc1ccc(OC)cc1)OCC]

To a stirred solution of 4-methoxyphenol (500 g, 4 mol) in DMSO (500 mL) was added KOH (400 g, 7.1 mol, 1.78 eq) at room temperature. After stirring for 20 min, the resulted mixture was heated to 120° C. 2-bromo-1,1-diethoxyethane (850 g, 4.3 mol) was added in drops within 2 hour at this temperature and stirred for another 2 hours. The mixture was treated with water (1000 mL) and PE (1000 mL), filtered through a celite pad. The liquid phase was extracted with PE (500 mL×2). The combined organics was washed with aqueous NaOH (2 N, 300 mL x 2), brine (500 mL×3), dried over anhydrate sodium sulfate and concentrated under reduced pressure to give the title compound (850 g, 88%) as a light yellow oil which was used into next step directly. $^1$H NMR (400 MHz, DMSO-d6) δ 6.98-6.78 (m, 4H), 4.76 (t, J=5.2 Hz, 1H), 3.88 (d, J=5.2 Hz, 2H), 3.71-3.68 (m, 3H), 3.69-3.61 (m, 2H), 3.60-3.50 (m, 2H), 1.17-1.10 (m, 6H) ppm.

Step B: 5-methoxybenzofuran

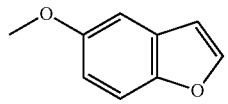

The mixture of the product of Step A (420 g, 1.87 mmol) and Amberlyst 15 (42 g) in toluene (2 L) was stirred at reflux for 6 hrs with concomitant azeotrope removal of EtOH generated in the reaction (keep the solvent more than 1.5 L). The resulting reaction mixture was filtered and the resin was washed with an excess of toluene. The combined filtrates were concentrated to dryness under reduced pressure. The crude product was distilled at 100° C. under reduced pressure through a lab oil pump to afford (105 g, 74° C. fraction). The solid was diluted with 1000 mL of PE and washed with NaOH (3 M, 200 mL x 2), brine (500 mL×3), dried over anhydrate sodium sulfate and concentrated under reduced pressure to give the title compounds (85 g, 33%) as a white solid. $^1$H NMR (400 MHz, CDCl$_3$) δ 7.59 (d, J=2.0 Hz, 1H), 7.39 (d, J=9.0 Hz, 1H), 7.05 (d, J=2.4 Hz, 1H), 6.90 (dd, J=9.0, 2.4 Hz, 1H), 6.73-6.68 (m, 1H), 3.84 (s, 3H) ppm.

Step C: benzofuran-5-ol

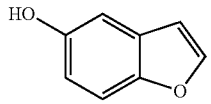

To a solution of the product of Step B (50 g, 0.34 mol) in CH$_2$Cl$_2$ (1200 mL) was added BBr$_3$ (32.5 mL, 0.34 mol) in drops at −20° C. under N$_2$. After the addition, the mixture was warmed to 20° C. and stirred for 2 hrs. The reaction mixture was cooled to 0° C. and added into a solution of NH$_3$/MeOH (3 mol/L, 500 mL) using a canula at −20° C. over a period of 15 min carefully. The mixture was concentrated and the residue was added EA (500 mL). The solid was filtered off through a silica pad and the filtrate was concentrated under reduced pressure to give the crude product (crude, 48 g) as an oil which was used for the next step directly. $^1$H NMR (400 MHz, DMSO-d6) δ 9.14 (s, 1H), 7.86 (d, J=2.0 Hz, 1H), 7.36 (d, J=8.8 Hz, 1H), 6.94 (d, J=2.4 Hz, 1H), 6.79 (dd, J=2.0, 0.9 Hz, 1H), 6.74 (dd, J=8.8, 2.4 Hz, 1H) ppm. MS: M/e 135 (M+1)$^+$.

Step D: (benzofuran-5-yloxy)trimethylsilane

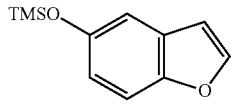

To a stirred solution of the product of Step C (350 g, 2.6 mol) and Et$_3$N (400 g, 3.9 mol) in DCM (2000 mL) was added a solution of TMSCl (290 g, 2.6 mol) in DCM (300 mL) at 0° C. The mixture was stirred at ambient temperature for 3 hours. Large amount of white solid precipitated and it was filtered with a silica-gel pad and the filter cake was washed with PE. The combined filtrates was concentrated and the resulted oil was distilled under high vacuum to give product (290 g, yield: 62% for 2 steps) as a colorless oil. $^1$H NMR (400 MHz, DMSO-d6) δ 7.69 (d, J=2.0 Hz, 1H), 7.21 (d, J=8.8 Hz, 1H), 6.84 (d, J=2.5 Hz, 1H), 6.61 (d, J=2.0 Hz, 1H), 6.56 (dd, J=8.8, 2.5 Hz, 1H), 0.00 (s, 9H) ppm.

Step E: ethyl 5-((trimethylsilyl)oxy)-1a,6b-dihydro-1H-cyclopropa[b]benzofuran-1-carboxylate

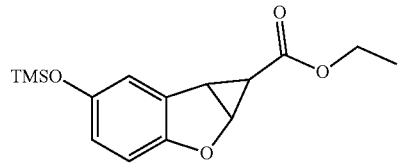

Copper (I) triflate (2:1 complex with toluene, 600 mg, 0.5%) and (S,S)-2,2'-Isopropylidene-bis(4-phenyl-2-oxazoline) (760 mg, 1%) were stirred in dichloromethane (10 mL) at ambient temperature under N$_2$ atmosphere for 1 hour. The product of Step D (47.2 g, 0.23 mol) was added, followed by a slow addition of ethyl diazoethanoate (78 g, 0.69 mol) in DCM (400 mL) during a period of 12 hours using a syringe pump. A solution of EDTA disodium (0.05 mol/L, 100 mL x 2) was added to the reaction mixture and stirred at room temperature for 1 hr. The organic phase was concentrated and the residue was distilled under reduced pressure (lab oil pump). The fraction of the title compound (43.5 g, 65%, light yellow oil) was collected at 125~140° C. $^1$H NMR (400 MHz, DMSO-d6) δ 6.79 (d, J=2.4 Hz, 1H), 6.59 (d, J=8.4 Hz, 1H), 6.42 (dd, J=8.4, 2.4 Hz, 1H), 4.95 (dd, J=5.4, 1.0 Hz, 1H), 3.08 (dd, J=5.4, 3.2 Hz, 1H), 1.02 (dd, J=3.1, 1.2 Hz, 1H), 0.00 (s, 9H) ppm.

Step F: ethyl 5-hydroxy-1a,6b-dihydro-1H-cyclopropa[b]benzofuran-1-carboxylate

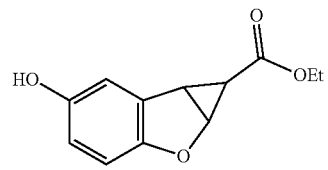 [SMILES: CCOC(=O)C1C2Oc3ccc(O)cc3C21]

A solution of the product of Step E (35 g, 0.12 mol) in MeOH (100 mL) was added a solution of HCl/EtOH (1 M, 0.1 mL) at ambient temperature and stirred for 1 hour. The mixture was concentrated and the resulted oil was diluted with 100 mL of PE/EA (3:1) and concentrated again to give the title compound (26.3 g, yield: >99%, ee %: 85%) as a light yellow solid.

$^1$H-NMR (600 MHz, CDCl$_3$) δ 7.01 (s, 1H), 6.89 (d, J=2.6 Hz, 1H), 6.68 (d, J=8.6 Hz, 1H), 6.63 (dd, J=8.6, 2.6 Hz,

1H), 5.02 (dd, J=5.6, 1.2 Hz, 1H), 4.15 (q, J=7.2 Hz, 2H), 3.19 (dd, J=5.4, 3.0 Hz, 1H), 1.26 (dd, J=3.0, 1.2 Hz, 1H), 1.26-1.23 (m, 3H) ppm.

Step G: (1S,1aS,6bR)-ethyl 5-hydroxy-1a,6b-dihydro-1H-cyclopropa[b]benzofuran-1-carboxylate

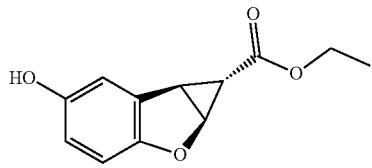 [SMILES: CCOC(=O)[C@@H]1[C@H]2Oc3ccc(O)cc3[C@H]21]

The phenol the product of Step F (46.0 g, purity: 100%; ee: 85.1%) in n-hexane/ethyl acetate (12/1, total 1400 mL) was stirred at reflux. After all solids dissolved and a homogenous solution was obtained, the solution was stirred at reflux for 0.5 h more. Then the solution was cooled to room temperature and phenol compound crystallized out as needle form crystals over 2 h time period. The mixture was filtered and the crystals (26.5 g, ee: 98.0%) were collected. 26 g of the 98.0% ee compound was subjected to a second round of re-crystallization (n -hexane/ethyl acetate 11/1, total 1000 mL) to give 18.3 g of crystals (the title compound) with 99.9% ee after filtration and drying. $^1$H NMR (400 MHz, DMSO-d6) δ 9.06 (s, 1H), 6.89 (d, J=2.8 Hz, 1H), 6.72 (d, J=8.8 Hz, 1H), 6.55 (dd, J=8.8, 2.4 Hz, 1H), 5.12 (d, J=5.6 Hz, 1H), 4.09 (q, J=7.2 Hz, 2H), 3.27 (dd, J=5.6, 2.8 Hz, 1H), 1.25-1.15 (m, 4H). MS: M/e 221 (M+1)$^+$.

Step H: (1S,1aS,6bR)-ethyl 5-((7-oxo-5,6,7,8-tetrahydro -1,8-naphthyridin-4-yl)oxy)-1a,6b-dihydro-1H-cyclopropa[b]benzofuran-1-carboxylate

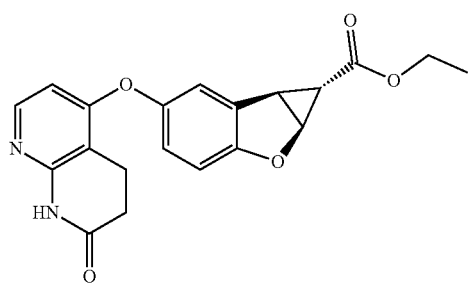 [SMILES: CCOC(=O)[C@@H]1[C@H]2Oc3ccc(Oc4ccnc5c4CCC(=O)N5)cc3[C@H]21]

The mixture of the product of Step G (66.3 g, 0.3 mol) and 5-fluoro-3,4-dihydro-1,8-naphthyridin-2(1H)-one (50 g, 0.3 mol) in DMF (850 mL) was added Potassium tert-butoxide (35.4 g, 0.32 mol) and the mixture was stirred at 120° C. under nitrogen for 2 hrs. The reaction was cooled to room temperature and filtered through a celite pad and the filtrate was removed half of the solvent. The residue was added into stirred 2 L water in drops. A solid was precipitated out of the solution. The solid was filtered, washed with water and dried in air. The dried title compound (108.2 g, 98%) as a gray solid was used into next step directly. $^1$H NMR (400 MHz, DMSO-d6) δ 10.43 (s, 1H), 7.92 (d, J=5.8 Hz, 1H), 7.30 (d, J=2.4 Hz, 1H), 6.98 (d, J=8.8 Hz, 1H), 6.94 (dd, J=8.8, 2.4 Hz, 1H), 6.21 (d, J=5.8 Hz, 1H), 5.26 (dd, J=5.4, 1.0 Hz, 1H), 4.08 (q, J=7.0 Hz, 2H), 3.34 (dd, J=5.4, 3.2 Hz, 1H), 2.89 (t, J=7.8 Hz, 2H), 2.51 (t, J=7.8 Hz, 2H), 1.34 (dd, J=3.2, 1.0 Hz, 1H), 1.18 (t, J=7.0 Hz, 3H) ppm. MS: M/e 367 (M+1)$^+$.

Step I: (1S,1aS,6bR)-5-((7-oxo-5,6,7,8-tetrahydro-1, 8-naphthyridin-4-yl) oxy)-1a,6b-dihydro-1H-cyclopropa[b]benzofuran-1-carboxylic acid

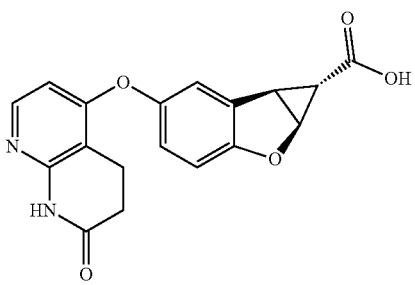 [SMILES: O=C1CCc2c(Oc3ccc4c(c3)[C@@H]3[C@H](O4)[C@H]3C(=O)O)ccnc2N1]

Sodium hydroxide aqueous solution (450 mL, 2 M, 0.9 mol) was added to a stirred solution of the product of Step H (216.4 g, 0.59 mol) in ethanol (1 L) at room temperature. The mixture was stirred at room temperature for 2 hours and 60° C. for 2 hours. The solvent was removed under reduced pressure and the residue was dissolved into water (1.2 L). The solution was neutralized with HCl (1 mol/L) to pH=7 and white solid precipitated out of solution. The white solid was collected by filtration and dried in air to give the title compound (164 g, 82%). $^1$H NMR (400 MHz, DMSO-d6) δ 12.59 (s, 1H), 10.43 (s, 1H), 7.92 (d, J=5.8 Hz, 1H), 7.29 (d, J=2.4 Hz, 1H), 6.97 (d, J=8.8 Hz, 1H), 6.93 (dd, J=8.8, 2.4 Hz, 1H), 6.21 (d, J=5.8 Hz, 1H), 5.21 (dd, J=5.4, 1.0 Hz, 1H), 3.27-3.25 (m, 1H), 2.89 (t, J=7.8 Hz, 2H), 2.51 (d, J=8.8 Hz, 2H), 1.19 (dd, J=3.0, 1.0 Hz, 1H) ppm. MS: M/e 339 (M+1)$^+$.

Step J: (1S,1aS,6bR)-5-((7-oxo-5,6,7,8-tetrahydro-1, 8-naphthyridin-4-yl)oxy)-1a,6b-dihydro-1H-cyclopropa[b]benzofuran-1-carbonyl azide (Intermediate I)

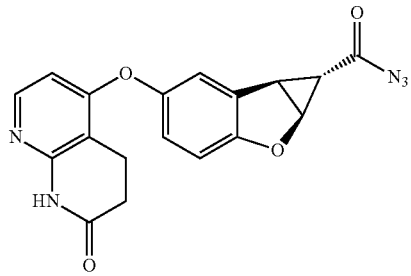 [SMILES: [N-]=[N+]=NC(=O)[C@@H]1[C@H]2Oc3ccc(Oc4ccnc5c4CCC(=O)N5)cc3[C@H]21]

To a 0° C. solution of the product of Step I (6.0 g, 17.7 mmol) in DMF (40 mL) was added Et$_3$N (4.5 g, 45 mmol) and followed by DPPA (5.9 g, 21.5 mmol). The resulted mixture was allowed warm to ambient temperature and stirred for 5 hours. 150 mL of H$_2$O was added and the mixture was extracted with EA (100 mL×3). The combined extracts was washed with brine (100 mL×3), dried over Na$_2$SO$_4$, concentrated under vacuum until about 30 mL of EA remained. 150 mL of PE was added and the mixture was stirred for 30 minutes. The white solid was filtered and washed with PE/EA (5:1, 100 mL), dried under high vacuum to give the title compound (6.17 g, yield: 95%) as a white solid. $^1$H NMR (400 MHz, CDCl$_3$) δ 8.80 (s, 1H), 8.02 (d, J=6.0 Hz, 1H), 7.15 (d, J=2.0 Hz, 1H), 7.00-6.85 (m, 2H), 6.26 (d, J=6.0 Hz, 1H), 5.22 (d, J=5.2 Hz, 1H), 3.43 (dd, J=5.2, 2.8 Hz, 1H), 3.07 (t, J=7.6 Hz, 2H), 2.71 (t, J=7.6 Hz, 2H), 1.36 (d, J=2.0 Hz, 1H). MS: M/e 364 (M+1)$^+$.

Step K: 1-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(3-(trifluoromethyl)phenyl)urea (Compound 1.1)

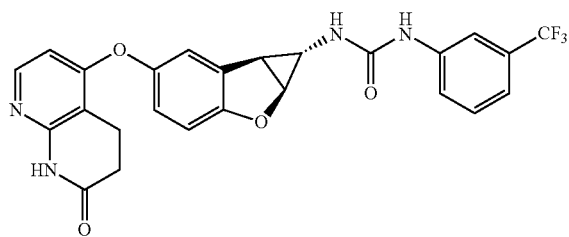 [SMILES: O=C1CCc2c(Oc3ccc4c(c3)[C@H]3[C@H](NC(=O)Nc5cccc(C(F)(F)F)c5)[C@H]3O4)ccnc2N1]

The mixture of the product of step J (1 g, 2.75 mmol) and 3-(trifluoromethyl) aniline (500 mg, 3.11 mmol) in 15 mL of anhydrous 1,4-dioxane was stirred at reflux for 2 hours. The reaction mixture was concentrated under reduced pressure and the resulted residue was purified by silica gel chromatography to give the crude compound. The solid was precipitated in hexane/EA (1:1, 50 mL) solution and filtered to afford the title compound (1.00 g, yield: 73%) as a white solid. $^1$H NMR (400 MHz, CD$_3$OD) δ 7.95 (d, J=6.4 Hz, 1H), 7.86 (s, 1H), 7.52 (d, J=9.0 Hz, 1H), 7.42 (t, J=8.0 Hz, 1H), 7.28-7.21 (m, 2H), 6.94-6.82 (m, 2H), 6.40 (d, J=6.4 Hz, 1H), 4.90 (d, J=6.0 Hz, 1H), 3.09 (t, J=7.6 Hz, 2H), 2.96 (dd, J=6.0, 2.0 Hz, 1H), 2.68 (t, J=7.6 Hz, 2H), 2.26 (d, J=2.0 Hz, 1H). MS: M/e 497 (M+1)$^+$.

Compounds 1.2-1.69 were prepared according to the procedures described for Compound 1.1 under appropriate conditions that could be recognized by one skilled in the art.

Compound 1.2

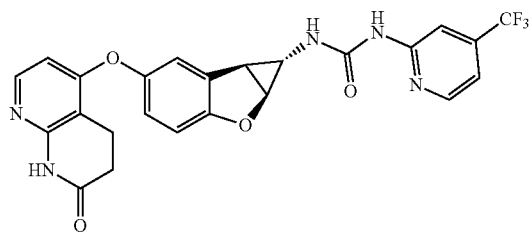 [SMILES: O=C1CCc2c(Oc3ccc4c(c3)[C@H]3[C@H](NC(=O)Nc5cc(C(F)(F)F)ccn5)[C@H]3O4)ccnc2N1]

$^1$H NMR (400 MHz, CD$_3$OD) δ 8.34 (d, J=5.6 Hz, 1H), 7.92 (d, J=6.4 Hz, 1H), 7.52 (s, 1H), 7.19 (d, J=2.4 Hz, 1H), 7.14 (d, J=4.4 Hz, 1H), 6.89-6.80 (m, 2H), 6.44 (d, J=6.4 Hz, 1H), 4.92 (d, J=5.6 Hz, 1H), 3.05 (t, J=7.6 Hz, 2H), 2.96 (dd, J=5.6, 2.0 Hz, 1H), 2.65 (t, J=7.6 Hz, 2H), 2.27 (d, J=2.0 Hz, 1H). MS: M/e 498 (M+1)$^+$.

Compound 1.3

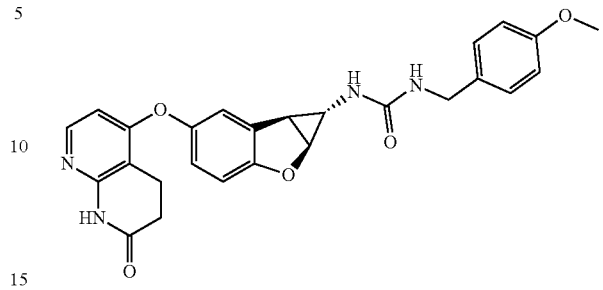

$^1$H NMR (400 MHz, DMSO-d6) δ 10.55 (s, 1H), 7.96 (d, J=6.0 Hz, 1H), 7.24-7.14 (m, 3H), 6.94-6.81 (m, 4H), 6.55-6.35 (m, 2H), 6.26 (d, J=6.0 Hz, 1H), 4.89 (d, J=5.6 Hz, 1H), 4.14 (s, 2H), 3.72 (s, 3H), 2.93 (t, J=7.6 Hz, 2H), 2.86 (dd, J=5.6, 1.6 Hz, 1H), 2.58-2.52 (m, 2H), 2.18 (s, 1H). MS: M/e 473 (M+1)$^+$

Compound 1.4

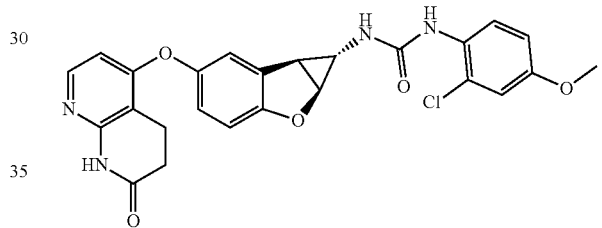

$^1$H NMR (400 MHz, DMSO-d6) δ 10.48 (s, 1H), 7.96 (d, J=6.4 Hz, 1H), 7.89-7.84 (m, 2H), 7.24-7.22 (m, 1H), 7.15-7.12 (m, 1H), 7.02 (d, J=2.8 Hz, 1H), 6.93-6.85 (m, 3H), 6.25 (d, J=6.4 Hz, 1H), 4.97 (d, J=5.6 Hz, 1H), 3.73 (s, 3H), 2.98-2.90 (m, 3H), 2.56-2.50 (m, 2H), 2.27-2.25 (m, 1H). MS: M/e 493 (M+1)$^+$

Compound 1.5

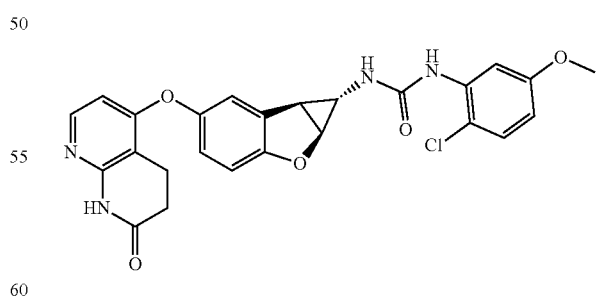

$^1$H NMR (400 MHz, DMSO-d6) δ 10.47 (s, 1H), 8.08-7.92 (m, 2H), 7.87 (d, J=2.8 Hz, 1H), 7.49-7.45 (m, 1H), 7.30 (d, J=8.8 Hz, 1H), 7.24-7.22 (m, 1H), 6.94-6.91 (m, 2H), 6.57 (dd, J=8.8, 3.2 Hz, 1H), 6.25 (d, J=5.6 Hz, 1H), 4.99 (d, J=5.6 Hz, 1H), 3.72 (s, 3H), 3.00-2.88 (m, 3H), 2.63-2.50 (m, 2H), 2.29-2.26 (m, 1H). MS: M/e 493 (M+1)$^+$.

Compound 1.6

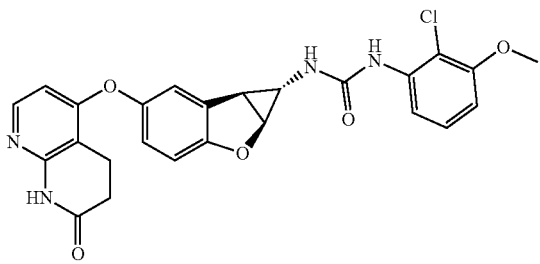 [SMILES: COc1cccc(NC(=O)N[C@@H]2[C@H]3Oc4ccc(Oc5ccnc6c5CCC(=O)N6)cc4[C@@H]23)c1Cl]

¹H NMR (400 MHz, DMSO-d6) δ 10.48 (s, 1H), 8.07-7.90 (m, 2H), 7.81-7.77 (m, 1H), 7.45-7.41 (m, 1H), 7.26-7.17 (m, 2H), 6.94-6.91 (m, 2H), 6.79-6.74 (m, 1H), 6.25 (d, J=5.6 Hz, 1H), 4.98 (d, J=5.6 Hz, 1H), 3.83 (s, 3H), 2.99-2.91 (m, 3H), 2.57-2.52 (m, 2H), 2.29-2.27 (m, 1H). MS: M/e 493 (M+1)⁺.

Compound 1.7

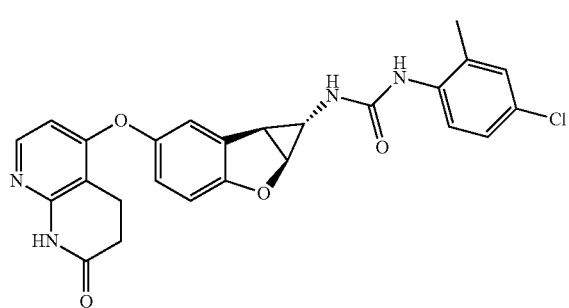 [SMILES: Cc1cc(Cl)ccc1NC(=O)N[C@@H]1[C@H]2Oc3ccc(Oc4ccnc5c4CCC(=O)N5)cc3[C@@H]12]

¹H NMR (400 MHz, DMSO-d6) δ 10.47 (s, 1H), 7.96 (d, J=5.6 Hz, 1H), 7.83 (d, J=5.6 Hz, 1H), 7.77 (s, 1H), 7.24-7.21 (m, 2H), 7.18-7.13 (m, 1H), 7.00-6.98 (m, 1H), 6.93-6.90 (m, 2H), 6.25 (d, J=5.6 Hz, 1H), 4.98 (d, J=5.6 Hz, 1H), 2.98-2.90 (m, 3H), 2.56-2.51 (m, 2H), 2.28-2.26 (m, 1H), 2.18 (s, 3H). MS: M/e 477 (M+1)⁺.

Compound 1.8

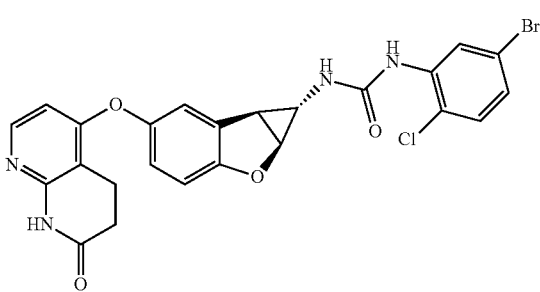 [SMILES: O=C1CCc2c(Oc3ccc4c(c3)[C@H]3[C@H](NC(=O)Nc5cc(Br)ccc5Cl)[C@H]3O4)ccnc2N1]

¹H NMR (400 MHz, DMSO-d6) δ 10.48 (s, 1H), 8.43 (d, J=2.4 Hz, 1H), 8.20 (s, 1H), 7.96 (d, J=5.6 Hz, 1H), 7.54-7.50 (m, 1H), 7.39 (d, J=8.4 Hz, 1H), 7.26-7.23 (m, 1H), 7.17 (dd, J=8.4, 2.4 Hz, 1H), 6.93-6.91 (m, 2H), 6.25 (d, J=5.6 Hz, 1H), 5.00 (d, J=5.6 Hz, 1H), 3.02-2.86 (m, 3H), 2.58-2.52 (m, 2H), 2.29-2.26 (m, 1H). MS: M/e 543 (M+1)⁺

Compound 1.9

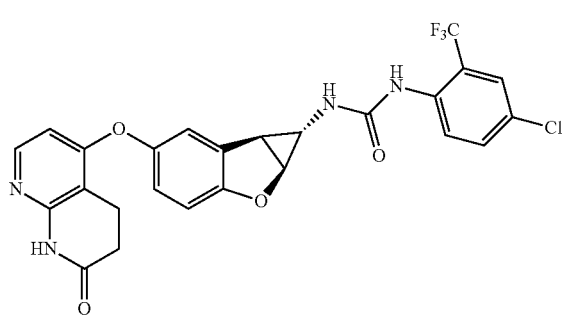 [SMILES: O=C1CCc2c(Oc3ccc4c(c3)[C@H]3[C@H](NC(=O)Nc5ccc(Cl)cc5C(F)(F)F)[C@H]3O4)ccnc2N1]

¹H NMR (400 MHz, DMSO-d6) δ 10.48 (s, 1H), 8.04-8.00 (m, 1H), 7.97-7.84 (m, 2H), 7.71-7.66 (m, 2H), 7.46-7.42 (m, 1H), 7.24-7.21 (m, 1H), 6.93-6.91 (m, 2H), 6.24 (d, J=6.0 Hz, 1H), 4.99 (d, J=5.6 Hz, 1H), 3.04-2.84 (m, 3H), 2.59-2.51 (m, 2H), 2.30-2.27 (m, 1H). MS: M/e 531 (M+1)⁺

Compound 1.10

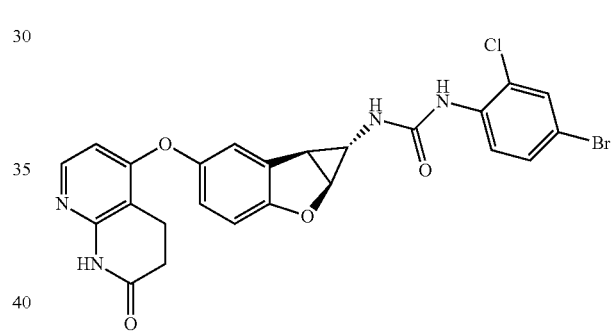

¹H NMR (400 MHz, DMSO-d6) δ 10.47 (s, 1H), 8.15-8.10 (m, 2H), 7.96 (d, J=5.6 Hz, 1H), 7.68 (d, J=2.4 Hz, 1H), 7.49-7.40 (m, 2H), 7.25-7.22 (m, 1H), 6.93-6.91 (m, 2H), 6.25 (d, J=5.6 Hz, 1H), 4.99 (d, J=5.6 Hz, 1H), 3.03-2.87 (m, 3H), 2.58-2.52 (m, 2H), 2.29-2.26 (m, 1H). MS: M/e 543 (M+1)⁺.

Compound 1.11

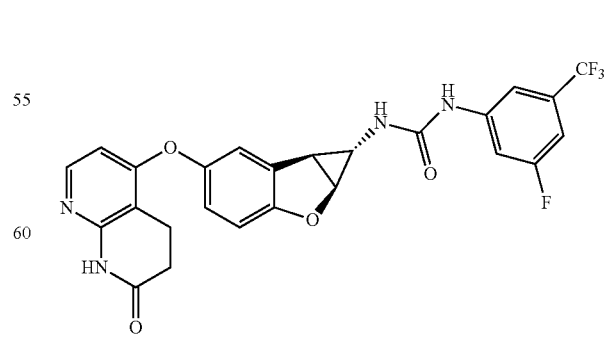

¹H NMR (400 MHz, DMSO-d6) δ 10.49 (s, 1H), 9.20 (s, 1H), 7.96 (d, J=5.6 Hz, 1H), 7.69 (s, 1H), 7.60 (d, J=11.4 Hz,

1H), 7.23 (s, 1H), 7.17 (d, J=8.5 Hz, 1H), 6.99-6.88 (m, 3H), 6.26 (d, J=5.6 Hz, 1H), 5.00 (d, J=5.6 Hz, 1H), 3.03-2.89 (m, 3H), 2.54 (t, J=7.6 Hz, 2H), 2.27 (s, 1H) ppm. MS: M/e 515 (M+1)+.

Compound 1.12

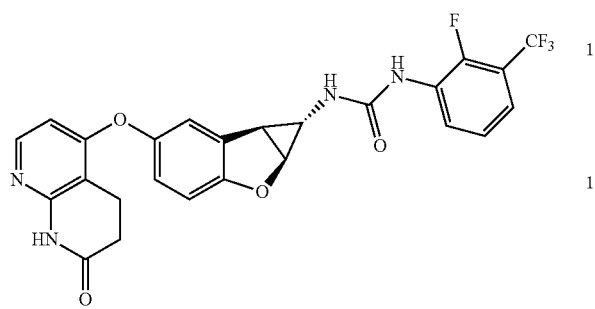

$^1$H NMR (400 MHz, DMSO-d6) δ 10.49 (s, 1H), 8.65 (s, 1H), 8.46-8.32 (m, 1H), 7.96 (d, J=5.6 Hz, 1H), 7.37-7.28 (m, 2H), 7.24 (s, 1H), 7.08 (d, J=1.9 Hz, 1H), 6.98-6.88 (m, 2H), 6.26 (d, J=5.6 Hz, 1H), 5.00 (d, J=5.6 Hz, 1H), 3.02-2.89 (m, 3H), 2.55 (d, J=7.6 Hz, 2H), 2.28 (s, 1H) ppm. MS: M/e 515 (M+1)+.

Compound 1.13

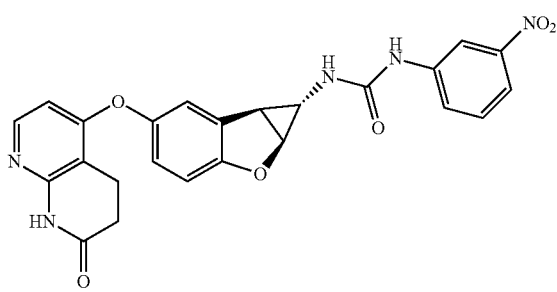 [SMILES: O=C1CCc2c(Oc3ccc4c(c3)[C@H]3[C@H](NC(=O)Nc5cccc([N+](=O)[O-])c5)[C@H]3O4)ccnc2N1]

$^1$H NMR (400 MHz, DMSO-d6) δ 10.51 (s, 1H), 9.19 (s, 1H), 8.53 (t, J=2.0 Hz, 1H), 7.97 (d, J=5.6 Hz, 1H), 7.78 (dd, J=8.4, 1.6 Hz, 1H), 7.71 (d, J=9.6 Hz, 1H), 7.52 (t, J=8.4 Hz, 1H), 7.24 (d, J=1.6 Hz, 1H), 6.97-6.86 (m, 3H), 6.26 (d, J=5.6 Hz, 1H), 5.00 (d, J=5.6 Hz, 1H), 2.99 (dd, J=5.6, 1.6 Hz, 1H), 2.94 (t, J=7.6 Hz, 2H), 2.55 (t, J=7.6 Hz, 2H), 2.29 (s, 1H) ppm. MS: M/e 474 (M+1)+.

Compound 1.14

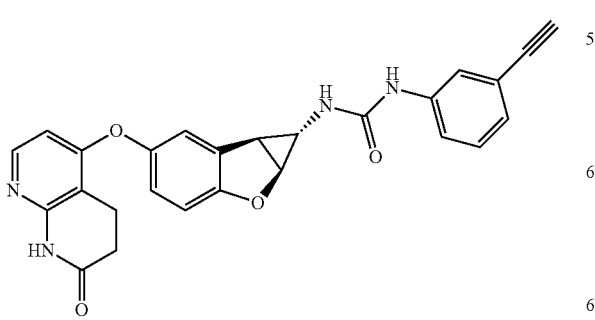

$^1$H NMR (400 MHz, DMSO-d6) δ 10.50 (s, 1H), 8.69 (s, 1H), 7.96 (d, J=5.6 Hz, 1H), 7.63 (s, 1H), 7.38 (d, J=8.4 Hz, 1H), 7.30-7.18 (m, 2H), 7.03 (d, J=7.6 Hz, 1H), 6.92 (s, 2H), 6.70 (s, 1H), 6.26 (d, J=5.6 Hz, 1H), 4.98 (d, J=5.6 Hz, 1H), 4.13 (s, 1H), 3.00-2.87 (m, 3H), 2.54 (t, J=8.0 Hz, 2H), 2.26 (s, 1H) ppm. MS: M/e 453 (M+1)+.

Compound 1.15

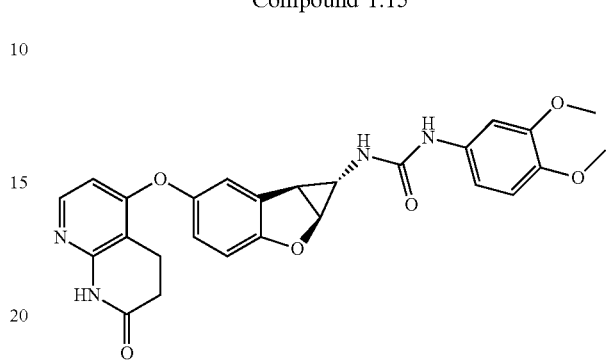

$^1$H NMR (400 MHz, DMSO-d6) δ 10.52 (s, 1H), 8.38 (s, 1H), 7.96 (d, J=5.6 Hz, 1H), 7.25-7.15 (m, 2H), 6.92 (s, 2H), 6.82 (s, 2H), 6.51 (s, 1H), 6.26 (d, J=5.6 Hz, 1H), 4.96 (d, J=5.6 Hz, 1H), 3.70 (s, 3H), 3.68 (s, 3H), 3.00-2.88 (m, 3H), 2.60-2.50 (m, 2H), 2.24 (s, 1H). MS: M/e 489 (M+1)+

Compound 1.16

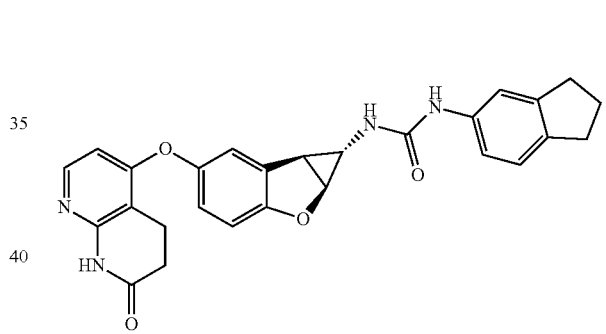

$^1$H NMR (400 MHz, DMSO-d6) δ 10.56 (s, 1H), 8.40 (s, 1H), 7.97 (d, J=5.6 Hz, 1H), 7.32 (s, 1H), 7.23 (s, 1H), 7.14-7.02 (m, 2H), 6.97-6.85 (m, 2H), 6.55 (s, 1H), 6.27 (d, J=5.6 Hz, 1H), 4.96 (d, J=5.6 Hz, 1H), 3.00-2.90 (m, 3H), 2.84-2.71 (m, 4H), 2.60-2.51 (m, 2H), 2.24 (s, 1H), 2.06-1.89 (m, 2H). MS: M/e 469 (M+1)+

Compound 1.17

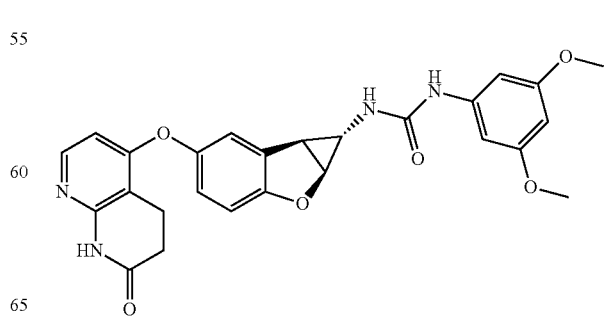

¹H NMR (400 MHz, DMSO-d6) δ 10.53 (s, 1H), 8.56 (s, 1H), 7.96 (d, J=6.0 Hz, 1H), 7.23 (s, 1H), 6.96-6.87 (m, 2H), 6.65 (d, J=2.0 Hz, 2H), 6.58 (s, 1H), 6.26 (d, J=6.0 Hz, 1H), 6.09 (t, J=2.0 Hz, 1H), 4.97 (d, J=5.6 Hz, 1H), 3.68 (s, 6H), 3.01-2.88 (m, 3H), 2.55 (t, J=7.6 Hz, 2H), 2.24 (s, 1H). MS: M/e 489 (M+1)⁺.

Compound 1.18

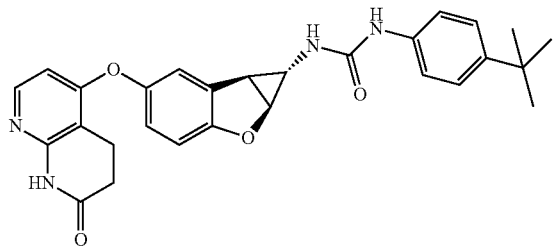 [SMILES: CC(C)(C)c1ccc(NC(=O)N[C@@H]2[C@H]3Oc4ccc(Oc5ccnc6c5CCC(=O)N6)cc4[C@@H]23)cc1]

¹H NMR (400 MHz, DMSO-d6) δ 10.56 (s, 1H), 8.46 (s, 1H), 7.97 (d, J=5.6 Hz, 1H), 7.36-7.28 (m, 2H), 7.27-7.20 (m, 3H), 6.96-6.86 (s, 2H), 6.56 (s, 1H), 6.27 (d, J=5.6 Hz, 1H), 4.96 (d, J=5.6 Hz, 1H), 2.98-2.90 (m, 3H), 2.55 (t, J=8.0 Hz, 2H), 2.25 (s, 1H), 1.24 (s, 9H). MS: M/e 485 (M+1)⁺.

Compound 1.19

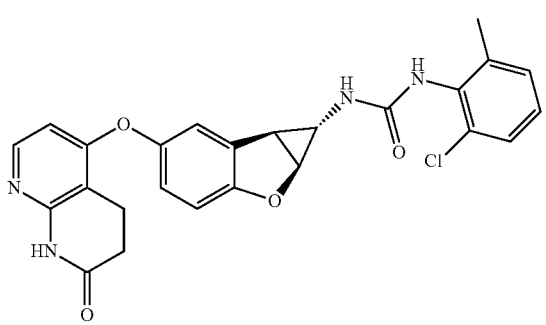 [SMILES: Cc1cccc(Cl)c1NC(=O)N[C@@H]1[C@H]2Oc3ccc(Oc4ccnc5c4CCC(=O)N5)cc3[C@@H]12]

¹H NMR (400 MHz, DMSO-d6) δ 10.48 (s, 1H), 7.95 (d, J=6.0 Hz, 1H), 7.88 (s, 1H), 7.31 (d, J=7.6 Hz, 1H), 7.23-7.12 (m, 3H), 6.95-6.87 (m, 2H), 6.76 (s, 1H), 6.24 (d, J=6.0 Hz, 1H), 4.95 (d, J=5.6 Hz, 1H), 2.97-2.87 (m, 3H), 2.58-2.52 (m, 2H), 2.26 (s, 1H), 2.21 (s, 3H). MS: M/e 477 (M+1)⁺.

Compound 1.20

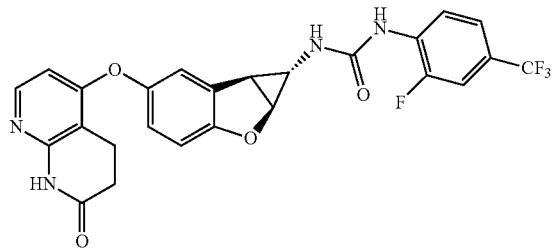 [SMILES: O=C1CCc2c(Oc3ccc4c(c3)[C@H]3[C@H](NC(=O)Nc5ccc(C(F)(F)F)cc5F)[C@H]3O4)ccnc2N1]

¹H NMR (400 MHz, DMSO-d6) δ 10.54 (s, 1H), 8.75 (s, 1H), 8.39 (t, J=8.4 Hz, 1H), 7.97 (d, J=6.0 Hz, 1H), 7.66 (d, J=10.0 Hz, 1H), 7.51 (d, J=8.8 Hz, 1H), 7.25 (s, 1H), 7.16 (s, 1H), 6.97-6.89 (m, 2H), 6.27 (d, J=6.0 Hz, 1H), 5.01 (d, J=5.6 Hz, 1H), 2.99 (d, J=5.6 Hz, 1H), 2.94 (t, J=7.6 Hz, 2H), 2.55 (t, J=7.6 Hz, 2H), 2.29 (s, 1H). MS: M/e 515 (M+1)⁺.

Compound 1.21

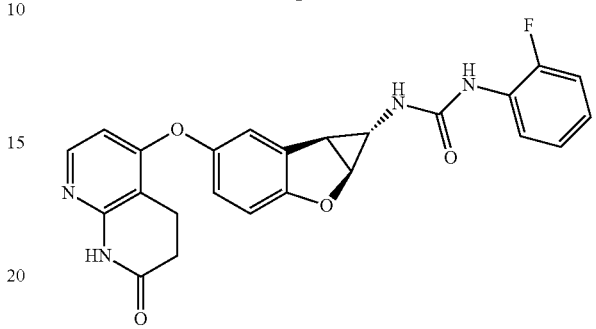

¹H NMR (400 MHz, DMSO-d6) δ 10.50 (s, 1H), 8.34 (s, 1H), 8.12-8.06 (m, 1H), 7.96 (d, J=5.6 Hz, 1H), 7.25-7.06 (m, 3H), 6.99-6.91 (m, 4H), 6.25 (d, J=5.6 Hz, 1H), 4.98 (d, J=6.0 Hz, 1H), 2.99-2.88 (m, 3H), 2.54 (t, J=7.2 Hz, 2H), 2.28-2.25 (m, 1H). MS: M/e 447 (M+1)⁺.

Compound 1.22

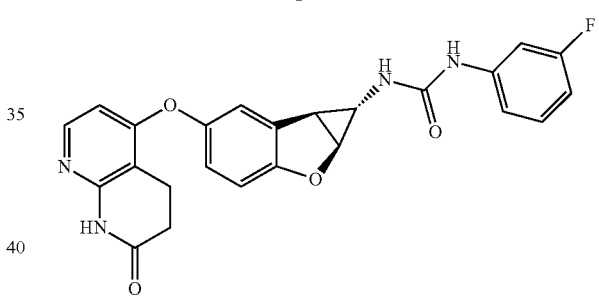

¹H NMR (400 MHz, DMSO-d6) δ 10.50 (s, 1H), 8.81 (s, 1H), 7.96 (d, J=5.6 Hz, 1H), 7.48-7.43 (m, 1H), 7.28-7.22 (m, 2H), 7.10-7.06 (m, 1H), 6.95-6.90 (m, 2H), 6.76-6.69 (m, 2H), 6.26 (d, J=5.6 Hz, 1H), 4.98 (d, J=5.6 Hz, 1H), 2.97-2.90 (m, 3H), 2.57-2.51 m, 2H), 2.27-2.24 (m, 1H). MS: M/e 447 (M+1)⁺.

Compound 1.23

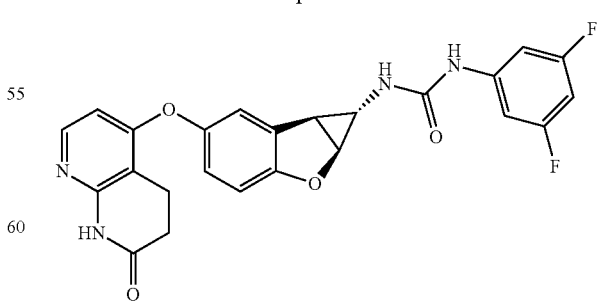

¹H NMR (400 MHz, DMSO-d6) δ 10.48 (s, 1H), 9.01 (s, 1H), 7.96 (d, J=6.0 Hz, 1H), 7.24-7.22 (m, 1H), 7.18-7.14 (m, 2H), 6.93-6.91 (m, 2H), 6.86-6.82 (m, 1H), 6.77-6.70

(m, 1H), 6.25 (d, J=6.0 Hz, 1H), 4.98 (d, J=6.0 Hz, 1H), 2.98-2.90 (m, 3H), 2.57-2.52 (m, 2H), 2.27-2.24 (m, 1H). MS: M/e 465 (M+1)⁺.

Compound 1.24

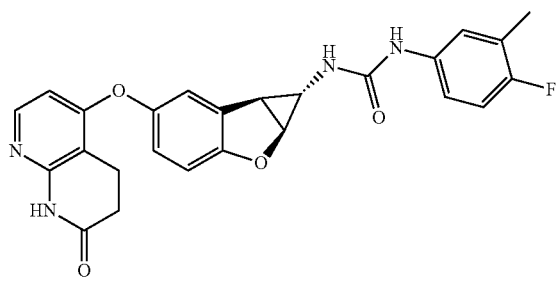 [SMILES: Cc1cc(NC(=O)N[C@@H]2[C@H]3Oc4ccc(Oc5ccnc6c5CCC(=O)N6)cc4[C@@H]23)ccc1F]

¹H NMR (400 MHz, DMSO-d6) δ 10.48 (s, 1H), 8.50 (s, 1H), 7.96 (d, J=6.0 Hz, 1H), 7.31 (dd, J=7.2, 2.4 Hz, 1H), 7.25-7.17 (m, 2H), 6.99 (t, J=9.2 Hz, 1H), 6.91 (d, J=2.0 Hz, 2H), 6.60 (s, 1H), 6.25 (d, J=6.0 Hz, 1H), 4.96 (d, J=5.6 Hz, 1H), 2.98-2.88 (m, 3H), 2.54 (t, J=7.8 Hz, 2H), 2.24 (s, 1H), 2.18 (s, 3H) ppm. MS: M/e 461 (M+1)⁺.

Compound 1.25

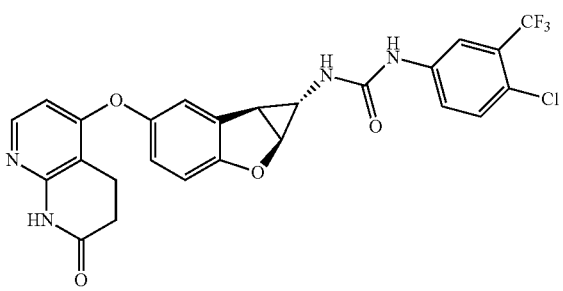 [SMILES: O=C1CCc2c(Oc3ccc4c(c3)[C@H]3[C@H](NC(=O)Nc5ccc(Cl)c(C(F)(F)F)c5)[C@H]3O4)ccnc2N1]

¹H NMR (400 MHz, DMSO-d6) δ 10.48 (s, 1H), 9.10 (s, 1H), 8.09 (d, J=2.4 Hz, 1H), 7.96 (d, J=6.0 Hz, 1H), 7.63 (dd, J=8.8, 2.4 Hz, 1H), 7.57 (d, J=8.8 Hz, 1H), 7.23 (d, J=2.0 Hz, 1H), 6.94-6.85 (m, 3H), 6.25 (d, J=6.0 Hz, 1H), 4.99 (d, J=5.6 Hz, 1H), 3.02-2.88 (m, 3H), 2.55 (d, J=7.8 Hz, 2H), 2.27 (s, 1H) ppm. MS: M/e 531 (M+1)⁺.

Compound 1.26

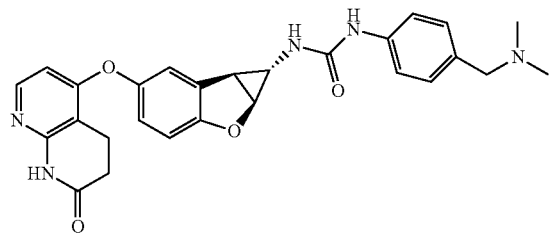 [SMILES: CN(C)Cc1ccc(NC(=O)N[C@@H]2[C@H]3Oc4ccc(Oc5ccnc6c5CCC(=O)N6)cc4[C@@H]23)cc1]

¹H NMR (400 MHz, DMSO-d6) δ 10.50 (s, 1H), 8.88 (s, 1H), 7.96 (d, J=6.0 Hz, 1H), 7.51 (d, J=8.4 Hz, 2H), 7.34 (d, J=8.4 Hz, 2H), 7.23 (s, 1H), 7.00-6.79 (m, 3H), 6.26 (d,

J=6.0 Hz, 1H), 4.97 (d, J=5.6 Hz, 1H), 4.17 (d, J=5.2 Hz, 2H), 3.00-2.85 (m, 3H), 2.71 (s, 3H), 2.69 (s, 3H), 2.54 (t, J=7.6 Hz, 2H), 2.27 (s, 1H) ppm. MS: M/e 486 (M+1)⁺.

Compound 1.27

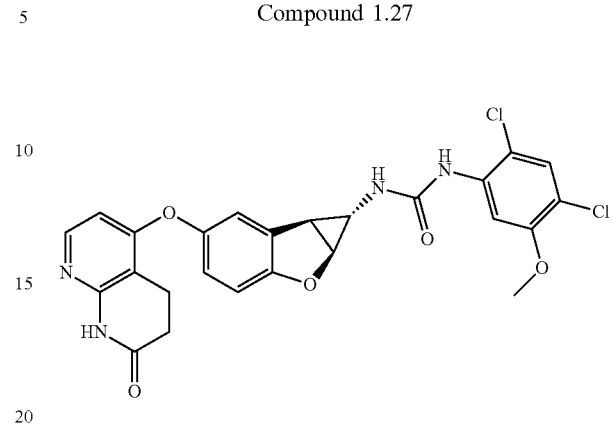

¹H NMR (400 MHz, DMSO-d6) δ 10.47 (s, 1H), 8.12 (d, J=2.4 Hz, 2H), 7.96 (d, J=6.0 Hz, 1H), 7.61-7.45 (m, 2H), 7.25 (s, 1H), 6.93 (d, J=1.6 Hz, 2H), 6.24 (d, J=6.0 Hz, 1H), 5.00 (d, J=5.6 Hz, 1H), 3.82 (s, 3H), 2.98 (dd, J=5.6, 2.4 Hz, 1H), 2.93 (t, J=8.0 Hz, 2H), 2.53 (t, J=8.0 Hz, 2H), 2.28 (s, 1H) ppm. MS: M/e 527 (M+1)⁺.

Compound 1.28

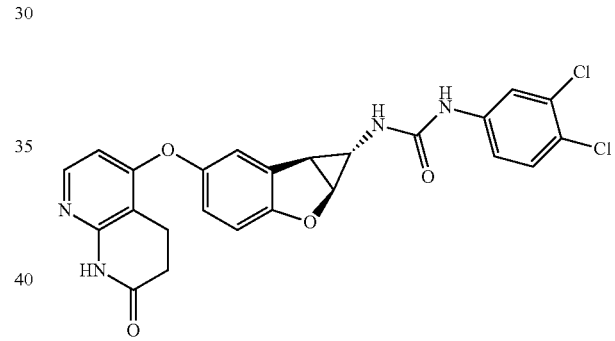

¹H NMR (400 MHz, DMSO-d6) δ 10.49 (s, 1H), 8.93 (s, 1H), 7.96 (d, J=6.0 Hz, 1H), 7.86 (d, J=2.4 Hz, 1H), 7.47 (d, J=8.8 Hz, 1H), 7.31 (dd, J=8.8, 2.4 Hz, 1H), 7.22 (d, J=1.6 Hz, 1H), 6.95-6.89 (m, 2H), 6.83 (s, 1H), 6.27 (d, J=6.0 Hz, 1H), 4.98 (d, J=5.6 Hz, 1H), 3.00-2.89 (m, 3H), 2.54 (t, J=7.6 Hz, 2H), 2.26 (s, 1H) ppm. MS: M/e 497 (M+1)⁺.

Compound 1.29

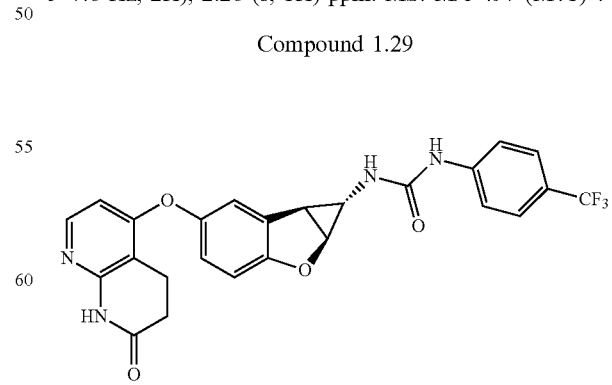

¹H NMR (400 MHz, DMSO-d6) δ 10.48 (s, 1H), 9.02 (s, 1H), 7.96 (d, J=6.0 Hz, 1H), 7.66-7.55 (m, 4H), 7.23 (d,

J=1.6 Hz, 1H), 6.95-6.89 (m, 2H), 6.80 (s, 1H), 6.25 (d, J=6.0 Hz, 1H), 4.99 (d, J=5.6 Hz, 1H), 3.00-2.89 (m, 3H), 2.54 (t, J=7.6 Hz, 2H), 2.28 (s, 1H) ppm. MS: M/e 497 (M+1)⁺.

Compound 1.30

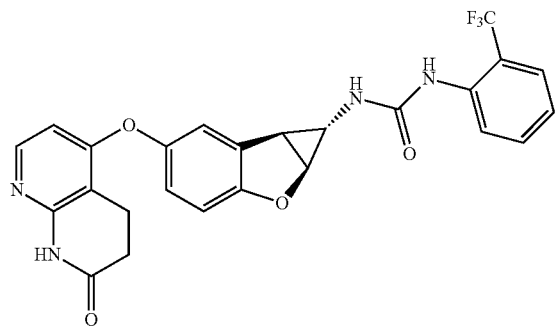 [SMILES: O=C1CCc2c(Oc3ccc4c(c3)[C@H]3[C@H](NC(=O)Nc5ccccc5C(F)(F)F)[C@H]3O4)ccnc2N1]

¹H NMR (400 MHz, DMSO-d6) δ 10.49 (s, 1H), 7.96 (d, J=6.0 Hz, 2H), 7.82 (s, 1H), 7.67-7.55 (m, 2H), 7.39 (d, J=2.4 Hz, 1H), 7.29-7.17 (m, 2H), 6.97-6.88 (m, 2H), 6.26 (d, J=6.0 Hz, 1H), 4.98 (d, J=6.0 Hz, 1H), 3.00-2.89 (m, 3H), 2.55 (t, J=7.6 Hz, 2H), 2.29 (s, 1H) ppm. MS: M/e 497 (M+1)⁺.

Compound 1.31

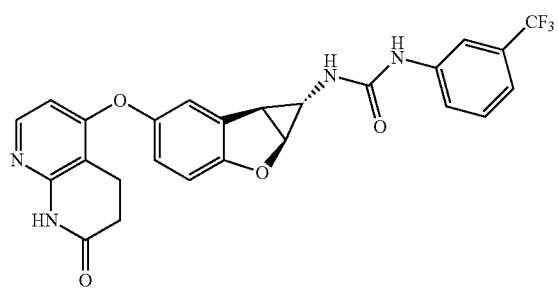 [SMILES: O=C1CCc2c(Oc3ccc4c(c3)[C@H]3[C@H](NC(=O)Nc5cccc(C(F)(F)F)c5)[C@H]3O4)ccnc2N1]

¹H NMR (400 MHz, DMSO-d6) δ 10.52 (s, 1H), 8.84 (s, 1H), 7.97 (d, J=6.0 Hz, 1H), 7.90 (d, J=1.6 Hz, 1H), 7.51-7.45 (m, 1H), 7.28 (d, J=8.4 Hz, 1H), 7.23 (d, J=1.2 Hz, 1H), 6.97-6.87 (m, 2H), 6.73 (d, J=2.0 Hz, 1H), 6.27 (d, J=6.0 Hz, 1H), 4.98 (d, J=5.6 Hz, 1H), 2.99-2.90 (m, 3H), 2.55 (t, J=7.6 Hz, 2H), 2.34 (d, J=1.6 Hz, 3H), 2.26 (s, 1H) ppm. MS: M/e 511 (M+1)⁺.

Compound 1.32

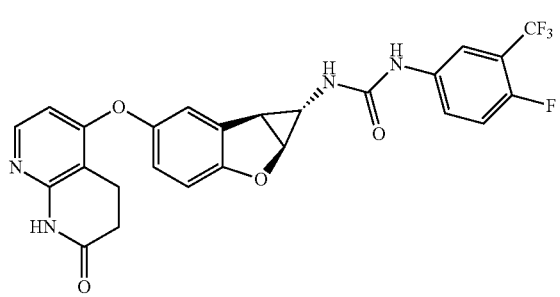 [SMILES: O=C1CCc2c(Oc3ccc4c(c3)[C@H]3[C@H](NC(=O)Nc5ccc(F)c(C(F)(F)F)c5)[C@H]3O4)ccnc2N1]

¹H NMR (400 MHz, DMSO-d6) δ 10.48 (s, 1H), 8.97 (s, 1H), 8.02-7.94 (m, 2H), 7.67-7.57 (m, 1H), 7.39 (t, J=9.6 Hz, 1H), 7.23 (s, 1H), 6.92 (s, 2H), 6.82 (s, 1H), 6.26 (d, J=6.0 Hz, 1H), 4.98 (d, J=5.6 Hz, 1H), 3.00-2.89 (m, 3H), 2.55 (t, J=7.6 Hz, 2H), 2.26 (s, 1H) ppm. MS: M/e 515 (M+1)⁺.

Compound 1.33

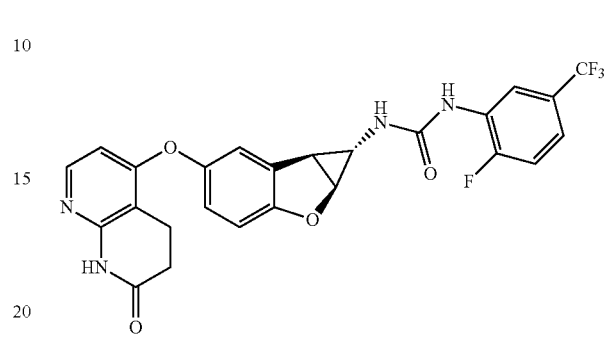

¹H NMR (400 MHz, DMSO-d6) δ 10.48 (s, 1H), 8.72 (s, 1H), 8.58 (d, J=5.6 Hz, 1H), 7.96 (d, J=6.0 Hz, 1H), 7.51-7.39 (m, 1H), 7.35 (s, 1H), 7.25 (d, J=1.6 Hz, 1H), 7.12 (s, 1H), 6.97-6.89 (m, 2H), 6.25 (d, J=6.0 Hz, 1H), 5.01 (d, J=5.6 Hz, 1H), 3.04-2.89 (m, 3H), 2.55 (t, J=7.6 Hz, 2H), 2.27 (s, 1H) ppm. MS: M/e 515 (M+1)⁺.

Compound 1.34

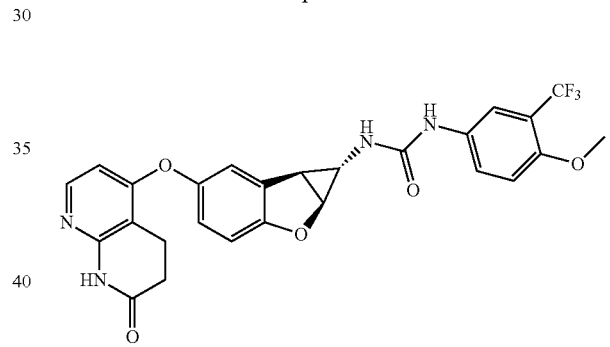

¹H NMR (400 MHz, DMSO-d6) δ 10.56 (s, 1H), 8.70 (s, 1H), 7.97 (d, J=6.0 Hz, 1H), 7.81 (d, J=2.4 Hz, 1H), 7.55 (dd, J=9.2, 2.4 Hz, 1H), 7.24 (s, 1H), 7.17 (d, J=9.2 Hz, 1H), 6.92 (s, 2H), 6.70 (s, 1H), 6.28 (d, J=6.0 Hz, 1H), 4.98 (d, J=5.6 Hz, 1H), 3.82 (s, 3H), 2.99-2.90 (m, 3H), 2.55 (t, J=7.6 Hz, 2H), 2.26 (s, 1H). MS: M/e 515 (M+1)⁺.

Compound 1.35

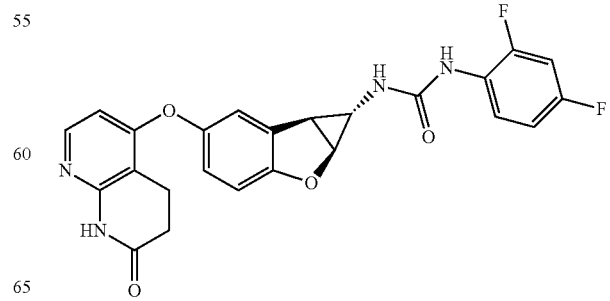

¹H NMR (400 MHz, DMSO-d6) δ 10.53 (s, 1H), 8.32 (s, 1H), 8.07-7.90 (m, 2H), 7.33-7.16 (m, 2H), 7.01 (t, J=8.8 Hz, 1H), 6.96-6.89 (m, 3H), 6.27 (d, J=6.0 Hz, 1H), 4.98 (d, J=5.6 Hz, 1H), 2.97-2.90 (m, 3H), 2.55 (t, J=8.0 Hz, 2H), 2.26 (s, 1H) ppm. MS: M/e 465 (M+1)⁺.

Compound 1.36

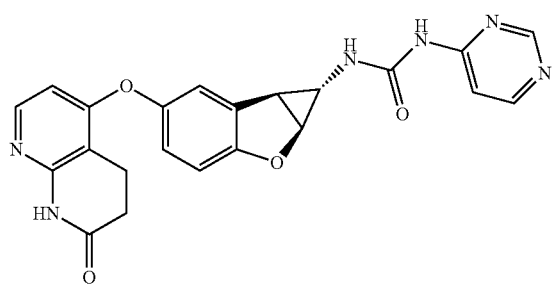 [SMILES: O=C1CCc2c(Oc3ccc4c(c3)[C@H]3[C@H](NC(=O)Nc5ccncn5)[C@H]3O4)ccnc2N1]

¹H NMR (400 MHz, DMSO-d6) δ 10.47 (s, 1H), 9.70 (s, 1H), 8.73 (s, 1H), 8.50 (d, J=6.0 Hz, 1H), 7.96 (d, J=6.0 Hz, 1H), 7.89 (s, 1H), 7.57 (d, J=5.6 Hz, 1H), 7.24 (d, J=2.0 Hz, 1H), 6.93 (d, J=2.4 Hz, 2H), 6.25 (d, J=6.0 Hz, 1H), 5.05 (d, J=5.6 Hz, 1H), 3.04 (dd, J=5.6, 2.0 Hz, 1H), 2.93 (t, J=7.6 Hz, 2H), 2.54 (t, J=7.6 Hz, 2H), 2.32 (s, 1H) ppm. MS: M/e 431 (M+1)⁺.

Compound 1.37

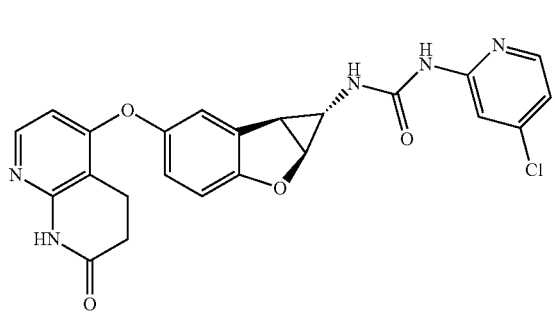 [SMILES: O=C1CCc2c(Oc3ccc4c(c3)[C@H]3[C@H](NC(=O)Nc5cc(Cl)ccn5)[C@H]3O4)ccnc2N1]

¹H NMR (400 MHz, DMSO-d6) δ 10.52 (s, 1H), 9.47 (s, 1H), 8.19 (d, J=5.6 Hz, 1H), 7.97 (d, J=6.0 Hz, 1H), 7.93 (s, 1H), 7.64 (s, 1H), 7.25 (s, 1H), 7.09 (dd, J=5.6, 2.0 Hz, 1H), 6.97-6.87 (m, 2H), 6.27 (d, J=6.0 Hz, 1H), 5.04 (d, J=5.6 Hz, 1H), 3.02 (dd, J=5.6, 1.6 Hz, 1H), 2.94 (t, J=7.6 Hz, 2H), 2.55 (t, J=7.6 Hz, 2H), 2.30 (s, 1H). MS: M/e 464 (M+1)⁺

Compound 1.38

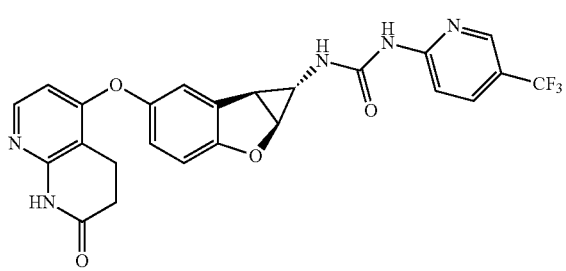 [SMILES: O=C1CCc2c(Oc3ccc4c(c3)[C@H]3[C@H](NC(=O)Nc5ccc(C(F)(F)F)cn5)[C@H]3O4)ccnc2N1]

¹H NMR (400 MHz, DMSO-d6) δ 10.47 (s, 1H), 9.72 (s, 1H), 8.58 (s, 1H), 8.12-8.04 (m, 1H), 7.98-7.93 (m, 2H), 7.73 (d, J=8.4 Hz, 1H), 7.24 (s, 1H), 6.95-6.88 (m, 2H), 6.26 (d, J=6.0 Hz, 1H), 5.05 (d, J=6.0 Hz, 1H), 3.05-3.01 (m, 1H), 2.94 (t, J=7.6 Hz, 2H), 2.55 (t, J=7.6 Hz, 2H), 2.33 (s, 1H) ppm. MS: M/e 498 (M+1)⁺.

Compound 1.39

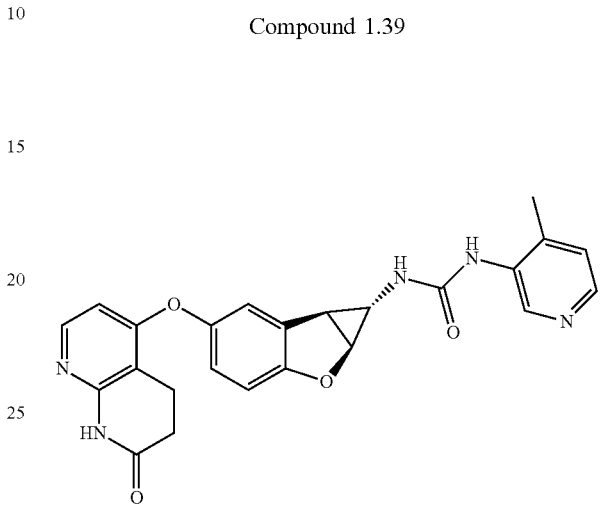

¹H NMR (400 MHz, DMSO-d6) δ 10.51 (s, 1H), 9.34 (s, 1H), 8.62 (s, 1H), 8.44 (d, J=6.0 Hz, 1H), 7.97 (d, J=6.0 Hz, 1H), 7.87 (d, J=5.6 Hz, 1H), 7.49 (s, 1H), 7.25 (s, 1H), 7.00-6.88 (m, 2H), 6.26 (d, J=6.0 Hz, 1H), 5.03 (d, J=5.6 Hz, 1H), 3.02 (dd, J=5.6, 1.6 Hz, 1H), 2.94 (t, J=8.0 Hz, 2H), 2.55 (t, J=8.0 Hz, 2H), 2.46 (s, 3H), 2.32 (s, 1H) ppm. MS: M/e 444 (M+1)⁺.

Compound 1.40

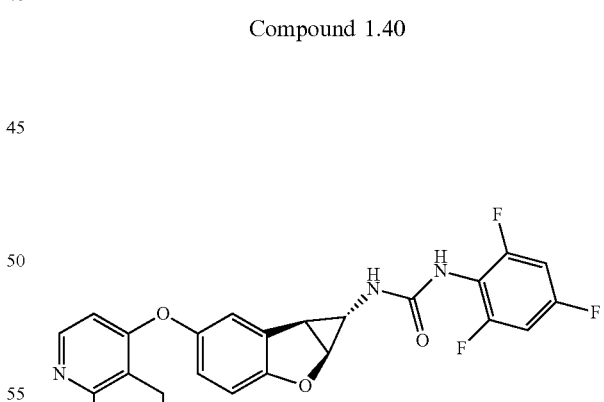

¹H NMR (400 MHz, DMSO-d6) δ 10.51 (s, 1H), 7.98 (s, 1H), 7.95 (d, J=5.6 Hz, 1H), 7.23-7.20 (m, 3H), 6.94-6.91 (m, 3H), 6.24 (d, J=5.6 Hz, 1H), 4.95 (d, J=5.6 Hz, 1H), 2.95-2.90 (m, 3H), 2.54 (t, J=8.0 Hz, 2H), 2.25-2.24 (m, 1H) ppm. MS: M/e 483 (M+1)⁺.

Compound 1.41

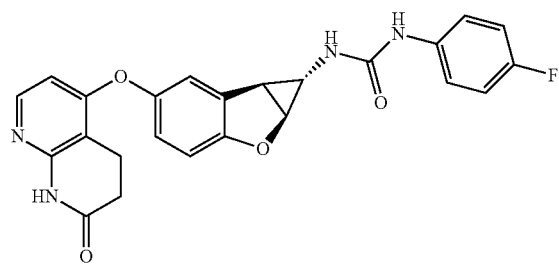 [SMILES: O=C1CCc2c(Oc3ccc4c(c3)[C@H]3[C@H](NC(=O)Nc5ccc(F)cc5)[C@H]3O4)ccnc2N1]

¹H NMR (400 MHz, DMSO-d6) δ 10.59 (s, 1H), 8.71 (s, 1H), 7.98 (d, J=6.0 Hz, 1H), 7.47-7.37 (m, 2H), 7.24 (s, 1H), 7.11-7.02 (m, 2H), 6.97-6.87 (m, 2H), 6.70 (s, 1H), 6.29 (d, J=6.0 Hz, 1H), 4.97 (d, J=5.6 Hz, 1H), 3.01-2.89 (m, 3H), 2.56 (t, J=7.6 Hz, 2H), 2.25 (s, 1H) ppm. MS: M/e 447 (M+1)⁺.

Compound 1.42

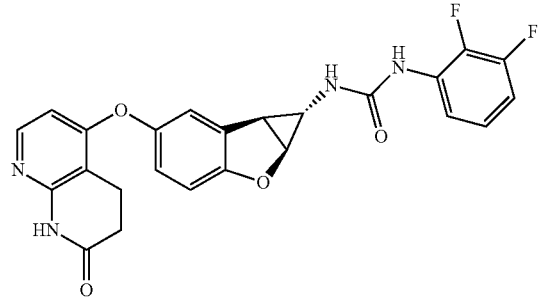 [SMILES: O=C1CCc2c(Oc3ccc4c(c3)[C@H]3[C@H](NC(=O)Nc5cccc(F)c5F)[C@H]3O4)ccnc2N1]

¹H NMR (400 MHz, DMSO-d6) δ 10.49 (s, 1H), 8.55 (s, 1H), 7.97 (s, 1H), 7.95-7.85 (m, 1H), 7.24 (s, 1H), 7.15-6.90 (m, 5H), 6.25 (d, J=6.0 Hz, 1H), 4.99 (d, J=5.6 Hz, 1H), 2.99-2.90 (m, 3H), 2.57-2.51 (m, 2H), 2.28-2.25 (m, 1H). MS: M/e 465 (M+1)⁺.

Compound 1.43

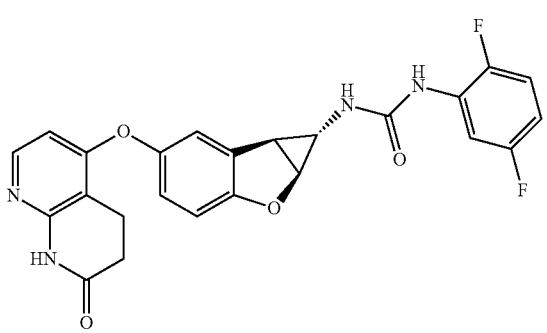 [SMILES: O=C1CCc2c(Oc3ccc4c(c3)[C@H]3[C@H](NC(=O)Nc5cc(F)ccc5F)[C@H]3O4)ccnc2N1]

¹H NMR (400 MHz, DMSO-d6) δ 10.52 (s, 1H), 8.58 (s, 1H), 8.05-7.93 (m, 2H), 7.30-7.20 (m, 2H), 7.09 (d, J=1.6 Hz, 1H), 6.93 (s, 2H), 6.84-6.72 (m, 1H), 6.26 (d, J=6.0 Hz, 1H), 4.99 (d, J=5.6 Hz, 1H), 3.01-2.89 (m, 3H), 2.55 (t, J=7.6 Hz, 2H), 2.27 (s, 1H) ppm. MS: M/e 465 (M+1)⁺.

Compound 1.44

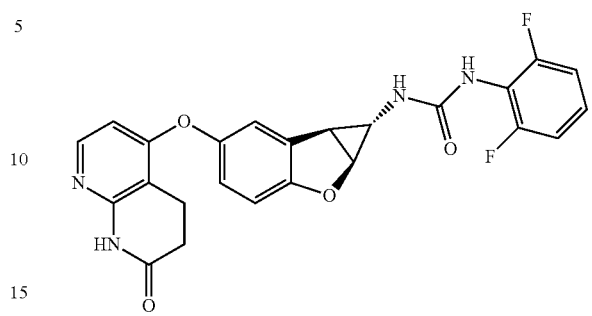

¹H NMR (400 MHz, DMSO-d6) δ 10.53 (s, 1H), 8.05 (s, 1H), 7.96 (d, J=6.0 Hz, 1H), 7.31-7.19 (m, 2H), 7.14-7.07 (m, 2H), 6.95-6.87 (m, 3H), 6.26 (d, J=6.0 Hz, 1H), 4.96 (d, J=5.6 Hz, 1H), 3.00-2.88 (m, 3H), 2.54 (t, J=7.6 Hz, 2H), 2.26 (s, 1H) ppm. MS: M/e 465 (M+1)⁺.

Compound 1.45

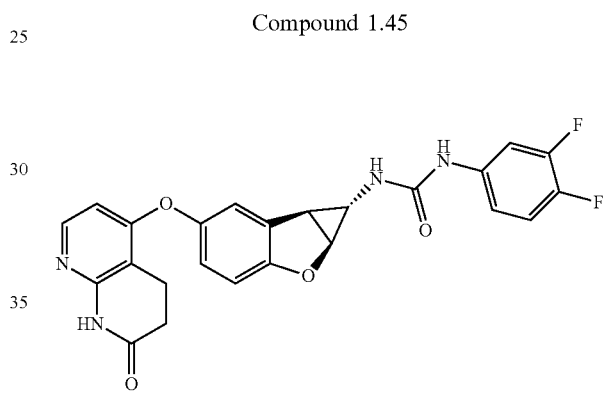

¹H NMR (400 MHz, DMSO-d6) δ 10.50 (s, 1H), 8.81 (s, 1H), 7.96 (d, J=5.6 Hz, 1H), 7.67-7.60 (m, 1H), 7.35-7.20 (m, 2H), 7.11-7.06 (m, 1H), 6.95-6.86 (m, 2H), 6.75-6.71 (s, 1H), 6.26 (d, J=5.6 Hz, 1H), 4.97 (d, J=5.6 Hz, 1H), 2.97-2.90 (m, 3H), 2.57-2.51 (m, 2H), 2.26-2.24 (m, 1H). MS: M/e 465 (M+1)⁺.

Compound 1.46

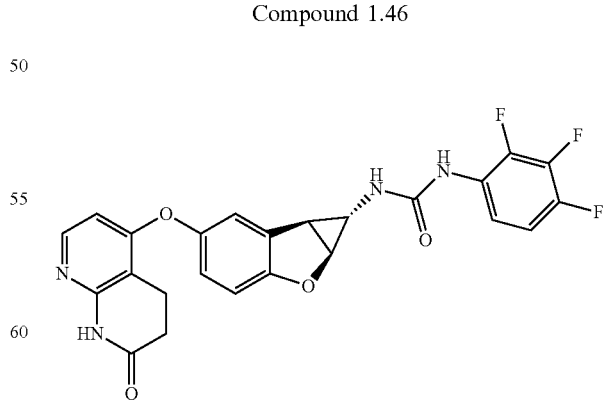

¹H NMR (400 MHz, DMSO-d6) δ 10.48 (s, 1H), 8.53 (s, 1H), 7.95 (d, J=5.6 Hz, 1H), 7.85-7.75 (m, 1H), 7.31-7.15 (m, 2H), 7.00 (d, J=2.0 Hz, 1H), 6.96-6.86 (m, 2H), 6.24 (d,

J=5.6 Hz, 1H), 4.98 (d, J=5.6 Hz, 1H), 3.00-2.88 (m, 3H), 2.54 (t, J=7.6 Hz, 2H), 2.26 (s, 1H) ppm. MS: M/e 483 (M+1)⁺.

Compound 1.47

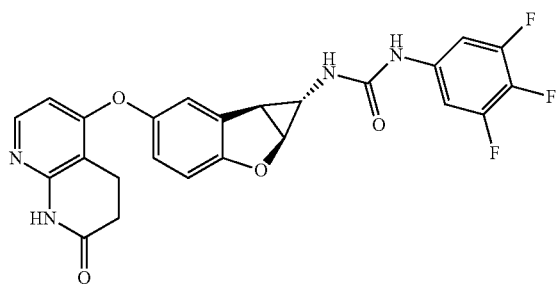 [SMILES: O=C1CCc2c(Oc3ccc4c(c3)[C@H]3[C@H](NC(=O)Nc5cc(F)c(F)c(F)c5)[C@H]3O4)ccnc2N1]

¹H NMR (400 MHz, DMSO-d6) δ 10.52 (s, 1H), 8.98 (s, 1H), 7.96 (d, J=6.0 Hz, 1H), 7.40-7.30 (m, 2H), 7.23 (s, 1H), 7.05-6.83 (m, 3H), 6.26 (d, J=6.0 Hz, 1H), 4.98 (d, J=5.6 Hz, 1H), 3.10-2.84 (m, 3H), 2.54 (t, J=7.2 Hz, 2H), 2.25 (s, 1H) ppm. MS: M/e 483 (M+1)⁺.

Compound 1.48

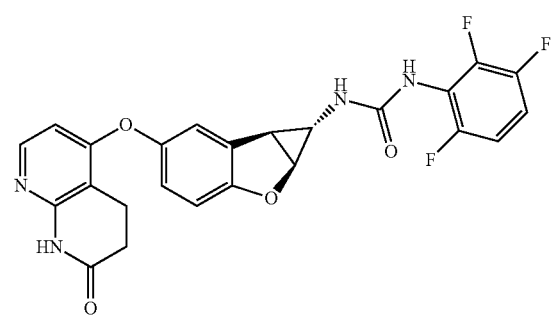 [SMILES: O=C1CCc2c(Oc3ccc4c(c3)[C@H]3[C@H](NC(=O)Nc5c(F)ccc(F)c5F)[C@H]3O4)ccnc2N1]

¹H NMR (400 MHz, DMSO-d6) δ 10.50 (s, 1H), 8.28 (s, 1H), 7.95 (d, J=6.0 Hz, 1H), 7.40-7.30 (m, 1H), 7.21 (s, 1H), 7.19-7.11 (m, 1H), 6.99 (s, 1H), 6.97-6.85 (m, 2H), 6.25 (d, J=6.0 Hz, 1H), 4.97 (d, J=6.0 Hz, 1H), 3.01-2.87 (m, 3H), 2.55 (t, J=8.0 Hz, 2H), 2.27 (s, 1H) ppm. MS: M/e 483 (M+1)⁺.

Compound 1.49

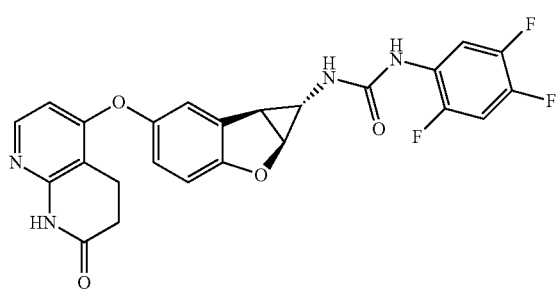

¹H NMR (400 MHz, DMSO-d6) δ 10.48 (s, 1H), 8.55 (s, 1H), 8.24-8.12 (m, 1H), 7.96 (d, J=5.6 Hz, 1H), 7.64-7.52 (m, 1H), 7.23 (s, 1H), 7.02 (s, 1H), 6.98-6.86 (m, 2H), 6.24 (d, J=5.6 Hz, 1H), 4.99 (d, J=5.6 Hz, 1H), 3.02-2.86 (m, 3H), 2.55 (d, J=8.0 Hz, 2H), 2.26 (s, 1H) ppm. MS: M/e 483 (M+1)⁺.

Compound 1.50

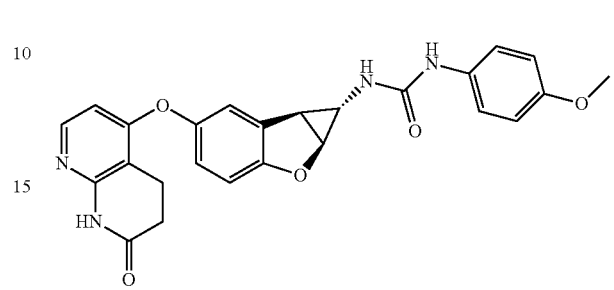

¹H NMR (400 MHz, DMSO-d6) δ 10.50 (s, 1H), 8.34 (s, 1H), 7.96 (d, J=5.6 Hz, 1H), 7.32-7.28 (m, 2H), 7.23-7.21 (m, 1H), 6.93-6.90 (m, 2H), 6.84-6.80 (m, 2H), 6.51-6.48 (m, 1H), 6.25 (d, J=5.6 Hz, 1H), 4.95 (d, J=5.6 Hz, 1H), 3.67 (s, 3H), 2.96-2.90 (m, 3H), 2.62-2.51 (m, 2H), 2.25-2.22 (m, 1H). MS: M/e 459 (M+1)⁺

Compound 1.51

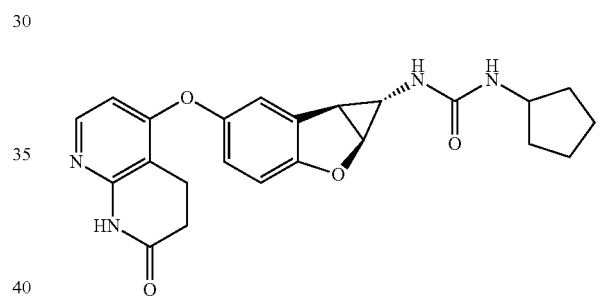

¹H NMR (400 MHz, DMSO-d6) δ 10.55 (s, 1H), 7.96 (d, J=5.6 Hz, 1H), 7.19 (s, 1H), 6.95-6.84 (m, 2H), 6.26 (d, J=5.6 Hz, 1H), 6.15 (s, 1H), 5.97 (s, 1H), 4.87 (d, J=5.6 Hz, 1H), 3.96-3.76 (m, 1H), 2.93 (t, J=7.6 Hz, 2H), 2.82 (dd, J=5.6, 1.6 Hz, 1H), 2.54 (t, J=7.6 Hz, 2H), 2.19-2.12 (m, 1H), 1.84-1.70 (m, 2H), 1.66-1.54 (m, 2H), 1.53-1.41 (m, 2H), 1.37-1.22 (m, 2H) ppm. MS: M/e 421 (M+1)⁺.

Compound 1.52

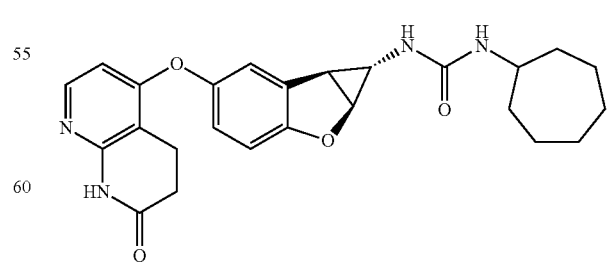

¹H NMR (400 MHz, DMSO-d6) δ 10.51 (s, 1H), 7.95 (d, J=6.0 Hz, 1H), 7.18 (s, 1H), 6.97-6.82 (m, 2H), 6.25 (d, J=6.0 Hz, 1H), 6.15 (s, 1H), 5.90 (s, 1H), 4.86 (d, J=5.6 Hz,

1H), 3.68-3.47 (m, 1H), 2.93 (t, J=7.6 Hz, 2H), 2.82 (dd, J=5.6, 1.6 Hz, 1H), 2.55 (t, J=7.6 Hz, 2H), 2.17-2.11 (m, 1H), 1.81-1.68 (m, 2H), 1.60-1.43 (m, 6H), 1.43-1.30 (m, 4H) ppm. MS: M/e 449 (M+1)+.

Compound 1.53

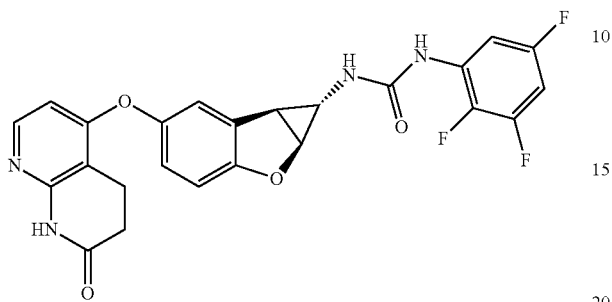

¹H NMR (400 MHz, DMSO-d6) δ 10.50 (s, 1H), 8.81 (s, 1H), 7.96 (d, J=6.0 Hz, 1H), 7.91-7.78 (m, 1H), 7.24 (s, 1H), 7.12 (s, 1H), 7.10-6.99 (m, 1H), 6.98-6.87 (m, 2H), 6.25 (d, J=6.0 Hz, 1H), 5.00 (d, J=6.0 Hz, 1H), 3.02-2.87 (m, 3H), 2.55 (d, J=7.6 Hz, 2H), 2.28-2.25 (m, 1H) ppm. MS: M/e 483 (M+1)+.

Compound 1.54

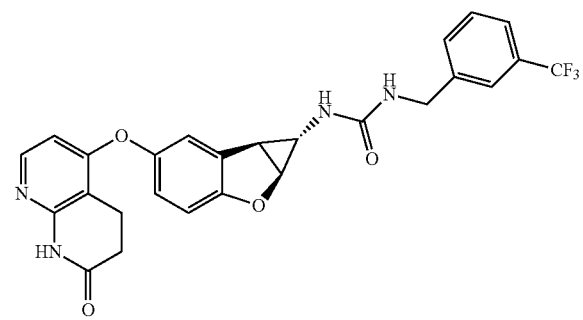 [SMILES: O=C1CCc2c(Oc3ccc4c(c3)[C@H]3[C@H](NC(=O)NCc5cccc(C(F)(F)F)c5)[C@H]3O4)ccnc2N1]

¹H NMR (400 MHz, DMSO-d6) δ 10.55 (s, 1H), 7.96 (d, J=6.0 Hz, 1H), 7.64-7.52 (m, 4H), 7.20 (s, 1H), 6.90 (s, 2H), 6.84-6.72 (m, 1H), 6.60 (s, 1H), 6.26 (d, J=6.0 Hz, 1H), 4.90 (d, J=5.6 Hz, 1H), 4.31 (d, J=5.6 Hz, 2H), 2.93 (t, J=7.6 Hz, 2H), 2.88 (dd, J=5.6, 1.6 Hz, 1H), 2.54 (t, J=7.6 Hz, 2H), 2.21 (s, 1H) ppm. MS: M/e 511 (M+1)+.

Compound 1.55

¹H NMR (400 MHz, DMSO-d6) δ 10.49 (s, 1H), 7.95 (d, J=5.6 Hz, 1H), 7.73-7.61 (m, 2H), 7.53 (d, J=7.6 Hz, 1H), 7.45 (t, J=7.6 Hz, 1H), 7.20 (s, 1H), 7.00-6.82 (m, 2H), 6.73-6.58 (m, 2H), 6.24 (d, J=5.6 Hz, 1H), 4.92 (d, J=5.6 Hz, 1H), 4.42 (d, J=5.6 Hz, 2H), 3.00-2.82 (m, 3H), 2.54 (d, J=8.0 Hz, 2H), 2.28-2.13 (m, 1H) ppm. MS: M/e 511 (M+1)+.

Compound 1.56

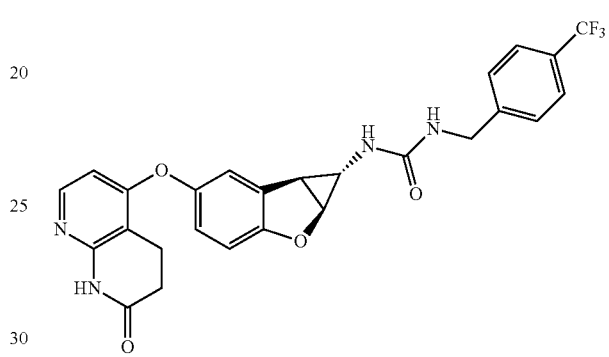

¹H NMR (400 MHz, DMSO-d6) δ 10.44 (s, 1H), 7.92 (d, J=6.0 Hz, 1H), 7.64 (d, J=8.0 Hz, 2H), 7.44 (d, J=8.0 Hz, 2H), 7.16 (s, 1H), 6.90-6.82 (m, 2H), 6.69 (s, 1H), 6.52 (s, 1H), 6.21 (d, J=6.0 Hz, 1H), 4.87 (d, J=5.6 Hz, 1H), 4.27 (d, J=5.2 Hz, 2H), 2.89 (t, J=7.6 Hz, 2H), 2.85 (dd, J=5.6, 1.6 Hz, 1H), 2.51 (t, J=7.6 Hz, 2H), 2.20-2.13 (m, 1H) ppm. MS: M/e 511 (M+1)+.

Compound 1.57

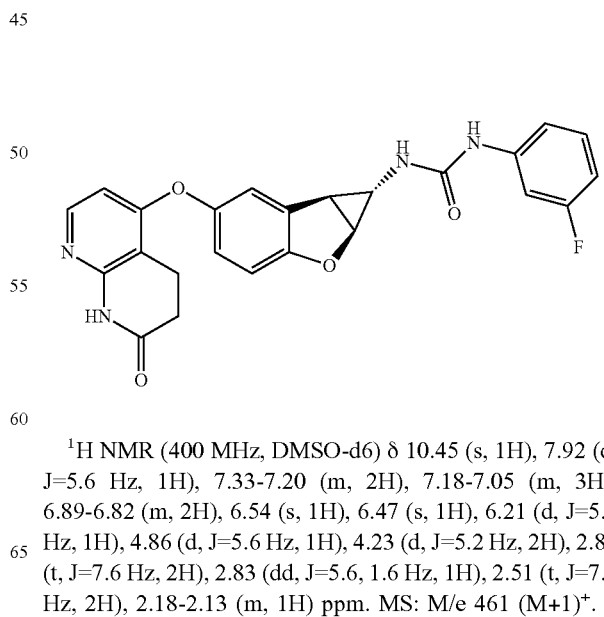

¹H NMR (400 MHz, DMSO-d6) δ 10.45 (s, 1H), 7.92 (d, J=5.6 Hz, 1H), 7.33-7.20 (m, 2H), 7.18-7.05 (m, 3H), 6.89-6.82 (m, 2H), 6.54 (s, 1H), 6.47 (s, 1H), 6.21 (d, J=5.6 Hz, 1H), 4.86 (d, J=5.6 Hz, 1H), 4.23 (d, J=5.2 Hz, 2H), 2.89 (t, J=7.6 Hz, 2H), 2.83 (dd, J=5.6, 1.6 Hz, 1H), 2.51 (t, J=7.6 Hz, 2H), 2.18-2.13 (m, 1H) ppm. MS: M/e 461 (M+1)+.

Compound 1.58

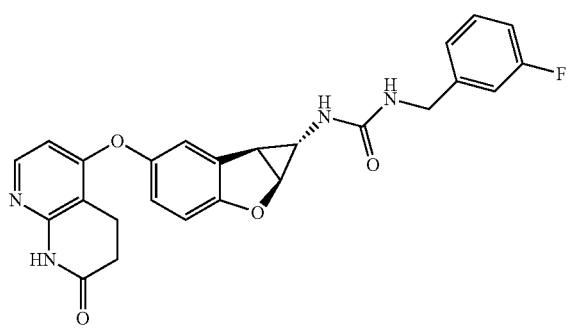 [SMILES: O=C1CCc2c(Oc3ccc4c(c3)[C@H]3[C@H](NC(=O)NCc5cccc(F)c5)[C@H]3O4)ccnc2N1]

¹H NMR (400 MHz, DMSO-d6) δ 10.48 (s, 1H), 7.95 (d, J=5.6 Hz, 1H), 7.38-7.31 (m, 1H), 7.20-7.18 (m, 1H), 7.13-7.00 (m, 3H), 6.90-6.88 (m, 2H), 6.68-6.63 (m, 1H), 6.54-6.50 (m, 1H), 6.24 (d, J=5.6 Hz, 1H), 4.90 (d, J=5.6 Hz, 1H), 4.23 (d, J=5.6 Hz, 2H), 3.95-2.85 (m, 3H), 2.56-2.52 (m, 2H), 2.21-2.19 (m, 1H). MS: M/e 461(M+1)⁺

Compound 1.59

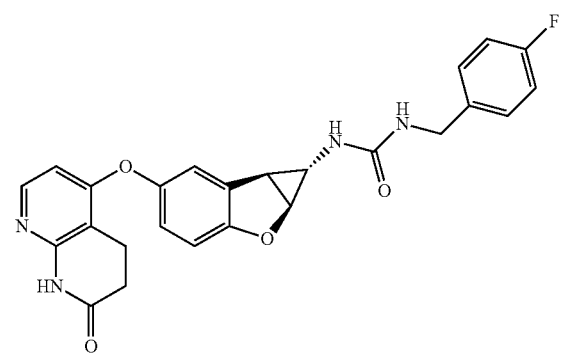 [SMILES: O=C1CCc2c(Oc3ccc4c(c3)[C@H]3[C@H](NC(=O)NCc5ccc(F)cc5)[C@H]3O4)ccnc2N1]

¹H NMR (400 MHz, DMSO-d6) δ 10.50 (s, 1H), 7.95 (d, J=5.6 Hz, 1H), 7.32-7.26 (m, 2H), 7.20-7.18 (m, 1H), 7.16-7.09 (m, 2H), 6.91-6.88 (m, 2H), 6.64-6.56 (m, 1H), 6.49-6.45 (m, 1H), 6.26-6.22 (m, 1H), 4.89 (d, J=5.6 Hz, 1H), 4.19 (d, J=5.6 Hz, 2H), 2.96-2.90 (m, 2H), 2.88-2.85 (m, 1H), 2.56-2.52 (m, 2H), 2.20-2.17 (m, 1H). MS: M/e 461(M+1)⁺

Compound 1.60

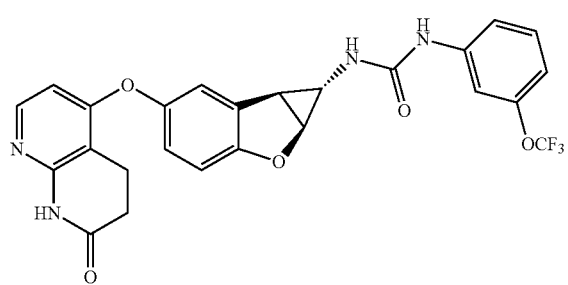 [SMILES: O=C1CCc2c(Oc3ccc4c(c3)[C@H]3[C@H](NC(=O)Nc5cccc(OC(F)(F)F)c5)[C@H]3O4)ccnc2N1]

¹H NMR (400 MHz, DMSO-d6) δ 10.51 (s, 1H), 8.92 (s, 1H), 7.96 (d, J=6.0 Hz, 1H), 7.67 (s, 1H), 7.35 (t, J=8.0 Hz, 1H), 7.28-7.20 (m, 2H), 6.95-6.85 (m, 3H), 6.76 (d, J=2.0 Hz, 1H), 6.26 (d, J=6.0 Hz, 1H), 4.98 (d, J=5.6 Hz, 1H), 3.01-2.88 (m, 3H), 2.54 (t, J=7.6 Hz, 2H), 2.27-2.25 (m, 1H) ppm. MS: M/e 513 (M+1)⁺.

Compound 1.61

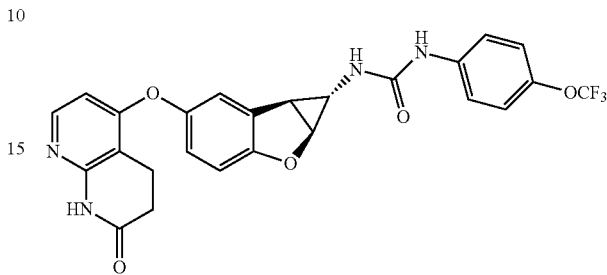

¹H NMR (400 MHz, DMSO-d6) δ 10.50 (s, 1H), 8.79 (s, 1H), 7.96 (d, J=5.6 Hz, 1H), 7.52 (d, J=9.2 Hz, 2H), 7.24-7.22 (m, 3H), 7.00-6.83 (m, 2H), 6.70 (s, 1H), 6.26 (d, J=5.6 Hz, 1H), 4.97 (d, J=5.6 Hz, 1H), 3.00-2.85 (m, 3H), 2.54 (t, J=8.0 Hz, 2H), 2.27-2.26 (m, 1H) ppm. MS: M/e 513 (M+1)⁺.

Compound 1.62

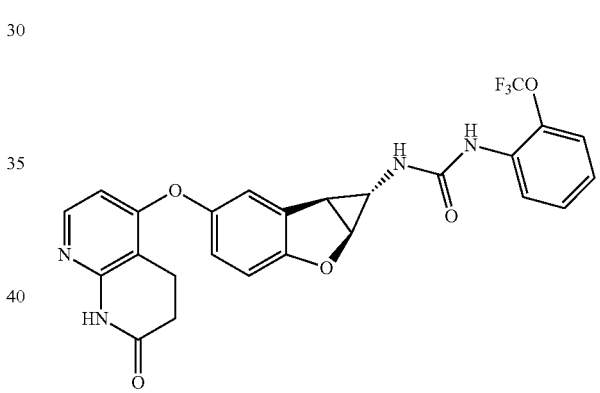

¹H NMR (400 MHz, DMSO-d6) δ 10.50 (s, 1H), 8.26-8.19 (m, 2H), 7.96 (d, J=5.6 Hz, 1H), 7.37-7.21 (m, 4H), 7.09-6.99 (m, 1H), 6.97-6.89 (m, 2H), 6.26 (d, J=5.6 Hz, 1H), 4.99 (d, J=5.6 Hz, 1H), 3.02-2.88 (m, 3H), 2.54 (t, J=7.6 Hz, 2H), 2.30-2.25 (m, 1H) ppm. MS: M/e 513 (M+1)⁺.

Compound 1.63

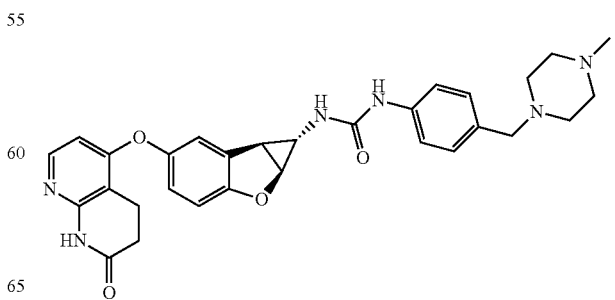

¹H NMR (400 MHz, DMSO-d6) δ 10.51 (s, 1H), 8.94 (s, 1H), 7.93 (d, J=5.6 Hz, 1H), 7.45 (d, J=8.0 Hz, 2H), 7.29 (d, J=8.0 Hz, 2H), 7.19 (s, 1H), 6.94 (s, 1H), 6.92-6.81 (m, 2H), 6.23 (d, J=5.6 Hz, 1H), 4.92 (d, J=5.6 Hz, 1H), 4.08 (s, 2H), 3.65-2.85 (m, 11H), 2.80 (s, 3H), 2.51 (t, J=7.6 Hz, 2H), 2.26-2.19 (m, 1H) ppm. MS: M/e 541 (M+1)⁺.

Compound 1.64

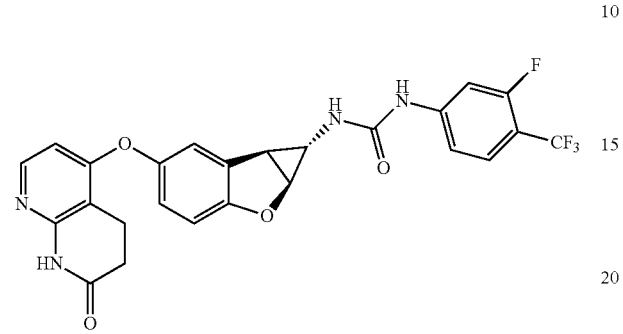

¹H NMR (400 MHz, DMSO-d6) δ 10.53 (s, 1H), 9.29 (s, 1H), 7.97 (d, J=6.0 Hz, 1H), 7.74-7.64 (m, 1H), 7.64 (t, J=8.8 Hz, 1H), 7.28 (d, J=8.8 Hz, 1H), 7.24-7.21 (m, 1H), 7.00-6.91 (m, 3H), 6.26 (d, J=6.0 Hz, 1H), 5.00 (d, J=5.6 Hz, 1H), 2.98 (dd, J=5.6, 2.0 Hz, 1H), 2.94 (t, J=7.6 Hz, 2H), 2.55 (t, J=7.6 Hz, 2H), 2.30-2.25 (m, 1H) ppm. MS: M/e 515(M+1)⁺.

Compound 1.65

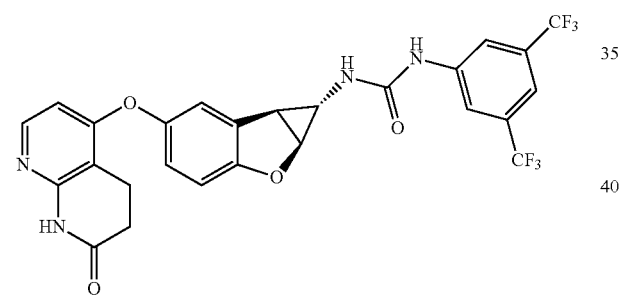

¹H NMR (400 MHz, DMSO-d6) δ 10.49 (s, 1H), 9.36 (s, 1H), 8.14 (s, 2H), 7.96 (d, J=5.6 Hz, 1H), 7.59 (s, 1H), 7.25-7.23 (m, 1H), 7.07 (s, 1H), 7.01-6.85 (m, 2H), 6.26 (d, J=5.6 Hz, 1H), 5.01 (d, J=5.6 Hz, 1H), 3.00 (d, J=4.0 Hz, 1H), 2.94 (t, J=7.6 Hz, 2H), 2.55 (d, J=7.6 Hz, 2H), 2.28 (s, 1H) ppm. MS: M/e 565(M+1)⁺.

Compound 1.66

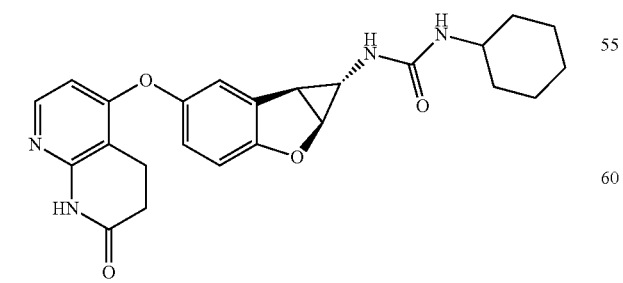

¹H NMR (400 MHz, DMSO-d6) δ 10.49 (d, J=8.0 Hz, 1H), 7.92 (d, J=6.0 Hz, 1H), 7.15 (s, 1H), 6.86 (s, 2H), 6.21 (d, J=6.0 Hz, 1H), 6.14 (s, 1H), 5.83 (s, 1H), 4.83 (d, J=5.6 Hz, 1H), 3.32 (s, 1H), 2.90 (t, J=7.6 Hz, 2H), 2.79 (dd, J=5.6, 2.0 Hz, 1H), 2.52 (t, J=7.6 Hz, 2H), 2.11 (s, 1H), 1.70-1.68 (m, 2H), 1.61-1.58 (m, 2H), 1.50-1.47 (m, 1H), 1.25-1.76 (m, 2H), 1.15-0.97 (m, 3H) ppm. MS: M/e 435 (M+1)⁺.

Compound 1.67

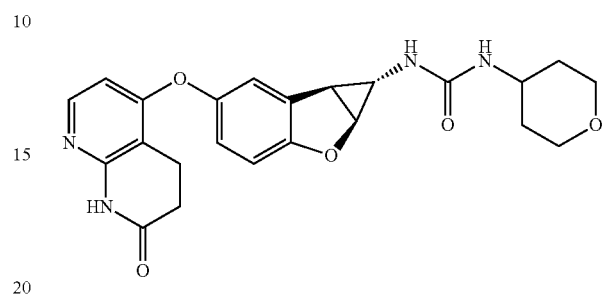

¹H NMR (400 MHz, DMSO-d6) δ 10.54 (s, 1H), 7.96 (d, J=6.0 Hz, 1H), 7.19 (s, 1H), 6.96-6.82 (m, 2H), 6.26 (d, J=6.0 Hz, 2H), 6.04 (s, 1H), 4.87 (d, J=5.6 Hz, 1H), 3.79 (d, J=11.2 Hz, 2H), 3.57 (s, 1H), 3.38-3.27 (m, 2H), 2.94 (t, J=7.6 Hz, 2H), 2.84 (dd, J=5.6, 16.8 Hz, 1H), 2.55 (t, J=7.6 Hz, 2H), 2.24-2.11 (m, 1H), 1.70 (d, J=12.0 Hz, 2H), 1.42-1.22 (m, 2H) ppm. MS: M/e 437 (M+1)⁺.

Compound 1.68

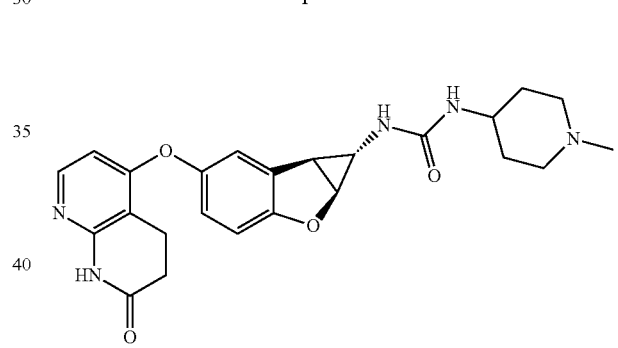

¹H NMR (400 MHz, DMSO-d6) δ 10.44 (s, 1H), 7.91 (d, J=5.6 Hz, 1H), 7.14 (s, 1H), 7.00-6.72 (m, 2H), 6.20 (d, J=5.6 Hz, 2H), 5.96 (s, 1H), 4.83 (d, J=5.2 Hz, 1H), 3.42-3.33 (m, 1H), 2.89 (t, J=7.6 Hz, 2H), 2.84-2.66 (m, 3H), 2.51 (t, J=7.6 Hz, 2H), 2.22 (s, 3H), 2.18-2.05 (m, 3H), 1.81-1.62 (m, 2H), 1.45-1.24 (m, 2H) ppm. MS: M/e 450 (M+1)⁺.

Compound 1.69

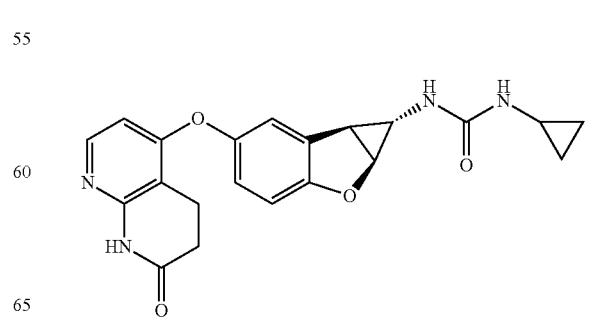

¹H NMR (400 MHz, DMSO-d6) δ 10.52 (d, J=19.2 Hz, 1H), 7.96 (d, J=6.0 Hz, 1H), 7.19 (s, 1H), 6.96-6.81 (m, 2H), 6.32-6.23 (m, 3H), 4.89 (d, J=5.6 Hz, 1H), 2.93 (t, J=7.6 Hz, 2H), 2.85 (dd, J=5.6, 2.0 Hz, 1H), 2.55 (t, J=7.6 Hz, 2H), 2.45-2.36 (m, 1H), 2.21-2.10 (m, 1H), 0.62-0.50 (m, 2H), 0.40-0.29 (m, 2H) ppm. MS: M/e 393 (M+1)⁺.

Compound 1.70: 1-(3-(2-aminopropan-2-yl)-5-(trifluoromethyl)phenyl)-3-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)urea

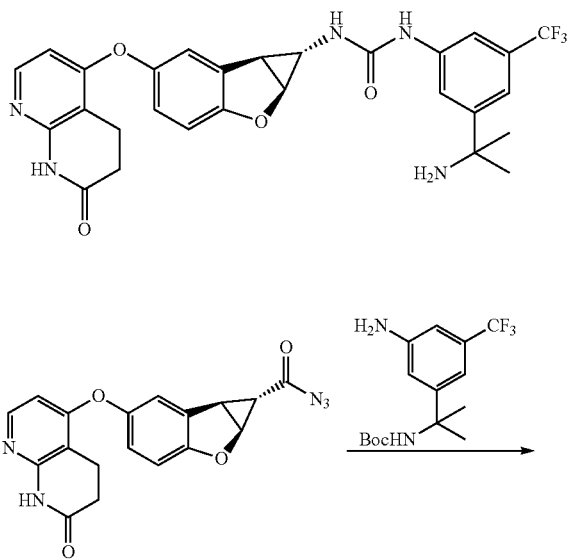

Intermediate I

Step A: tert-butyl (2-(3-(3-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)ureido)-5-(trifluoromethyl)phenyl)propan-2-yl)carbamate

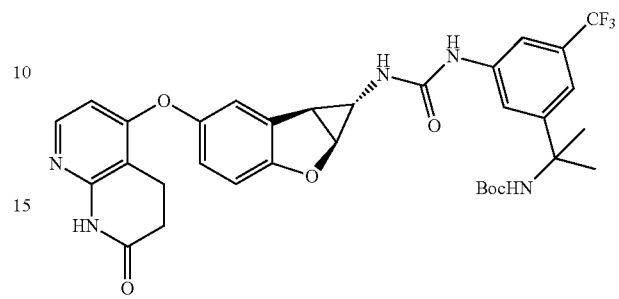

The mixture of Intermediate I (azide compound) (50 mg, 0.14 mmol) and tert-butyl (2-(3-amino-5-(trifluoromethyl)phenyl)propan-2-yl)carbamate (43.8 mg, 0.14 mmol) in 1,4-dioxane (1 mL) was stirred at reflux for 2 hours. The reaction mixture was concentrated under reduced pressure and the residue was purified by prep-HPLC to afford the title compound (42.31 mg, yield: 46.2%) as a white solid. ¹H NMR (400 MHz, DMSO-d6) δ 10.51 (s, 1H), 8.96 (s, 1H), 7.96 (d, J=6.0 Hz, 1H), 7.81 (br. s, 1H), 7.52 (s, 1H), 7.36 (br. s, 1H), 7.23 (d, J=1.6 Hz, 1H), 7.16 (s, 1H), 6.97-6.88 (m, 2H), 6.74 (s, 1H), 6.26 (d, J=6.0 Hz, 1H), 5.00 (d, J=5.6 Hz, 1H), 3.00-2.89 (m, 3H), 2.54 (t, J=7.6 Hz, 2H), 2.26 (s, 1H), 1.48 (s, 6H), 1.40-1.21 (m, 9H). ppm. MS: M/e 654 (M+1)⁺.

Step B: 1-(3-(2-aminopropan-2-yl)-5-(trifluoromethyl)phenyl)-3-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)urea (Compound 1.70)

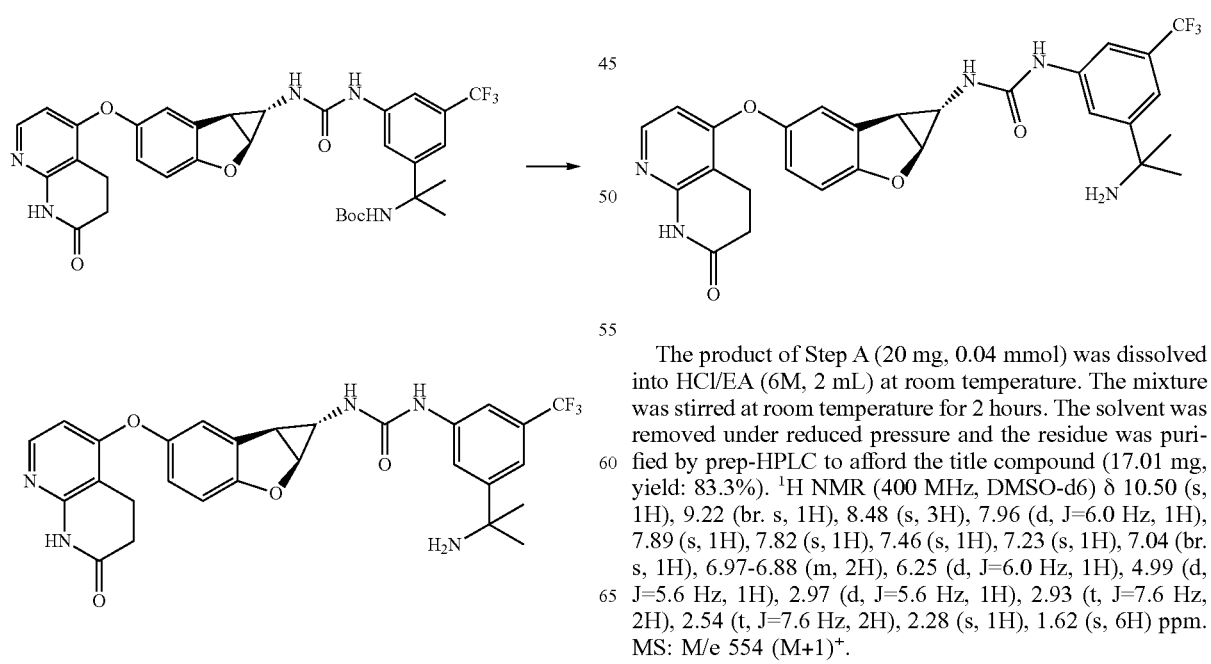

The product of Step A (20 mg, 0.04 mmol) was dissolved into HCl/EA (6M, 2 mL) at room temperature. The mixture was stirred at room temperature for 2 hours. The solvent was removed under reduced pressure and the residue was purified by prep-HPLC to afford the title compound (17.01 mg, yield: 83.3%). ¹H NMR (400 MHz, DMSO-d6) δ 10.50 (s, 1H), 9.22 (br. s, 1H), 8.48 (s, 3H), 7.96 (d, J=6.0 Hz, 1H), 7.89 (s, 1H), 7.82 (s, 1H), 7.46 (s, 1H), 7.23 (s, 1H), 7.04 (br. s, 1H), 6.97-6.88 (m, 2H), 6.25 (d, J=6.0 Hz, 1H), 4.99 (d, J=5.6 Hz, 1H), 2.97 (d, J=5.6 Hz, 1H), 2.93 (t, J=7.6 Hz, 2H), 2.54 (t, J=7.6 Hz, 2H), 2.28 (s, 1H), 1.62 (s, 6H) ppm. MS: M/e 554 (M+1)⁺.

83

Compound 1.71: 1-((1R,1aR,6bR)-5-((7-oxo-5,6,7,8-tetrahydro-1,8-naphthyridin-4-yl)oxy)-1a,6b-dihydro-1H-cyclopropa[b]benzofuran-1-yl)-3-(3-(trifluoromethyl)phenyl)urea

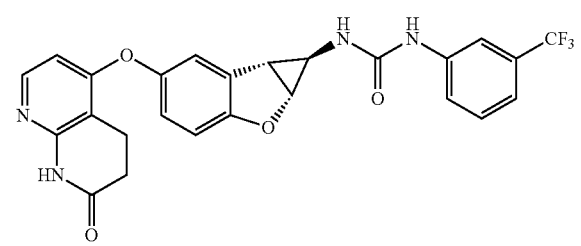

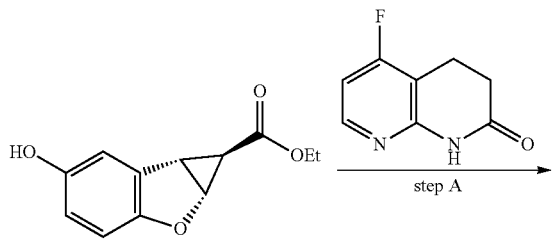

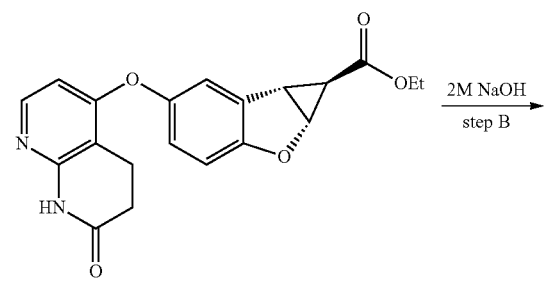

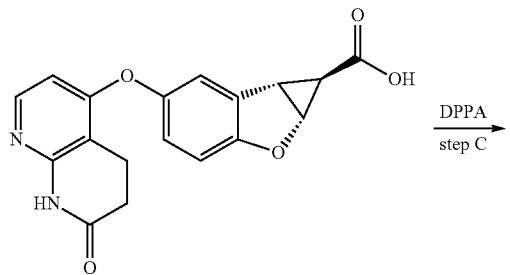

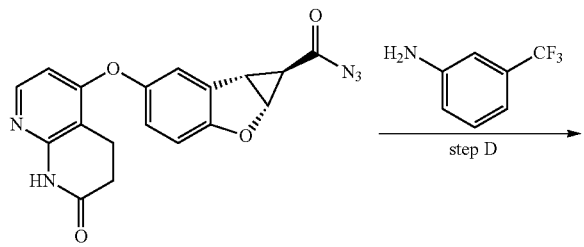

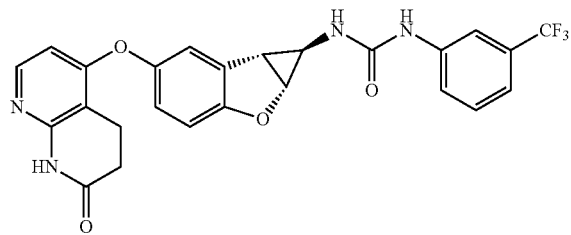

84

Step A: (1R,1aR,6bS)-ethyl 5-((7-oxo-5,6,7,8-tetrahydro-1,8-naphthyridin-4-yl) oxy)-1a,6b-dihydro-1H-cyclopropa[b]benzofuran-1-carboxylate

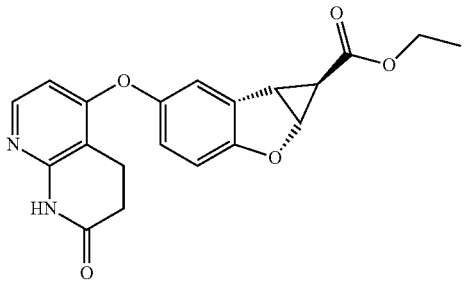

The mixture of (1R,1aR,6bS)-ethyl 5-hydroxy-1a,6b-dihydro-1H-cyclopropa [b]benzofuran-1-carboxylate (2.2 g, 0.01 mol) which was separated the product from Step F in synthesis of Compound 1.1 by Chiral SFC (column: Chiralpak AD-H), 5-fluoro-3,4-dihydro-1,8-naphthyridin-2(1H)-one (1.67 g, 0.01 mol) and t-BuOK (1.45 g, 0.013 mol) in DMF (10 mL) was stirred at 100° C. for 5 hours. The reaction was cooled to room temperature and filtered through a celite pad. The filtrate was concentrated to half of original volume. Water (30 mL) was added dropwise and a solid was precipitated out of the solution. The solid was filtered and dried in air. The title compound (3.5 g, crude) was obtained as a black solid. MS: M/e 367 (M+1)$^+$.

Step B: (1R,1aR,6bS)-5-((7-oxo-5,6,7,8-tetrahydro-1,8-naphthyridin-4-yl)oxy)-1a,6b-dihydro-1H-cyclopropa[b]benzofuran-1-carboxylic acid

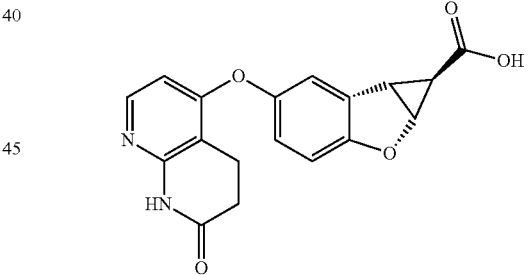

Sodium hydroxide aqueous solution (10 mL, 2 mol/L, 20 mmol) was added to a stirred solution of the crude product of Step A (2.8 g, 7.7 mmol) in methanol (20 mL) at room temperature. The mixture was stirred at 60° C. for 3 hours. The solvent was removed under reduced pressure and the residue was dissolved into water (20 mL), extracted with dichloromethane (2×20 mL). The aqueous layer was collected and neutralized with HCl (2 mol/L) to pH about 3 and white solid was precipitated out of solution. The white solid was collected by filtration and dried in air to give the title compound (2.1 g, 66% for two steps). $^1$H-NMR (400 MHz, DMSO-d$_6$) δ 12.60 (brs 1H), 10.49 (s, 1H), 7.95 (d, J=5.6 Hz, 1H), 7.33 (d, J=2.4 Hz, 1H), 7.02-6.95 (m, 2H), 6.24 (d, J=5.6 Hz, 1H), 5.27-5.23 (m, 1H), 3.34-3.29 (m, 1H), 2.93 (t, J=7.6 Hz, 2H), 2.53 (t, J=7.6 Hz, 2H), 1.24-1.21 (m, 1H) ppm. MS: M/e 339 (M+1)$^+$.

Step C: (1R,1aR,6bS)-5-((7-oxo-5,6,7,8-tetrahydro-1,8-naphthyridin-4-yl) oxy)-1a,6b-dihydro-1H-cyclopropa[b]benzofuran-1-carbonyl azide

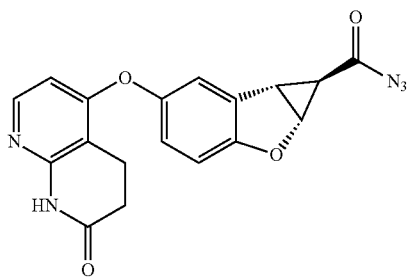 [SMILES: [N-]=[N+]=NC(=O)[C@H]1[C@@H]2Oc3ccc(Oc4ccnc5c4CCC(=O)N5)cc3[C@@H]21]

To a 0° C. solution of the product of Step B (0.5 g, 1.48 mmol) in DMF (1 mL) was added Et$_3$N (0.3 mL) and followed by DPPA (0.5 g, 1.82 mmol). The resulted mixture was allowed warm to ambient temperature and stirred for 5 hours. 10 mL of H$_2$O was added and the mixture was extracted with EA (10 mL×3). The combined extracts was washed with brine (10 mL×3), dried over Na$_2$SO$_4$, concentrated under vacuum until about 2 mL of EA remained. 10 mL of PE was added and the mixture was stirred for 30 minutes. The white solid was filtered and washed with PE/EA (5:1, 100 mL), dried under high vacuum to give the title compound (0.5 g, yield: 93.1%) as a white solid. $^1$H NMR (400 MHz, DMSO-d$_6$) δ 10.49 (s, 1H), 7.95 (d, J=5.6 Hz, 1H), 7.34 (d, J=2.4 Hz, 1H), 7.10-6.96 (m, 2H), 6.25 (d, J=5.6 Hz, 1H), 5.42 (dd, J=5.2, 0.8 Hz, 1H), 3.56 (dd, J=5.2, 3.2 Hz, 1H), 2.92 (t, J=8.0 Hz, 2H), 2.54 (t, J=8.0 Hz, 2H), 1.51 (dd, J=3.2, 0.8 Hz, 1H) ppm. MS: M/e 364 (M+1)$^+$.

Step D: 1-((1R,1aR,6bR)-5-((7-oxo-5,6,7,8-tetrahydro-1,8-naphthyridin-4-yl) oxy)-1a,6b-dihydro-1H-cyclopropa[b]benzofuran-1-yl)-3-(3-(trifluoromethyl)phenyl)urea (Compound 1.71)

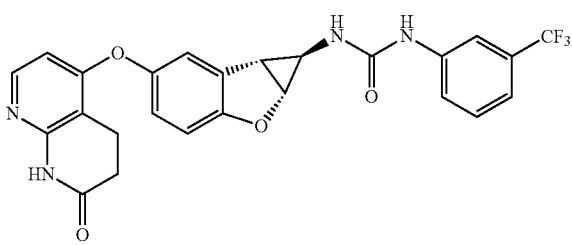 [SMILES: O=C1CCc2c(Oc3ccc4c(c3)[C@@H]3[C@@H](NC(=O)Nc5cccc(C(F)(F)F)c5)[C@@H]3O4)ccnc2N1]

The mixture of the product of step C (40 mg, 0.11 mmol) and 3-(trifluoromethyl) aniline (18.6 mg, 0.12 mmol) in toluene (1 mL) was stirred at 100° C. for 2 hours. The reaction mixture was concentrated under reduced pressure and the resulted residue was purified by prep-HPLC to afford the title compound (24.7 mg, yield: 45.2%). $^1$H NMR (400 MHz, DMSO-d6) δ 10.50 (s, 1H), 8.97 (s, 1H), 8.05-7.91 (m, 2H), 7.60-7.41 (m, 2H), 7.29-7.20 (m, 2H), 6.99-6.87 (m, 2H), 6.80 (s, 1H), 6.26 (s, 1H), 5.00 (s, 1H), 3.02-2.88 (m, 3H), 2.54 (t, J=7.6 Hz, 2H), 2.27 (s, 1H) ppm. MS: M/e 497 (M+1)$^+$ Compound 1.72 was prepared according to the procedures described for Compound 1.71 under appropriate conditions that could be recognized by one skilled in the art.

Compound 1.72

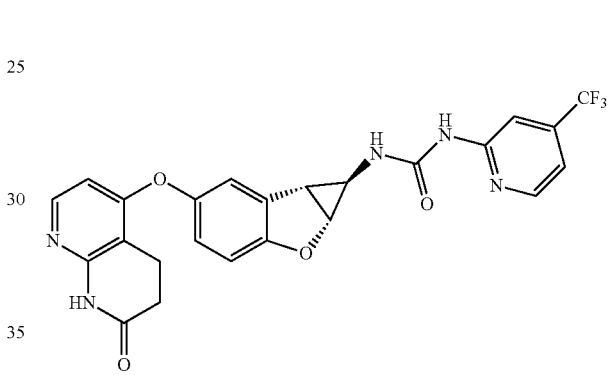

$^1$H NMR (400 MHz, DMSO-d6) δ 10.49 (s, 1H), 9.63 (s, 1H), 8.47 (d, J=5.2 Hz, 1H), 8.03-7.92 (m, 2H), 7.72 (s, 1H), 7.31 (d, J=6.0 Hz, 1H), 7.25 (d, J=1.6 Hz, 1H), 6.98-6.88 (m, 2H), 6.25 (d, J=6.0 Hz, 1H), 5.05 (d, J=6.0 Hz, 1H), 3.06-3.00 (m, 1H), 2.94 (t, J=7.6 Hz, 2H), 2.55 (t, J=7.6 Hz, 2H), 2.30 (s, 1H). ppm. MS: M/e 498 (M+1)$^+$.

Compound 1.73: 1-(4-((4-ethylpiperazin-1-yl)methyl)-3-(trifluoromethyl) phenyl)-3-((1S,1aS,6bS)-5-((7-oxo-5,6,7,8-tetrahydro-1, 8-naphthyridin-4-yl)oxy)-1a,6b-dihydro-1H-cyclopropa[b]benzofuran-1-yl)urea

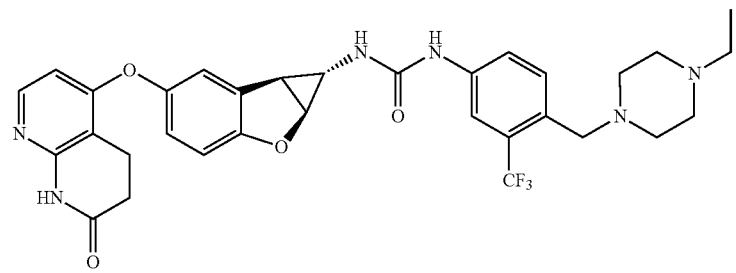

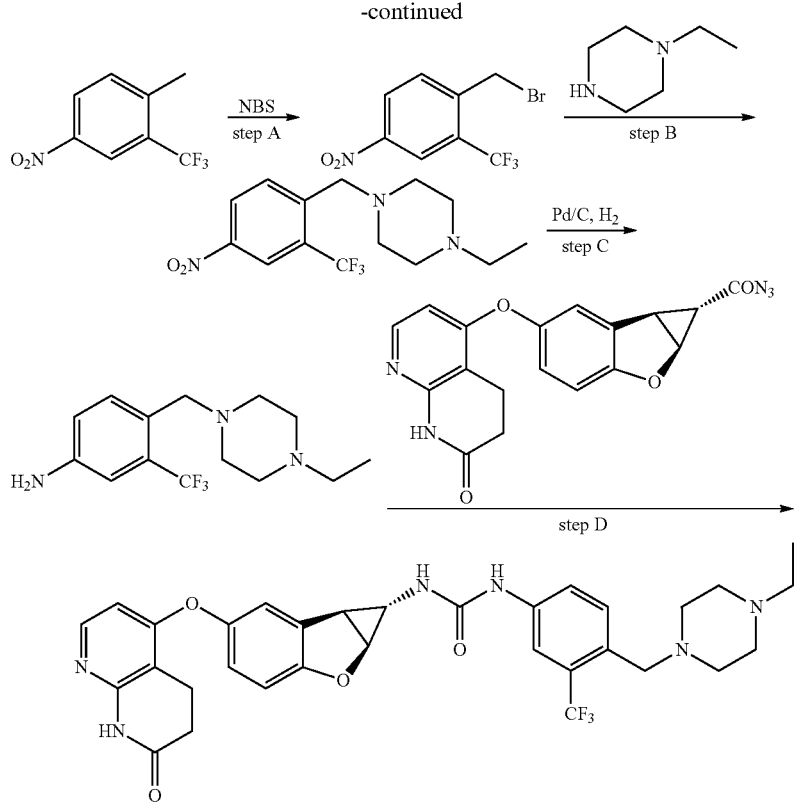

Step A: 1-(bromomethyl)-4-nitro-2-(trifluoromethyl)benzene

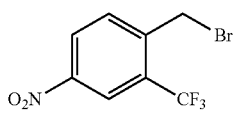

To the solution of 1-methyl-4-nitro-2-(trifluoromethyl)benzene (500 mg, 2.44 mmol) and benzoyl peroxide (58 mg, 0.24 mmol) in $CCl_4$ (15 mL) was added N-bromosuccinimide (434 mg, 2.44 mmol) at room temperature. The solution was stirred at 80° C. for 4 hours. TLC (PE/EA=5/1) showed the reaction was completed. The resulting solution was concentrated and the residue was extracted with DCM (20 mL×2) and washed by water (20 mL). The combined organic layer was dried over $Na_2SO_4$ and concentrated to get the crude product (690 mg, yield: 99%) as yellow oil, which was used in next step directly.

Step B: 1-ethyl-4-(4-nitro-2-(trifluoromethyl)benzyl)piperazine

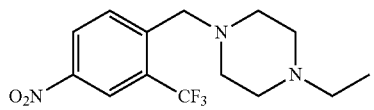

To the solution of product of Step A (690 mg, 2.44 mmol) in DCM (10 mL) was added 1-ethylpiperazine (279 mg, 2.44 mmol) followed by $Et_3N$ (247 mg, 2.44 mmol). The solution was stirred at room temperature for 4 hours. TLC (PE/EA=5/1) showed the reaction was completed. The resulting solution was concentrated and the residue (770 mg, yield: 99%) was used in next step directly. MS: M/e 318 (M+1)$^+$.

Step C: 4-((4-ethylpiperazin-1-yl)methyl)-3-(trifluoromethyl)aniline

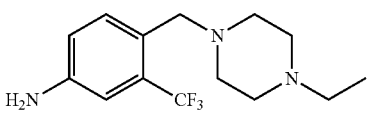 [SMILES: CCN1CCN(Cc2ccc([N+](=O)[O-])cc2C(F)(F)F)CC1]

To the solution of the product of Step B (770 mg, 2.43 mmol) in methanol (10 mL) was added Pd/C (70 mg). The solution was stirred at room temperature under hydrogen (4 atm) for 2 hours. TLC (DCM/MeOH=20/1) showed the reaction was completed. The resulting solution was filtered through a silica pad, the filtrate was concentrated and purified by silica gel chromatography (silica weight: 10 g, eluting: DCM/MeOH=20/1) to afford the title compound (500 mg, yield: 71%) as yellow oil. MS: M/e 288(M+1)$^+$.

Step D: 1-(4-((4-ethylpiperazin-1-yl)methyl)-3-(trifluoromethyl)phenyl)-3-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)urea (Compound 1.73)

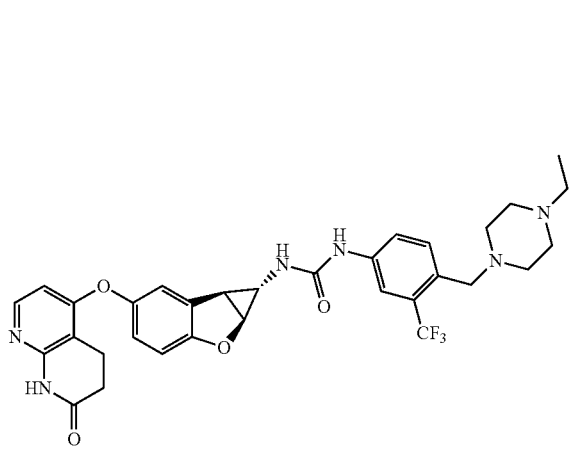 [SMILES: CCN1CCN(Cc2ccc(NC(=O)N[C@@H]3[C@H]4Oc5ccc(Oc6ccnc7c6CCC(=O)N7)cc5[C@@H]34)cc2C(F)(F)F)CC1]

A mixture of the product of Step C (49 mg, 0.17 mmol) and Intermediate I (50 mg, 0.14 mmol) in 1,4-dioxane (2 mL) was stirred at 100° C. under $N_2$ for 2 hours (monitored by LCMS). The resulting solution was concentrated under reduced pressure and purified by prep-HPLC to get the title compound (20 mg, 23%) as a white solid. $^1$H NMR (400 MHz, DMSO-d6) δ 10.44 (s, 1H), 8.86 (s, 1H), 7.92 (d, J=5.6 Hz, 1H), 7.90 (d, J=1.6 Hz, 1H), 7.59-7.44 (m, 2H), 7.20 (s, 1H), 6.97-6.82 (m, 2H), 6.70 (s, 1H), 6.21 (d, J=5.6 Hz, 1H), 4.95 (d, J=5.6 Hz, 1H), 3.47 (s, 2H), 2.99-2.82 (m, 3H), 2.54-2.48 (m, 4H), 2.43-2.20 (m, 9H), 0.94 (t, J=7.2 Hz, 3H) ppm. MS: M/e 623 (M+1)$^+$.

Compound 1.74 was prepared according to the procedures described for Compound 1.73 under appropriate conditions that could be recognized by one skilled in the art.

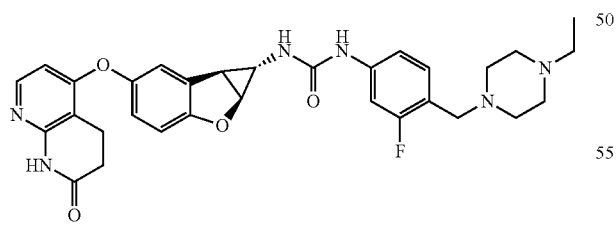

$^1$H NMR (400 MHz, DMSO-d6) δ 10.48 (s, 1H), 8.80 (s, 1H), 7.96 (d, J=6.0 Hz, 1H), 7.42 (dd, J=12.8, 1.6 Hz, 1H), 7.27-7.14 (m, 2H), 7.05 (dd, J=8.0, 1.6 Hz, 1H), 6.97-6.86 (m, 2H), 6.71 (s, 1H), 6.25 (d, J=6.0 Hz, 1H), 4.97 (d, J=5.6 Hz, 1H), 3.42 (s, 2H), 2.99-2.88 (m, 3H), 2.56-2.50 (m, 4H), 2.48-2.26 (m, 8H), 2.27-2.21 (m, 1H), 0.98 (t, J=7.2 Hz, 3H) ppm. MS: M/e 573 (M+1)$^+$.

Compound 1.75: 1-(2-methoxypyridin-4-yl)-3-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)urea

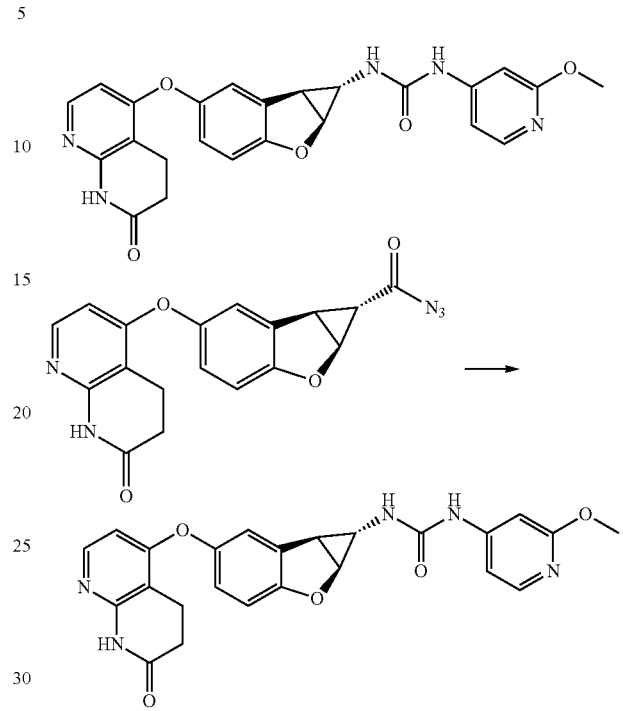

The mixture of Intermediate I (azide compound) (50 mg, 0.14 mmol) in toluene (1 mL) was stirred at reflux for 30 min. To the stirred mixture was added 2-methoxypyridin-4-amine (17 mg, 0.14 mmol) at reflux. The reaction was stirred at reflux for another 30 min. The mixture was concentrated under reduced pressure and the residue was purified by prep-HPLC to afford the title compound (25 mg, yield: 39.7%) as a white solid. $^1$H NMR (400 MHz, DMSO-d6) δ 10.63 (s, 1H), 10.14 (s, 1H), 8.07 (d, J=6.4 Hz, 1H), 7.99 (d, J=6.0 Hz, 1H), 7.61 (s, 1H), 7.38 (s, 1H), 7.25 (s, 1H), 7.14 (d, J=6.0 Hz, 1H), 6.98-6.90 (m, 2H), 6.29 (d, J=6.0 Hz, 1H), 5.01 (d, J=5.6 Hz, 1H), 3.96 (s, 3H), 3.01 (dd, J=5.6, 2.0 Hz, 1H), 2.95 (t, J=7.6 Hz, 2H), 2.56 (t, J=7.6 Hz, 2H), 2.31 (s, 1H) ppm. MS: M/e 460 (M+1)$^+$.

Compounds 1.76-1.85 were prepared according to the procedures described for Compound 1.1 under appropriate conditions that could be recognized by one skilled in the art.

Compound 1.76

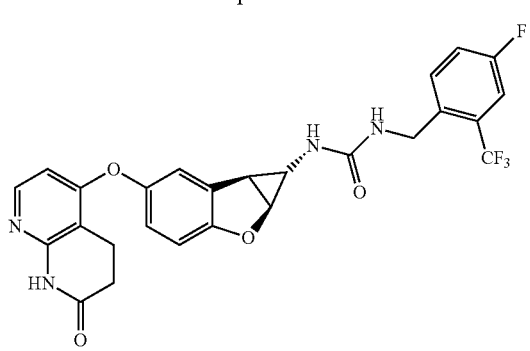

¹H NMR (400 MHz, DMSO-d6) δ 10.49 (s, 1H), 7.95 (d, J=5.6 Hz, 1H), 7.65-7.48 (m, 3H), 7.20 (s, 1H), 6.95-6.85 (m, 2H), 6.70 (m, 1H), 6.66 (s, 1H), 6.24 (d, J=5.6 Hz, 1H), 4.91 (d, J=5.6 Hz, 1H), 4.38 (d, J=5.2 Hz, 2H), 2.97-2.85 (m, 3H), 2.54 (t, J=7.6 Hz, 2H), 2.24-2.17 (m, 1H) ppm. MS: M/e 529 (M+1)⁺.

Compound 1.77

¹H NMR (400 MHz, DMSO-d6) δ 10.47 (s, 1H), 8.31 (s, 1H, HCOOH), 7.95 (d, J=5.6 Hz, 1H), 7.25-7.20 (m, 1H), 7.19 (s, 1H), 7.17-7.10 (m, 2H), 7.10-7.03 (m, 1H), 6.93-6.85 (m, 2H), 6.40 (d, J=8.4 Hz, 1H), 6.27-6.22 (m, 2H), 4.91 (d, J=5.6 Hz, 1H), 4.83-4.73 (m, 1H), 2.93 (t, J=7.6 Hz, 2H), 2.88 (dd, J=5.6, 2.0 Hz, 1H), 2.80-2.62 (m, 2H), 2.54 (t, J=7.6 Hz, 2H), 2.26-2.19 (m, 1H), 1.93-1.62 (m, 4H) ppm. MS: M/e 483 (M+1)⁺.

Compound 1.80

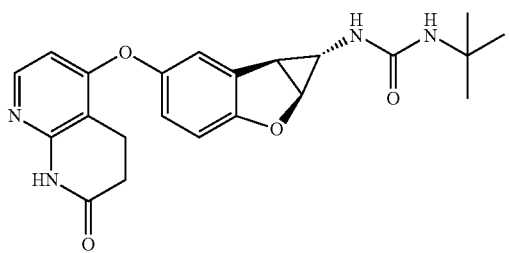 [SMILES: CC(C)(C)NC(=O)N[C@@H]1[C@H]2Oc3ccc(Oc4ccnc5c4CCC(=O)N5)cc3[C@@H]12]

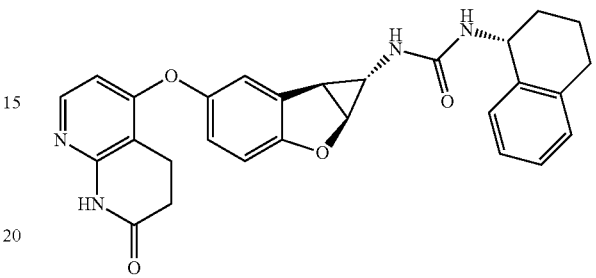

¹H NMR (400 MHz, DMSO-d6) δ 10.51 (s, 1H), 7.95 (d, J=5.6 Hz, 1H), 7.20 (s, 1H), 6.97-6.83 (m, 2H), 6.23 (d, J=5.6 Hz, 1H), 6.08 (s, 1H), 5.69 (s, 1H), 4.84 (d, J=5.6 Hz, 1H), 2.93 (t, J=7.6 Hz, 2H), 2.80 (dd, J=5.6, 2.0 Hz, 1H), 2.54 (t, J=7.6 Hz, 2H), 2.14-2.08 (m, 1H), 1.22 (s, 9H) ppm. MS: M/e 409 (M+1)⁺.

¹H NMR (400 MHz, DMSO-d6) δ 10.48 (s, 1H), 8.30 (s, 1H—HCOOH), 7.95 (d, J=5.6 Hz, 1H), 7.30-7.21 (m, 1H), 7.15 (s, 1H), 7.13-7.09 (m, 2H), 7.08-7.03 (m, 1H), 6.94-6.85 (m, 2H), 6.39 (d, J=8.8 Hz, 1H), 6.26 (s, 1H), 6.40 (d, J=5.6 Hz, 1H), 4.92 (d, J=5.6 Hz, 1H), 4.83-4.72 (m, 1H), 2.92 (t, J=7.6 Hz, 2H), 2.87 (dd, J=5.6, 2.0 Hz, 1H), 2.81-2.61 (m, 2H), 2.54 (t, J=7.6 Hz, 2H), 2.25-2.20 (m, 1H), 1.92-1.61 (m, 4H) ppm. MS: M/e 483 (M+1)⁺.

Compound 1.81

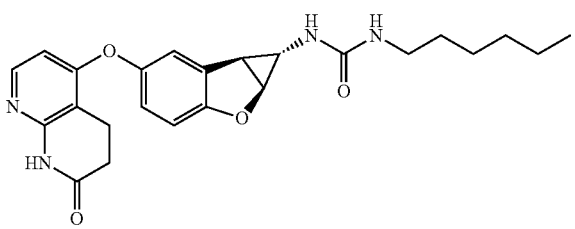 [SMILES: CCCCCCNC(=O)N[C@@H]1[C@H]2Oc3ccc(Oc4ccnc5c4CCC(=O)N5)cc3[C@@H]12]

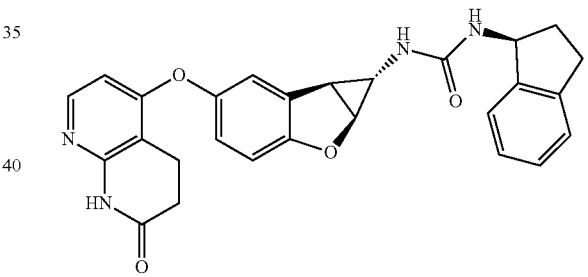

Compound 1.78

¹H NMR (400 MHz, DMSO-d6) δ 10.49 (s, 1H), 7.95 (d, J=6.0 Hz, 1H), 7.18 (s, 1H), 6.92-6.86 (m, 2H), 6.27 (s, 1H), 6.24 (d, J=6.0 Hz, 1H), 5.99 (s, 1H), 4.87 (d, J=6.0 Hz, 1H), 3.02-2.88 (m, 4H), 2.82 (dd, J=5.6, 2.0 Hz, 1H), 2.54 (t, J=8.0 Hz, 2H), 2.17-2.11 (m, 1H), 1.41-1.31 (m, 2H), 1.31-1.18 (m, 6H), 0.86 (t, J=7.2 Hz, 3H) ppm. MS: M/e 437 (M+1)⁺.

Compound 1.79

¹H NMR (400 MHz, DMSO-d6) δ 10.50 (s, 1H), 7.95 (d, J=5.6 Hz, 1H), 7.29-7.13 (m, 5H), 6.97-6.84 (m, 2H), 6.41 (d, J=8.8 Hz, 1H), 6.31 (s, 1H), 6.25 (d, J=5.6 Hz, 1H), 5.18-5.05 (m, 1H), 4.92 (d, J=5.6 Hz, 1H), 2.97-2.83 (m, 4H), 2.83-2.70 (m, 1H), 2.55 (t, J=7.6 Hz, 2H), 2.44-2.31 (m, 1H), 2.26-2.19 (m, 1H), 1.80-1.66 (m, 1H) ppm. MS: M/e 469 (M+1)⁺.

Compound 1.82

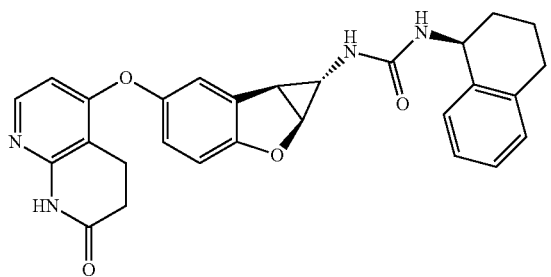 [SMILES: O=C1CCc2c(Oc3ccc4c(c3)[C@H]3[C@H](NC(=O)N[C@H]5CCCc6ccccc65)[C@H]3O4)ccnc2N1]

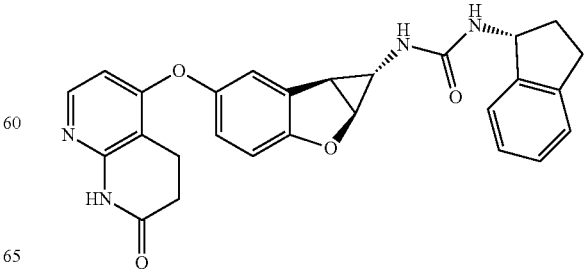

¹H NMR (400 MHz, DMSO-d6) δ 10.49 (s, 1H), 7.95 (d, J=5.6 Hz, 1H), 7.23-7.12 (m, 5H), 6.94-6.86 (m, 2H), 6.40 (d, J=8.4 Hz, 1H), 6.31 (s, 1H), 6.25 (d, J=5.6 Hz, 1H), 5.10 (q, J=8.0 Hz, 1H), 4.93 (d, J=5.6 Hz, 1H), 2.96-2.83 (m, 4H), 2.82-2.71 (m, 1H), 2.54 (t, J=7.6 Hz, 2H), 2.44-2.31 (m, 1H), 2.25-2.20 (m, 1H), 1.79-1.64 (m, 1H) ppm. MS: M/e 469 (M+1)⁺.

Compound 1.83

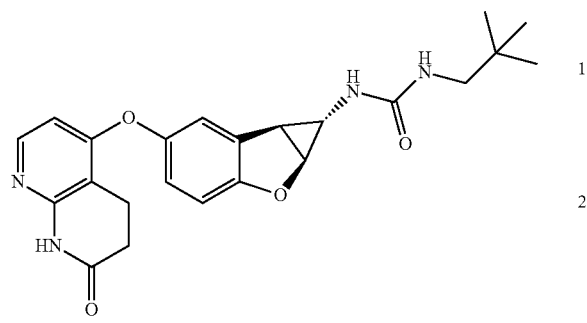

¹H NMR (400 MHz, DMSO-d6) δ 10.49 (s, 1H), 7.95 (d, J=5.6 Hz, 1H), 7.18 (s, 1H), 6.95-6.84 (m, 2H), 6.25-6.23 (m, 2H), 5.97 (t, J=6.0 Hz, 1H), 4.87 (d, J=5.6 Hz, 1H), 2.93 (t, J=7.6 Hz, 2H), 2.87-2.77 (m, 3H), 2.55 (t, J=7.6 Hz, 2H), 2.22-2.13 (m, 1H), 0.82 (s, 9H) ppm. MS: M/e 423 (M+1)⁺.

Compound 1.84

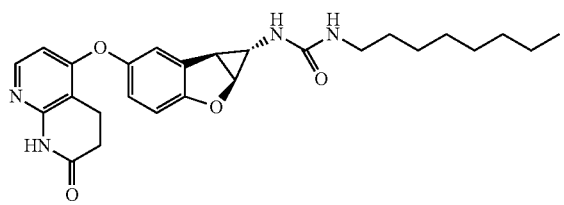 [SMILES: CCCCCCCCNC(=O)N[C@@H]1[C@H]2Oc3ccc(Oc4ccnc5c4CCC(=O)N5)cc3[C@@H]12]

¹H NMR (400 MHz, DMSO-d6) δ 10.49 (s, 1H), 7.95 (d, J=5.6 Hz, 1H), 7.18 (s, 1H), 6.94-6.84 (m, 2H), 6.27 (s, 1H), 6.24 (d, J=5.6 Hz, 1H), 6.00 (s, 1H), 4.86 (d, J=5.6 Hz, 1H), 3.03-2.88 (m, 4H), 2.82 (dd, J=5.6, 1.6 Hz, 1H), 2.54 (t, J=7.6 Hz, 2H), 2.18-2.11 (m, 1H), 1.41-1.31 (m, 2H), 1.30-1.18 (m, 10H), 0.85 (t, J=6.8 Hz, 3H) ppm. MS: M/e 465 (M+1)⁺.

Compound 1.85

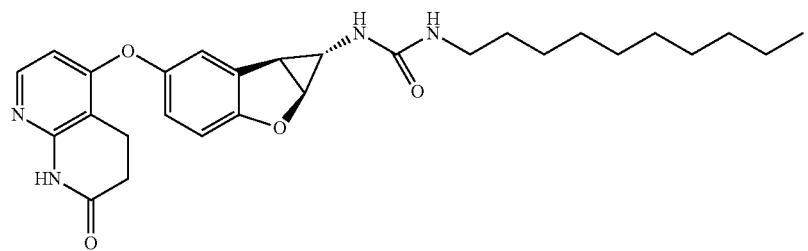 [SMILES: CCCCCCCCCCNC(=O)N[C@@H]1[C@H]2Oc3ccc(Oc4ccnc5c4CCC(=O)N5)cc3[C@@H]12]

¹H NMR (400 MHz, DMSO-d6) δ 10.48 (s, 1H), 7.95 (d, J=5.6 Hz, 1H), 7.18 (s, 1H), 6.94-6.84 (m, 2H), 6.27 (s, 1H), 6.24 (d, J=5.6 Hz, 1H), 6.00 (s, 1H), 4.85 (d, J=5.6 Hz, 1H), 3.01-2.88 (m, 4H), 2.82 (d, J=5.6 Hz, 1H), 2.54 (t, J=7.6 Hz, 2H), 2.16-2.12 (m, 1H), 1.41-1.31 (m, 2H), 1.30-1.15 (m, 14H), 0.85 (t, J=6.4 Hz, 3H) ppm. MS: M/e 493 (M+1)⁺.

Compound 1.86: 1-(4-(4-methylpiperazin-1-yl)-3-(trifluoromethyl)phenyl)-3-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)urea

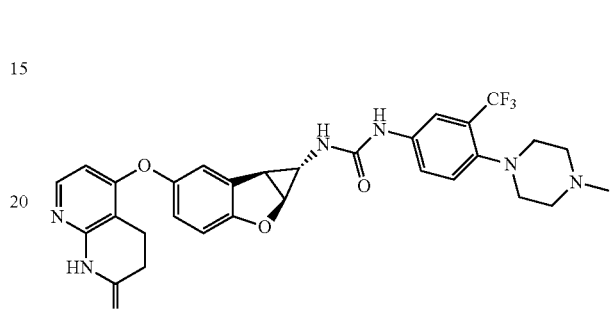

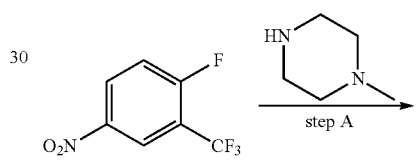

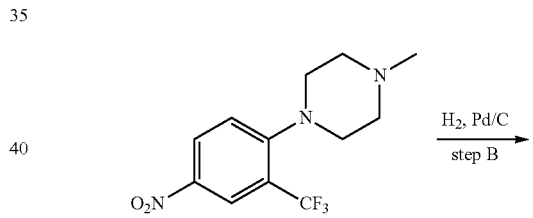

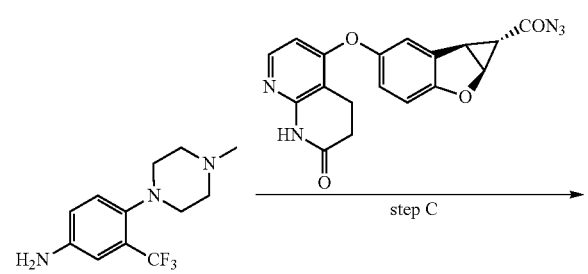

-continued

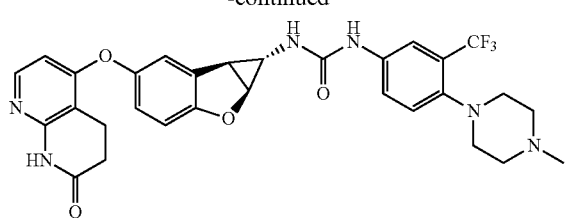

Step A: 1-methyl-4-(4-nitro-2-(trifluoromethyl)phenyl)piperazine

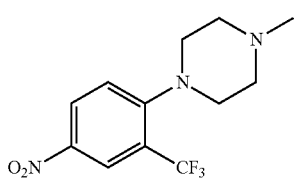 [SMILES: CN1CCN(c2ccc([N+](=O)[O-])cc2C(F)(F)F)CC1]

A solution of 1-fluoro-4-nitro-2-(trifluoromethyl)benzene (500 mg, 2.39 mmol), 1-methylpiperazine (286 mg, 2.86 mmol) and $Cs_2CO_3$ (1.16 g, 3.58 mmol) in DMF (10 mL) was stirred at 60° C. for 1 hour. The resulting solution was concentrated, the residue was diluted by ethyl acetate (10 mL), the solution was filtered to remove $Cs_2CO_3$, the filtrate was concentrated to get crude title compound (670 mg, yield: 97%) as yellow oil, which was used in next step directly.

Step B: 4-(4-methylpiperazin-1-yl)-3-(trifluoromethyl)aniline

Pd/C (67 mg) was added to the solution of the product of Step A (670 mg, 2.32 mmol) in MeOH (10 mL). The solution was stirred under 4 atm $H_2$ at room temperature overnight. The resulting solution was filtered, the filtrate was concentrated to get crude title product (600 mg, yield: 100%) as a yellow solid, which was used in next step directly. MS: M/e 260 (M+1)$^+$.

Step C: 1-(4-(4-methylpiperazin-1-yl)-3-(trifluoromethyl)phenyl)-3-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)urea (Compound 1.86)

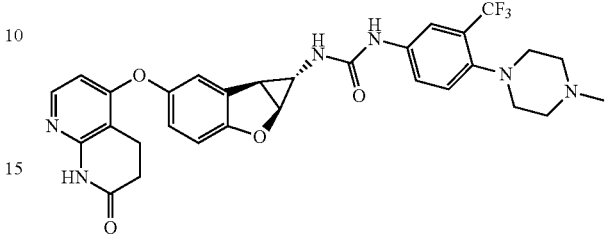

A mixture of Intermediate I (60 mg, 0.16 mmol) and the product of Step B (51 mg, 0.20 mmol) in dioxane (3 mL) was stirred at 100° C. under $N_2$ for 2 hours. The resulting solution was concentrated and purified by prep-HPLC to get title compound (26 mg, yield: 30%) as a white solid. $^1$H NMR (400 MHz, DMSO-d6) δ 10.49 (s, 1H), 9.67 (s, 1H—$CF_3COOH$), 9.03 (s, 1H), 7.96 (d, J=6.0 Hz, 1H), 7.92 (s, 1H), 7.62 (d, J=10.8 Hz, 1H), 7.47 (d, J=8.8 Hz, 1H), 7.23 (s, 1H), 6.96-6.79 (m, 3H), 6.25 (d, J=6.0 Hz, 1H), 4.98 (d, J=5.6 Hz, 1H), 3.49 (d, J=11.6 Hz, 2H), 3.17-2.98 (m, 6H), 2.96 (dd, J=5.6, 2.0 Hz, 1H), 2.93 (t, J=7.6 Hz, 2H), 2.89 (d, J=4.0 Hz, 3H), 2.54 (t, J=7.6 Hz, 2H), 2.30-2.23 (m, 1H) ppm. MS: M/e 595 (M+1)$^+$.

Compound 1.87 was prepared according to the procedures described for Compound 1.86 under appropriate conditions that could be recognized by one skilled in the art.

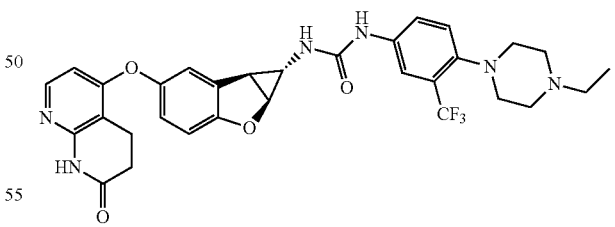

$^1$H NMR (400 MHz, DMSO-d6) δ 10.49 (s, 1H), 9.46 (s, 1H—CF3COOH), 9.02 (s, 1H), 7.96 (d, J=5.6 Hz, 1H), 7.93 (s, 1H), 7.63 (d, J=8.4 Hz, 1H), 7.47 (d, J=8.8 Hz, 1H), 7.23 (s, 1H), 6.98-6.81 (m, 3H), 6.25 (d, J=5.6 Hz, 1H), 4.98 (d, J=5.6 Hz, 1H), 3.56-3.55 (m, 2H), 3.30-3.18 (m, 2H), 3.13-2.99 (m, 6H), 2.96 (dd, J=5.6, 2.0 Hz, 1H), 2.93 (t, J=7.6 Hz, 2H), 2.54 (t, J=7.6 Hz, 2H), 2.33-2.20 (m, 1H), 1.24 (t, J=7.2 Hz, 3H) ppm. MS: M/e 609 (M+1)$^+$

EXAMPLE 2

Synthesis of Compounds 2.1-2.16

Compound 2.1: 1-(2,4-difluorophenyl)-3-((1S,1aS,6bS)-5-(pyrimidin-4-yloxy)-1a,6b-dihydro-1H-cyclopropa[b]benzofuran-1-yl)urea

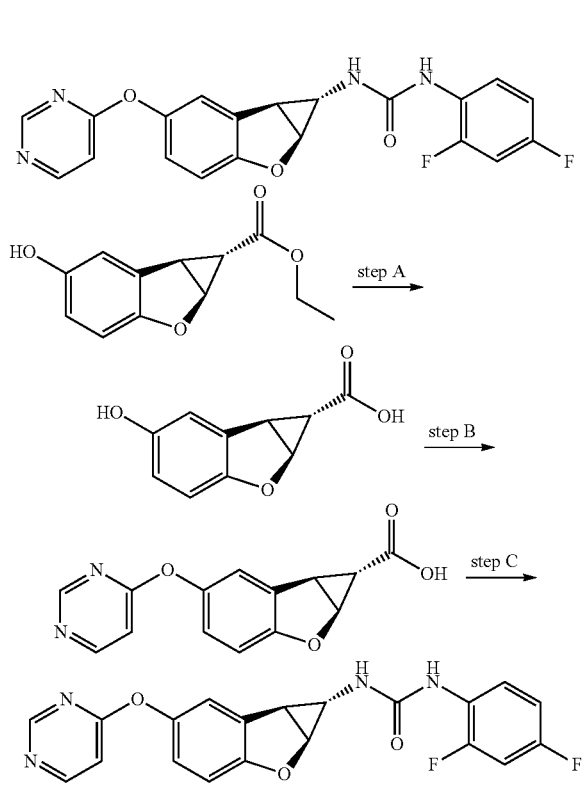

Step A: (1S,1aS,6bR)-5-hydroxy-1a,6b-dihydro-1H-cyclopropa[b]benzofuran-1-carboxylic acid

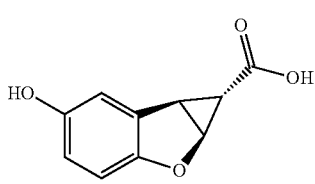

A mixture of (1S,1aS,6bR)-ethyl 5-hydroxy-1a,6b-dihydro-1H-cyclopropa[b]benzofuran-1-carboxylate (the product of Step G in synthesis of Compound 1.1, 4.4 g, 20 mmol) in NaOH (2N, 20 mL) in THF (40 mL) was stirred at 60° C. for 2 hours. The solvent was removed under reduced pressure and the residue was dissolved into water. The aqueous phase was adjusted to pH=3-4 by HCl (2 mol/L). The white solid was collected and dried in air to afford the title compound (3.8 g, 99%). $^1$H NMR (400 MHz, DMSO-d6) δ 12.51 (s, 1H), 9.03 (s, 1H), 6.88 (d, J=2.4 Hz, 1H), 6.71 (d, J=8.8 Hz, 1H), 6.54 (dd, J=8.8, 2.4 Hz, 1H), 5.07 (dd, J=5.6, 1.2 Hz, 1H), 3.21 (dd, J=5.6, 3.2 Hz, 1H), 1.06 (dd, J=3.2, 1.2 Hz, 1H) ppm.

Step B: (1S,1aS,6bR)-5-(pyrimidin-4-yloxy)-1a,6b-dihydro-1H-cyclopropa[b]benzofuran-1-carboxylic acid

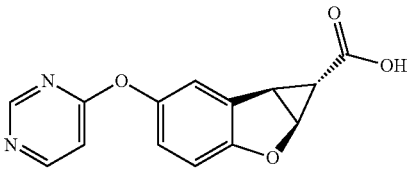

A mixture of the product of step A (576 mg, 3 mmol), 4-chloropyrimidine hydrochloride (344 mg, 3 mmol) and Cesium carbonate (2.9 g, 9 mmol) in DMF (10 mL) was stirred at 100° C. for 2 hours. The mixture was concentrated under reduced pressure and the residue was suspended with H$_2$O (20 mL). The water phase was adjusted to pH about 5-6 by HCl (2 mol/L). The mixture was filtered and the filtrate was lyophilized and suspended with DCM:MeOH (5:1, 100 mL). The mixture was filtered, the filtrate was concentrated under reduced pressure and purified by prep-HPLC to afford the title compound (100 mg, yield: 12%) as a yellow solid. $^1$H NMR (400 MHz, DMSO-d6) δ 8.76 (s, 1H), 8.66 (d, J=6.0 Hz, 1H), 7.38 (d, J=2.4 Hz, 1H), 7.11 (dd, J=6.0, 1.0 Hz, 1H), 7.02-6.99 (m, 2H), 5.25 (dd, J=5.2, 0.8 Hz, 1H), 3.32 (dd, J=5.2, 3.2 Hz, 1H), 1.22 (dd, J=3.2, 0.8 Hz, 1H) ppm.

Step C: 1-(2,4-difluorophenyl)-34(1S,1aS,6bS)-5-(pyrimidin-4-yloxy)-1a,6b-dihydro-1H-cyclopropa[b]benzofuran-1-yl)urea (Compound 2.1)

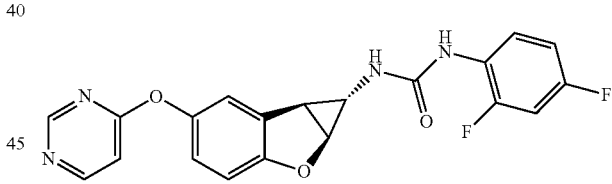

To a solution of the product of step B (50 mg, 0.19 mmol) and Et$_3$N (48 mg, 0.48 mmol) in 1,4-dioxane (2 mL) was added DPPA (63 mg, 0.23 mmol). The reaction mixture was stirred at room temperature for 2 hours. The 2,4-difluoroaniline (25 mg, 0.19 mmol) was added and the resulting mixture was stirred at 100° C. for 2 hours. The mixture was concentrated under reduced pressure. The residue was diluted with EA (40 mL), washed with brine (15 mL) and dried over anhydrous sodium sulfate. Then the mixture was filtered and concentrated under reduced pressure. The residue was purified by prep-HPLC to afford the title compound (30 mg, 40%) as a yellow solid. $^1$H NMR (400 MHz, DMSO-d6) δ 8.77 (s, 1H), 8.66 (d, J=6.0 Hz, 1H), 8.33 (s, 1H), 8.05-7.97 (m, 1H), 7.33-7.20 (m, 2H), 7.12-7.09 (m, 1H), 7.04-6.90 (m, 4H), 4.99 (d, J=6.0 Hz, 1H), 2.96 (dd, J=6.0, 1.6 Hz, 1H), 2.27-2.25 (m, 1H) ppm. MS: M/e 397(M+1)$^+$.

Compound 2.2 was prepared according to the procedures described for Compound 2.1 under appropriate conditions that could be recognized by one skilled in the art.

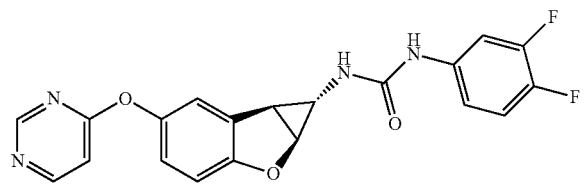 [SMILES: O=C(Nc1ccc(F)c(F)c1)N[C@@H]1[C@H]2Oc3ccc(Oc4ccncn4)cc3[C@@H]12]

$^1$H NMR (400 MHz, DMSO-d6) δ 8.83 (s, 1H), 8.77 (s, 1H), 8.66 (d, J=6.0 Hz, 1H), 7.68-7.60 (m, 1H), 7.35-7.25 (m, 2H), 7.15-7.06 (m, 2H), 6.99-6.89 (m, 2H), 6.77-6.73 (m, 1H), 4.98 (d, J=5.6 Hz, 1H), 2.95 (dd, J=5.6, 1.6 Hz, 1H), 2.28-2.23 (m, 1H) ppm. MS: M/e 397(M+1)$^+$.

Compound 2.3: 1-((1S,1aS,6bS)-5-((2-oxo-2,4-di-hydro-1H-pyrido[2,3-d][1,3] oxazin-5-yl)oxy)-1a, 6b-dihydro-1H-cyclopropa[b]benzofuran-1-yl)-3-(2,4,5-trifluorophenyl)urea

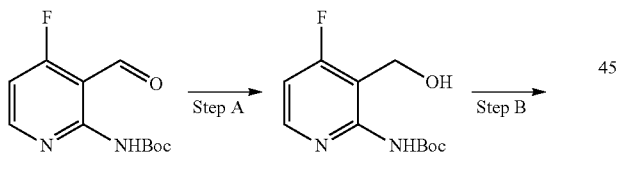

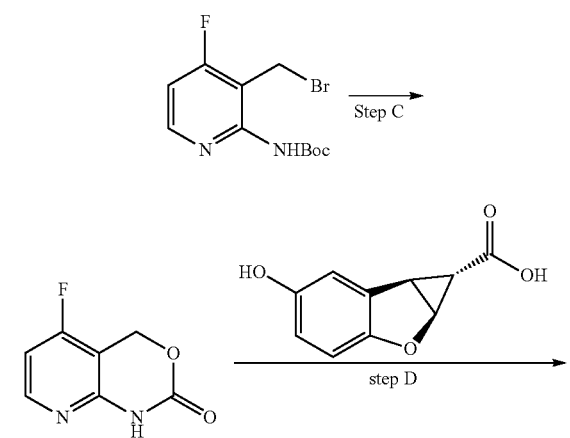

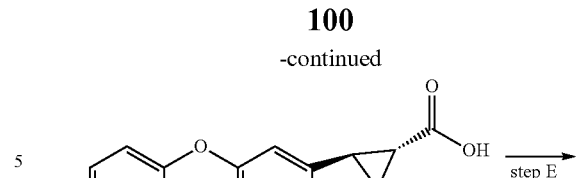

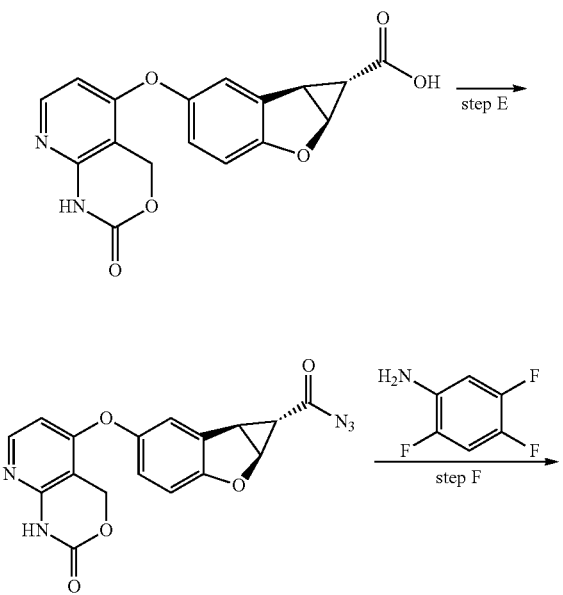

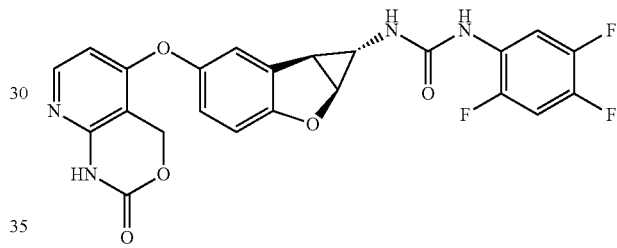

Step A: tert-butyl 4-fluoro-3-(hydroxymethyl)pyridin-2-ylcarbamate

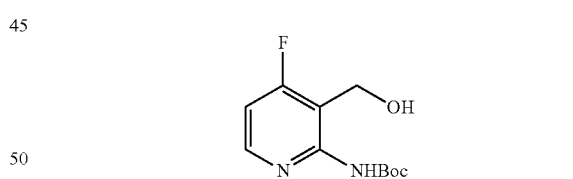

To a solution of tert-butyl (4-fluoro-3-formylpyridin-2-yl)carbamate (480 mg, 2 mmol) in MeOH (3 mL) was added NaBH$_4$ (76 mg, 2 mmol) at 0° C. The reaction was stirred at 0° C. for 30 min. The reaction was quenched with saturated NH$_4$Cl (1 mL) and water (5 mL), extracted with ethyl acetate (2×15 mL). The combined organic phase was dried over anhydrous sodium sulfate, filtered and concentrated under reduced pressure to obtain the title compound (460 mg, 95%) as a white solid which was used directly in the next step. $^1$H-NMR (600 MHz, DMSO-d$_6$) δ 9.20 (s, 1H), 8.31-8.28 (m, 1H), 7.11-7.09 (m, 1H), 5.26 (t, J=6.0 Hz, 1H), 4.48 (d, J=6.0 Hz, 2H), 1.45 (s, 9H) ppm. MS: M/e 243 (M+1)$^+$.

Step B: tert-butyl
3-(bromomethyl)-4-fluoropyridin-2-ylcarbamate

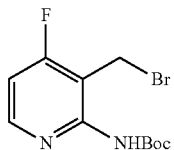 [SMILES: CC(C)(C)OC(=O)Nc1nccc(F)c1CBr]

CBr$_4$ (531 mg, 1.6 mmol) was added to a solution of the product of Step A (242 mg, 1 mmol) in THF (3 mL). Then a solution of triphenylphosphine in THF (1 mL) was added dropwise and the mixture was stirred at room temperature for 3 hours. The mixture was loaded onto a silica gel column. Eluted with (EtOAc:PE=1:3) to afford the title compound (160 mg, 52%) as a white solid. $^1$H-NMR (400 MHz, CDCl$_3$) δ 8.38-8.35 (m, 1H), 7.09 (s, 1H), 6.90-6.86 (m, 1H), 4.61 (s, 2H), 1.54 (s, 9H) ppm MS: M/e 305 (M+1)$^+$.

Step C:
5-fluoro-1H-pyrido[2,3-d][1,3]oxazin-2(4H)-one

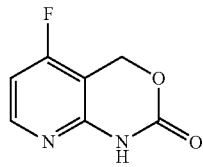 [SMILES: O=C1Nc2nccc(F)c2CO1]

The solution of the product of Step B (120 mg, 0.4 mmol) in DMSO (1 mL) was stirred at 60° C. for 4 hours under N$_2$. Then water (10 mL) was added and extracted with ethyl acetate (3×15 mL). The combined organic phase was washed with brine, dried over anhydrous sodium sulfate and concentrated under reduce pressure. The residue was purified by pre-TLC (EtOAc:PE=1:1) to give the title compound (20 mg, 30%) as a solid. $^1$H-NMR (600 MHz, DMSO-d$_6$) δ 10.95 (s, 1H), 8.21-8.18 (m, 1H), 6.97-6.94 (m, 1H), 5.37 (s, 2H) ppm. MS: M/e 169 (M+1)$^+$.

Step D: (1S,1aS,6bR)-5-((2-oxo-2,4-dihydro-1H-pyrido[2,3-d][1,3]oxazin-5-yl) oxy)-1a,6b-dihydro-1H-cyclopropa[b]benzofuran-1-carboxylic acid

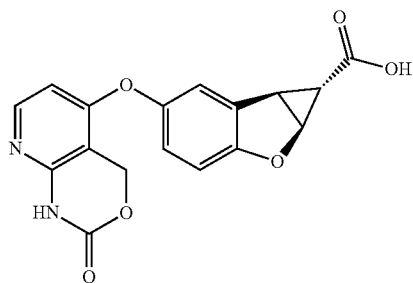 [SMILES: O=C1Nc2nccc(Oc3ccc4c(c3)[C@@H]3[C@H](O4)[C@H]3C(=O)O)c2CO1]

A mixture of the product of Step A in synthesis of Compound 2.1 (103 mg, 0.536 mmol), the product of step C (90 mg, 0.536 mmol) and Cs$_2$CO$_3$ (528 mg, 1.61 mmol) in DMF (3 mL) was stirred at 100° C. for 2 hours. Most of DMF was removed to give the residue, which was treated with H$_2$O (10 mL), acidified to pH=3-4 with aq.HCl (2.0 M), extracted with EtOAc (30 mL×4). The combined organic layers were washed with brine, dried over Na$_2$SO$_4$, concentrated and purified by prep-HPLC to give the target compound (30 mg, 16.5%) as a white solid. MS: M/e 341(M+1)$^+$.

Step E: (1S,1aS,6bR)-5-((2-oxo-2,4-dihydro-1H-pyrido[2,3-d][1,3]oxazin-5-yl) oxy)-1a,6b-dihydro-1H-cyclopropa[b]benzofuran-1-carbonyl azide

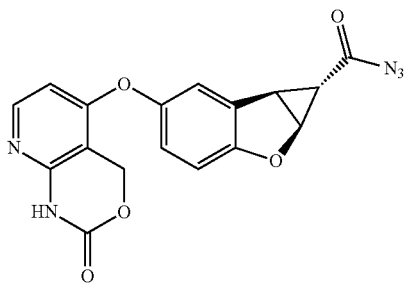 [SMILES: [N-]=[N+]=NC(=O)[C@@H]1[C@H]2Oc3ccc(Oc4ccnc5c4COC(=O)N5)cc3[C@H]21]

The product of step D (30 mg, 0.088 mmol) and Et$_3$N (8.9 mg, 0.088 mmol) were dissolved in DMF (2 mL), then DPPA (24 mg, 0.088 mmol) was added at room temperature. After the addition, the reaction was stirred for 4 hours at room temperature. The reaction mixture was treated with H$_2$O (20 mL) and extracted with EtOAc (15 mL×3). The combined organic layers were washed with brine, dried over Na$_2$SO$_4$ and concentrated to give crude product (100%), which was directly used to the next step. MS: M/e 366 (M+1)$^+$.

Step F: 1-((1S,1aS,6bS)-5-((2-oxo-2,4-dihydro-1H-pyrido[2,3-d][1,3]oxazin-5-yl) oxy)-1a,6b-dihydro-1H-cyclopropa[b]benzofuran-1-yl)-3-(2,4,5-trifluorophenyl)urea (Compound 2.3)

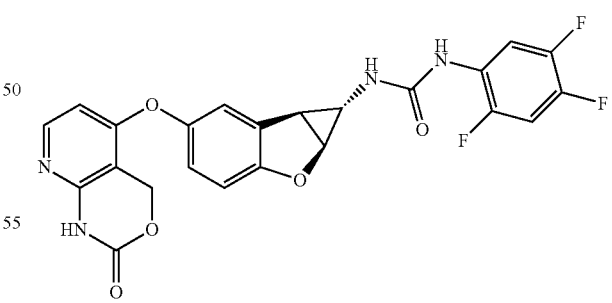

A mixture of the product of step E (crude, 0.088 mmol) and 2,4,5-trifluoroaniline (13 mg, 0.088 mmol) in dioxane (1 mL) was stirred at 80° C. for an hour. The reaction mixture was concentrated to give the residue, which was purified by prep-HPLC to give the target compound (12 mg, 28%) as a white solid. $^1$H NMR (400 MHz, DMSO-d6) δ 10.73 (s, 1H), 8.56 (s, 1H), 8.15-8.12 (m, 1H), 8.03 (d, J=6.0 Hz, 1H), 7.59-7.56 (m, 1H), 7.28 (d, J=1.2 Hz, 1H), 7.04 (d, J=0.8 Hz, 1H), 6.95 (s, 2H), 6.27 (d, J=6.0 Hz, 1H), 5.42 (s, 2H), 4.99 (d, J=5.6 Hz, 1H), 2.99-2.97 (m, 1H), 2.25-2.27 (m, 1H) ppm. MS: M/e 485 (M+1)+.

Compound 2.4: 1-(4-fluoro-3-(trifluoromethyl)phenyl)-3-((1S,1aS,6bS)-5-((2-oxo-1,2,3,4-tetrahydropyrido[2,3-d]pyrimidin-5-yl)oxy)-1a,6b-dihydro-1H-cyclopropa[b]benzofuran-1-yl) urea

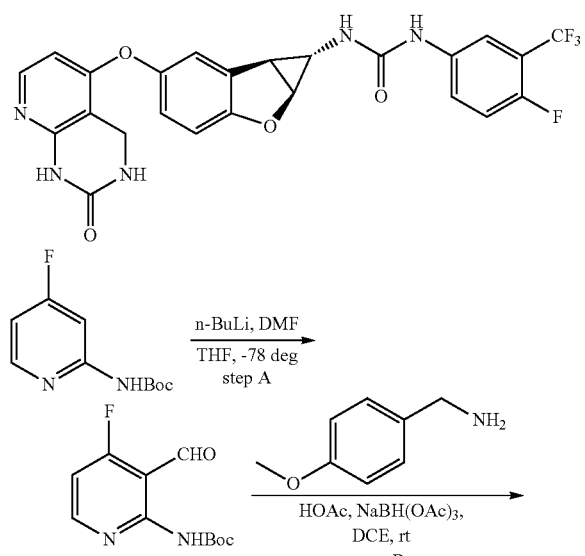

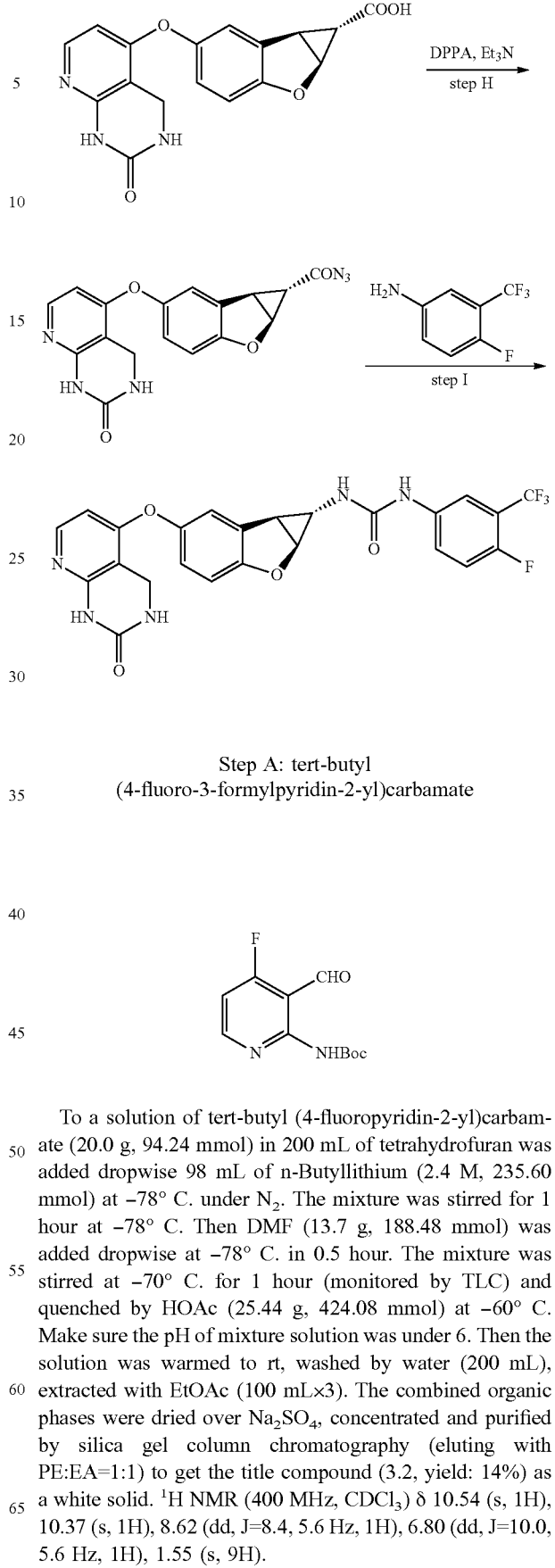

Step A: tert-butyl (4-fluoro-3-formylpyridin-2-yl)carbamate

To a solution of tert-butyl (4-fluoropyridin-2-yl)carbamate (20.0 g, 94.24 mmol) in 200 mL of tetrahydrofuran was added dropwise 98 mL of n-Butyllithium (2.4 M, 235.60 mmol) at −78° C. under $N_2$. The mixture was stirred for 1 hour at −78° C. Then DMF (13.7 g, 188.48 mmol) was added dropwise at −78° C. in 0.5 hour. The mixture was stirred at −70° C. for 1 hour (monitored by TLC) and quenched by HOAc (25.44 g, 424.08 mmol) at −60° C. Make sure the pH of mixture solution was under 6. Then the solution was warmed to rt, washed by water (200 mL), extracted with EtOAc (100 mL×3). The combined organic phases were dried over $Na_2SO_4$, concentrated and purified by silica gel column chromatography (eluting with PE:EA=1:1) to get the title compound (3.2, yield: 14%) as a white solid. $^1H$ NMR (400 MHz, $CDCl_3$) δ 10.54 (s, 1H), 10.37 (s, 1H), 8.62 (dd, J=8.4, 5.6 Hz, 1H), 6.80 (dd, J=10.0, 5.6 Hz, 1H), 1.55 (s, 9H).

Step B: tert-butyl (4-fluoro-3-(((4-methoxybenzyl)amino)methyl)pyridin-2-yl) carbamate

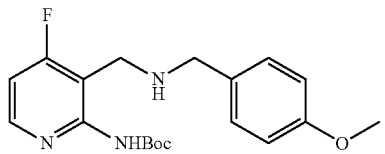 [SMILES: COc1ccc(CNCc2c(F)ccnc2NC(=O)OC(C)(C)C)cc1]

To the solution of the product of Step A (2.67 g, 11.11 mmol) and (4-methoxyphenyl)methanamine (1.83 g, 13.33 mmol) in 1,2-dichloroethane (30 mL) was added acetic acid (666 mg, 11.11 mmol). The solution was stirred at room temperature for 10 min. To this solution was added NaBH(OAc)$_3$ (11.77 g, 55.55 mmol). The solution was stirred at room temperature for 5 hours. TLC (PE/EA=1/1) showed the reaction was completed. The resulting solution was quenched by NaHCO$_3$ aqueous solution, extracted with EA (100 mL×3). The combined organic layers were dried over Na$_2$SO$_4$, concentrated and purified by silica gel column chromatography (eluting with PE:EA=1:1) to get the title compound (2 g, yield: 50%) as yellow oil. MS: M/e 362 (M+1)$^+$.

Step C: 4-fluoro-3-(((4-methoxybenzyl)amino)methyl)pyridin-2-amine

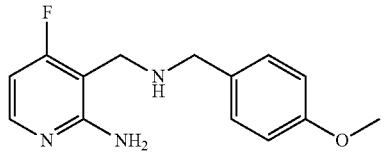 [SMILES: COc1ccc(CNCc2c(F)ccnc2N)cc1]

To the solution of the product of Step B (2 g, 5.53 mmol) in DCM (2 mL) was added TFA (5 mL). The solution was stirred at room temperature for 5 hours. TLC (DCM/MeOH=20/1) showed the reaction was completed. The resulting solution was concentrated under reduced pressure, the residue was neutralized by NaHCO$_3$ aqueous solution till pH=7-8, then extracted with DCM (50 mL×3). The combined organic layer was dried over Na$_2$SO$_4$, concentrated and purified by silica gel column chromatography (weight of silica: 10 g, eluting with DCM/MeOH=20:1) to get the title compound (900 mg, yield=64%) as yellow oil. MS: M/e 262 (M+1)$^+$.

Step D: 5-fluoro-3-(4-methoxybenzyl)-3,4-dihydropyrido[2,3-d]pyrimidin-2(1H)-one

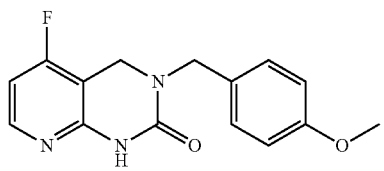 [SMILES: COc1ccc(CN2Cc3c(F)ccnc3NC2=O)cc1]

A mixture of the product of Step C (880 mg, 3.36 mmol), CDI (1.64 g, 10.10 mmol) in CH$_3$CN (10 mL) was stirred at 50° C. under N$_2$ for 2 hours. TLC (PE/EA=1/1) showed the reaction was completed. The resulting solution was filtered, the solid was washed by water (10 mL) followed by methanol (10 mL) to get the title compound (300 mg, yield: 31%) as a white solid. MS: M/e 288 (M+1)$^+$.

Step E: 5-fluoro-3,4-dihydropyrido[2,3-d]pyrimidin-2(1H)-one

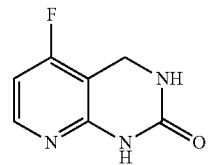 [SMILES: O=C1NCc2c(F)ccnc2N1]

The product of Step D (300 mg, 1.04 mmol) was dissolved in TFA (3 mL) in sealing tube. The solution was stirred at 85° C. overnight. The resulting solution was cooled, concentrated under reduced pressure to get the residue (170 mg, yield: 98%) which was used in next step directly. MS: M/e 168 (M+1)$^+$.

Step F: (1S,1aS,6bR)-ethyl 5-((2-oxo-1,2,3,4-tetrahydropyrido[2,3-d]pyrimidin-5-yl)oxy)-1a,6b-dihydro-1H-cyclopropa[b]benzofuran-1-carboxylate

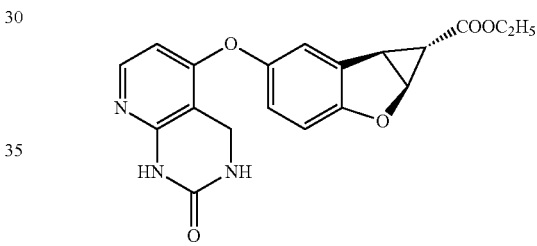

A mixture of the product of Step E (100 mg, 0.60 mmol), (1S,1aS,6bR)-ethyl 5-hydroxy-1a,6b-dihydro-1H-cyclopropa[b]benzofuran-1-carboxylate (the product of Step G in synthesis of Compound 1.1, 131 mg, 0.60 mmol) and Potassium tert-butoxide (71 mg, 0.63 mmol) in DMF (2 mL) was stirred at 120° C. for 2 hours (monitored by LC_MS). The resulting solution was concentrated under reduced pressure to remove excess solvent, the residue was washed by water (2 mL), the black solid was formed and filtered to get the crude product (120 mg, yield: 55%) which was used in next step directly. MS: M/e 368 (M+1)$^+$.

Step G: (1S,1aS,6bR)-5-((2-oxo-1,2,3,4-tetrahydropyrido[2,3-d]pyrimidin-5-yl)oxy)-1a,6b-dihydro-1H-cyclopropa[b]benzofuran-1-carboxylic acid

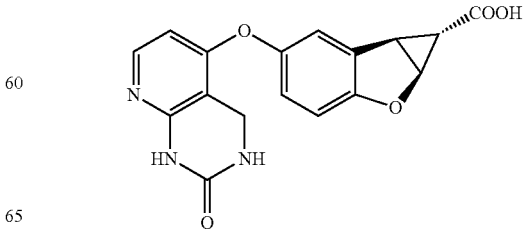

The product of Step F (120 mg, 0.33 mmol) was diluted in ethanol (3 mL), added NaOH (26 mg, 0.66 mmol) in H$_2$O (2 mL) dropwise. The solution was stirred at room temperature for 2 hours, then added HCl (2 mol/L) aqueous solution till pH=5-6. The resulting solution was concentrated and the residue was washed by water (5 mL). The solid was formed and filtered to get the title compound (88 mg, yield: 79%) as a black solid, which was used into next step directly. MS: M/e 340 (M+1)$^+$.

Step H: (1S,1aS,6bR)-5-((2-oxo-1,2,3,4-tetrahydro-pyrido[2,3-d]pyrimidin-5-yl) oxy)-1a,6b-dihydro-1H-cyclopropa[b]benzofuran-1-carbonyl azide

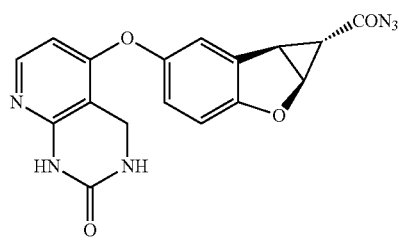

To a 0° C. solution of the product of Step G (60 mg, 0.18 mmol) in 1,4-dioxane (5 mL) was added Et$_3$N (45 mg, 0.44 mmol) followed by DPPA (59 mg, 0.22 mmol). The resulted mixture was warmed to ambient temperature and stirred for 5 hours. The resulting solution was used in next step directly.

Step I: 1-(4-fluoro-3-(trifluoromethyl)phenyl)-3-((1S,1aS,6bS)-5-((2-oxo-1,2,3,4-tetrahydropyrido[2,3-d]pyrimidin-5-yl)oxy)-1a,6b-dihydro-1H-cyclopropa[b]benzofuran-1-yl)urea (Compound 2.4)

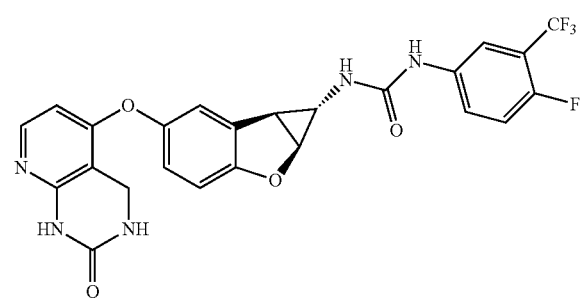 [SMILES: O=C1NCc2c(Oc3ccc4c(c3)[C@H]3[C@H](NC(=O)Nc5ccc(F)c(C(F)(F)F)c5)[C@H]3O4)ccnc2N1]

To the solution of Step H in 1,4-dioxane (2 mL) was added 4-fluoro-3-(trifluoromethyl)aniline (35 mg, 0.2 mmol). The solution was stirred at 100° C. under N$_2$ for 2 hours (monitored by LC_MS). The resulting solution was concentrated under reduced pressure and purified by prep-HPLC to get the title compound (4.5 mg, 5%) as a white solid. $^1$H NMR (400 MHz, DMSO-d6) δ 9.46 (s, 1H), 9.03 (s, 1H), 7.95 (d, J=4.4 Hz, 1H), 7.88 (d, J=5.6 Hz, 1H), 7.58 (s, 1H), 7.35 (t, J=10.0 Hz, 1H), 7.21 (s, 1H), 6.97 (s, 1H), 6.93-6.82 (m, 3H), 6.10 (d, J=5.6 Hz, 1H), 4.95 (d, J=5.6 Hz, 1H), 4.36 (s, 2H), 2.93 (d, J=5.6 Hz, 1H), 2.27-2.17 (m, 1H) ppm. MS: M/e 516 (M+1)$^+$.

Compound 2.5 was prepared according to the procedures described for Compound 2.4 under appropriate conditions that could be recognized by one skilled in the art.

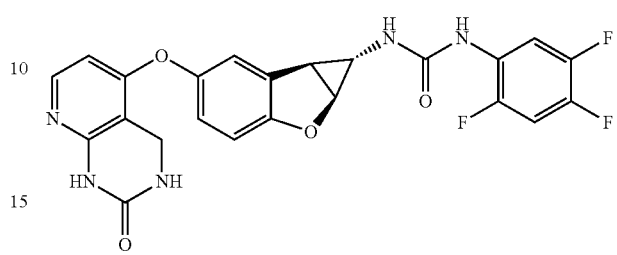

$^1$H NMR (400 MHz, DMSO-d6) δ 9.45 (s, 1H), 8.52 (s, 1H), 8.17-8.04 (m, 1H), 7.87 (d, J=6.0 Hz, 1H), 7.55-7.51 (m, 1H), 7.21 (s, 1H), 6.99 (d, J=8.4 Hz, 2H), 6.89 (d, J=1.6 Hz, 2H), 6.10 (d, J=6.0 Hz, 1H), 4.95 (d, J=5.6 Hz, 1H), 4.36 (s, 2H), 2.93 (d, J=4.0 Hz, 1H), 2.24-2.18 (m, 1H) ppm. MS: M/e 484 (M+1)$^+$.

Compound 2.6: N-methyl-4-(((1S,1aS,6bS)-1-(3-(3-(trifluoromethyl)phenyl) ureido)-1a,6b-dihydro-1H-cyclopropa[b]benzofuran-5-yl)oxy)picolinamide

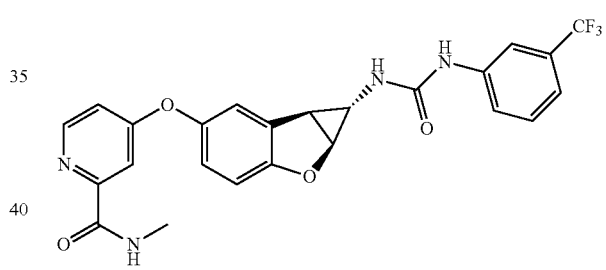

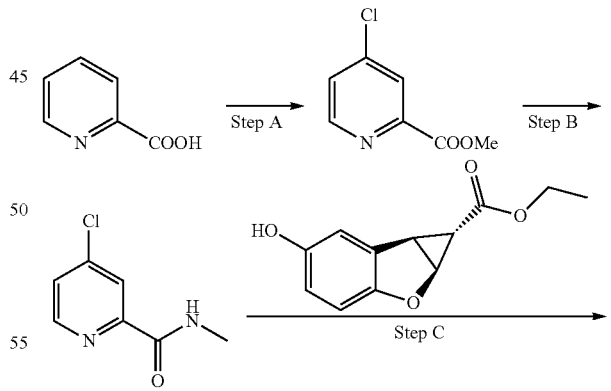

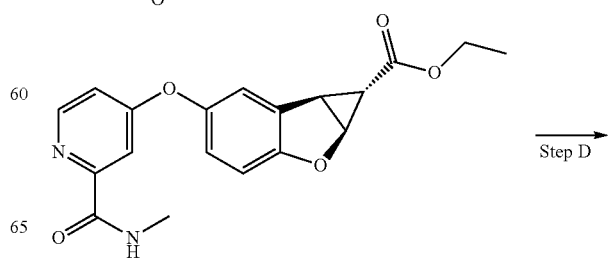

-continued

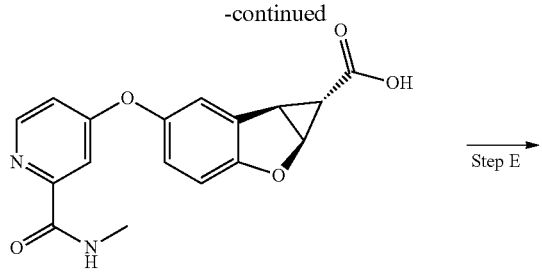

Step E

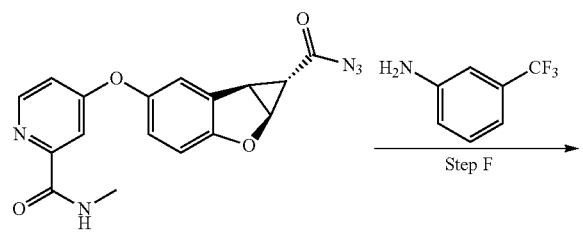

Step F

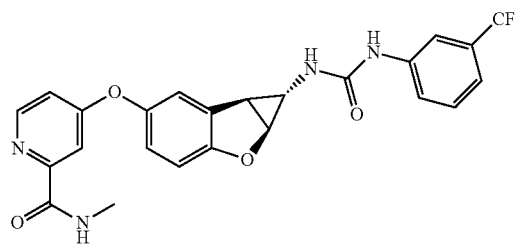

Step A: methyl 4-chloropicolinate

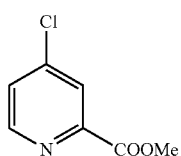 [SMILES: COC(=O)c1cc(Cl)ccn1]

Anhydrous DMF (1 mL) was slowly added to sulfurous dichloride (30 mL) at 45° C. The solution was stirred at room temperature for 10 min, and then picolinic acid (10 g, 81 mmol) was added over 30 min. The resulting solution was heated at 72° C. for 16 hours to generate yellow solid. The mixture was cooled to room temperature, diluted with toluene (50 mL) and concentrated to 20 mL. The toluene addition/concentration process was repeated twice. The resulting solution and solid was added into 20 mL methanol at ice bath to keep the internal temperature below 55° C. The mixture was stirred at room temperature for 45 min, cooled to 5° C. and treated with ethyl ether (20 mL) dropwisely. The resulting solid was filtered, washed with ethyl ether (20 mL) and dried under 35° C. to provide a white yellow solid. After the solid were solvated to hot water (50 mL, 45° C.), sodium bicarbonate aqueous solution was added to adjust pH to 8~9. The mixture was extracted with ethyl acetate (2×30 mL) and the organic phase was concentrated to give desired compound (5.5 g, yield: 39.6%) as off-white solid.

Step B: 4-chloro-N-methylpicolinamide

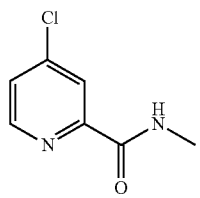

To a solution of the product of Step A (5.5 g, 32.2 mmol) in methanol (60 mL) was added methylamine in methanol (2.2 mL) at 5° C. The mixture was stirred at 0~5° C. for 2 hours. The solvent was evaporated at 40~50° C. to give the title compound (6.2 g, yield: 90%) as a yellow solid. $^1$H NMR (400 MHz, DMSO-d6) δ 8.85 (br, 1H), 8.63 (d, J=5.2 Hz, 1H), 8.05-8.02 (m, 1H), 7.76 (dd, J=5.2, 2.0 Hz, 1H), 2.85 (d, J=4.8 Hz, 3H). MS: M/e 171 (M+1)$^+$.

Step C: (1S,1aS,6bR)-ethyl 5-((2-(methylcarbamoyl)pyridin-4-yl)oxy)-1a,6b-dihydro-1H-cyclopropa[b]benzofuran-1-carboxylate

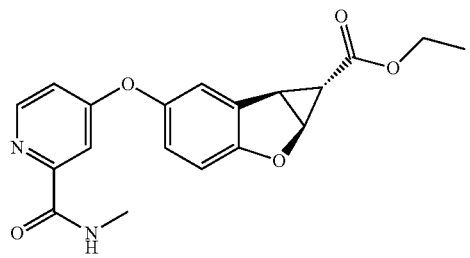 [SMILES: CCOC(=O)[C@@H]1[C@H]2Oc3ccc(Oc4ccnc(C(=O)NC)c4)cc3[C@H]21]

The mixture of the product of Step B (1.5 g, 8.82 mmol), Intermediate I (1.94 g, 8.82 mmol) and Cesium carbonate (3.45 g, 10.6 mmol) in DMF (20 mL) was stirred at 110° C. for 2 hours. Water (20 mL) was added to quench the reaction which was extracted with ethyl acetate (2×20 mL). The combined organic phase was washed with brine, dried over anhydrous sodium sulfate and concentrated under reduced pressure. The residue was purified by silica gel chromatography (silica gel weight: 30 g, elute: EA/PE: 1/3) to afford the title product (1.4 g, yield: 44.9%) as a yellow solid. MS: M/e 355 (M+1)$^+$.

Step D: (1S,1aS,6bR)-5-((2-(methylcarbamoyl)pyridin-4-yl)oxy)-1a,6b-dihydro-1H-cyclopropa[b]benzofuran-1-carboxylic acid

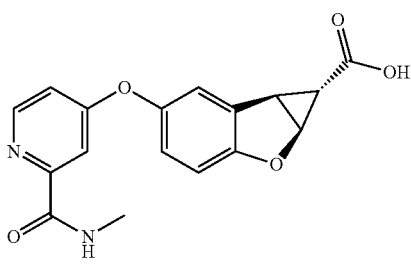 [SMILES: CNC(=O)c1cc(Oc2ccc3c(c2)[C@@H]2[C@H](O3)[C@H]2C(=O)O)ccn1]

To a stirred solution of the product of step C (1.4 g, 4.0 mmol) in THF/H₂O (8 mL/2 mL) was added sodium hydroxide aqueous solution (4 mL, 2 mol/L) at room temperature. The mixture was stirred at 60° C. for 2 hours. The solvent was concentrated and the residue was dissolved into 20 mL water. Hydrochloric acid (2 mol/L) was added to adjust pH to 7. The mixture was extracted with ethyl acetate (2×20 mL). The organic phase was washed with brine, dried over anhydrous sodium sulfate and concentrated under reduced pressure. The residue (800 mg, yield: 61.5%) as a yellow solid which was used into next step directly. MS: M/e 327 (M+1)⁺.

Step E: (1S,1aS,6bR)-5-((2-(methylcarbamoyl)pyridin-4-yl)oxy)-1a,6b-dihydro-1H-cyclopropa[b]benzofuran-1-carbonyl azide

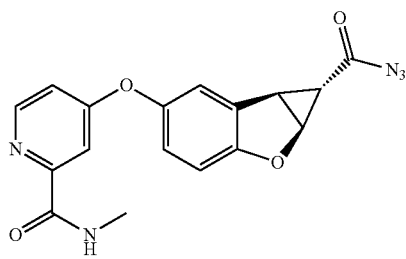 [SMILES: CNC(=O)c1cc(Oc2ccc3c(c2)[C@@H]2[C@H](O3)[C@H]2C(=O)N=[N+]=[N-])ccn1]

To a solution of the product of Step D (400 mg, 1.23 mmol) in DMF (10 mL) was added Et₃N and followed by DPPA at 0° C. The resulted mixture was warmed to room temperature and stirred for 5 hours. Water (20 mL) was added and the mixture was extracted with ethyl acetate (3×20 mL). The combined extracted phase was washed with brine, dried over anhydrous sodium sulfate and concentrated under reduced pressure. The residue (300 mg, yield: 69.8%) as yellow oil was used into next step directly. MS: M/e 352 (M+1)⁺.

Step F: N-methyl-4-(((1S,1aS,6bS)-1-(3-(3-(trifluoromethyl)phenyl)ureido)-1a,6b-dihydro-1H-cyclopropa[b]benzofuran-5-yl)oxy)picolinamide (Compound 2.6)

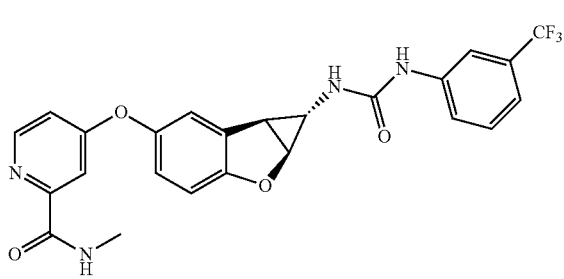 [SMILES: CNC(=O)c1cc(Oc2ccc3c(c2)[C@H]2[C@H](NC(=O)Nc4cccc(C(F)(F)F)c4)[C@H]2O3)ccn1]

The mixture of the product of Step E (100 mg, 0.28 mmol) and 3-(trifluoromethyl)aniline (45.9 mg, 0.28 mmol) in 1,4-dioxane (2 mL) was stirred at reflux for 2 hours. The reaction mixture was concentrated under reduced pressure and the residue was purified by prep-HPLC to afford the title compound (40.09 mg, yield: 29%) as a white solid. ¹H NMR (400 MHz, DMSO-d6) δ 8.97 (s, 1H), 8.84-8.72 (m, 1H), 8.50 (d, J=5.6 Hz, 1H), 7.99 (s, 1H), 7.56 (d, J=8.0 Hz, 1H), 7.46 (t, J=8.0 Hz, 1H), 7.38 (d, J=2.4 Hz, 1H), 7.31 (s, 1H), 7.26 (d, J=8.0 Hz, 1H), 7.12 (dd, J=5.6, 2.4 Hz, 1H), 7.02-6.94 (m, 2H), 6.80 (d, J=2.0 Hz, 1H), 5.02 (d, J=5.6 Hz, 1H), 3.00 (dd, J=5.6, 2.0 Hz, 1H), 2.79 (d, J=4.8 Hz, 3H), 2.36-2.25 (m, 1H) ppm. MS: M/e 485 (M+1)⁺.

Compounds 2.7-2.8 were prepared according to the procedures described for Compound 2.6 under appropriate conditions that could be recognized by one skilled in the art.

Compound 2.7

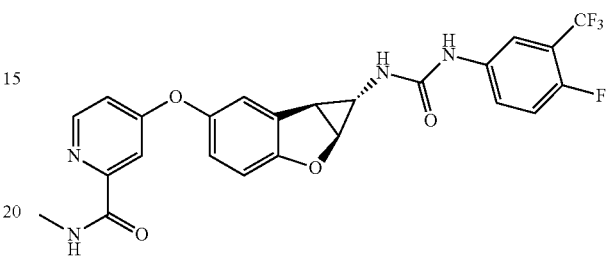

¹H NMR (400 MHz, DMSO-d6) δ 8.98 (s, 1H), 8.82-8.74 (m, 1H), 8.50 (d, J=5.6 Hz, 1H), 7.98 (dd, J=6.4, 2.4 Hz, 1H), 7.69-7.59 (m, 1H), 7.44-7.35 (m, 2H), 7.31 (s, 1H), 7.12 (dd, J=5.6, 2.4 Hz, 1H), 7.01-6.95 (m, 2H), 6.84 (s, 1H), 5.01 (d, J=5.6 Hz, 1H), 2.99 (dd, J=5.6, 1.6 Hz, 1H), 2.79 (d, J=4.8 Hz, 3H), 2.33-2.27 (m, 1H) ppm. MS: M/e 503 (M+1)⁺.

Compound 2.8

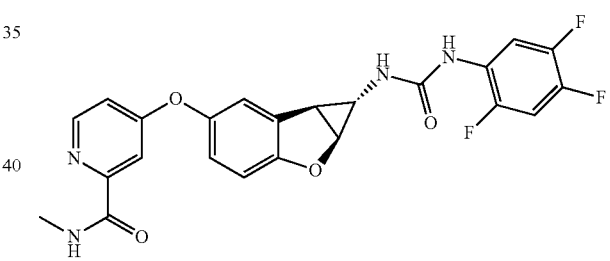

¹H NMR (400 MHz, DMSO-d6) δ 8.84-8.70 (m, 1H), 8.56 (s, 1H), 8.50 (d, J=5.6 Hz, 1H), 8.24-8.07 (m, 1H), 7.65-7.50 (m, 1H), 7.37 (d, J=2.4 Hz, 1H), 7.31 (s, 1H), 7.12 (dd, J=5.6, 2.4 Hz, 1H), 7.03 (d, J=1.6 Hz, 1H), 6.98 (s, 2H), 5.02 (d, J=5.6 Hz, 1H), 2.99 (dd, J=5.6, 1.6 Hz, 1H), 2.79 (d, J=4.8 Hz, 3H), 2.33-2.26 (m, 1H) ppm. MS: M/e 471 (M+1)⁺.

Compound 2.9: 1-((1S,1aS,6bS)-5-((2-aminopyridin-4-yl)oxy)-1a,6b-dihydro-1H-cyclopropa[b]benzofuran-1-yl)-3-(2,4-difluorophenyl)urea

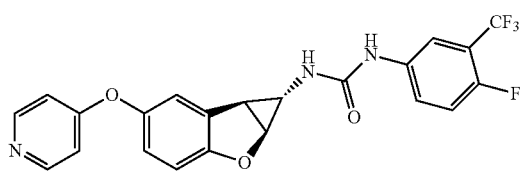

-continued

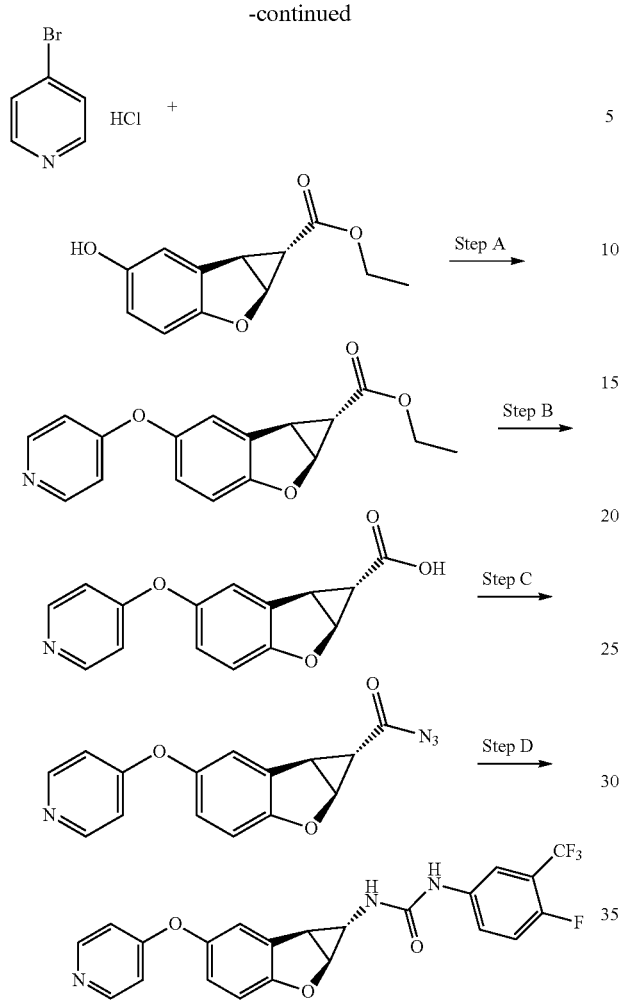

Step A: (1S,1aS,6bR)-ethyl 5-(pyridin-4-yloxy)-1a, 6b-dihydro-1H-cyclopropa[b]benzofuran-1-carboxylate

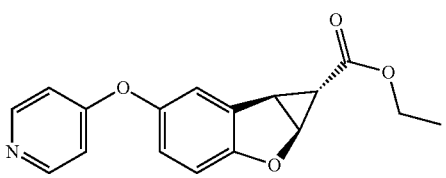 [SMILES: CCOC(=O)[C@@H]1[C@H]2Oc3ccc(Oc4ccncc4)cc3[C@H]21]

The mixture of (1S,1aS,6bR)-ethyl 5-hydroxy-1a,6b-dihydro-1H-cyclopropa[b]benzofuran-1-carboxylate (the product of Step G in synthesis of compound 1.1, 2.2 g, 10 mmol), 4-bromopyridine hydrochloride (1.95 g, 10 mmol), cesium carbonate (9.8 g, 30 mmol) and copper(I) iodide (cat.) in DMF (30 mL) was stirred at 130° C. for 8 hrs. The reaction was filtered through a celite pad. The filtrate was concentrated, diluted with EA (400 mL), washed with brine (100 mL×3), dried over sodium sulfate anhydrous and concentrated. The residue was purified by column chromatography (petroleum ether/EtOAc 2:3) to give the target compound (0.41 g, 15%) as oil. $^1$H NMR (400 MHz, DMSO-d6) δ 8.47 (s, 2H), 7.36 (d, J=2.4 Hz, 1H), 7.11-6.96 (m, 2H), 6.89 (br.s, 2H), 5.30 (dd, J=5.2, 1.2 Hz, 1H), 4.11 (q, J=7.2, 12 Hz, 2H), 3.37 (dd, J=5.2, 3.2 Hz, 1H), 1.39 (dd, J=3.2, 1.2 Hz, 1H), 1.21 (t, J=7.2 Hz, 3H). ppm.

Step B: (1S,1aS,6bR)-5-(pyridin-4-yloxy)-1a,6b-dihydro-1H-cyclopropa[b]benzofuran-1-carboxylic acid

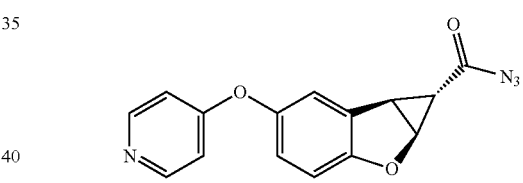

A mixture of the product of step A (400 mg, 1.3 mmol) in NaOH (2N, 2 mL, 4 mmol) and THF (8 mL) was stirred at 60° C. for 4 hrs. Removing THF, the residue was diluted with H$_2$O (10 mL) and adjusted to pH=6 by 2N HCl. The solid was collected and dried to afford the product (270 mg, 77%) as offwhite solid. $^1$H NMR (400 MHz, DMSO-d6) δ 12.65 (br.s, 1H), 8.43 (br.s, 2H), 7.36 (d, J=2.0 Hz, 1H), 7.11-6.95 (m, 2H), 6.89 (s, 2H), 5.24 (d, J=5.2 Hz, 1H), 3.32-3.30 (m, 1H), 1.20-1.16 (m, 1H). ppm.

Step C: (1S,1aS,6bR)-5-(pyridin-4-yloxy)-1a,6b-dihydro-1H-cyclopropa[b]benzofuran-1-carbonyl azide

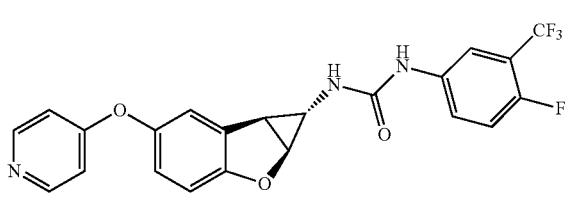 [SMILES: O=C(Nc1ccc(F)c(C(F)(F)F)c1)N[C@@H]1[C@H]2Oc3ccc(Oc4ccncc4)cc3[C@@H]12]

To a solution of the product of step B (270 mg, 1 mmol) and Et$_3$N (303 mg, 3 mmol) in DMF (5 mL) was added DPPA (330 mg, 1.2 mmol) at rt. The reaction mixture was stirred at rt for 2 h. The resulting mixture was diluted with EA (150 mL), washed with brine (30 mL×3), dried over anhydrous sodium sulfate, concentrated to give the crude product (280 mg, 92%) as brown oil which was directly used in the next step.

Step D: 1-((1S,1aS,6bS)-5-((2-aminopyridin-4-yl)oxy)-1a,6b-dihydro-1H-cyclopropa[b]benzofuran-1-yl)-3-(2,4-difluorophenyl)urea (Compound 2.9)

To a mixture of the product of step C (90 mg, 0.25 mmol) and 4-fluoro-3-(trifluoromethyl)aniline (50 mg, 0.28 mmol)

in dioxane (2 mL) was stirred at 100° C. for 2 h. Concentrated, the residue was directly purified prep-TLC (petroleum ether/EtOAc 1:3) and further purified by prep-HPLC to get title compound (10 mg, 12%) as a white solid. $^1$H NMR (400 MHz, DMSO-d6) δ 9.03 (s, 1H), 8.45-8.40 (m, 2H), 7.98 (dd, J=6.4, 2.8 Hz, 1H), 7.66-7.60 (m, 1H), 7.39 (t, J=10.0 Hz, 1H), 7.27-7.25 (m, 1H), 6.97-6.93 (m, 2H), 6.90-6.85 (m, 3H), 4.99 (d, J=5.6 Hz, 1H), 2.98 (dd, J=5.6, 1.6 Hz, 1H), 2.29-2.27 (m, 1H). MS: M/e 446 (M+1)$^+$ Compounds 2.10-2.11 were prepared according to the procedures described for Compound 2.9 under appropriate conditions that could be recognized by one skilled in the art.

Compound 2.10

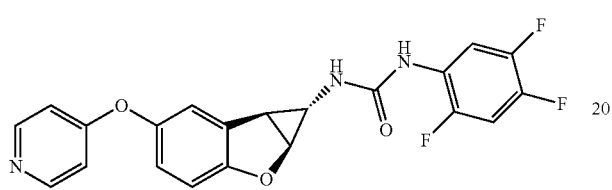

$^1$H NMR (400 MHz, DMSO-d6) δ 8.73-8.68 (m, 2H), 8.60-8.55 (m, 1H), 8.19-8.09 (m, 1H), 7.64-7.55 (m, 1H), 7.40-7.38 (m, 1H), 7.36-7.30 (m, 2H), 7.08-7.00 (m, 3H), 5.05 (d, J=5.6 Hz, 1H), 3.01 (dd, J=5.6, 2.0 Hz, 1H), 2.31-2.90 (m, 1H). MS: M/e 414(M+1)$^+$

Compound 2.11

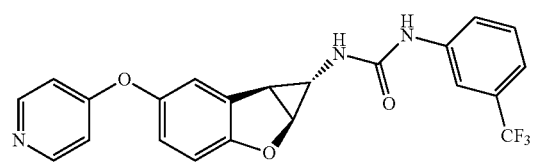 [SMILES: O=C(Nc1cccc(C(F)(F)F)c1)N[C@@H]1[C@H]2Oc3ccc(Oc4ccncc4)cc3[C@@H]12]

$^1$H NMR (400 MHz, DMSO-d6) δ 9.32-9.25 (m, 1H), 8.65-8.55 (m, 2H), 8.01 (s, 1H), 7.57-8.53 m, 1H), 7.46 (t, J=8.0 Hz, 1H), 7.36-7.34 (m, 1H), 7.27-7.23 (m, 1H), 7.20-7.09 (m, 3H), 7.03-6.98 (m, 2H), 5.02 (d, J=5.6 Hz, 1H), 2.99 (dd, J=5.6, 2.0 Hz, 1H), 2.31-2.28 (m, 1H). MS: M/e 428 (M+1)$^+$

Compound 2.12: 1-((1S,1aS,6bS)-5-((9H-purin-6-yl)oxy)-1a,6b-dihydro-1H-cyclopropa[b]benzofuran-1-yl)-3-(4-fluoro-3-(trifluoromethyl)phenyl)urea

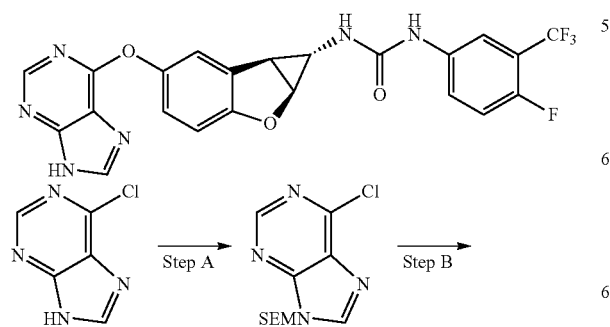

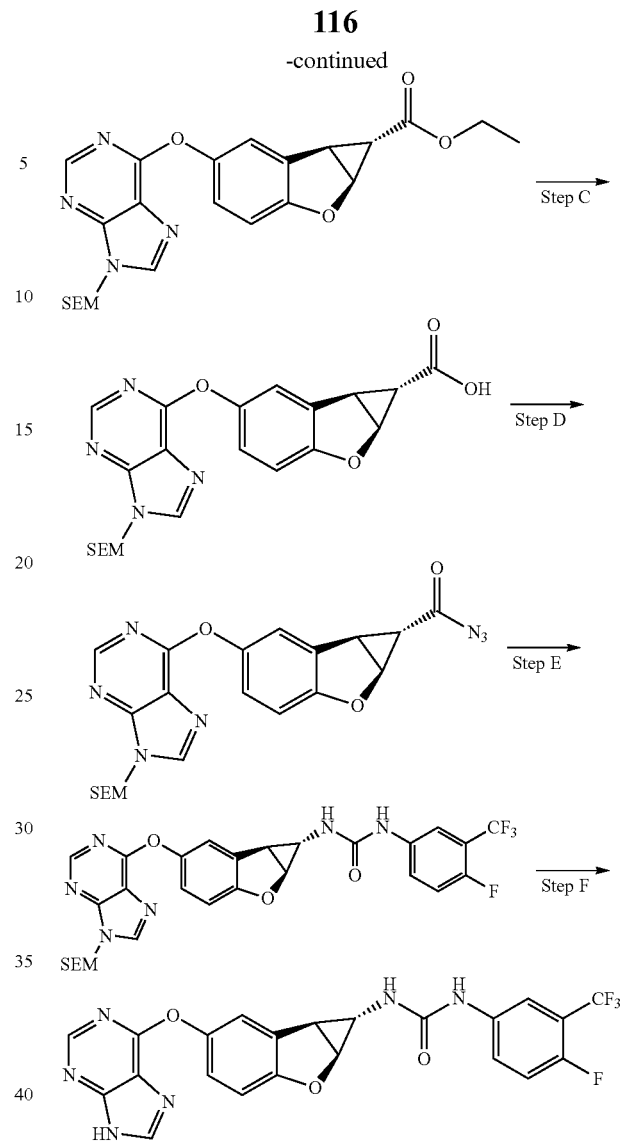

Step A: 6-chloro-9-((2-(trimethylsilyl)ethoxy)methyl)-9H-purine

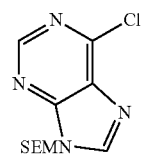 [SMILES: C[Si](C)(C)CCOCn1cnc2c(Cl)ncnc21]

To a solution of 6-chloro-9H-purine (2 g, 13 mmol) and Potassium carbonate (3.6 g, 26 mmol) in DMF (30 mL) was added (2-(chloromethoxy)ethyl)trimethylsilane (3.3 g, 19.5 mmol) at room temperature. The mixture was stirred at room temperature overnight. Water (50 mL) was added to quench the reaction and EA (2×30 mL) extracted. The combined organic phase were washed with brine, dried over anhydrous sodium sulfate and concentrated under reduced pressure. The residue was purified by silica gel chromatography (elute: EA/PE: 1/10) to afford the title compound (2.1 g, yield: 65.6%) as colorless liquid. $^1$H NMR (400 MHz, CDCl$_3$) δ 8.81 (s, 1H), 8.35 (s, 1H), 5.73 (s, 2H), 3.67 (t, J=2.4 Hz, 2H), 0.98 (t, J=2.4 Hz, 2H), 0.00 (s, 9H) ppm. MS: M/e 285 (M+1)$^+$ Step B: (1S,1aS,6bR)-ethyl 5-((9-((2-(trimethylsilyl)ethoxy)methyl)-9H-purin-6-yl)oxy)-1a,6b-dihydro-1H-cyclopropa[b]benzofuran-1-carboxylate

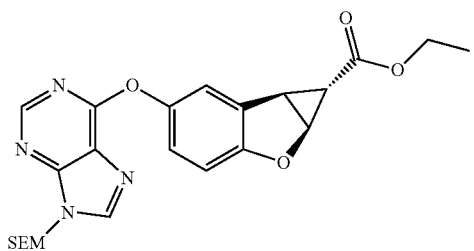 [SMILES: CCOC(=O)[C@@H]1[C@H]2Oc3ccc(Oc4ncnc5c4ncn5COCC[Si](C)(C)C)cc3[C@H]21]

A mixture of the product from Step A (1.5 g, 8.3 mmol), (1S,1aS,6bR)-ethyl 5-hydroxy-1a,6b-dihydro-1H-cyclopropa[b]benzofuran-1-carboxylate (the product of Step G in synthesis of Compound 1.1, 1.9 g, 8.6 mmol), Pd$_2$(dba)$_3$ (700 mg, 0.76 mmol), X-Phos (500 mg, 1.05 mmol) and K$_2$CO$_3$ (2.8 g, 20.3 mmol) in toluene (25 mL) was refluxed under N$_2$ for 2 hours. The mixture was added 50 mL of EA, filtered through a celite pad and the filtrate was concentrated under reduced pressure. The residue was purified by silica-gel column chromatography (eluting: PE/EA: 5/1~2/1) to obtain the title product (0.92 g, 24%) as a brown oil. MS: M/e 469 (M+1)$^+$.

Step C: (1S,1aS,6bR)-5-((9-((2-(trimethylsilyl)ethoxy)methyl)-9H-purin-6-yl) oxy)-1a,6b-dihydro-1H-cyclopropa[b]benzofuran-1-carboxylic acid

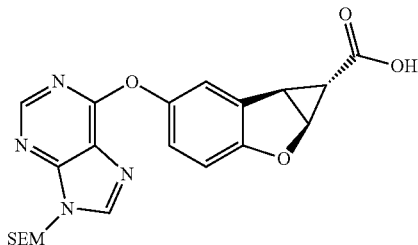 [SMILES: C[Si](C)(C)CCOCn1cnc2c(Oc3ccc4c(c3)[C@@H]3[C@H](O4)[C@H]3C(=O)O)ncnc21]

To a solution of the product from Step B (800 mg, 1.71 mmol) in THF (15 mL) was added aqueous solution of NaOH (2 M, 5 mL) at ambient temperature and stirred at this temperature for 16 hours. HCl (1 M) was added in drops to adjust the pH to 3. EA (15 mL×3) was added to extract the product. The combined extracts was washed with brine (20 mL×2), dried and concentrated to obtain the title product (720 mg, 96%) as a brown solid. $^1$H NMR (400 MHz, DMSO-d6) δ 12.59 (s, 1H), 8.66 (s, 1H), 8.49 (s, 1H), 7.45 (d, J=2.4 Hz, 1H), 7.09 (dd, J=8.8, 2.4 Hz, 1H), 7.00 (d, J=8.8 Hz, 1H), 5.65 (s, 2H), 5.26 (dd, J=5.6, 1.2 Hz, 1H), 3.65-3.56 (m, 2H), 3.36-3.30 (m, 1H), 1.23 (dd, J=3.2, 1.2 Hz, 1H), 0.90-0.82 (m, 2H), −0.07 (s, 9H). MS: M/e 441 (M+1)$^+$.

Step D: (1S,1aS,6bR)-5-((9-((2-(trimethylsilyl)ethoxy)methyl)-9H-purin-6-yl) oxy)-1a,6b-dihydro-1H-cyclopropa[b]benzofuran-1-carbonyl azide

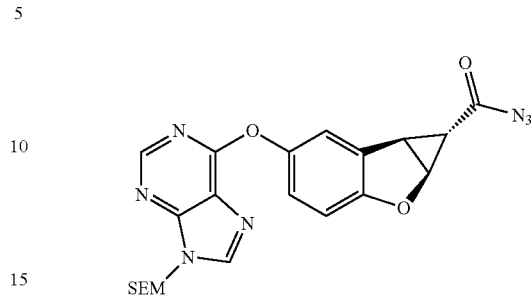

To a solution of the product of Step C (1.0 g, 2.3 mmol) and Et$_3$N (586 mg, 5.8 mmol) in DMF (10 mL) was added DPPA (770 mg, 2.8 mmol) at 0° C. The reaction mixture was stirred at room temperature for 2 hours. The resulting mixture was diluted with EA (200 mL) and washed with brine (50 mL×3). The organic phase was dried over anhydrous sodium sulfate and concentrated under reduced pressure. The residue was purified by silica gel chromatography (silica weight: 10 g, petroleum ether/EA: 3/2, 500 mL) to give the target compound (1.0 g, 93%). $^1$H NMR (400 MHz, DMSO-d6) δ 8.63 (s, 1H), 8.46 (s, 1H), 7.43 (d, J=2.4 Hz, 1H), 7.15-7.08 (m, 1H), 7.08-6.97 (m, 1H), 5.62 (s, 2H), 5.41 (dd, J=5.2, 0.8 Hz, 1H), 3.62-3.49 (m, 3H), 1.49 (dd, J=3.2, 0.8 Hz, 1H), 0.86-0.80 (m, 2H), −0.11 (s, 9H) ppm.

Step E: 1-(4-fluoro-3-(trifluoromethyl)phenyl)-3-((1S,1aS,6bS)-5-((9-((2-(trimethyl silyl)ethoxy)methyl)-9H-purin-6-yl)oxy)-1a,6b-dihydro-1H-cyclopropa[b]benzofuran-1-yl)urea

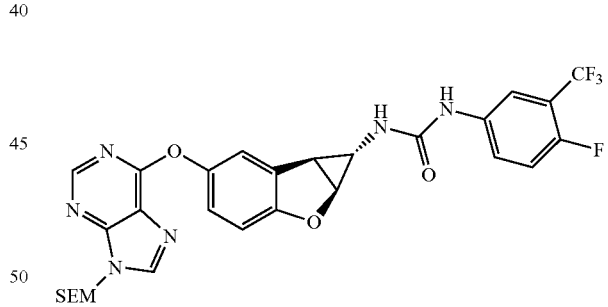

To a mixture of the product of step D (230 mg, 0.5 mmol) and 4-fluoro-3-(trifluoromethyl) aniline (107 mg, 0.6 mmol) in 1,4-dioxane (5 mL) was stirred at 100° C. for 2 hours. The mixture was concentrated under reduced pressure and the residue was directly purified by silica gel chromatography (silica weight 5 g, petroleum ether/EA: 1/2, 500 mL) to give the target compound (200 mg, 65%). $^1$H NMR (400 MHz, DMSO-d6) δ 8.94 (s, 1H), 8.63 (s, 1H), 8.47 (s, 1H), 7.95 (dd, J=6.6, 2.6 Hz, 1H), 7.64-7.56 (m, 1H), 7.43-7.28 (m, 2H), 7.01-6.97 (m, 1H), 6.92-6.88 (m, 1H), 6.79 (d, J=2.0 Hz, 1H), 5.62 (s, 2H), 4.98 (d, J=5.6 Hz, 1H), 3.58 (t, J=8.0 Hz, 2H), 2.95 (dd, J=5.6, 1.6 Hz, 1H), 2.27-2.24 (m, 1H), 0.84 (t, J=8.4 Hz, 2H), −0.10 (s, 9H) ppm.

Step F: 1-((1S,1aS,6bS)-5-((9H-purin-6-yl)oxy)-1a,6b-dihydro-1H-cyclopropa[b]benzofuran-1-yl)-3-(4-fluoro-3-(trifluoromethyl)phenyl)urea (Compound 2.12)

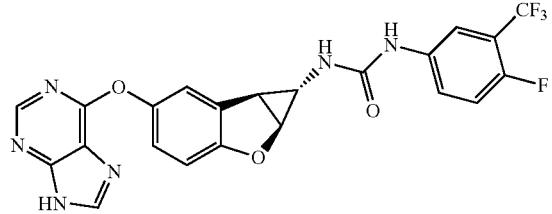 [SMILES: O=C(Nc1ccc(F)c(C(F)(F)F)c1)N[C@@H]1[C@H]2Oc3ccc(Oc4ncnc5[nH]cnc45)cc3[C@@H]12]

A solution of the product of step B (50 mg, 0.08 mmol) in HCl (g)/EtOH (5M, 8 mL) was stirred at room temperature for 4 hours. Then the mixture was poured into $NH_3$ (g)/MeOH (10.0 M, 10 mL) at −20° C. The mixture was concentrated under reduced pressure and the residue was diluted with DCM (30 mL). The organic phase was washed with $H_2O$ (15 mL×2). The aqueous phase was concentrated under reduced pressure and added DCM (30 mL). The mixture was filtered and the filtrate was concentrated. The residue was purified by prep-HPLC to afford the title compound (10 mg, 27%) as a white solid. $^1$H NMR (400 MHz, DMSO-d6) δ 9.01-8.98 (m, 1H), 8.52 (s, 1H), 8.43 (s, 1H), 7.99 (dd, J=6.4, 2.8 Hz, 1H), 7.66-7.60 (m, 1H), 7.42-7.34 (m, 2H), 7.04-7.00 (m, 1H), 6.95-6.91 (m, 1H), 6.87-6.83 (m, 1H), 5.00 (d, J=5.6 Hz, 1H), 2.98 (dd, J=5.6, 1.6 Hz, 1H), 2.30-2.28 (m, 1H) ppm. MS: M/e 487 (M+1)$^+$.

Compound 2.13 was prepared according to the procedures described for Compound 2.12 under appropriate conditions that could be recognized by one skilled in the art.

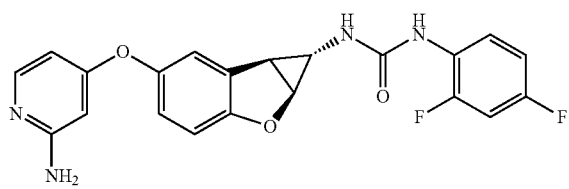

$^1$H NMR (400 MHz, DMSO-d6) δ 8.49 (s, 1H), 8.40 (s, 1H), 8.29 (s, 1H), 8.03-7.93 (m, 1H), 7.32 (d, J=2.4 Hz, 1H), 7.27-7.19 (m, 1H), 7.02-6.87 (m, 4H), 4.96 (d, J=5.6 Hz, 1H), 2.94 (d, J=4.0 Hz, 1H), 2.25 (s, 1H). MS: M/e 437(M+1)$^+$.

Compound 2.14: 1-((1S,1aS,6bS)-5-((2-aminopyridin-4-yl)oxy)-1a,6b-dihydro-1H-cyclopropa[b]benzofuran-1-yl)-3-(2,4-difluorophenyl)urea

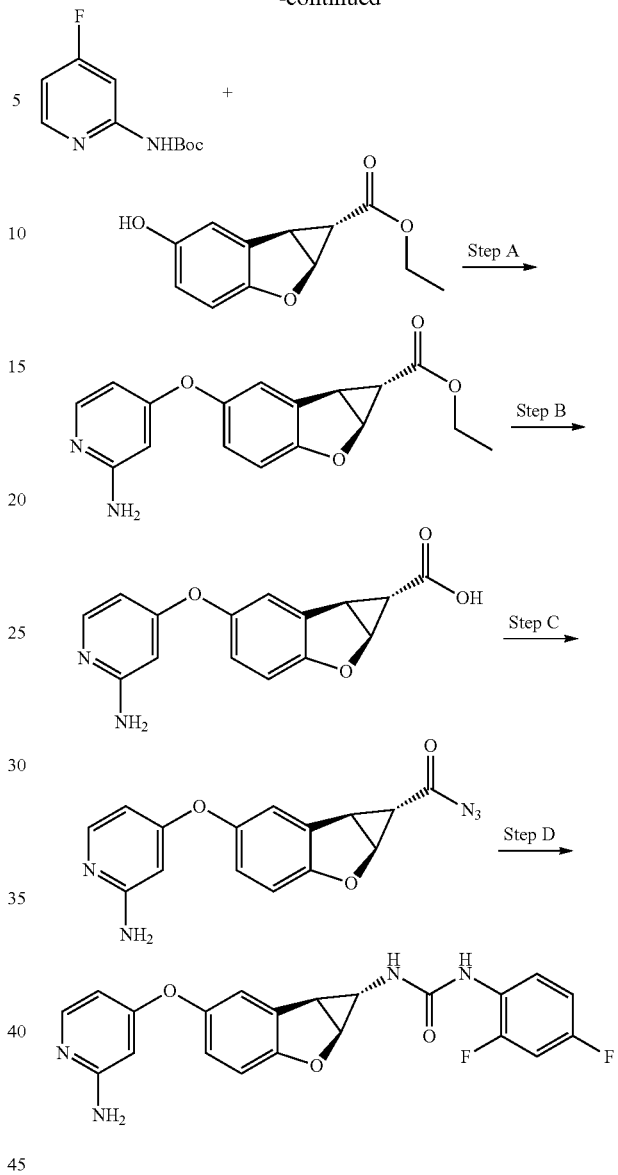

Step A: (1S,1aS,6bR)-ethyl 5-((2-aminopyridin-4-yl)oxy)-1a,6b-dihydro-1H-cyclopropa[b]benzofuran-1-carboxylate The mixture of (1S,1aS,6bR)-ethyl 5-hydroxy-1a,6b-dihydro-1H-cyclopropa[b]benzofuran-1-carboxylate (the product of Step G in synthesis of Compound 1.1, 2.2 g, 10 mmol), tert-butyl (4-fluoropyridin-2-yl)carbamate (2.1 g, 10 mmol) and cesium carbonate (6.5 g, 20 mmol) in DMF (50 mL) was stirred at 100° C. for 2 hours. The reaction was filtered through a celite pad. The filtrate was concentrated under reduced pressure. The residue was diluted with EA (300 mL), washed with brine (100 mL×3), dried over anhydrous sodium sulfate and concentrated under reduced pressure. The residue was purified by silica gel chromatography (silica weight: 20 g, petroleum ether/EA: 2/3, 1500 mL) to give the target compound (1.0 g, 30%) as brown oil. ¹H NMR (400 MHz, DMSO-d6) δ 7.83 (d, J=6.0 Hz, 1H), 7.37 (d, J=2.4 Hz, 1H), 7.08-6.96 (m, 2H), 6.16 (dd, J=6.0, 2.4 Hz, 1H), 5.95 (s, 2H), 5.81 (d, J=2.4 Hz, 1H), 5.35 (dd, J=5.2, 1.2 Hz, 1H), 4.17 (q, J=7.2 Hz, 2H), 3.44 (dd, J=5.2, 3.2 Hz, 1H), 1.39 (dd, J=3.2, 1.2 Hz, 1H), 1.27 (t, J=7.2 Hz, 3H) ppm.

Step B: (1S,1aS,6bR)-5-((2-aminopyridin-4-yl)oxy)-1a,6b-dihydro-1H-cyclopropa[b]benzofuran-1-carboxylic acid

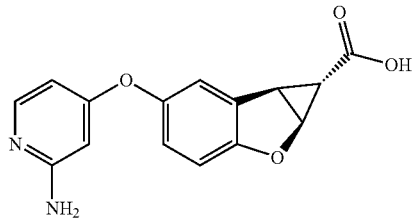 [SMILES: Nc1cc(Oc2ccc3c(c2)[C@@H]2[C@H](O3)[C@H]2C(=O)O)ccn1]

A mixture of the product of step A (600 mg, 2 mmol) in sodium hydroxide aqueous solution (2 mol/L, 2 mL, 4 mmol) and THF (8 mL) was stirred at 60° C. for 2 hours. The solvent was removed under reduced pressure, the residue was diluted with H₂O (8 mL) and adjusted to pH about 6 by HCl (2 mol/L). The solid was collected and dried in air to afford the title compound (500 mg, yield: 88%) as a white solid. ¹H NMR (400 MHz, DMSO-d6) δ 7.73 (d, J=5.6 Hz, 1H), 7.27 (d, J=2.4 Hz, 1H), 6.97-6.88 (m, 2H), 6.09 (dd, J=5.6, 2.4 Hz, 1H), 5.90 (s, 2H), 5.71 (d, J=2.0 Hz, 1H), 5.19 (d, J=5.2 Hz, 1H), 3.27 (dd, J=5.2, 2.8 Hz, 1H), 1.15-1.13 (m, 1H) ppm.

Step C: (1S,1aS,6bR)-5-((2-aminopyridin-4-yl)oxy)-1a,6b-dihydro-1H-cyclopropa[b]benzofuran-1-carbonyl azide

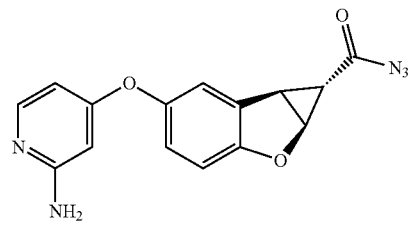 [SMILES: [N-]=[N+]=NC(=O)[C@@H]1[C@H]2Oc3ccc(Oc4ccnc(N)c4)cc3[C@H]21]

To a solution of the product of step B (100 mg, 0.35 mmol) and Et₃N (89 mg, 0.88 mmol) in DMF (5 mL) was added DPPA (116 mg, 0.42 mmol) at room temperature. The reaction mixture was stirred at room temperature for 2 hours. The resulting mixture was diluted with EA (60 mL) and washed with brine (20 mL×3). The organic phase was dried over anhydrous sodium sulfate and concentrated under reduced pressure to afford the crude product (100 mg, 93%) which was directly used in the next step. ¹H NMR (400 MHz, DMSO-d6) δ 7.95 (s, 1H), 7.78 (d, J=5.6 Hz, 1H), 7.35-7.31 (m, 1H), 7.06-7.03 (m, 1H), 7.01-6.97 (m, 1H), 6.14 (dd, J=5.6, 2.0 Hz, 1H), 6.03 (s, 2H), 5.78 (d, J=2.0 Hz, 1H), 5.43 (dd, J=5.2, 1.2 Hz, 1H), 3.58 (dd, J=5.2, 3.2 Hz, 1H), 1.45 (dd, J=3.2, 1.2 Hz, 1H) ppm.

Step D: 1-((1S,1aS,6bS)-5-((2-aminopyridin-4-yl)oxy)-1a,6b-dihydro-1H-cyclopropa [b]benzofuran-1-yl)-3-(2,4-difluorophenyl)urea (Compound 2.14)

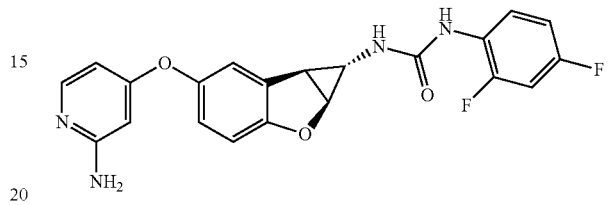

To a mixture of the product of step C (50 mg, 0.16 mmol) and 2,4-difluoro aniline (25 mg, 0.19 mmol) in 1,4-dioxane (2 mL) was stirred at 100° C. for 2 hours. The mixture was concentrated under reduced pressure and the residue was directly purified by prep-HPLC to afford the title compound (5 mg, 8%) as a white solid. ¹H NMR (400 MHz, DMSO-d6) δ 8.34 (s, 1H), 8.04-7.96 (m, 1H), 7.93 (d, J=7.2 Hz, 1H), 7.72 (s, 2H), 7.35 (s, 1H), 7.31-7.19 (m, 2H), 7.05-6.95 (m, 4H), 6.65 (dd, J=7.2, 2.4 Hz, 1H), 6.04 (d, J=2.4 Hz, 1H), 5.04 (d, J=5.6 Hz, 1H), 3.00 (dd, J=5.6, 2.0 Hz, 1H), 2.27-2.26 (m, 1H) ppm.

Compound 2.15 was prepared according to the procedures described for Compound 2.14 under appropriate conditions that could be recognized by one skilled in the art.

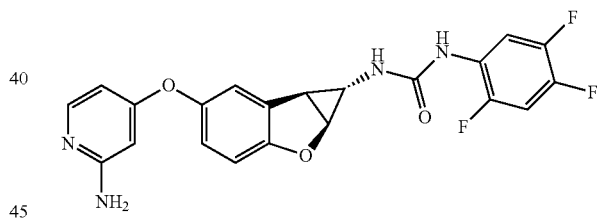

¹H NMR (400 MHz, DMSO-d6) δ 8.59 (s, 1H), 8.28-8.08 (m, 1H, HOOH), 7.77 (d, J=5.6 Hz, 1H), 7.63-7.53 (m, 1H), 7.20 (d, J=2.0 Hz, 1H), 7.08 (s, 1H), 7.00-6.85 (m, 2H), 6.11 (dd, J=6.0, 2.0 Hz, 1H), 5.90 (s, 2H), 5.77 (d, J=2.0 Hz, 1H), 4.97 (d, J=5.6 Hz, 1H), 2.97 (d, J=4.0 Hz, 1H), 2.24 (s, 1H) ppm. MS: M/e 429(M+1)⁺.

Compounds 2.16 was prepared according to the procedures described for Compound 2.6 under appropriate conditions that could be recognized by one skilled in the art.

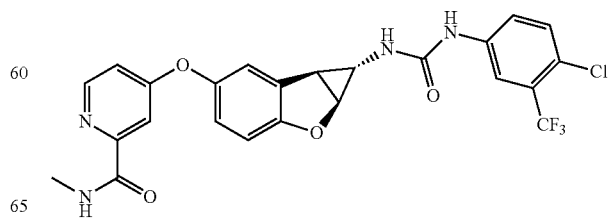

¹H NMR (400 MHz, DMSO-d6) δ 9.12 (s, 1H), 8.82-8.74 (m, 1H), 8.50 (d, J=5.6 Hz, 1H), 8.09 (d, J=2.4 Hz, 1H), 7.64 (dd, J=8.8, 2.4 Hz, 1H), 7.57 (d, J=8.8 Hz, 1H), 7.38 (d, J=2.4 Hz, 1H), 7.33-7.28 (m, 1H), 7.12 (dd, J=5.6, 2.4 Hz, 1H), 7.02-6.96 (m, 2H), 6.90 (d, J=2.4 Hz, 1H), 5.02 (d, J=5.6 Hz, 1H), 3.00 (dd, J=5.6, 1.6 Hz, 1H), 2.79 (d, J=4.8 Hz, 3H), 2.34-2.26 (m, 1H) ppm. MS: M/e 519 (M+1)⁺

Raf IC$_{50}$ Assay Protocol

Compounds disclosed herein were tested against B-Raf (V600E) (PV3849, from Invitrogen) or C-Raf (Y340D/Y341D) (PV3805, from Invitrogen) in a time-resolved fluorescence energy transfer assay. The assay was carried out in reactions (10 µL) containing 0.0625 nM B-Raf or 0.5 nM C-Raf, 25 mM Tris pH7.4, 10 mM MgCl$_2$, 0.5 mM EGTA, 0.5 mM Na$_3$VO4, 5 mM beta-glycerophosphate, 0.01% Triton X-100, 2.5 mM DTT, 0.1% BSA, 0.1 mM ATP, 13.7 nM GST-tagged MEK1 (Full-length protein with K97R mutation, recombinant protein purified from bacterial expression system) and 0-5 µM compounds disclosed herein (final concentration of 1% DMSO). The enzyme was incubated with the compounds at room temperature for 60 minutes and the reactions were initiated by the addition of ATP and GST-MEK1. After reaction at room temperature for 60 minutes, an equal volume of stop/detection solution was added according to the manufacture's instruction (CisBio Bioassays). The stop/detection solution contained Eu$^{3+}$ cryptate-conjugated anti-phospho MEK1/2 (Ser217/221) rabbit polyclonal antibody and d2-conjugated anti-GST mouse monoclonal antibody in buffer containing 25 mM Tris pH7.4, 400 mM KF, 50 mM EDTA, 0.01% BSA and 0.01% Triton X-100. Plates were sealed and incubated at room temperature for 2 hours, and the TR-FRET signals (ratio of fluorescence emission at 665 nm over emission at 620 nm with excitation at 337 nm wavelength) were recorded on a PHERAstar FS plate reader (BMG Labtech). Phosphorylation of MEK1 led to the binding of anti-phospho-MEK1/2 antibody to GST-MEK1 protein that place fluorescent donor (Eu$^{3+}$ crypate) in close proximity to the accepter d2 on the anti-GST antibody, thus resulting in a high degree of fluorescence resonance energy transfer from the donor fluorophore (at 620 nm) to the acceptor fluorophore (at 665 nm). Inhibition of RAF kinase activity resulted in decrease of the TR-FRET signal. The IC$_{50}$ for each compound was derived from fitting the dose-response % inhibition data to the four-parameter logistic model by Graphpad Prism software.

WT B-Raf IC$_{50}$ Assay Protocol

Compounds disclosed herein were tested against wild type B-Raf (PV3848, from Invitrogen) in a time-resolved fluorescence energy transfer assay. The assay was carried out in reactions (10 µL) containing 0.5 nM B-Raf, 25 mM Tris pH7.4, 10 mM MgCl$_2$, 0.5 mM EGTA, 0.5 mM Na$_3$VO$_4$, 5 mM beta-glycerophosphate, 0.01% Triton X-100, 2.5 mM DTT, 0.1% BSA, 2.9 µM or 2.5 mM ATP, 10 nM GST-tagged MEK1 (Full-length protein with K97R mutation, recombinant protein purified from bacterial expression system) and 0-10 µM compounds disclosed herein (final concentration of 1% DMSO). The enzyme was incubated with the compounds at room temperature for 120 minutes and the reactions were initiated by the addition of ATP and GST-MEK1. After incubating at room temperature for 60 minutes, an equal volume of stop buffer containing 25 mM Tris pH7.4, 400 mM KF, 50 mM EDTA, 0.1% BSA, 0.01% Triton X-100, 1 test of Eu3+ Cryptate-conjugated rabbit polyclonal antibody anti-Phospho MEK1/2 (Ser217/221) and 1 test of d2-conjugated mouse monoclonal antibody anti-glutathione S-transferase was added to stop the reactions. Plates were sealed and incubated at room temperature for 1.5 hours, and then the TR-FRET signals were read on BMG PHERAstar FS instrument. The IC$_{50}$ for each compound was calculated by non linear regression by Graphpad Prism software.

P61-A375 Cell Expression

To express p61 in mammalian cells, cDNA encoding the p61 (Poulikakos et al., Nature. 2011 Nov. 23; 480(7377): 387-90) was synthesized by Genscript and cloned into pLVX-IRES-Puro vector (Clontech). The cDNA was a modified form of p61 in which sequencing encoding the flag-epitope had been inserted to the C-terminus, resulting in the expression of flag-tagged forms of protein. A375 cells were stably transfected with the Flag-p61 expressing plasmid and selected with DMEM containing 0.3 ng/mL puromycin (Invitrogen). Cells were cloned by limiting dilution in a 96-wells plate and the clones screened by western blot analysis using a monoclonal antibody directed against the flag-epitope.

ERK Phosphorylation Inhibition IC50 Assay Protocol

To determine inhibition of ERK phosphorylation, A375, p61-A375, Calu-6 and HeLa were seeded at $3\times10^4$ per well of a 96-wells plate and left to attach for 16 hours. Growth medium was then replaced with 100 µL of serum free DMEM, cells were then treated with a 10-point titration of compounds disclosed herein. After 1 hour compound treatment, 50 µL of lysis buffer (Cisbio) were added to each well and incubated at room temperature with shaking for 30 minutes. A total of 16 µL of cell lysate from each well of a 96-well plate was transferred to a 384-well small volume white plate. Lysate from each well was incubated with 2 µL of Eu$^{3+}$-cryptate (donor) labeled anti-ERK antibody (Cisbio) and 2 µL of D2 (acceptor) labeled anti-phospho-ERK antibody (Cisbio) for 2 hours at room temperature. When donor and acceptor are in close proximity, excitation of the donor with laser triggers a Fluorescence Resonance Energy Transfer (FRET) towards the acceptor, which in turn fluoresces at 655 nm wavelength. Fluorescence values were measured using a BMG reader.

IC$_{50}$ values for ERK inhibition were calculated by fitting dose-dependent data to the four-parameter logistic model using GraphPad Prism software.

Anti-Proliferative Activity EC50 Assay Protocol

The growth-inhibitory activity of compounds in A375 and p61-A375, was determined using CellTiter-Glo luminescent cell viability assay (Promega). The 2,000 cells were seeded per well of a 96-well plate to ensure logarithmic growth could occur over the 3 days treatment period. Cells were left to attach for 16 hours, cells were treated in duplicate with a 10-point dilution series. Following a 3-day exposure to compounds disclosed herein, a volume of CellTiter-Glo reagent equal to the volume of cell culture medium present in each well was added. Mixture was mixed on an orbital shaker for 2 minutes to allow cell lysis, followed by 10 minutes incubation at room temperature to allow stabilization of luminescent signal, which corresponded to quantitation of ATP and thus the quantitation of metabolically active cells. Luminescent signal was measured using Pherastar FS reader (BMG Labtech).

EC$_{50}$ values for cell viability were calculated with GraphPad Prism software and are the mean of 3 independent assays. EC$_{50}$ values for growth inhibition were calculated by fitting dose-dependent data to the four-parameter logistic model using GraphPad Prism software.

Compounds 1.1-1.87 and 2.1-2.16 inhibited B-Raf (wild type, V600E)/C-Raf with IC$_{50}$ values ranging from 0.1 nM to 10 µM.

Compounds 1.1-1.87 and 2.1-2.16 inhibited ERK phosphorylation, p61-A375, Calu-6 and HeLa cell with $IC_{50}$ values ranging from 0.1 nM to 10 μM.

Compounds 1.1-1.87 and 2.1-2.16 inhibited cell proliferation in A375 and p61-A375 with $EC_{50}$ values ranging from 0.1 nM to 10 μM.

TABLE 1

$IC_{50}$s and $EC_{50}$s

| Compound No. | IC50 (nM) | | | | IC50 (nM) | Cell Proliferation | |
| | | | | | | EC50 (nM) | |
| | $B\_Raf^{V600E}$ | C-Raf | $B\text{-}Raf^{WT}Km$ ATP | $B\text{-}Raf^{WT}$ 2.5 mM ATP | p61-A375 pERK | A375 | p61-A375 |
|---|---|---|---|---|---|---|---|
| 1.1 | 8.3 | 1.6 | 13 | 43 | | 109 | |
| 1.2 | 4 | 0.77 | 6.3 | 18 | | 122 | |
| 1.3 | 40 | 0.54 | 56% at 100 nM | | | | |
| 1.4 | 1.8 | | 99% at 100 nM | | | | |
| 1.5 | 2.2 | | 102% at 100 nM | | | | |
| 1.6 | 1.9 | 0.33 | 4.5 | 11 | | 229 | |
| 1.7 | 1.1 | 0.35 | 2.6 | | | | |
| 1.8 | 8.7 | | 95% at 100 nM | | | | |
| 1.9 | 9.5 | 1.6 | 21 | | | | |
| 1.10 | 6.3 | | 95% at 100 nM | | | | |
| 1.11 | 5.5 | 1.8 | 30 | 110 | | 147 | |
| 1.12 | 4.7 | 1.1 | 23 | 86 | | 106 | |
| 1.13 | 1.8 | | 102% at 100 nM | | | | |
| 1.14 | 1.9 | | 2.8 | 8.5 | | 127 | |
| 1.15 | 2.3 | | 98% at 100 nM | | | | |
| 1.16 | 2.6 | | 100% at 100 nM | | | | |
| 1.17 | 1.5 | | 100% at 100 nM | | | | |
| 1.18 | 16 | | 77% at 100 nM | | | | |
| 1.19 | 5.1 | | 99% at 100 nM | | | 503 | |
| 1.20 | 13 | 2.7 | 23 | | | | |
| 1.21 | 1.1 | 0.066 | 0.87 | 2.5 | | 128 | |
| 1.22 | 1.3 | 0.18 | 1.7 | 4.2 | | 87 | |
| 1.23 | 1.8 | 0.3 | 3.7 | 12 | 253 | 109 | 479 |
| 1.24 | 1.5 | 0.37 | 2.7 | 7.7 | | 25 | |
| 1.25 | 27 | 2.3 | 33 | | | 25 | |
| 1.26 | 2675 | | 7% at 100 nM | | | | |
| 1.27 | 11 | | 85% at 100 nM | | | | |
| 1.28 | 5.5 | 0.77 | 16 | 49 | | 40 | |
| 1.29 | 6.9 | | 101% at 100 nM | | | 222 | |
| 1.30 | 3 | | 101% at 100 nM | | | 583 | |
| 1.31 | 17 | 1.4 | 26 | | | | |
| 1.32 | 7.7 | 1.2 | 17 | 58 | 433 | 55 | 527 |
| 1.33 | 9.5 | | 19 | 75 | | 137 | |
| 1.34 | 12.6 | | 87% at 100 nM | | | | |
| 1.35 | 0.59 | 0.25 | 1 | 4.1 | 314 | 143 | 1134 |
| 1.36 | 1.3 | | 93% at 100 nM | | | | |
| 1.37 | 0.85 | | 100% at 100 nM | | | | |
| 1.38 | 4 | | 95% at 100 nM | | | | |
| 1.39 | 2.6 | | 99% at 100 nM | | | | |
| 1.40 | 1.6 | 0.2 | 2 | | | | |
| 1.41 | 0.8 | 0.15 | 0.57 | | | 65 | |
| 1.42 | 0.94 | 0.24 | 1.5 | | | 178 | |
| 1.43 | 1.2 | 0.26 | 2.1 | 5.9 | | 96 | |
| 1.44 | 1.3 | 0.21 | 1.9 | | | 702 | |
| 1.45 | 1.1 | 0.30 | 2.7 | 6.7 | 325 | 32 | 645 |
| 1.46 | 0.78 | 0.22 | 1.7 | 6 | | 109 | |
| 1.47 | 4.1 | 0.53 | 6.4 | 23 | | 140 | |
| 1.48 | 0.74 | | 2.5 | 7.9 | | 686 | |
| 1.49 | 1.2 | 0.19 | 2.5 | 7.9 | 153 | 17 | 639 |
| 1.50 | 0.8 | | 97% at 100 nM | | | | |
| 1.51 | 0.59 | | | | | 273 | |
| 1.52 | 1.4 | 0.25 | 1.7 | | 173 | 47.7 | |
| 1.53 | 2.9 | | 96% at 100 nM | | | 77 | 1315 |
| 1.54 | 1.9 | | 91% at 100 nM | | | 2700 | |
| 1.55 | 1.7 | 0.34 | 2.2 | | | 178 | |
| 1.56 | 158 | | | | | | |
| 1.57 | 0.71 | | | | | 840 | |
| 1.58 | 0.77 | | 96% at 100 nM | | | 534 | |
| 1.59 | 0.84 | | 101% at 100 nM | | | 891 | |
| 1.60 | 8.6 | | | | | 193 | |
| 1.61 | 7.4 | | | | | 975 | |
| 1.62 | 6.3 | | | | | 302 | |

TABLE 1-continued

IC$_{50}$s and EC$_{50}$s

| Compound No. | IC50 (nM) | | | | Cell Proliferation | | |
|---|---|---|---|---|---|---|---|
| | B_Raf$^{V600E}$ | C-Raf | B-Raf$^{WT}$Km ATP | B-Raf$^{WT}$2.5 mM ATP | IC50 (nM) p61-A375 pERK | EC50 (nM) A375 | p61-A375 |
| 1.63 | >5000 | | | | | | |
| 1.64 | 27 | | | | | | |
| 1.65 | 116 | | | | | | |
| 1.66 | 2.3 | 0.25 | 2.3 | | | 101 | |
| 1.67 | 4.2 | | | | | 4174 | |
| 1.68 | 20 | | | | | | |
| 1.69 | 30 | | | | | | |
| 1.70 | 7.4 | 0.81 | 15 | | | | |
| 1.71 | 3 | 0.34 | 91% at 100 nM | | | | |
| 1.72 | 1.9 | | 83% at 100 nM | | | | |
| 1.73 | 13 | 0.84 | 13 | | | 1331 | |
| 1.74 | 821 | | | | | | |
| 1.75 | 2.2 | 0.27 | 2.4 | | | 405 | |
| 1.76 | 3.4 | | | | | 1310 | |
| 1.77 | 4.5 | | | | | 4535 | |
| 1.78 | 0.72 | | | | | 1897 | |
| 1.79 | 3.2 | 0.39 | | | | 222 | |
| 1.80 | 4 | 0.50 | | | | 132 | |
| 1.81 | 2.7 | | | | | 159 | |
| 1.82 | 2.4 | | | | | 867 | |
| 1.83 | 3 | | | | | 291 | |
| 1.84 | 12 | | | | | 4326 | |
| 1.85 | 129 | | | | | | |
| 1.86 | 183 | | | | | | |
| 1.87 | 227 | | | | | | |
| 2.1 | 1098 | | | | | | |
| 2.2 | 111 | | | | | | |
| 2.3 | 2.6 | | | | | 190 | |
| 2.4 | 11 | | | | | 374 | |
| 2.5 | 2.3 | | | | | 769 | |
| 2.6 | 26 | | 77% at 100 nM | | | 624 | |
| 2.7 | 33 | | 70% at 100 nM | | | 464 | |
| 2.8 | 13 | 3 | 17 | | | | |
| 2.9 | 24 | | 65% at 100 nM | | | | |
| 2.10 | 50 | | 58% at 100 nM | | | | |
| 2.11 | 58 | | 36% at 100 nM | | | | |
| 2.12 | 10 | | | | | | |
| 2.13 | 24 | | | | | | |
| 2.14 | 36 | | | | | | |
| 2.15 | 18 | | | | | 10,000 | |
| 2.16 | 88 | | | | | | |
| Vemurafenib | 33 | 31 | 58 | 3700 | >10,000 | 178 | >10,000 |

TABLE 2

IC$_{50}$s

| Compound No. | IC$_{50}$ (nM) | |
|---|---|---|
| | Calu-6 (pERK) | HeLa (pERK) |
| 1.23 | 101 | 189 |
| 1.32 | 301 | 536 |
| 1.35 | 75 | 610 |
| 1.45 | 84 | 265 |
| 1.49 | 112 | 498 |
| 1.52 | 411 | 5,428 |
| Vemurafenib | >10,000 | 5,818 |

The invention claimed is:

1. A compound of Formula (I):

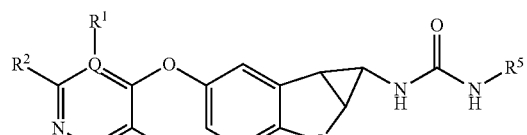

or a stereoisomer thereof, or a pharmaceutically acceptable salt thereof, wherein:

Q is selected from C and N;

$R^1$, $R^2$, $R^3$, and $R^4$, which may be the same or different, are each selected from hydrogen, halogen, alkyl, alkenyl, cycloalkyl, aryl, heterocyclyl, heteroaryl, alkynyl, —CN, —NR⁶R⁷, —OR⁶, —COR⁶, —CO₂R⁶, —CONR⁶R⁷, —C(=NR⁶)NR⁷R⁸, —NR⁶COR⁷, —NR⁶CONR⁷R⁸, —NR⁶CO₂R⁷, —SO₂R⁶, —NR⁶SO₂NR⁷R⁸, —NR⁶SO₂R⁷, and —NR⁶SO₂aryl, wherein the alkyl, alkenyl, alkynyl, cycloalkyl, heteroaryl, aryl, and heterocyclyl are independently optionally substituted with at least one substituent R⁹, or (R¹ and R²), and/or (R³ and R⁴), together with the ring to which they are attached, form a fused ring selected from heterocyclyl and heteroaryl rings optionally substituted with at least one substituent R⁹; provided that R¹ is absent when Q is N;

R⁵ is selected from alkyl, cycloalkyl, heterocyclyl, aryl, heteroaryl rings, each of which is optionally substituted with at least one substituent R⁹;

R⁶, R⁷ and R⁸, which may be the same or different, are each selected from H, alkyl, alkenyl, alkynyl, cycloalkyl, heterocyclyl, aryl, and heteroaryl; or (R⁶ and R⁷), and/or (R⁷ and R⁸) together with the atom(s) to which they are attached, each form a ring selected from heterocyclyl and heteroaryl rings optionally substituted with at least one substituent R⁹;

R⁹ is selected from halogen, haloalkyl, alkyl, alkenyl, cycloalkyl, aryl, heteroaryl, heterocyclyl, alkynyl, oxo, -alkyl-NR'R", —CN, —OR', —NR'R", —COR', —CO₂R', —CONR'R", —C(=NR')NR"R''', nitro, —NR'COR", —NR'CONR'R", —NR'CO₂R", —SO₂R', —SO₂aryl, —NR'SO₂NR"R''', NR'SO₂R", and —NR'SO₂aryl, wherein the cycloalkyl, aryl, heteroaryl, or heterocyclyl group are each independently optionally substituted by one, two or three substituents selected from halo, alkyl and haloalkyl, wherein R', R", and R''' are independently selected from H, haloalkyl, alkyl, alkenyl, alkynyl, cycloalkyl, heterocyclyl, aryl, and heteroaryl, or (R' and R"), and/or (R" and R''') together with the atoms to which they are attached, form a ring selected from heterocyclyl optionally substituted by halogen and alkyl, and heteroaryl rings optionally substituted by halogen and alkyl.

2. The compound of claim 1, wherein Q is C.

3. The compound of claim 1, wherein R¹ and R², which may be the same or different, are each selected from hydrogen, halogen, and alkyl optionally substituted with at least one substituent R⁹.

4. The compound of claim 1, wherein R³ and R⁴, which may be the same or different, are each selected from hydrogen, halogen, alkyl optionally substituted with at least one substituent R⁹, —NR⁶R⁷, or —CONR⁶R⁷, wherein R⁶ and R⁷ are each selected from hydrogen or alkyl.

5. The compound of claim 1, wherein R³ is —NR⁶R⁷ or —CONR⁶R⁷; and R⁴ is hydrogen, wherein R⁶ and R⁷ are each selected from hydrogen or alkyl.

6. The compound of claim 1, wherein R³ and R⁴ together with the ring to which they are attached, form a fused ring selected from naphthyridinyl, pyridooxazinyl, pyridopyrimidinyl, and purinyl, said ring being optionally substituted with oxo.

7. The compound of claim 1, wherein R³ and R⁴ together with the ring to which they are attached, form a fused ring selected from heterocyclyl or heteroaryl rings optionally substituted with at least one substituent R⁹, which is represented by

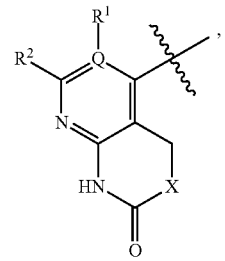

wherein R¹ and R² are defined as in Formula (I) of claim 1, and X is selected from —O—, —NR'— or —CR'R", wherein R' and R" are independently selected from H, haloalkyl, or alkyl.

8. The compound of claim 1, wherein R³ and R⁴ together with the ring to which they are attached, form a fused ring selected from heterocyclyl and heteroaryl rings, which is represented by

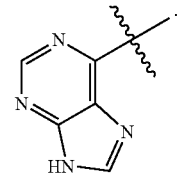

9. The compound of claim 1, wherein R⁵ is methyl, ethyl, propyl, isopropyl, butyl, tert-butyl, pentyl, neopentyl, hexyl, octyl, nonyl or decyl, each of which is optionally substituted with one or two or three halogen.

10. The compound of claim 1, wherein R⁵ is phenyl or naphthyl, each of which is optionally substituted with one or two or three substituent R⁹ as defined in Formula (I) of claim 1.

11. The compound of claim 1, wherein R⁵ is phenyl or naphthyl, each of which is optionally substituted with one or two or three substituent R⁹ selected from halogen, haloalkyl, alkyl, alkenyl, alkynyl, -alkyl-NR'R", —CN, —OR', —NR'R", or nitro, wherein R' and R" are independently selected from H, haloalkyl, or alkyl, or (R' and R") together with the nitrogen atom to which they are attached, form a ring selected from heterocyclyl optionally substituted by halogen and alkyl.

12. The compound of claim 1, wherein R⁵ is pyridinyl or pyrimidinyl, each of which is optionally substituted with one or two or three substituent R⁹ as defined in Formula (I) of claim 1.

13. The compound of claim 1, wherein R⁵ is pyridinyl or pyrimidinyl, each of which is optionally substituted with one or two or three substituent R⁹ selected from halogen, haloalkyl, alkyl, alkenyl, alkynyl, -alkyl-NR'R", —CN, —OR', —NR'R", or nitro, wherein R' and R" are independently selected from H, haloalkyl, or alkyl, or (R' and R") together with the nitrogen atom to which they are attached, form a ring selected from heterocyclyl optionally substituted by halogen and alkyl.

14. The compound of claim 1, wherein R⁵ is tetrahydropyranyl or piperidinyl, each of which is optionally substituted with one or two or three substituent R⁹ as defined in Formula (I) of claim 1.

15. The compound of claim 1, wherein R⁵ is tetrahydropyranyl or piperidinyl, each of which is optionally substituted with one or two or three substituent R⁹ selected from halogen, haloalkyl, alkyl, alkenyl, alkynyl, -alkyl-NR'R", —CN, —OR', —NR'R", or nitro, wherein R' and R" are independently selected from H, haloalkyl, or alkyl, or (R' and R") together with the nitrogen atom to which they are attached, form a ring selected from heterocyclyl optionally substituted by halogen and alkyl.

16. The compound of claim 1, wherein $R^5$ is monocyclic or bicyclic cycloalkyl group each of which is optionally substituted with one or two or three substituent $R^9$ as defined in Formula (I) of claim 1.

17. The compound of claim 1, wherein $R^5$ is monocyclic cycloalkyl group selected from cyclopropyl, cyclobutyl, cyclopentyl, cyclohexyl, cycloheptyl or cyclooctyl; or bicyclic cycloalkyl group selected from those arranged as a bicyclic ring selected from [4,4], [4,5], [5,5], [5,6] and [6,6] ring systems, each of which is optionally substituted with one or two or three substituent $R^9$ selected from halogen, haloalkyl, alkyl, alkenyl, alkynyl, -alkyl-NR'R", —CN, —OR', —NR'R", or nitro, wherein R' and R" are independently selected from H, haloalkyl, and alkyl, or (R' and R") together with the nitrogen atom to which they are attached, form a ring selected from heterocyclyl optionally substituted by halogen and alkyl.

18. The compound of claim 7, the compound is in either of the following configurations:

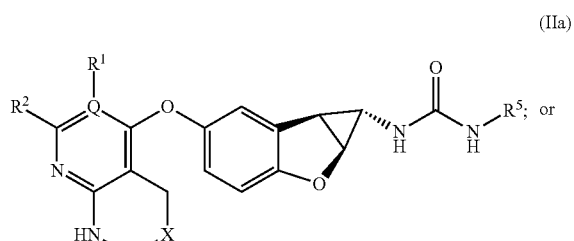

(IIa)

(IIb)

19. The compound of claim 1, wherein the compound is selected from compounds of Formula III:

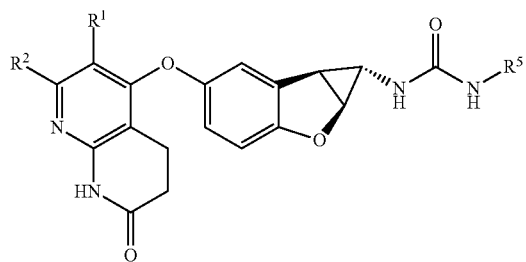

III or a stereoisomer thereof, or a pharmaceutically acceptable salt thereof, wherein:

$R^1$ and $R^2$, which may be the same or different, are each selected from hydrogen, halogen, or alkyl, optionally substituted with at least one substituent $R^9$, $R^5$ is selected from alkyl, cycloalkyl, heterocyclyl, aryl, or heteroaryl rings, each of which is optionally substituted with at least one substituent $R^9$;

$R^9$ is selected from halogen, haloalkyl, alkyl, alkenyl, cycloalkyl, aryl, heteroaryl, heterocyclyl, alkynyl, oxo, -alkyl-NR'R", —CN, —OR', —NR'R", —COR', —CO₂R', —CONR'R", —C(=NR')NR"R'", nitro, —NR'COR", —NR'CONR'R", —NR'CO₂R", —SO₂R', —SO₂aryl, —NR'SO₂NR"R'", NR'SO₂R", or —NR'SO₂aryl, wherein the cycloalkyl, aryl, heteroaryl, or heterocyclyl group are each independently optionally substituted by one, two or three substituents selected from halo, alkyl and haloalkyl, wherein R', R", and R'" are independently selected from H, haloalkyl, alkyl, alkenyl, alkynyl, cycloalkyl, heterocyclyl, aryl, or heteroaryl, or (R' and R"), and /or (R" and R'") together with the atoms to which they are attached, form a ring selected from heterocyclyl optionally substituted by halogen and alkyl, and heteroaryl rings optionally substituted by halogen and alkyl.

20. A pharmaceutical composition comprising at least one pharmaceutically acceptable carrier and as an active ingredient a therapeutically effective amount of a compound of claim 1 or a stereoisomer thereof, or a pharmaceutically acceptable salt thereof.

21. A method of treating cancer responsive to inhibition of Raf kinase and/or Raf kinase dimer comprising administering to a subject in need thereof a compound of claim 1, or a stereoisomer thereof, or a pharmaceutically acceptable salt thereof.

22. The method of claim 21 wherein the cancer is selected from one or more of the group consisting of melanomas and thyroid cancer, Barret's adenocarcinoma, breast cancer, cervical cancer, colorectal cancer, gastric cancer, lung cancer, ovarian cancer, pancreatic cancer, prostate cancer, hematologic cancers, cancer of Billary Tract, non-small-cell lung cancer, endometrium cancer, blood cancer, large intestinal colon carcinoma, histiocytic lymphoma, and lung adenocarcinoma.

23. The compound of claim 19, wherein $R^5$ is phenyl optionally substituted with one or two or three substituent $R^9$ selected from halogen, haloalkyl, alkyl, alkenyl, alkynyl, -alkyl-NR'R", —CN, —OR', —NR'R", or nitro, wherein R' and R" are independently selected from H, haloalkyl, or alkyl, or (R' and R") together with the nitrogen atom to which they are attached, form a ring selected from heterocyclyl optionally substituted by halogen and alkyl.

24. The compound of claim 1, wherein the compound is selected from:

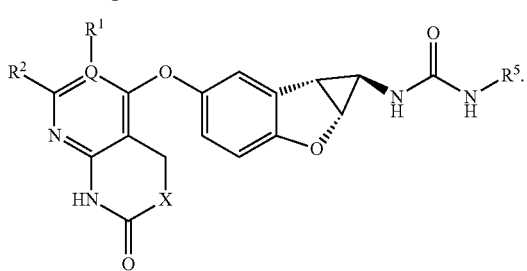

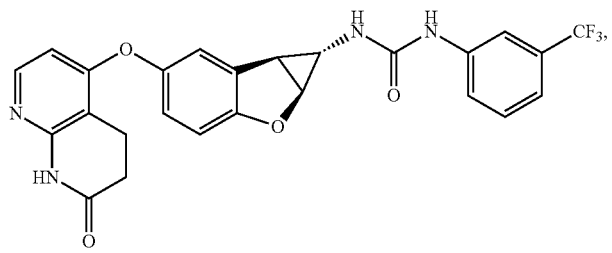
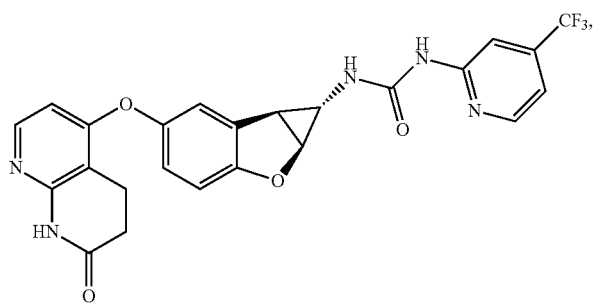
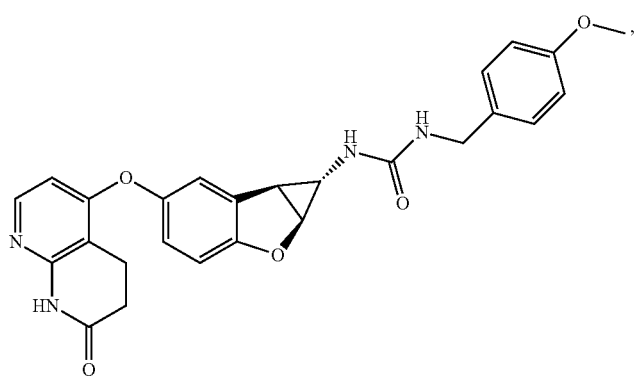
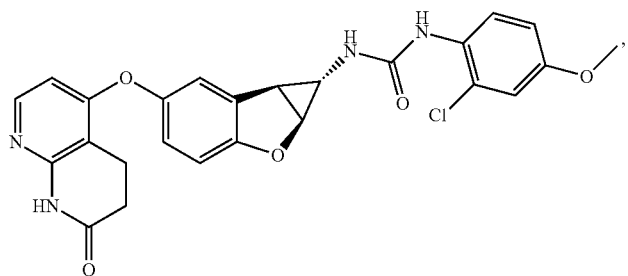
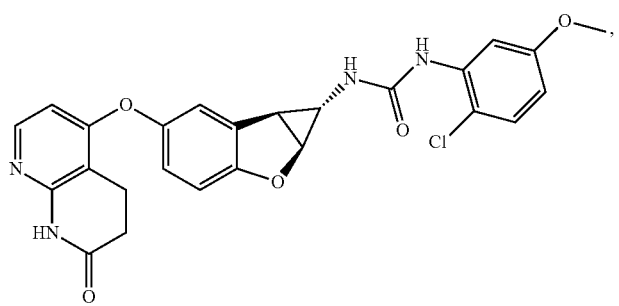

-continued
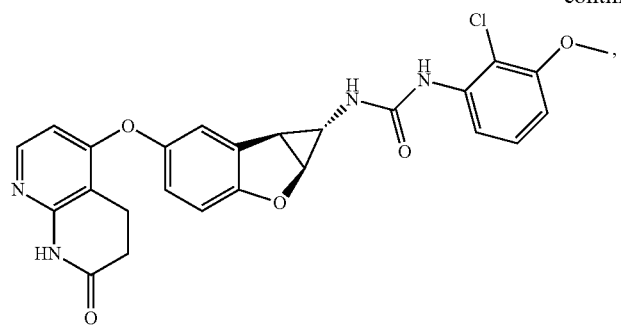
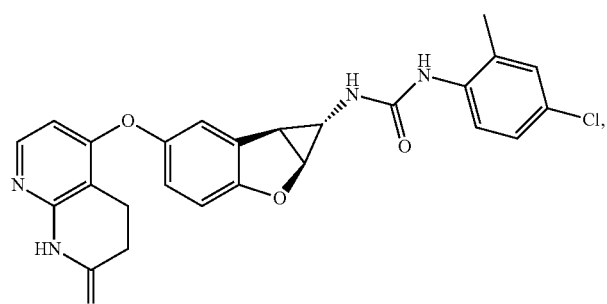
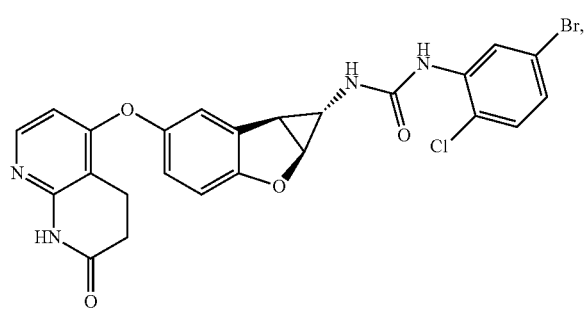
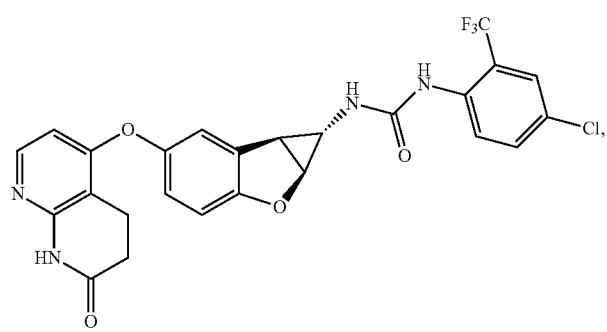
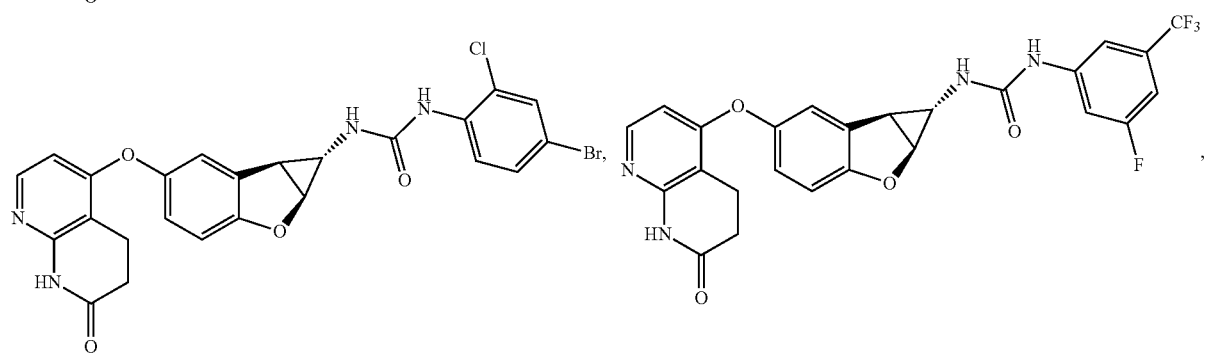
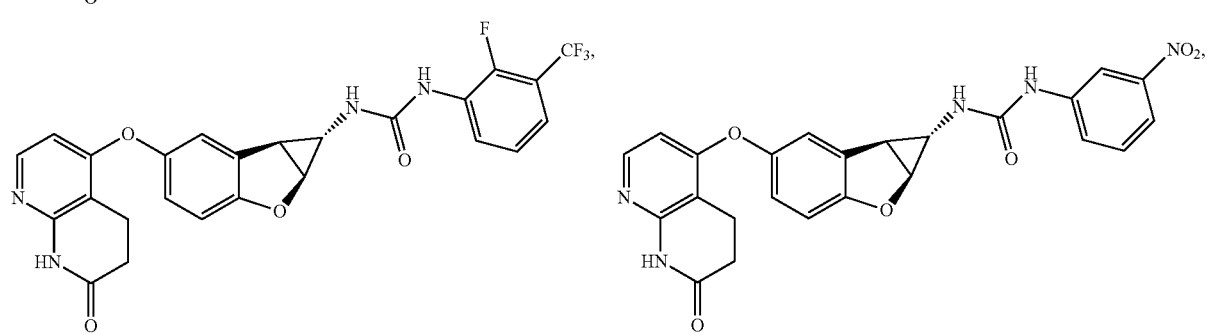

-continued
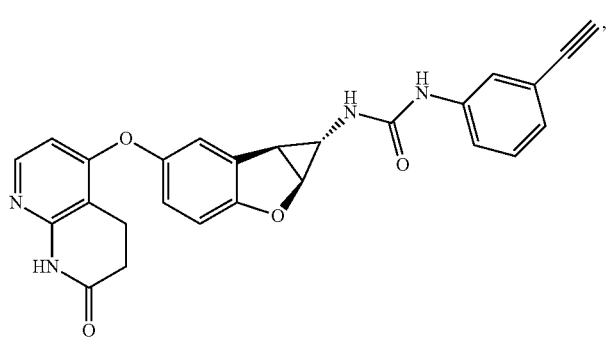
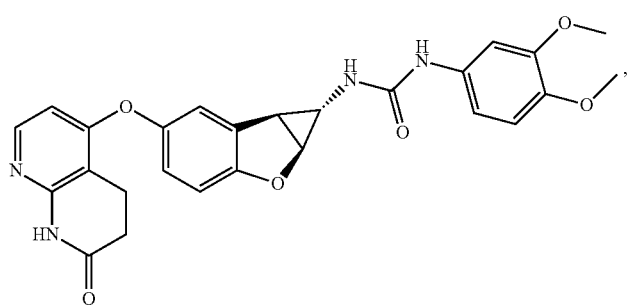
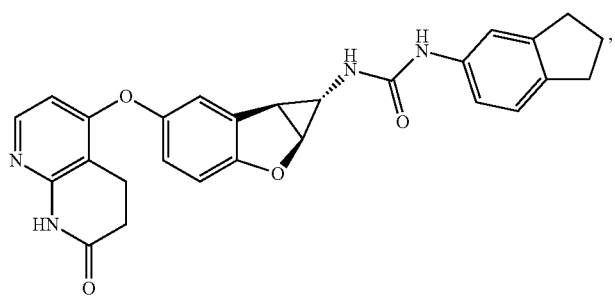
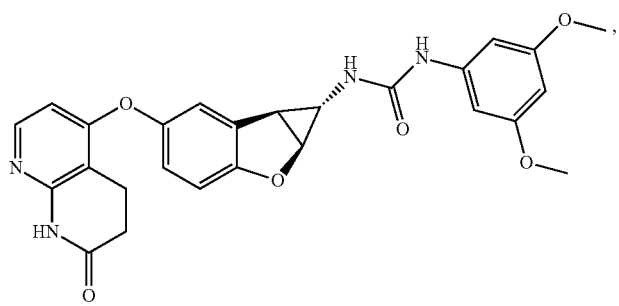
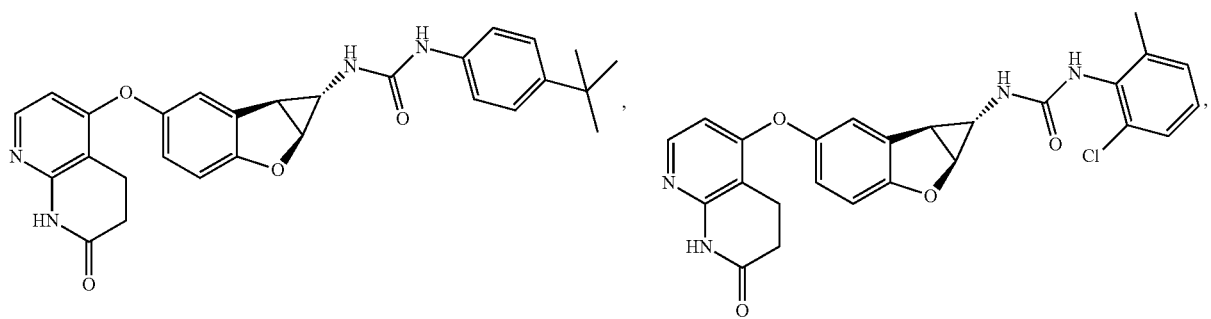

-continued
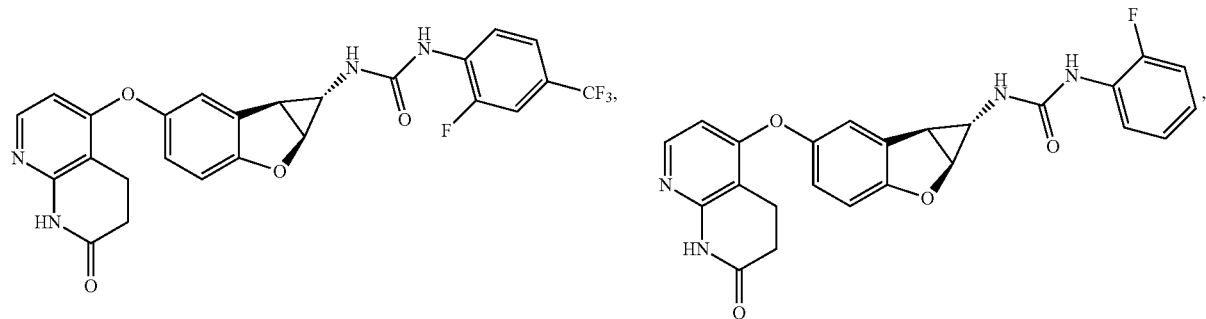
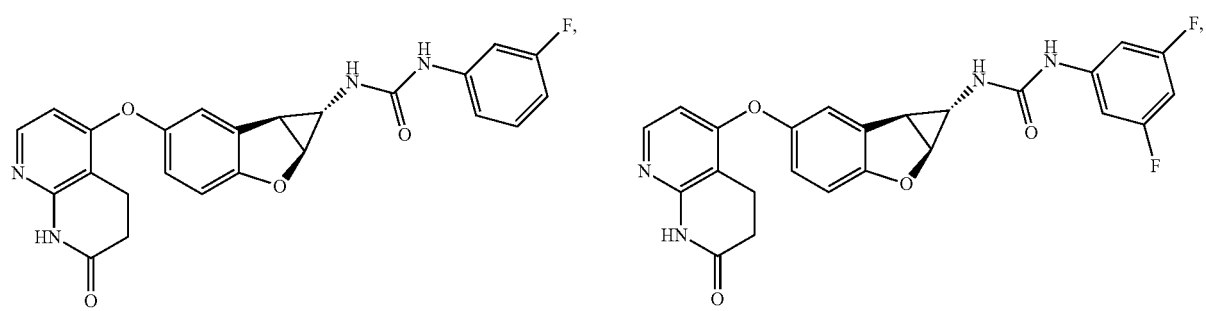
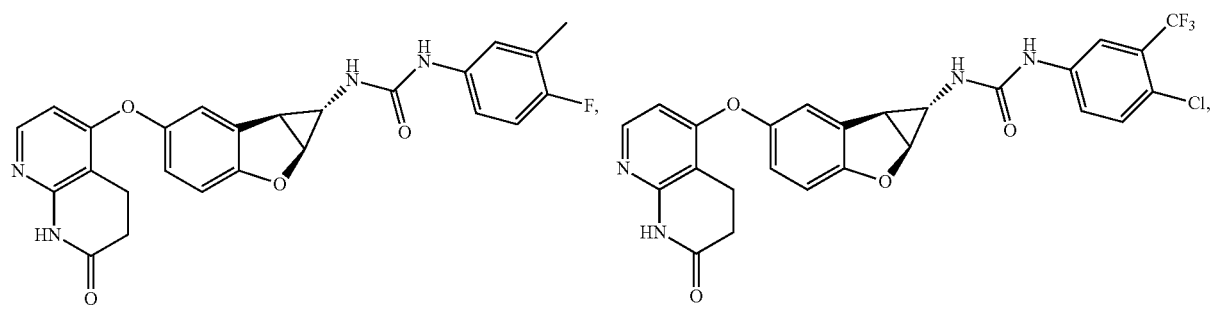
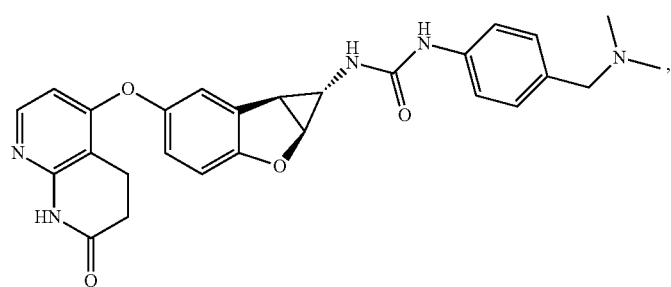
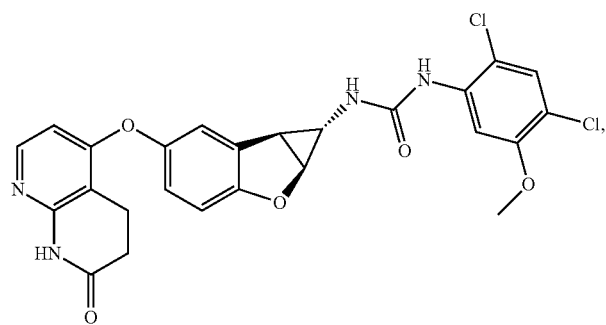

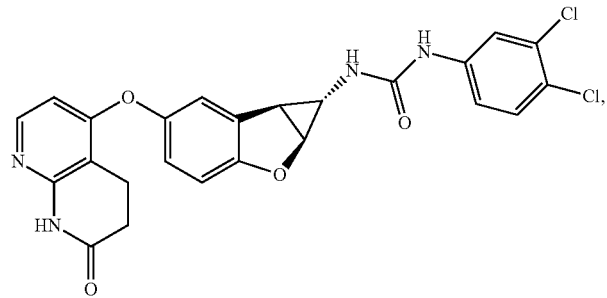
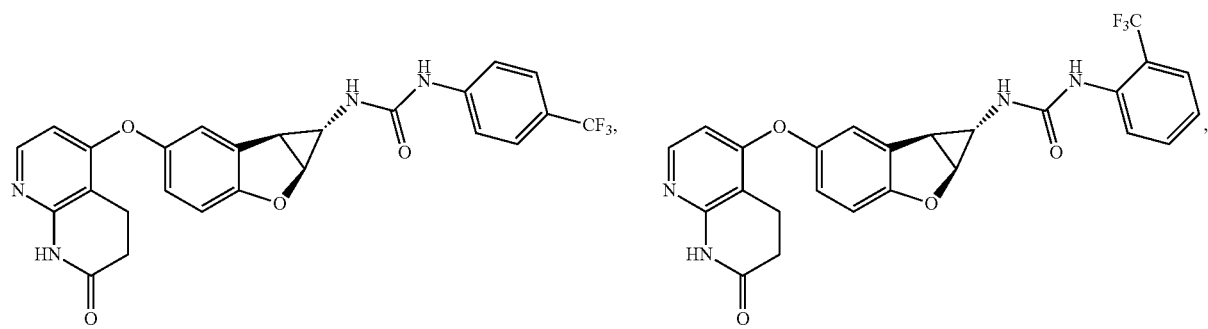
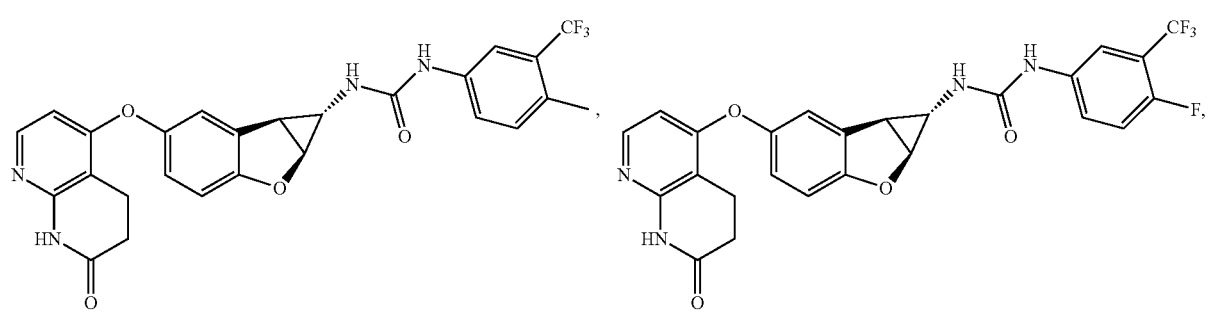
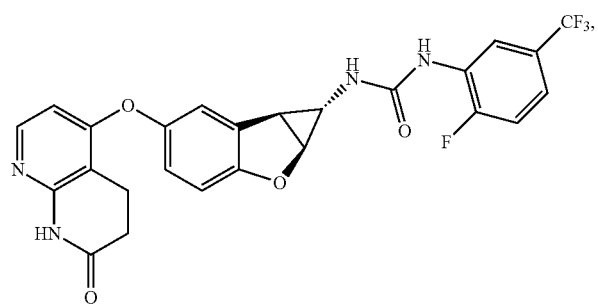
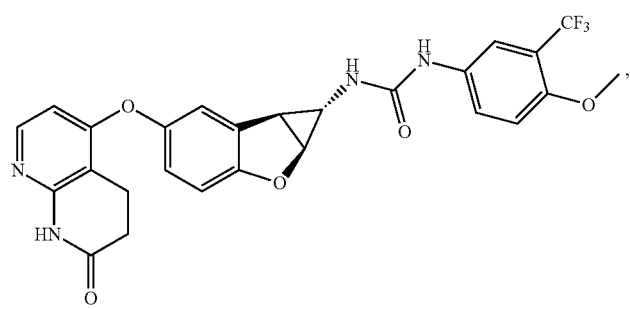

143
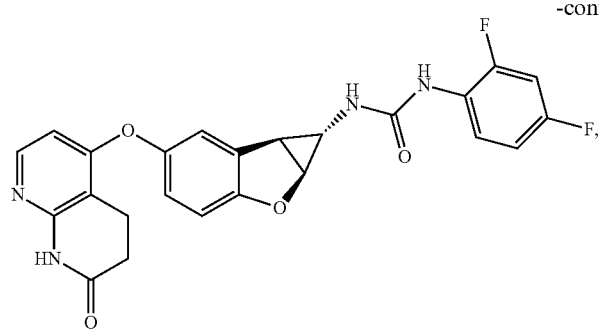
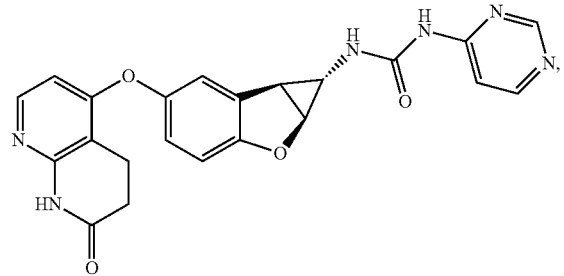
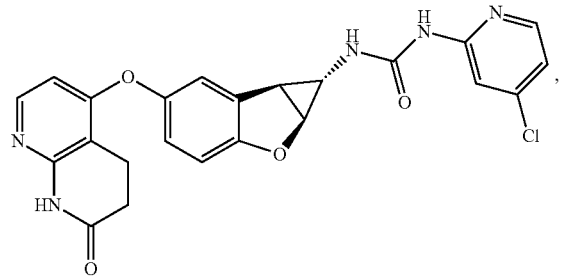
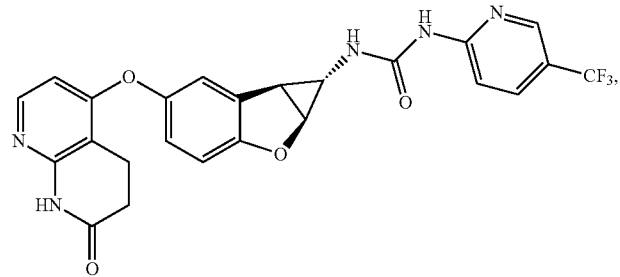
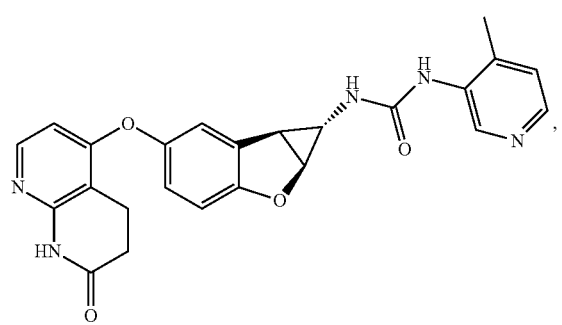
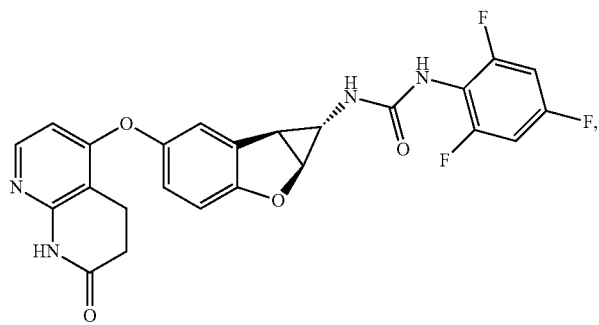
-continued
144
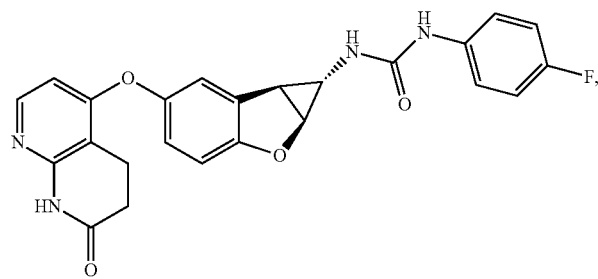
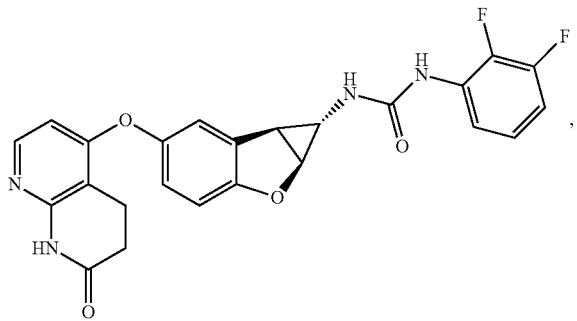
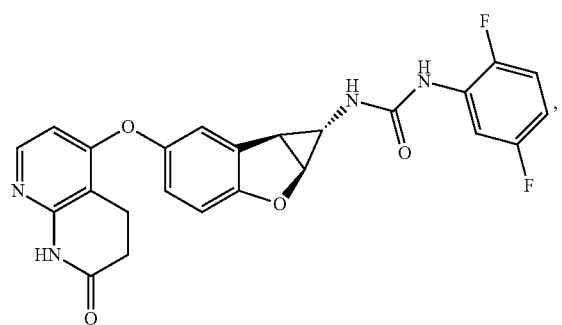
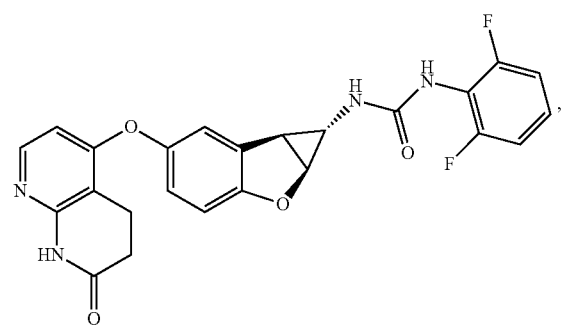

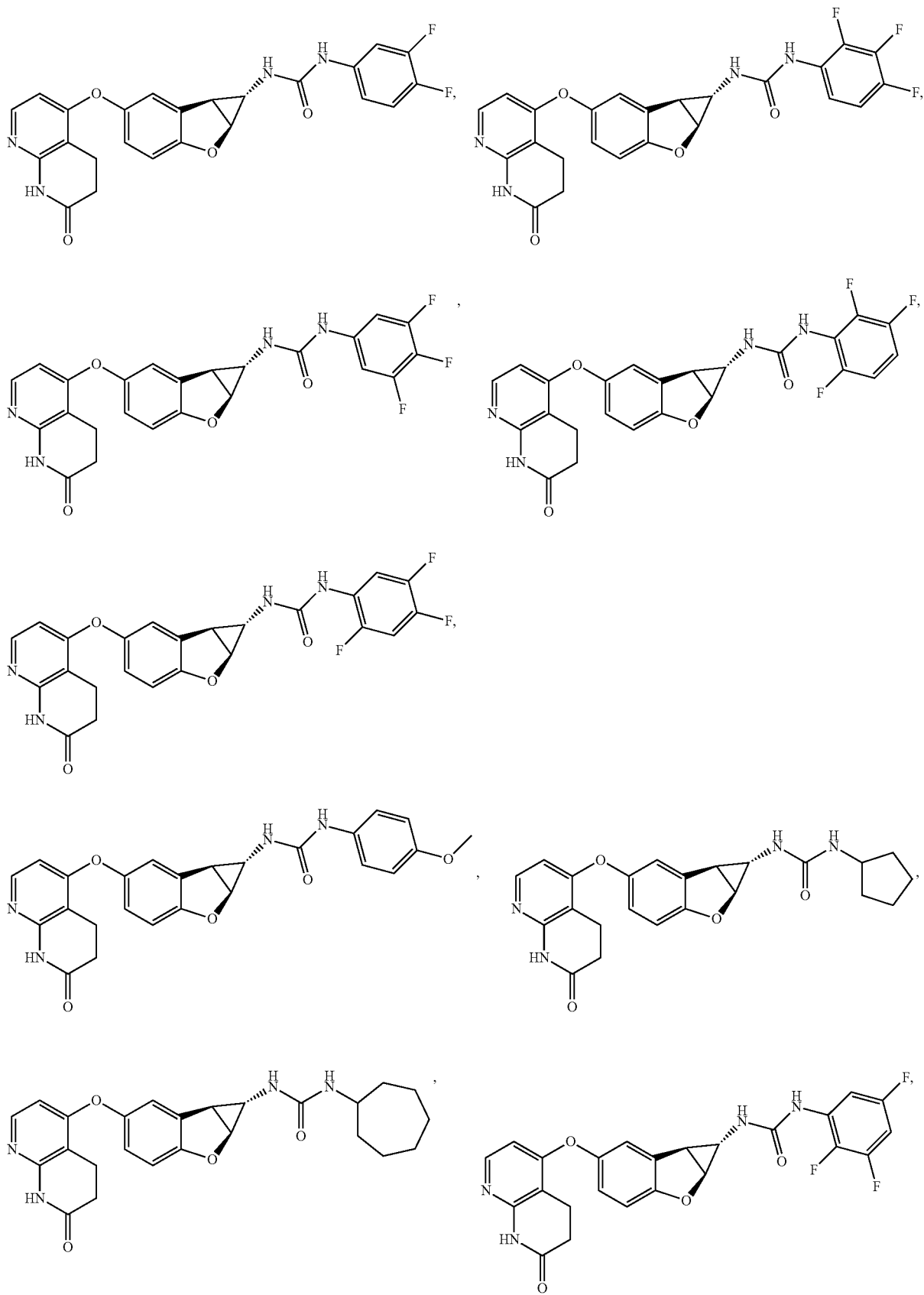

-continued
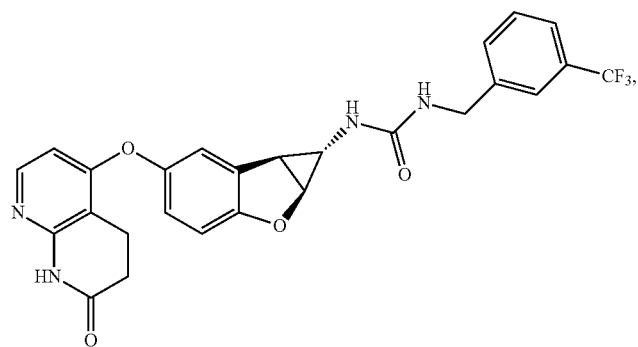
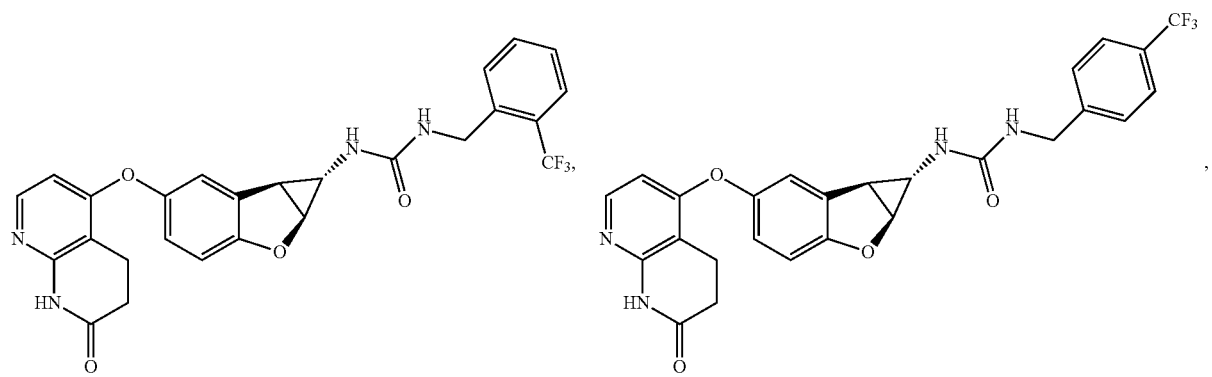
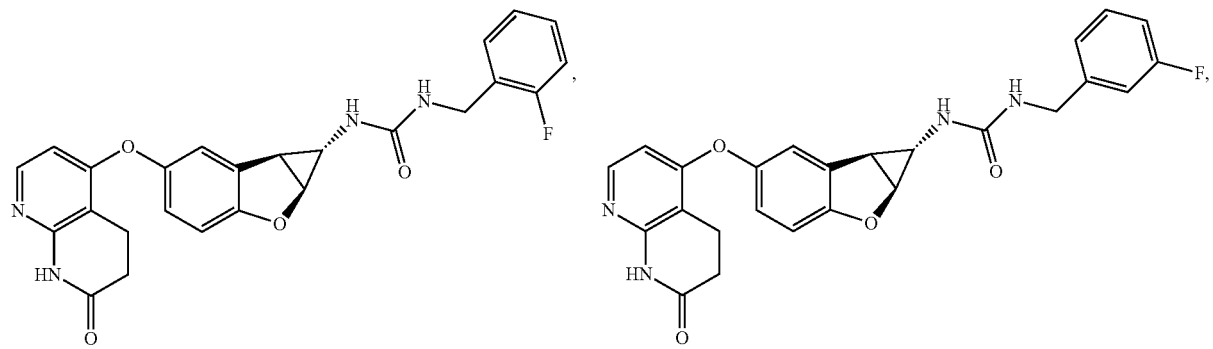
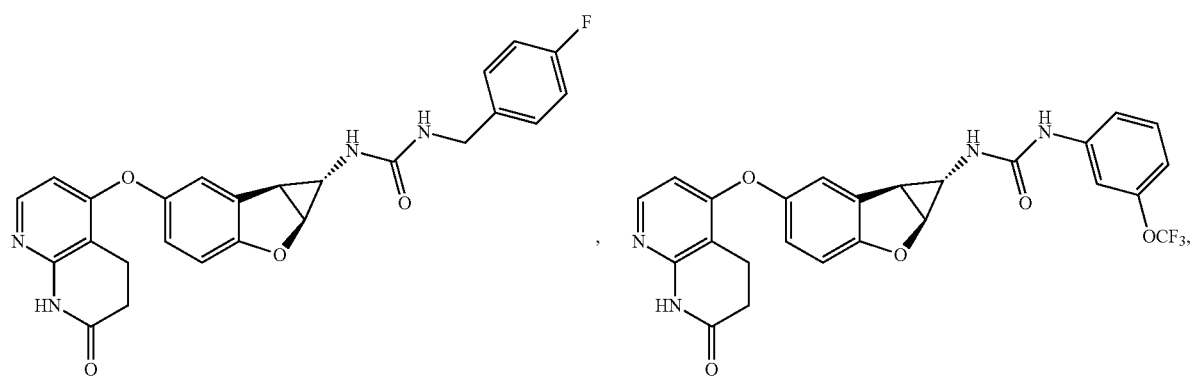

-continued
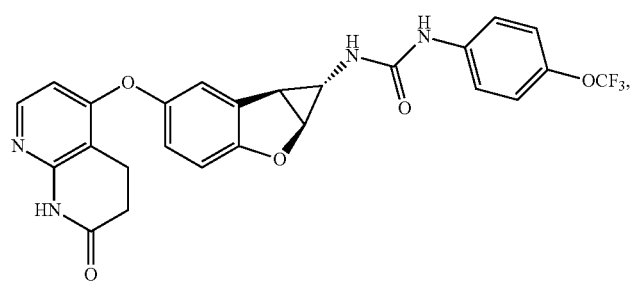 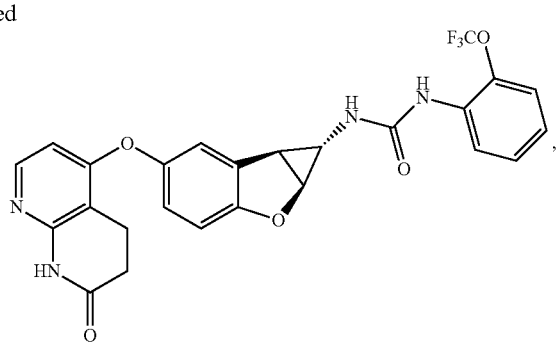
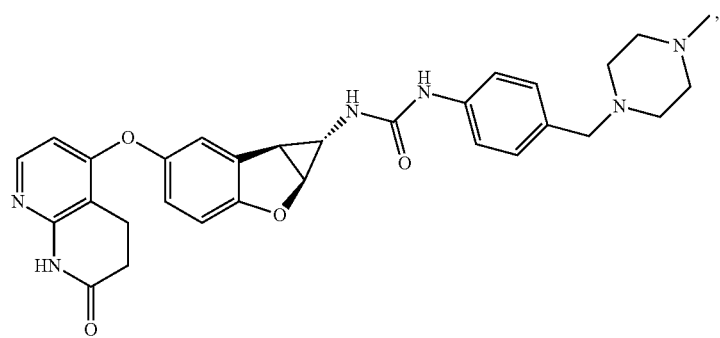
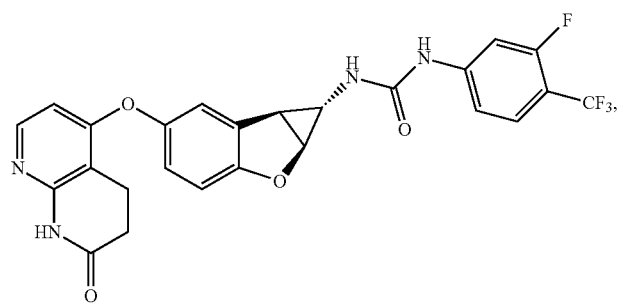
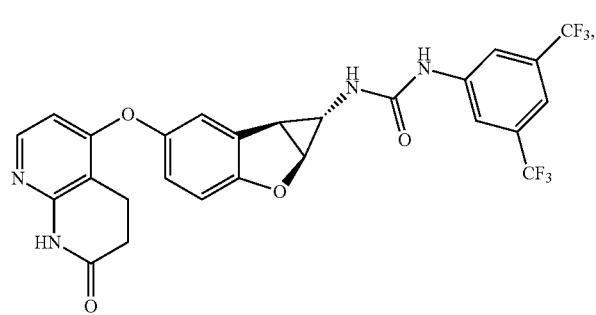 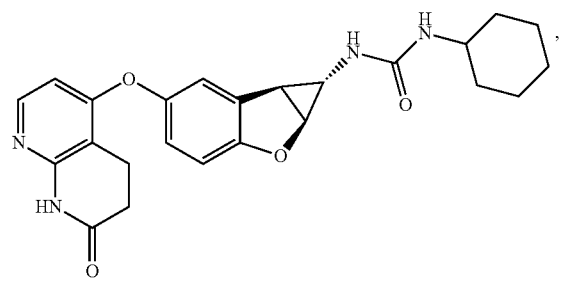
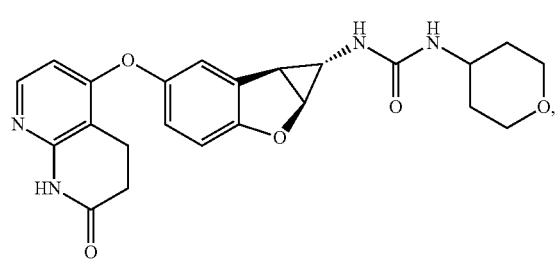 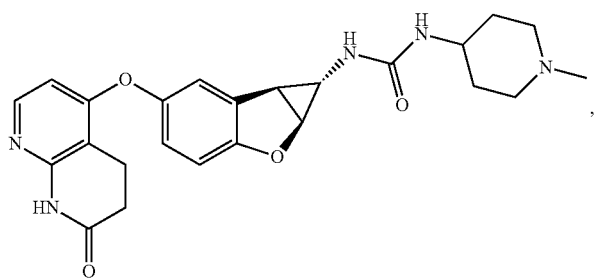

-continued
151
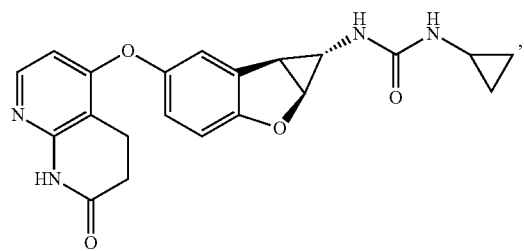
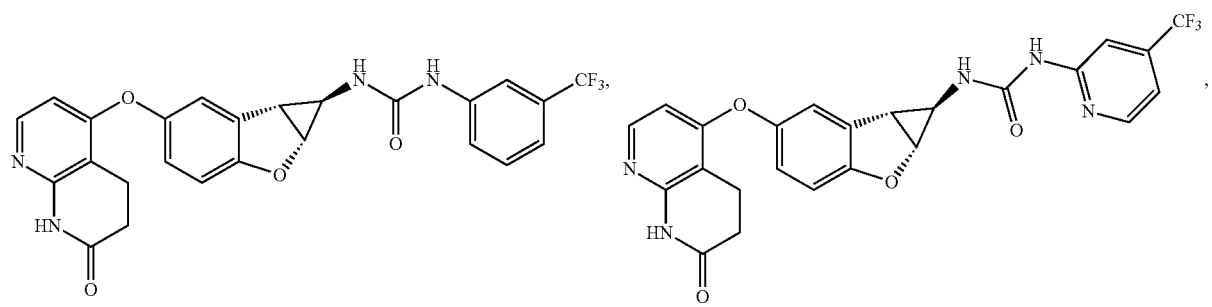
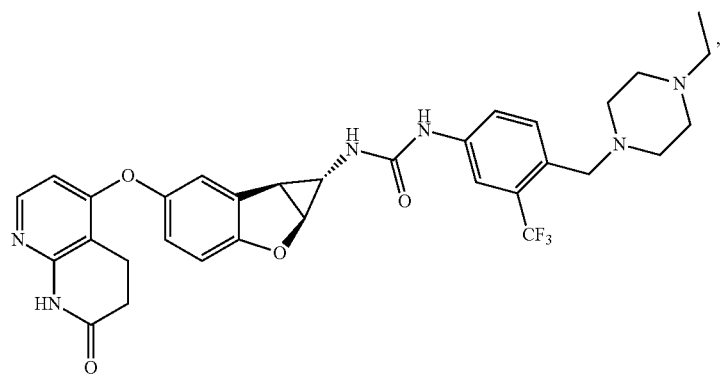
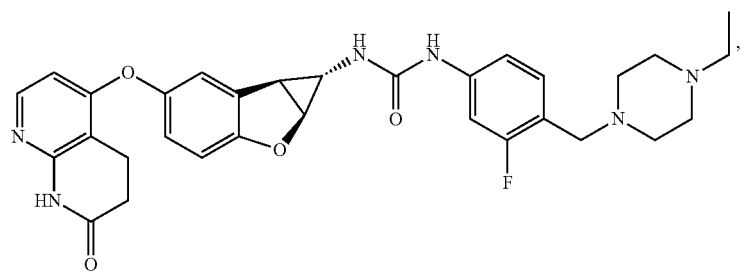
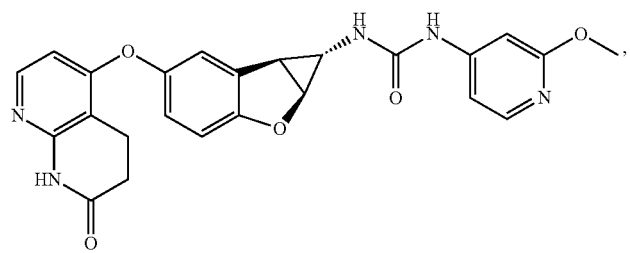
152
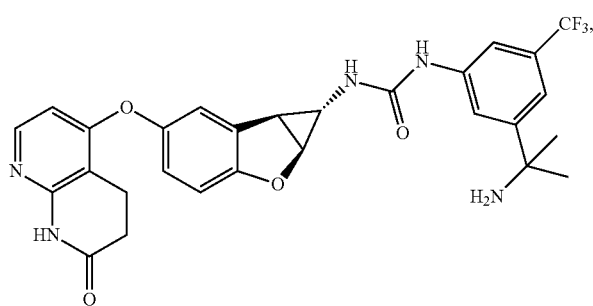

153 154
-continued
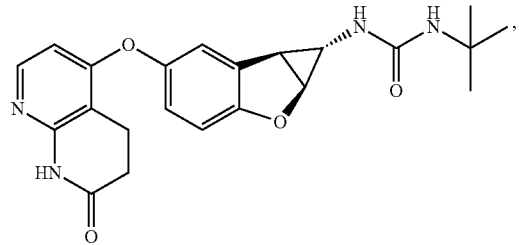
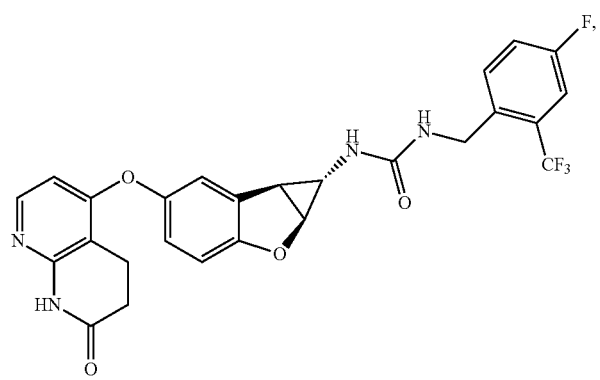
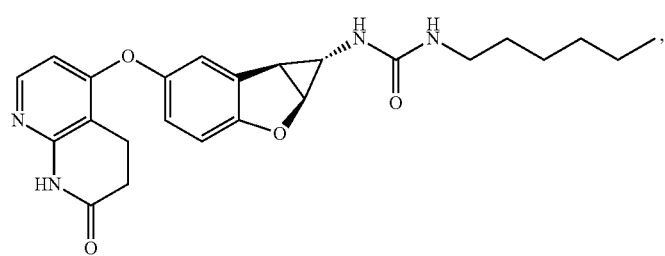
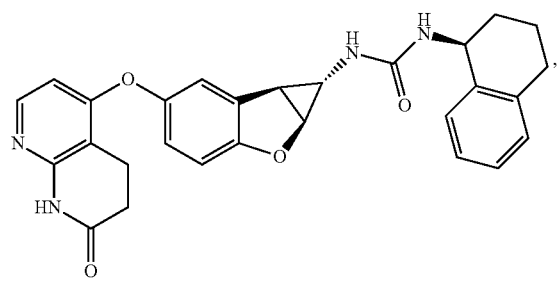
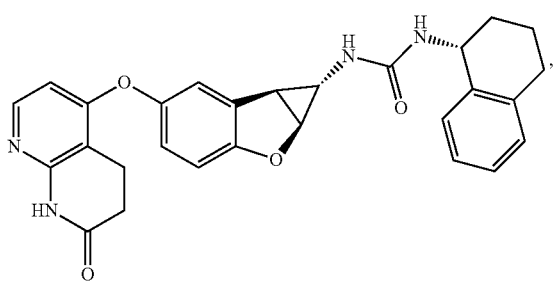
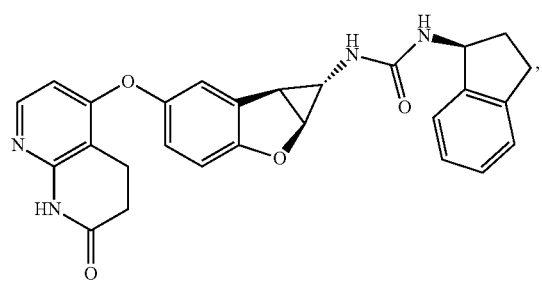
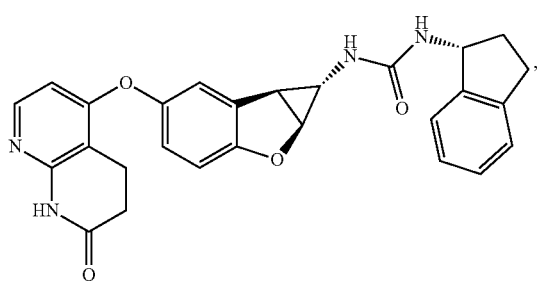
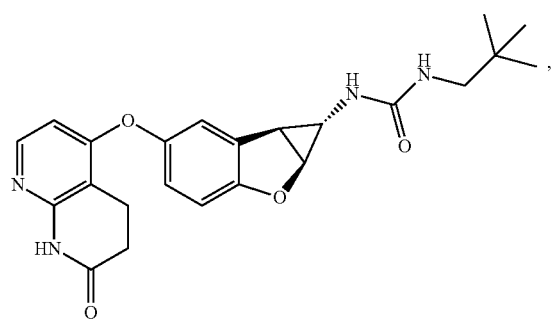

-continued
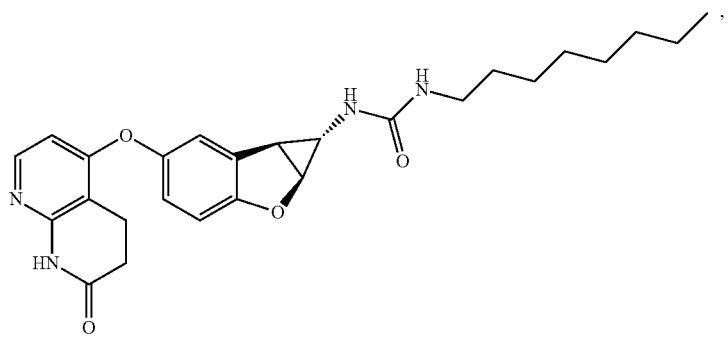
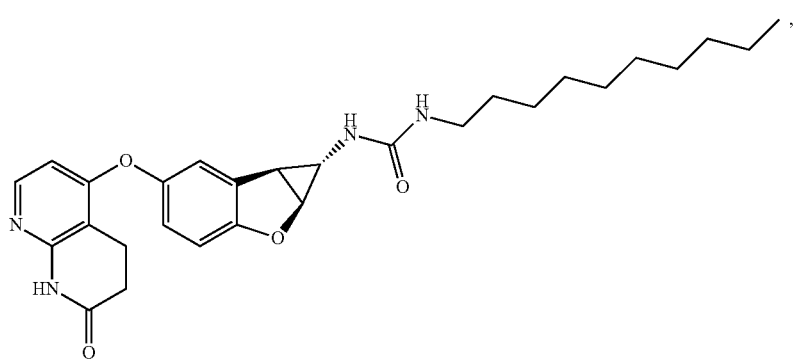
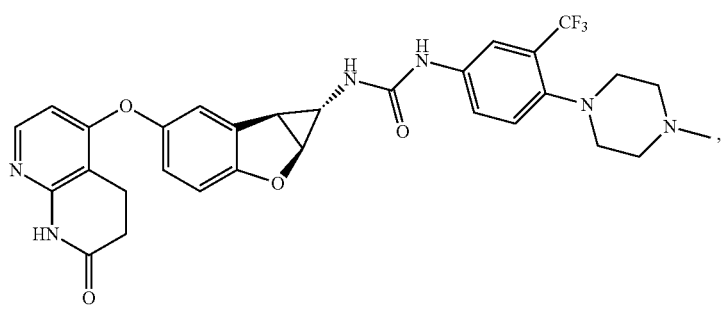
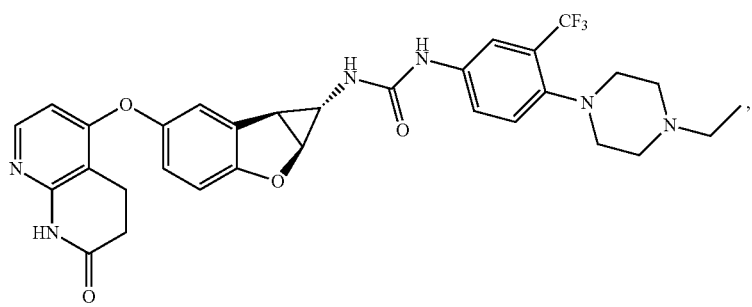
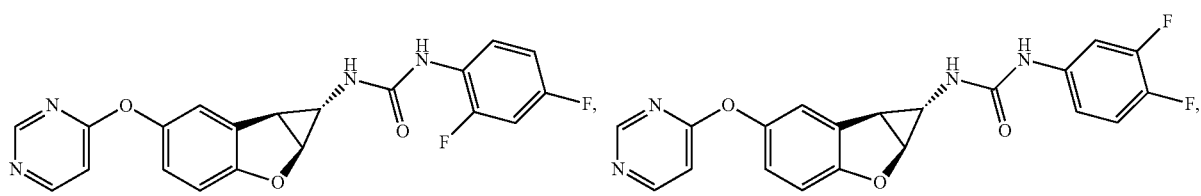

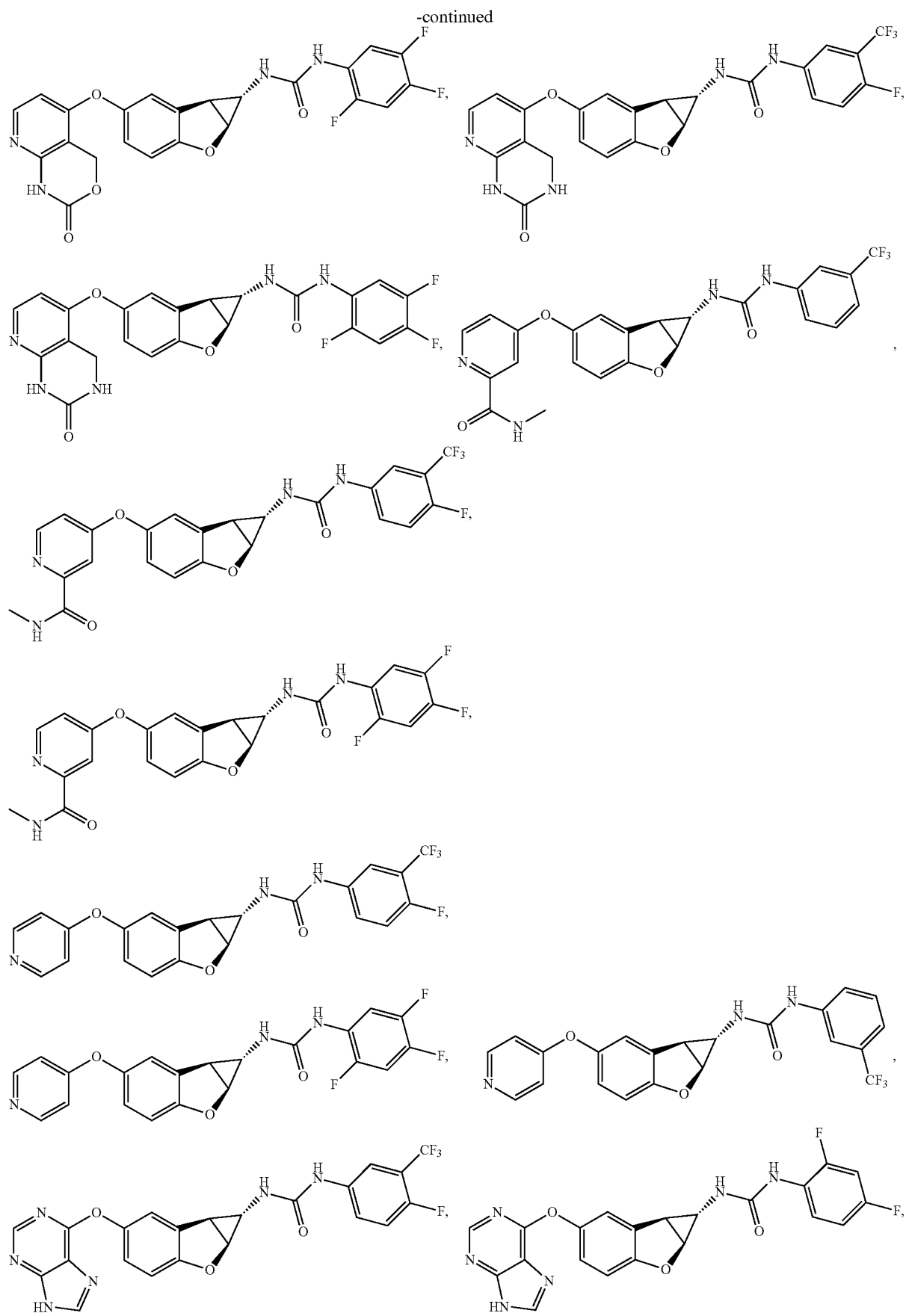

-continued
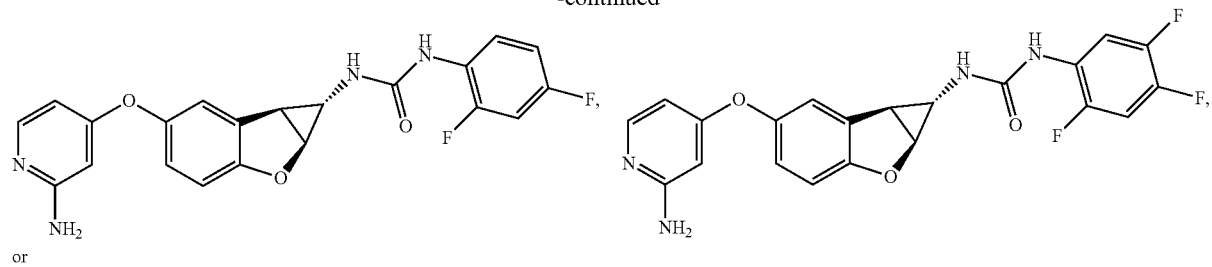
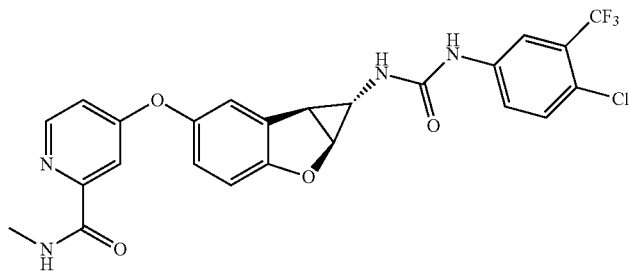
or a stereoisomer thereof, or a pharmaceutically acceptable salt thereof.
* * * * *